(12) United States Patent
Blumberg et al.

(10) Patent No.: US 12,173,066 B2
(45) Date of Patent: Dec. 24, 2024

(54) HUMANIZED AND AFFINITY-MATURED ANTI-CEACAM1 ANTIBODIES

(71) Applicant: The Brigham and Women's Hospital, Inc., Boston, MA (US)

(72) Inventors: Richard S. Blumberg, Weston, MA (US); Yu-Hwa Huang, Weston, MA (US); Amit Gandhi, Billerica, MA (US); Monica Bertagnolli, Newton, MA (US); Charles Yoon, Brookline, MA (US); Robert George Edward Holgate, Royston (GB); Arron Robert Hearn, Ely (GB); Susan Dana Jones, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 790 days.

(21) Appl. No.: 17/311,258

(22) PCT Filed: Dec. 9, 2019

(86) PCT No.: PCT/US2019/065212
§ 371 (c)(1),
(2) Date: Jun. 4, 2021

(87) PCT Pub. No.: WO2020/118295
PCT Pub. Date: Jun. 11, 2020

(65) Prior Publication Data
US 2022/0025040 A1 Jan. 27, 2022

Related U.S. Application Data

(60) Provisional application No. 62/776,877, filed on Dec. 7, 2018.

(51) Int. Cl.
| | | |
|---|---|---|
| C07K 16/28 | (2006.01) | |
| A61K 39/00 | (2006.01) | |
| A61P 35/00 | (2006.01) | |
| C07K 16/30 | (2006.01) | |

(52) U.S. Cl.
CPC .......... *C07K 16/2803* (2013.01); *A61P 35/00* (2018.01); *C07K 16/30* (2013.01); *A61K 2039/505* (2013.01); *C07K 2317/24* (2013.01); *C07K 2317/33* (2013.01); *C07K 2317/41* (2013.01); *C07K 2317/622* (2013.01); *C07K 2317/73* (2013.01); *C07K 2317/76* (2013.01); *C07K 2317/92* (2013.01)

(58) Field of Classification Search
CPC .......... C07K 16/2803; C07K 16/30; C07K 2317/24; C07K 2317/33; C07K 2317/41; C07K 2317/622; C07K 2317/73; C07K 2317/76; C07K 2317/92; C07K 2299/00; C07K 2317/34; C07K 2317/52; C07K 2317/70; C07K 2317/74; C07K 2319/00; A61P 35/00; A61K 2039/505; A61K 2039/876
See application file for complete search history.

(56) References Cited

U.S. PATENT DOCUMENTS

| | | | |
|---|---|---|---|
| 9,556,271 B2 * | 1/2017 | Blumberg | .......... A61K 47/6853 |
| 9,771,431 B2 | 9/2017 | Markel et al. | |
| 10,081,679 B2 * | 9/2018 | Ben-Moshe | ....... C07K 16/2827 |
| 10,550,196 B2 * | 2/2020 | Ben-Moshe | ............ A61P 11/00 |
| 11,866,509 B2 * | 1/2024 | Ben-Moshe | ............ A61P 11/00 |
| 2011/0305687 A1 | 12/2011 | Weng et al. | |
| 2014/0328841 A1 | 11/2014 | Blumberg et al. | |
| 2016/0176966 A1 | 6/2016 | Markel et al. | |
| 2017/0051058 A1 | 2/2017 | Lang et al. | |
| 2018/0153986 A1 | 6/2018 | Blumberg et al. | |

FOREIGN PATENT DOCUMENTS

| | | |
|---|---|---|
| WO | 2015166484 A1 | 11/2015 |
| WO | 2018174629 A1 | 9/2018 |

OTHER PUBLICATIONS

Huang et al. CEACAM1 regulates TIM-3-mediated tolerance and exhaustion. Nature, 517: 386-390 (2015). (Year: 2015).*
Ladner. Mapping the Epitopes of Antibodies. Biotechnology and Genetic Engineering Reviews, 24(1): 1-30 (2007). (Year: 2007).*
Schreiber et al. 3D-Epitope-Explorer (3DEX): localization of conformational epitopes within three-dimensional structures of proteins. J Comput Chem. 26(9):879-87 (2005). (Year: 2005).*
Blythe et al., Benchmarking B cell epitope prediction: Underperformance of existing methods, Protein Science. 14:246-248; (2005) (Year: 2005).*
Gershoni et al. Epitope Mapping, Biodrugs. 21 (3): 145-156 (2007) (Year: 2007).*
Gray-Owen et al: "CEACAM1: contact-dependent control of immunity", Nature Reviews Immunology, Nature Publishing Group UK, London, vol. 6, No. 6, Jun. 1, 2006 (Jun. 1, 2006), pp. 433-446.
Beauchemin et al: "Carcinoembryonic antigen-related cell adhesion molecules (CEACAMs) in cancer progression and metastasis", Cancer Metastasis, Kluwer Academic Publishers, Dordrecht, NL, vol. 32, No. 3, Aug. 1, 2013 (Aug. 1, 2013), pp. 643-671.

* cited by examiner

*Primary Examiner* — Julie Wu
*Assistant Examiner* — Amber K Faust
(74) *Attorney, Agent, or Firm* — Fox Rothschild LLP

(57) ABSTRACT

Provided herein are recombinant antibodies and antigen-binding fragments thereof useful for binding to and inhibiting carcinoembryonic antigen-related cell adhesion molecule 1 (CEACAM1). Also provided are methods of using the disclosed CEACAM1 antibodies and antigen-binding fragments thereof for reducing T-cell tolerance and for the treatment of cancer.

23 Claims, 43 Drawing Sheets
Specification includes a Sequence Listing.

```
       10         20         30         40         50         60         70         80         90        100
GAGGTGCAGTTGTTGGAGTCTGGGGGAGGCTTGGTGCAGCCTGGGGGGTCCCTGAGACTCTCCTGTGCAGCCTCTGGATTCATTTCAGTAGCCATGCA    Kabat
 E  V  Q  L  L  E  S  G  G  G  L  V  Q  P  G  G  S  L  R  L  S  C  A  A  S  G  F  I  F  S  S  H  G   Primary
                      10                   20                              30
                      10                   20                              30

110        120        130        140        150        160        170        180        190        200
TGTCTTGGGTTCGCCAGGCTCCAGGGAAGGGGCTGGAGTGGGTCGCAACCATTAGCAGTGGTGGTACTTACACCTATTACCCAGACAGTGTGAAGGGCG    Kabat
 M  S  W  V  R  Q  A  P  G  K  G  L  E  W  V  A  T  I  S  S  G  G  T  Y  T  Y  Y  P  D  S  V  K  G  R   Primary
                  40                              50   52 A              60
                  40                              50                      60

210        220        230        240        250        260        270        280        290        300
ATTCACCATATCCAGAGACAATTCCAAAAACACCCTGTACCTGCAAATGAACAGTCTGAAGGCCGAGGACACAGCCATGTATTACTGTGCAAGACACGAC    Kabat
 F  T  I  S  R  D  N  S  K  N  T  L  Y  L  Q  M  N  S  L  K  A  E  D  T  A  M  Y  Y  C  A  R  H  D   Primary
              70                      80  82 A B C              90
              70                              80                  90                              100

310        320        330        340        350        360
TTTGATTACGACGCGGGCTGGTTTGCTTACTGGGGCCAAGGGACCCTGGTCACCGTCTCCTCA                                        Kabat
 F  D  Y  D  A  W  F  A  Y  W  G  Q  G  T  L  V  T  V  S  S                                            Primary
 97  100 A B C D              110                        120
              100                        110                        120
```

FIG. 3A

```
        10         20         30         40         50         60         70         80         90        100
GAGGTGCAGTTGTTGGAGTCTGGGGGAGGCTTGGTGCAGCCTGGGGGGTCCCTGAGACTCTCCTGTGCAGCCTCTGGATTCATTTCAGTAGCCATGGCA   Kabat
 E  V  Q  L  L  E  S  G  G  G  L  V  Q  P  G  G  S  L  R  L  S  C  A  A  S  G  F  I  F  S  S  H  G    Primary
                   10                  20                                     30
                                                                              30

110        120        130        140        150        160        170        180        190        200
TGTCTTGGGTTCGCCAGGCTCCAGGGAAGGGGCTGGAGTGGGTCGCAACCATTAGCAGTGGTGGTACTTACACCTATTACCCAGACAGTGTGAAGGGCG   Kabat
 M  S  W  V  R  Q  A  P  G  K  G  L  E  W  V  A  T  I  S  S  G  G  T  Y  T  Y  Y  P  D  S  V  K  G  R  Primary
             40                                  50  52 A              60
             40                                  50                    60

210        220        230        240        250        260        270        280        290        300
ATTCACCATATCCAGAGACAATTCCAAAAACACCCTGTACCTGCAAATGAACAGTCTGAAGGCCGAGGACACAGCCATGTATTACTGTGCAAGACACGAC   Kabat
 F  T  I  S  R  D  N  S  K  N  T  L  Y  L  Q  M  N  S  L  K  A  E  D  T  A  M  Y  Y  C  A  R  H  D    Primary
       70                             80  82 A B C             90                          100
       70                             80                       90

310        320        330        340        350        360
TTTGATTACGACGGCGTCTGGTTTGCTTACTGGGGCCAAGGGACCCTGGTCACCGTCTCCTCA   Kabat
 F  D  Y  F  P  W  F  A  H  W  G  Q  G  T  L  V  T  V  S  S        Primary
97       100 A B C D                  110                  120
                                      110
```

FIG. 3B

```
         10         20         30         40         50         60         70         80         90        100
GAAATTGTTCTCACCCAGTCTCCAGCAACCCTGTCTTTGTCTCCAGGGGAAAGAGCCACCCTCTCCTGCAGGGCCAACTCAGCTGTAAGTTACATGTATT   Kabat
 E  I  V  L  T  Q  S  P  A  T  L  S  L  S  P  G  E  R  A  T  L  S  C  R  A  N  S  A  V  S  Y  M  Y     Primary
                10                  20                                      27 29 30
                10                  20                                         30
```
```
        110        120        130        140        150        160        170        180        190        200
GGTATCAACAGAAGCCAGGCCAGGCTCCCAGGCCCTGGATTTATCTCACATCCAACAGGCTACTGGAGTCCCTGCTCGCTTCAGTGGCAGTGGGTCTGG   Kabat
 W  Y  Q  Q  K  P  G  Q  A  P  R  P  W  I  Y  L  T  S  N  R  A  T  G  V  P  A  R  F  S  G  S  G  S  G   Primary
                40                          50                          60
                40                          50                          60
```
```
        210        220        230        240        250        260        270        280        290        300
GACCGACTATACTCTCACAATCAGCAGCCTAGAGCCTGAAGATTTTGCCGTTTATTACTGCCAGCAGTGGAGTAGTAACCCCACGTTCGGCCAGGGG   Kabat
 T  D  Y  T  L  T  I  S  S  L  E  P  E  D  F  A  V  Y  Y  C  Q  Q  W  S  S  N  P  T  F  G  Q  G        Primary
                70                          80                          90                     100
                70                          80                          90                     100
```
```
        310
ACAAAGCTGGAGATCAAA                                                                                      Kabat
 T  K  L  E  I  K                                                                                       Primary
       106 A
       106
```

FIG. 3C

VH CDR1

```
         26        35
    CAASGFIFSSHGMSW
    ----XXXXXXXXX-
```

VH CDR3 Block1 (B1)

```
       94         102
    CARHDFDYDAAWFAYW
    --XXXXXX--------
```

VH CDR3 Block2 (B2)

```
       94         102
    CARHDFDYDAAWFAYW
    --------XXXXXXX-
```

VL CDR3

```
      90    96
    CQQWSSNPPTF
    --XXXXXX--
```

FIG. 7

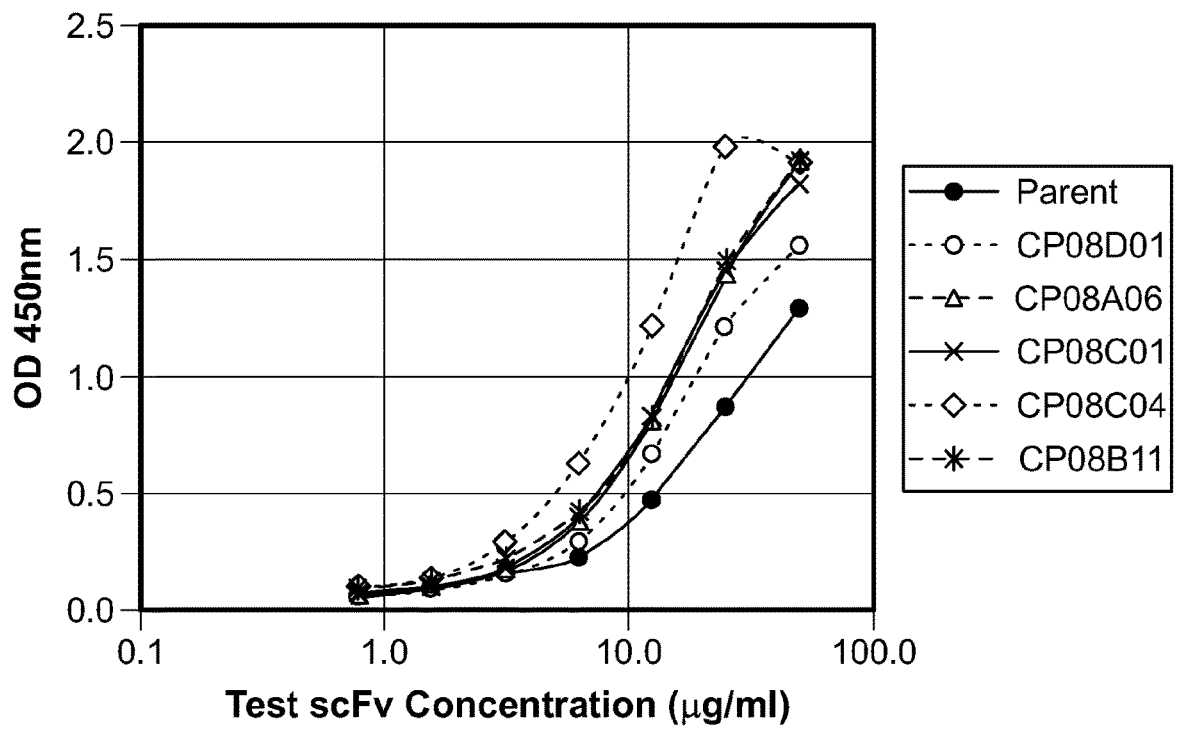
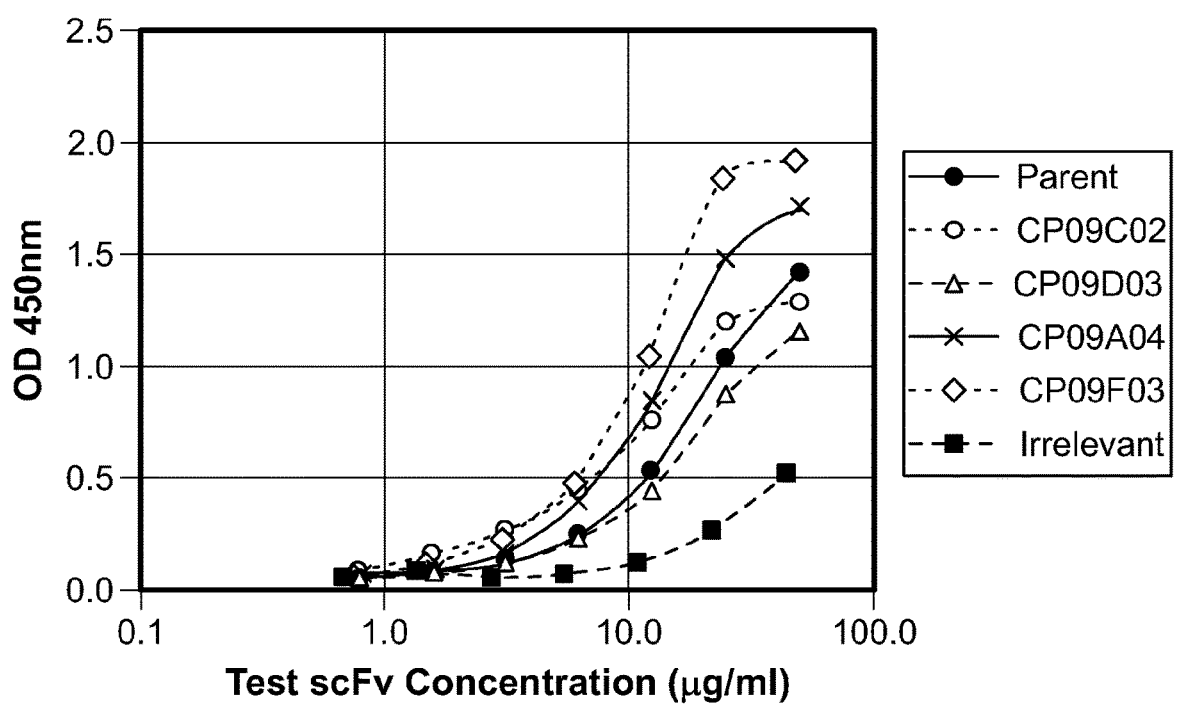
FIG. 10

|   | C4 | C7 | C8 | C5 | C3 | C1 | C6 |
|---|---|---|---|---|---|---|---|
| 1: C4 \| O75871 \| 36-139 | 100.00 | 44.23 | 50.00 | 47.12 | 50.96 | 47.12 | 50.96 |
| 2: C7 \| Q14002 \| 36-142 | 44.23 | 100.00 | 64.15 | 66.04 | 63.21 | 65.09 | 66.04 |
| 3: C8 \| P31997 \| 35-142 | 50.00 | 64.15 | 100.00 | 71.30 | 68.52 | 72.22 | 72.22 |
| 4: C5 \| P06731 \| 35-144 | 47.12 | 66.04 | 71.30 | 100.00 | 86.11 | 88.89 | 88.89 |
| 5: C3 \| P40198 \| 35-142 | 50.96 | 63.21 | 68.52 | 86.11 | 100.00 | 87.96 | 89.81 |
| 6: C1 \| P13688 \| 35-142 | 47.12 | 65.09 | 72.22 | 88.89 | 87.96 | 100.00 | 89.81 |
| 7: C6 \| P40199 \| 35-142 | 50.96 | 66.04 | 72.22 | 88.89 | 89.81 | 89.81 | 100.00 |

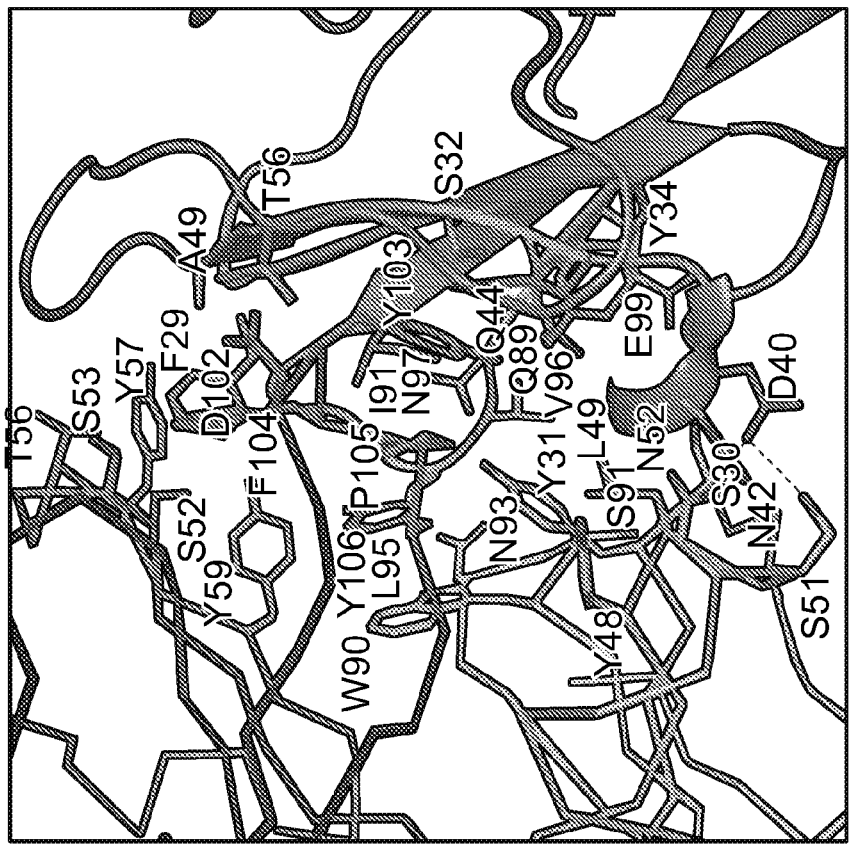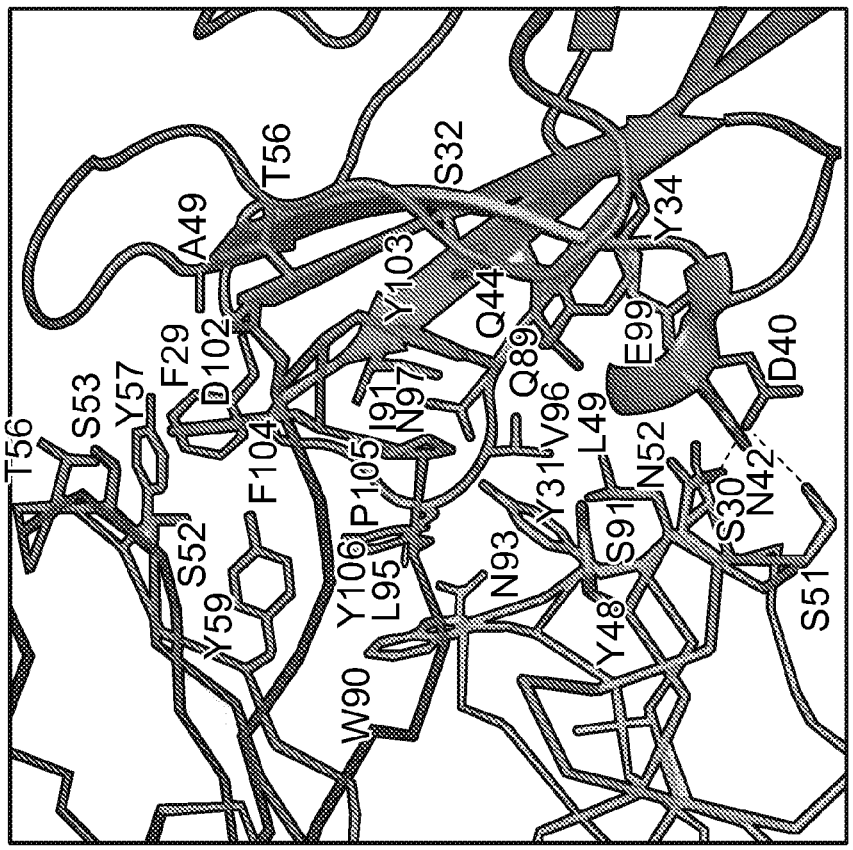
FIG. 18

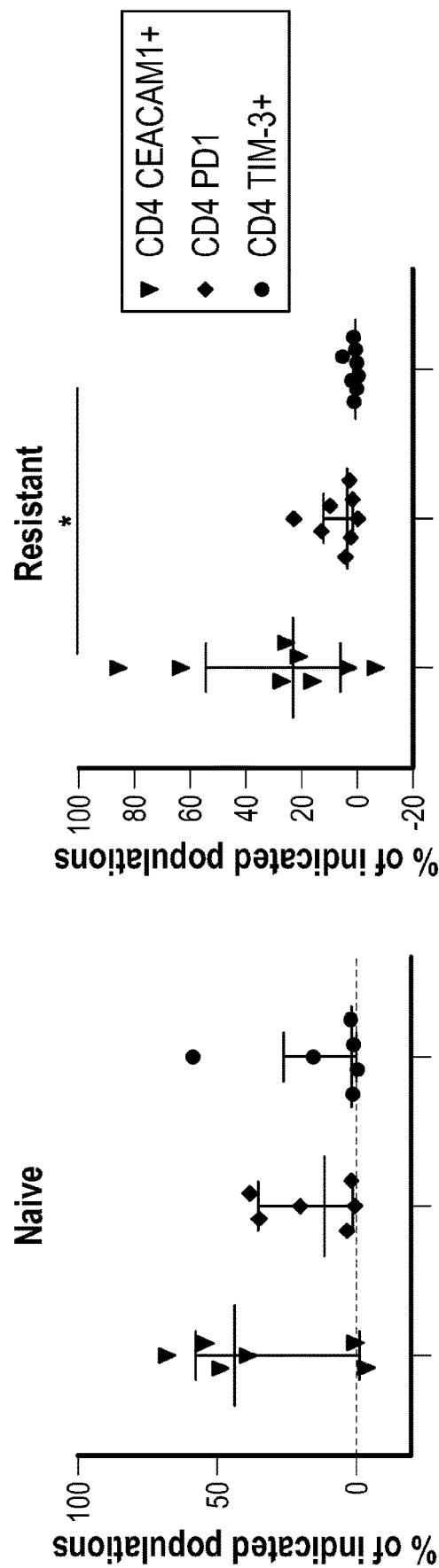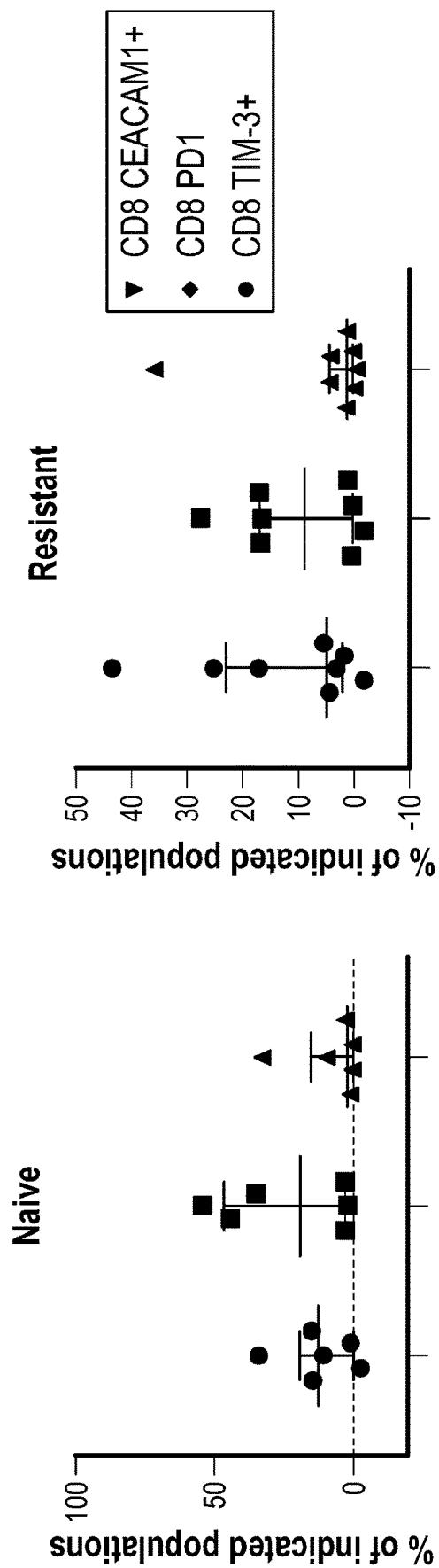
FIG. 27

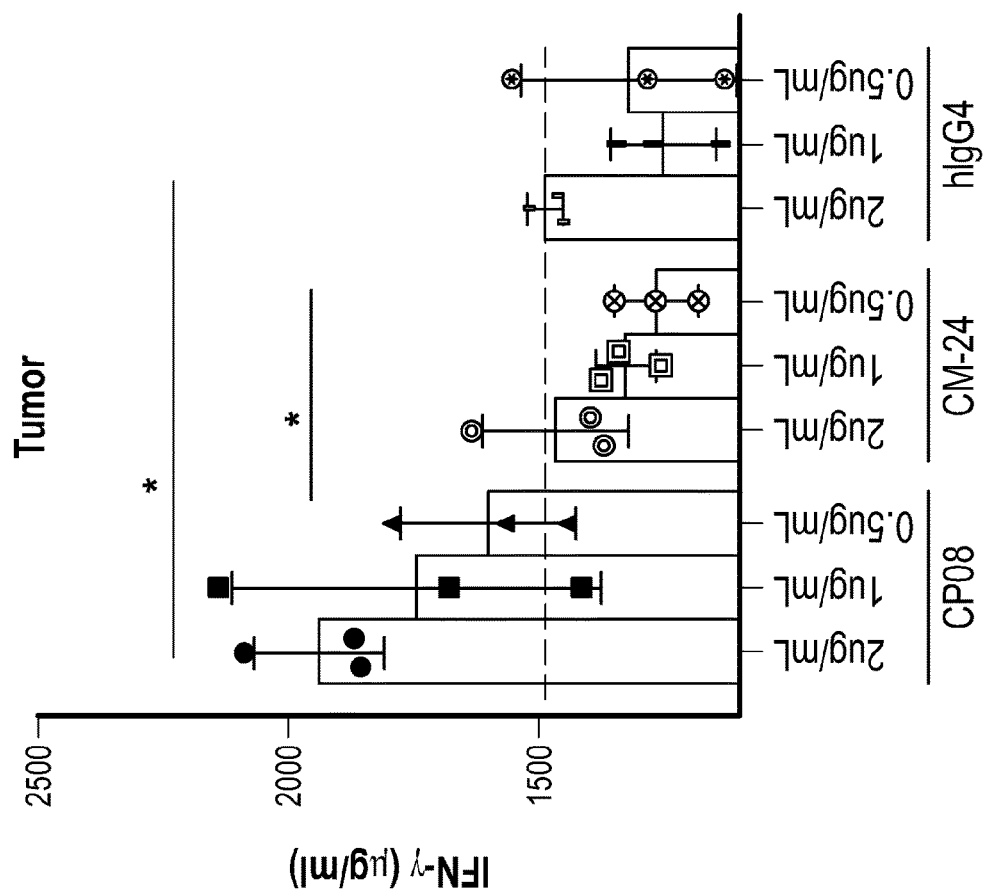
FIG. 32C
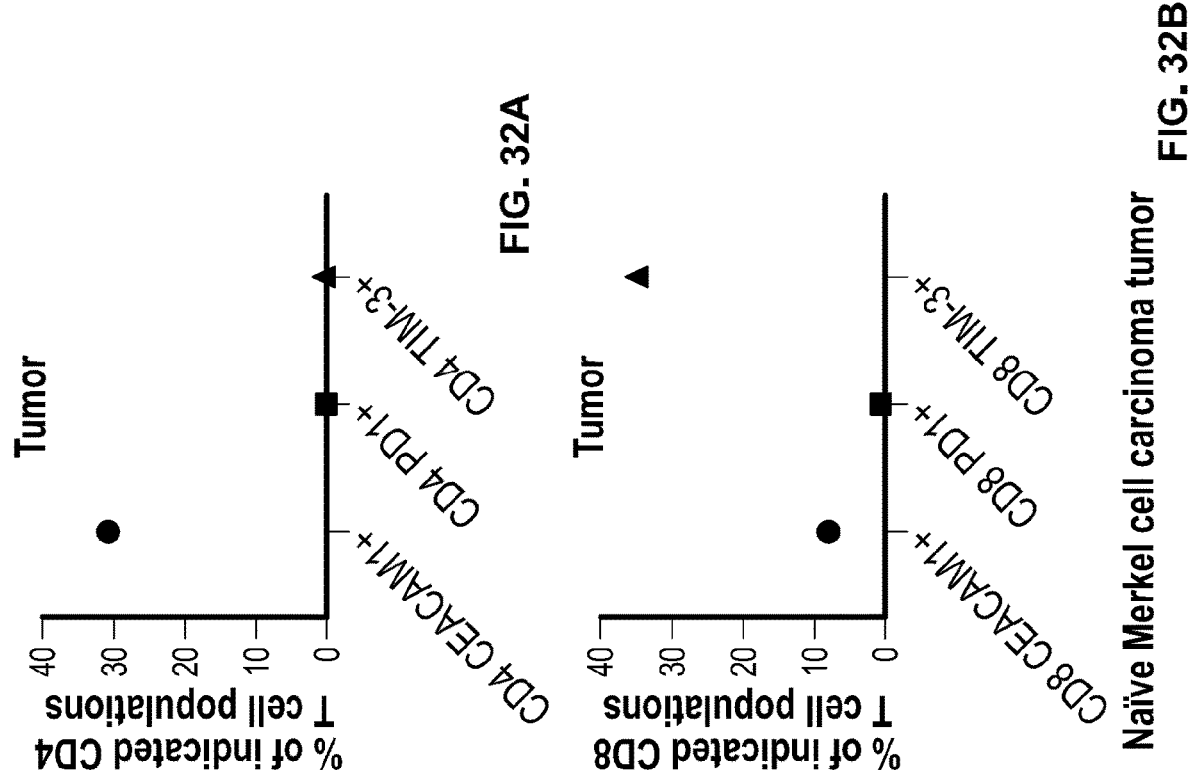
FIG. 32A
FIG. 32B
Naïve Merkel cell carcinoma tumor

SEQUENCE LISTING

```
<160> NUMBER OF SEQ ID NOS: 96

<210> SEQ ID NO 1
<211> LENGTH: 5
<212> TYPE: PRT
<213> ORGANISM: Artificial Sequence
<220> FEATURE:
<223> OTHER INFORMATION: CDR1H
<220> FEATURE:
<221> NAME/KEY: MISC_FEATURE
<222> LOCATION: (1)..(1)
<223> OTHER INFORMATION: A, D, N, or S
<220> FEATURE:
<221> NAME/KEY: MISC_FEATURE
<222> LOCATION: (3)..(3)
<223> OTHER INFORMATION: A or G
<220> FEATURE:
<221> NAME/KEY: MISC_FEATURE
<222> LOCATION: (4)..(4)
<223> OTHER INFORMATION: an amino acid with a hydrophobic side chain
      including I or M

<400> SEQUENCE: 1

Xaa His Xaa Xaa Ser
1               5

<210> SEQ ID NO 2
<211> LENGTH: 17
<212> TYPE: PRT
<213> ORGANISM: Artificial Sequence
<220> FEATURE:
<223> OTHER INFORMATION: CDR2H

<400> SEQUENCE: 2

Thr Ile Ser Ser Gly Gly Thr Tyr Thr Tyr Tyr Pro Asp Ser Val Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: CDR3H
<220> FEATURE:
```

```
<221> NAME/KEY: MISC_FEATURE
<222> LOCATION: (2)..(2)
<223> OTHER INFORMATION: D, G, or P
<220> FEATURE:
<221> NAME/KEY: MISC_FEATURE
<222> LOCATION: (3)..(3)
<223> OTHER INFORMATION: F or P
<220> FEATURE:
<221> NAME/KEY: MISC_FEATURE
<222> LOCATION: (6)..(6)
<223> OTHER INFORMATION: D or F
<220> FEATURE:
<221> NAME/KEY: MISC_FEATURE
<222> LOCATION: (8)..(8)
<223> OTHER INFORMATION: A or Y
<220> FEATURE:
<221> NAME/KEY: MISC_FEATURE
<222> LOCATION: (12)..(12)
<223> OTHER INFORMATION: L, H, or F

<400> SEQUENCE: 3

His Xaa Xaa Asp Tyr Xaa Pro Xaa Trp Phe Ala Xaa
1               5                   10

<210> SEQ ID NO 4
<211> LENGTH: 10
<212> TYPE: PRT
<213> ORGANISM: Artificial Sequence
<220> FEATURE:
<223> OTHER INFORMATION: CDR1L

<400> SEQUENCE: 4

Arg Ala Asn Ser Ala Val Ser Tyr Met Tyr
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CDR2L

<400> SEQUENCE: 5

Leu Thr Ser Asn Arg Ala Thr
1               5

<210> SEQ ID NO 6
<211> LENGTH: 9
<212> TYPE: PRT
<213> ORGANISM: Artificial Sequence
<220> FEATURE:
<223> OTHER INFORMATION: CDR3L
<220> FEATURE:
<221> NAME/KEY: MISC_FEATURE
<222> LOCATION: (3)..(3)
<223> OTHER INFORMATION: W or N
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (5)..(5)
<223> OTHER INFORMATION: A or an amino acid with a neutral hydrophilic
      side chain including S, N, and T
<220> FEATURE:
<221> NAME/KEY: MISC_FEATURE
<222> LOCATION: (6)..(6)
<223> OTHER INFORMATION: L, F, or N
<220> FEATURE:
<221> NAME/KEY: MISC_FEATURE
<222> LOCATION: (8)..(8)
<223> OTHER INFORMATION: P or F
```

<400> SEQUENCE: 6

Gln Gln Xaa Xaa Xaa Xaa Pro Xaa Thr
1               5

<210> SEQ ID NO 7
<211> LENGTH: 12
<212> TYPE: PRT
<213> ORGANISM: Artificial Sequence
<220> FEATURE:
<223> OTHER INFORMATION: CDR3H
<220> FEATURE:
<221> NAME/KEY: MISC_FEATURE
<222> LOCATION: (2)..(2)
<223> OTHER INFORMATION: D, G, or P
<220> FEATURE:
<221> NAME/KEY: MISC_FEATURE
<222> LOCATION: (3)..(3)
<223> OTHER INFORMATION: F or P
<220> FEATURE:
<221> NAME/KEY: MISC_FEATURE
<222> LOCATION: (12)..(12)
<223> OTHER INFORMATION: L, H, or F

<400> SEQUENCE: 7

His Xaa Xaa Asp Tyr Phe Pro Tyr Trp Phe Ala Xaa
1               5                   10

<210> SEQ ID NO 8
<211> LENGTH: 9
<212> TYPE: PRT
<213> ORGANISM: Artificial Sequence
<220> FEATURE:
<223> OTHER INFORMATION: CDR3L
<220> FEATURE:
<221> NAME/KEY: MISC_FEATURE
<222> LOCATION: (3)..(3)
<223> OTHER INFORMATION: W or N
<220> FEATURE:
<221> NAME/KEY: MISC_FEATURE
<222> LOCATION: (6)..(6)
<223> OTHER INFORMATION: L, F, or N
<220> FEATURE:
<221> NAME/KEY: MISC_FEATURE
<222> LOCATION: (8)..(8)
<223> OTHER INFORMATION: P or F

<400> SEQUENCE: 8

Gln Gln Xaa Ser Ser Xaa Pro Xaa Thr
1               5

<210> SEQ ID NO 9
<211> LENGTH: 5
<212> TYPE: PRT
<213> ORGANISM: Artificial Sequence
<220> FEATURE:
<223> OTHER INFORMATION: CDR1H

<400> SEQUENCE: 9

Ser His Gly Met Ser
1               5

<210> SEQ ID NO 10
<211> LENGTH: 12
<212> TYPE: PRT
<213> ORGANISM: Artificial Sequence
<220> FEATURE:
<223> OTHER INFORMATION: CDR3H

<400> SEQUENCE: 10

```
His Asp Phe Asp Tyr Phe Pro Tyr Trp Phe Ala His
1               5                   10
```

<210> SEQ ID NO 11
<211> LENGTH: 9
<212> TYPE: PRT
<213> ORGANISM: Artificial Sequence
<220> FEATURE:
<223> OTHER INFORMATION: CDR3L

<400> SEQUENCE: 11

```
Gln Gln Trp Ser Ser Asn Pro Pro Thr
1               5
```

<210> SEQ ID NO 12
<211> LENGTH: 9
<212> TYPE: PRT
<213> ORGANISM: Artificial Sequence
<220> FEATURE:
<223> OTHER INFORMATION: CDR3L

<400> SEQUENCE: 12

```
Gln Gln Trp Thr Ser Asn Pro Pro Thr
1               5
```

<210> SEQ ID NO 13
<211> LENGTH: 121
<212> TYPE: PRT
<213> ORGANISM: Artificial Sequence
<220> FEATURE:
<223> OTHER INFORMATION: heavy chain variable region

<400> SEQUENCE: 13

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Ser His
            20                  25                  30

Gly Met Ser Trp Val Arg Gln Ala Pro Gly Lys Gly Leu Glu Trp Val
        35                  40                  45

Ala Thr Ile Ser Ser Gly Gly Thr Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Ala Glu Asp Thr Ala Met Tyr Tyr Cys
                85                  90                  95

Ala Arg His Asp Phe Asp Tyr Phe Pro Tyr Trp Phe Ala His Trp Gly
            100                 105                 110

Gln Gly Thr Leu Val Thr Val Ser Ser
        115                 120
```

<210> SEQ ID NO 14
<211> LENGTH: 106
<212> TYPE: PRT
<213> ORGANISM: Artificial Sequence
<220> FEATURE:
<223> OTHER INFORMATION: light chain variable region

<400> SEQUENCE: 14

```
Glu Ile Val Leu Thr Gln Ser Pro Ala Thr Leu Ser Leu Ser Pro Gly
1               5                   10                  15

Glu Arg Ala Thr Leu Ser Cys Arg Ala Asn Ser Ala Val Ser Tyr Met
            20                  25                  30
```

```
Tyr Trp Tyr Gln Gln Lys Pro Gly Gln Ala Pro Arg Pro Trp Ile Tyr
            35                  40                  45

Leu Thr Ser Asn Arg Ala Thr Gly Val Pro Ala Arg Phe Ser Gly Ser
 50                  55                  60

Gly Ser Gly Thr Asp Tyr Thr Leu Thr Ile Ser Ser Leu Glu Pro Glu
 65                  70                  75                  80

Asp Phe Ala Val Tyr Tyr Cys Gln Gln Trp Ser Ser Asn Pro Pro Thr
                 85                  90                  95

Phe Gly Gln Gly Thr Lys Leu Glu Ile Lys
                100                 105
```

```
<210> SEQ ID NO 15
<211> LENGTH: 106
<212> TYPE: PRT
<213> ORGANISM: Artificial Sequence
<220> FEATURE:
<223> OTHER INFORMATION: light chain variable region

<400> SEQUENCE: 15

Glu Ile Val Leu Thr Gln Ser Pro Ala Thr Leu Ser Leu Ser Pro Gly
 1               5                  10                  15

Glu Arg Ala Thr Leu Ser Cys Arg Ala Asn Ser Ala Val Ser Tyr Met
             20                  25                  30

Tyr Trp Tyr Gln Gln Lys Pro Gly Gln Ala Pro Arg Pro Trp Ile Tyr
            35                  40                  45

Leu Thr Ser Asn Arg Ala Thr Gly Val Pro Ala Arg Phe Ser Gly Ser
 50                  55                  60

Gly Ser Gly Thr Asp Tyr Thr Leu Thr Ile Ser Ser Leu Glu Pro Glu
 65                  70                  75                  80

Asp Phe Ala Val Tyr Tyr Cys Gln Gln Trp Thr Ser Asn Pro Pro Thr
                 85                  90                  95

Phe Gly Gln Gly Thr Lys Leu Glu Ile Lys
                100                 105
```

```
<210> SEQ ID NO 16
<211> LENGTH: 106
<212> TYPE: PRT
<213> ORGANISM: Artificial Sequence
<220> FEATURE:
<223> OTHER INFORMATION: light chain variable region

<400> SEQUENCE: 16

Glu Ile Val Leu Thr Gln Ser Pro Ala Thr Leu Ser Leu Ser Pro Gly
 1               5                  10                  15

Glu Arg Ala Thr Leu Ser Cys Arg Ala Asn Ser Ser Val Ser Tyr Met
             20                  25                  30

Tyr Trp Tyr Gln Gln Lys Pro Gly Gln Ala Pro Arg Pro Trp Ile Tyr
            35                  40                  45

Leu Thr Ser Asn Arg Ala Thr Gly Val Pro Ala Arg Phe Ser Gly Ser
 50                  55                  60

Gly Ser Gly Thr Asp Tyr Thr Leu Thr Ile Ser Ser Leu Glu Pro Glu
 65                  70                  75                  80

Asp Phe Ala Val Tyr Tyr Cys Gln Gln Trp Ser Ser Asn Pro Pro Thr
                 85                  90                  95

Phe Gly Gln Gly Thr Lys Leu Glu Ile Lys
                100                 105
```

```
<210> SEQ ID NO 17
```

<211> LENGTH: 492
<212> TYPE: PRT
<213> ORGANISM: Artificial Sequence
<220> FEATURE:
<223> OTHER INFORMATION: The mature form of CEACAM1 (without signal
      sequence)

<400> SEQUENCE: 17

```
Gln Leu Thr Thr Glu Ser Met Pro Phe Asn Val Ala Glu Gly Lys Glu
1               5                   10                  15

Val Leu Leu Leu Val His Asn Leu Pro Gln Gln Leu Phe Gly Tyr Ser
            20                  25                  30

Trp Tyr Lys Gly Glu Arg Val Asp Gly Asn Arg Gln Ile Val Gly Tyr
        35                  40                  45

Ala Ile Gly Thr Gln Gln Ala Thr Pro Gly Pro Ala Asn Ser Gly Arg
    50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro Glu Leu Pro Lys
            100                 105                 110

Pro Ser Ile Ser Ser Asn Asn Ser Asn Pro Val Glu Asp Lys Asp Ala
        115                 120                 125

Val Ala Phe Thr Cys Glu Pro Glu Thr Gln Asp Thr Thr Tyr Leu Trp
    130                 135                 140

Trp Ile Asn Asn Gln Ser Leu Pro Val Ser Pro Arg Leu Gln Leu Ser
145                 150                 155                 160

Asn Gly Asn Arg Thr Leu Thr Leu Leu Ser Val Thr Arg Asn Asp Thr
                165                 170                 175

Gly Pro Tyr Glu Cys Glu Ile Gln Asn Pro Val Ser Ala Asn Arg Ser
            180                 185                 190

Asp Pro Val Thr Leu Asn Val Thr Tyr Gly Pro Asp Thr Pro Thr Ile
        195                 200                 205

Ser Pro Ser Asp Thr Tyr Tyr Arg Pro Gly Ala Asn Leu Ser Leu Ser
    210                 215                 220

Cys Tyr Ala Ala Ser Asn Pro Pro Ala Gln Tyr Ser Trp Leu Ile Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Thr Cys His Ala Asn Asn Ser Val Thr
            260                 265                 270

Gly Cys Asn Arg Thr Thr Val Lys Thr Ile Ile Val Thr Glu Leu Ser
        275                 280                 285

Pro Val Val Ala Lys Pro Gln Ile Lys Ala Ser Lys Thr Thr Val Thr
    290                 295                 300

Gly Asp Lys Asp Ser Val Asn Leu Thr Cys Ser Thr Asn Asp Thr Gly
305                 310                 315                 320

Ile Ser Ile Arg Trp Phe Phe Lys Asn Gln Ser Leu Pro Ser Ser Glu
                325                 330                 335

Arg Met Lys Leu Ser Gln Gly Asn Thr Thr Leu Ser Ile Asn Pro Val
            340                 345                 350

Lys Arg Glu Asp Ala Gly Thr Tyr Trp Cys Glu Val Phe Asn Pro Ile
        355                 360                 365

Ser Lys Asn Gln Ser Asp Pro Ile Met Leu Asn Val Asn Tyr Asn Ala
```

```
                370                 375                 380
Leu Pro Gln Glu Asn Gly Leu Ser Pro Gly Ala Ile Ala Gly Ile Val
385                 390                 395                 400

Ile Gly Val Val Ala Leu Val Ala Leu Ile Ala Val Ala Leu Ala Cys
                405                 410                 415

Phe Leu His Phe Gly Lys Thr Gly Arg Ala Ser Asp Gln Arg Asp Leu
                420                 425                 430

Thr Glu His Lys Pro Ser Val Ser Asn His Thr Gln Asp His Ser Asn
                435                 440                 445

Asp Pro Pro Asn Lys Met Asn Glu Val Thr Tyr Ser Thr Leu Asn Phe
450                 455                 460

Glu Ala Gln Gln Pro Thr Gln Pro Thr Ser Ala Ser Pro Ser Leu Thr
465                 470                 475                 480

Ala Thr Glu Ile Ile Tyr Ser Glu Val Lys Lys Gln
                485                 490

<210> SEQ ID NO 18
<211> LENGTH: 10
<212> TYPE: PRT
<213> ORGANISM: Artificial Sequence
<220> FEATURE:
<223> OTHER INFORMATION: CDR1 of the light chain variable region

<400> SEQUENCE: 18

Arg Ala Asn Ser Ser Val Ser Tyr Met Tyr
1               5                   10

<210> SEQ ID NO 19
<211> LENGTH: 121
<212> TYPE: PRT
<213> ORGANISM: Artificial Sequence
<220> FEATURE:
<223> OTHER INFORMATION: heavy variable chain

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Ser His
                20                  25                  30

Gly Met Ser Trp Val Arg Gln Ala Pro Gly Lys Gly Leu Glu Trp Val
            35                  40                  45

Ala Thr Ile Ser Ser Gly Gly Thr Tyr Thr Tyr Tyr Pro Asp Ser Val
        50                  55                  60

Lys Gly Arg Phe Thr Ile Ser Arg Asp Asn Lys Asn Thr Leu Tyr
65                  70                  75                  80

Leu Gln Met Asn Ser Leu Lys Ala Glu Asp Thr Ala Met Tyr Tyr Cys
                85                  90                  95

Ala Arg His Asp Phe Asp Tyr Asp Ala Ala Trp Phe Ala Tyr Trp Gly
                100                 105                 110

Gln Gly Thr Leu Val Thr Val Ser Ser
            115                 120

<210> SEQ ID NO 20
<211> LENGTH: 8
<212> TYPE: PRT
<213> ORGANISM: Artificial Sequence
<220> FEATURE:
<223> OTHER INFORMATION: CDR1H
<220> FEATURE:
<221> NAME/KEY: MISC_FEATURE
```

```
<222> LOCATION: (1)..(1)
<223> OTHER INFORMATION: G or E
<220> FEATURE:
<221> NAME/KEY: MISC_FEATURE
<222> LOCATION: (2)..(2)
<223> OTHER INFORMATION: an aromatic side chain including F or Y
<220> FEATURE:
<221> NAME/KEY: MISC_FEATURE
<222> LOCATION: (3)..(3)
<223> OTHER INFORMATION: T, S, or I
<220> FEATURE:
<221> NAME/KEY: MISC_FEATURE
<222> LOCATION: (5)..(5)
<223> OTHER INFORMATION: a polar uncharged side chain including S, T, or
      N
<220> FEATURE:
<221> NAME/KEY: MISC_FEATURE
<222> LOCATION: (6)..(6)
<223> OTHER INFORMATION: A, D, N, or S
<220> FEATURE:
<221> NAME/KEY: MISC_FEATURE
<222> LOCATION: (8)..(8)
<223> OTHER INFORMATION: A or G

<400> SEQUENCE: 20

Xaa Xaa Xaa Phe Xaa Xaa His Xaa
1               5

<210> SEQ ID NO 21
<211> LENGTH: 7
<212> TYPE: PRT
<213> ORGANISM: Artificial Sequence
<220> FEATURE:
<223> OTHER INFORMATION: CDR1H (IMGT definition)

<400> SEQUENCE: 21

Gly Phe Ile Phe Ser His Gly
1               5

<210> SEQ ID NO 22
<211> LENGTH: 10
<212> TYPE: PRT
<213> ORGANISM: Artificial Sequence
<220> FEATURE:
<223> OTHER INFORMATION: CDR1H
<220> FEATURE:
<221> NAME/KEY: MISC_FEATURE
<222> LOCATION: (1)..(1)
<223> OTHER INFORMATION: G or E
<220> FEATURE:
<221> NAME/KEY: MISC_FEATURE
<222> LOCATION: (2)..(2)
<223> OTHER INFORMATION: aromatic side chain including F or Y
<220> FEATURE:
<221> NAME/KEY: MISC_FEATURE
<222> LOCATION: (3)..(3)
<223> OTHER INFORMATION: T, S, or I
<220> FEATURE:
<221> NAME/KEY: MISC_FEATURE
<222> LOCATION: (5)..(5)
<223> OTHER INFORMATION: a polar uncharged side chain including S, T, or
      N
<220> FEATURE:
<221> NAME/KEY: MISC_FEATURE
<222> LOCATION: (6)..(6)
<223> OTHER INFORMATION: A, D, N, or S
<220> FEATURE:
<221> NAME/KEY: MISC_FEATURE
<222> LOCATION: (8)..(8)
<223> OTHER INFORMATION: A or G
<220> FEATURE:
<221> NAME/KEY: MISC_FEATURE
<222> LOCATION: (9)..(9)
<223> OTHER INFORMATION: a hydrophobic side chain including I or M
```

```
<400> SEQUENCE: 22

Xaa Xaa Xaa Phe Xaa Xaa His Xaa Xaa Ser
1               5                   10

<210> SEQ ID NO 23
<211> LENGTH: 10
<212> TYPE: PRT
<213> ORGANISM: Artificial Sequence
<220> FEATURE:
<223> OTHER INFORMATION: CDR1H

<400> SEQUENCE: 23

Gly Phe Ile Phe Ser Ser His Gly Met Ser
1               5                   10

<210> SEQ ID NO 24
<211> LENGTH: 13
<212> TYPE: PRT
<213> ORGANISM: Artificial Sequence
<220> FEATURE:
<223> OTHER INFORMATION: CDR3H
<220> FEATURE:
<221> NAME/KEY: MISC_FEATURE
<222> LOCATION: (1)..(1)
<223> OTHER INFORMATION: R or K
<220> FEATURE:
<221> NAME/KEY: MISC_FEATURE
<222> LOCATION: (3)..(3)
<223> OTHER INFORMATION: D, G, or P
<220> FEATURE:
<221> NAME/KEY: MISC_FEATURE
<222> LOCATION: (4)..(4)
<223> OTHER INFORMATION: F or P
<220> FEATURE:
<221> NAME/KEY: MISC_FEATURE
<222> LOCATION: (7)..(7)
<223> OTHER INFORMATION: D or F
<220> FEATURE:
<221> NAME/KEY: MISC_FEATURE
<222> LOCATION: (9)..(9)
<223> OTHER INFORMATION: A or Y
<220> FEATURE:
<221> NAME/KEY: MISC_FEATURE
<222> LOCATION: (13)..(13)
<223> OTHER INFORMATION: L, H, or F

<400> SEQUENCE: 24

Xaa His Xaa Xaa Asp Tyr Xaa Pro Xaa Trp Phe Ala Xaa
1               5                   10

<210> SEQ ID NO 25
<211> LENGTH: 13
<212> TYPE: PRT
<213> ORGANISM: Artificial Sequence
<220> FEATURE:
<223> OTHER INFORMATION: CDR3H

<400> SEQUENCE: 25

Arg His Asp Phe Asp Tyr Phe Pro Tyr Trp Phe Ala His
1               5                   10

<210> SEQ ID NO 26
<211> LENGTH: 526
<212> TYPE: PRT
<213> ORGANISM: Homo sapiens

<400> SEQUENCE: 26

Met Gly His Leu Ser Ala Pro Leu His Arg Val Arg Val Pro Trp Gln
1               5                   10                  15
```

```
Gly Leu Leu Leu Thr Ala Ser Leu Leu Thr Phe Trp Asn Pro Pro Thr
             20                  25                  30

Thr Ala Gln Leu Thr Thr Glu Ser Met Pro Phe Asn Val Ala Glu Gly
         35                  40                  45

Lys Glu Val Leu Leu Val His Asn Leu Pro Gln Gln Leu Phe Gly
 50                  55                  60

Tyr Ser Trp Tyr Lys Gly Glu Arg Val Asp Gly Asn Arg Gln Ile Val
 65                  70                  75                  80

Gly Tyr Ala Ile Gly Thr Gln Gln Ala Thr Pro Gly Pro Ala Asn Ser
             85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
                180                 185                 190

Leu Ser Asn Gly Asn Arg Thr Leu Thr Leu Leu Ser Val Thr Arg Asn
        195                 200                 205

Asp Thr Gly Pro Tyr Glu Cys Glu Ile Gln Asn Pro Val Ser Ala Asn
    210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
        260                 265                 270

Ile Asn Gly Thr Phe Gln Gln Ser Thr Gln Glu Leu Phe Ile Pro Asn
    275                 280                 285

Ile Thr Val Asn Asn Ser Gly Ser Tyr Thr Cys His Ala Asn Asn Ser
290                 295                 300

Val Thr Gly Cys Asn Arg Thr Thr Val Lys Thr Ile Ile Val Thr Glu
305                 310                 315                 320

Leu Ser Pro Val Val Ala Lys Pro Gln Ile Lys Ala Ser Lys Thr Thr
                325                 330                 335

Val Thr Gly Asp Lys Asp Ser Val Asn Leu Thr Cys Ser Thr Asn Asp
            340                 345                 350

Thr Gly Ile Ser Ile Arg Trp Phe Phe Lys Asn Gln Ser Leu Pro Ser
        355                 360                 365

Ser Glu Arg Met Lys Leu Ser Gln Gly Asn Thr Thr Leu Ser Ile Asn
    370                 375                 380

Pro Val Lys Arg Glu Asp Ala Gly Thr Tyr Trp Cys Glu Val Phe Asn
385                 390                 395                 400

Pro Ile Ser Lys Asn Gln Ser Asp Pro Ile Met Leu Asn Val Asn Tyr
                405                 410                 415

Asn Ala Leu Pro Gln Glu Asn Gly Leu Ser Pro Gly Ala Ile Ala Gly
        420                 425                 430

Ile Val Ile Gly Val Val Ala Leu Val Ala Leu Ile Ala Val Ala Leu
```

```
                     435                 440                 445
Ala Cys Phe Leu His Phe Gly Lys Thr Gly Arg Ala Ser Asp Gln Arg
    450                 455                 460

Asp Leu Thr Glu His Lys Pro Ser Val Ser Asn His Thr Gln Asp His
465                 470                 475                 480

Ser Asn Asp Pro Pro Asn Lys Met Asn Glu Val Thr Tyr Ser Thr Leu
                    485                 490                 495

Asn Phe Glu Ala Gln Gln Pro Thr Gln Pro Thr Ser Ala Ser Pro Ser
                500                 505                 510

Leu Thr Ala Thr Glu Ile Ile Tyr Ser Glu Val Lys Lys Gln
            515                 520                 525

<210> SEQ ID NO 27
<211> LENGTH: 121
<212> TYPE: PRT
<213> ORGANISM: Artificial Sequence
<220> FEATURE:
<223> OTHER INFORMATION: Variant VH0

<400> SEQUENCE: 27

Glu Val Gln Leu Val Glu Ser Gly Gly Asp Leu Val Lys Pro Gly Gly
1               5                   10                  15

Ser Leu Lys Leu Ala Cys Ala Ala Ser Gly Phe Ile Phe Ser Ser His
            20                  25                  30

Gly Met Ser Trp Val Arg Gln Thr Pro Asp Lys Arg Leu Glu Trp Val
        35                  40                  45

Ala Thr Ile Ser Ser Gly Gly Thr Tyr Thr Tyr Tyr Pro Asp Ser Val
    50                  55                  60

Lys Gly Arg Phe Thr Ile Ser Arg Asp Asn Asp Lys Asn Thr Leu Tyr
65                  70                  75                  80

Leu Gln Met Asn Ser Leu Lys Ser Glu Asp Thr Ala Met Tyr Tyr Cys
                85                  90                  95

Ala Arg His Asp Phe Asp Tyr Asp Ala Ala Trp Phe Ala Tyr Trp Gly
            100                 105                 110

Gln Gly Thr Leu Val Thr Val Ser Ser
        115                 120

<210> SEQ ID NO 28
<211> LENGTH: 121
<212> TYPE: PRT
<213> ORGANISM: Artificial Sequence
<220> FEATURE:
<223> OTHER INFORMATION: Variant VH2

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Ser His
            20                  25                  30

Gly Met Ser Trp Val Arg Gln Ala Pro Gly Lys Gly Leu Glu Trp Val
        35                  40                  45

Ala Thr Ile Ser Ser Gly Gly Thr Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95
```

Ala Arg His Asp Phe Asp Tyr Asp Ala Ala Trp Phe Ala Tyr Trp Gly
        100                 105                 110

Gln Gly Thr Leu Val Thr Val Ser Ser
        115                 120

<210> SEQ ID NO 29
<211> LENGTH: 121
<212> TYPE: PRT
<213> ORGANISM: Artificial Sequence
<220> FEATURE:
<223> OTHER INFORMATION: Variant VH3

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Ser His
            20                  25                  30

Gly Met Ser Trp Val Arg Gln Ala Pro Gly Lys Gly Leu Glu Trp Val
        35                  40                  45

Ala Thr Ile Ser Ser Gly Gly Thr Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg His Asp Phe Asp Tyr Asp Ala Ala Trp Phe Ala Tyr Trp Gly
            100                 105                 110

Gln Gly Thr Leu Val Thr Val Ser Ser
        115                 120

<210> SEQ ID NO 30
<211> LENGTH: 121
<212> TYPE: PRT
<213> ORGANISM: Artificial Sequence
<220> FEATURE:
<223> OTHER INFORMATION: Variant VH4

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Ser His
            20                  25                  30

Gly Met Ser Trp Val Arg Gln Ala Pro Gly Lys Gly Leu Glu Trp Val
        35                  40                  45

Ser Thr Ile Ser Ser Gly Gly Thr Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Asp Phe Asp Tyr Asp Ala Ala Trp Phe Ala Tyr Trp Gly
            100                 105                 110

Gln Gly Thr Leu Val Thr Val Ser Ser
        115                 120

<210> SEQ ID NO 31
<211> LENGTH: 106
<212> TYPE: PRT
<213> ORGANISM: Artificial Sequence
<220> FEATURE:
<223> OTHER INFORMATION: Variant Vk0 light chain

<400> SEQUENCE: 31

Gln Ile Val Leu Thr Gln Ser Pro Ala Leu Met Ser Ala Ser Pro Gly
1               5                   10                  15

Val Lys Val Thr Met Thr Cys Ser Ala Asn Ser Ser Val Ser Tyr Met
            20                  25                  30

Tyr Trp Tyr Arg Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65              70                  75                  80

Asp Ala Ala Thr Tyr Tyr Cys Gln Gln Trp Ser Asn Pro Pro Thr
                85                  90                  95

Phe Gly Ser Gly Thr Lys Leu Glu Ile Lys
            100                 105

<210> SEQ ID NO 32
<211> LENGTH: 106
<212> TYPE: PRT
<213> ORGANISM: Artificial Sequence
<220> FEATURE:
<223> OTHER INFORMATION: Variant Vk1 light chain

<400> SEQUENCE: 32

Gln Ile Val Leu Thr Gln Ser Pro Ala Leu Leu Ser Leu Ser Pro Gly
1               5                   10                  15

Glu Arg Ala Thr Met Ser Cys Ser Ala Asn Ser Ser Val Ser Tyr Met
            20                  25                  30

Tyr Trp Tyr Arg Gln Lys Pro Gly Gln Ala Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Asp Tyr Thr Leu Thr Ile Ser Ser Leu Glu Ala Glu
65              70                  75                  80

Asp Phe Ala Thr Tyr Tyr Cys Gln Gln Trp Ser Ser Asn Pro Pro Thr
                85                  90                  95

Phe Gly Gln Gly Thr Lys Leu Glu Ile Lys
            100                 105

<210> SEQ ID NO 33
<211> LENGTH: 106
<212> TYPE: PRT
<213> ORGANISM: Artificial Sequence
<220> FEATURE:
<223> OTHER INFORMATION: Variant Vk2 light chain

<400> SEQUENCE: 33

Glu Ile Val Leu Thr Gln Ser Pro Ala Thr Leu Ser Leu Ser Pro Gly
1               5                   10                  15

Glu Arg Ala Thr Leu Ser Cys Arg Ala Asn Ser Ser Val Ser Tyr Met
            20                  25                  30

Tyr Trp Tyr Gln Gln Lys Pro Gly Gln Ala Pro Arg Pro Trp Ile Tyr
        35                  40                  45

Leu Thr Ser Asn Arg Ala Thr Gly Val Pro Ala Arg Phe Ser Gly Ser
    50                  55                  60

```
Gly Ser Gly Thr Asp Tyr Thr Leu Thr Ile Ser Ser Leu Glu Pro Glu
65                  70                  75                  80

Asp Phe Ala Thr Tyr Tyr Cys Gln Gln Trp Ser Ser Asn Pro Pro Thr
                85                  90                  95

Phe Gly Gln Gly Thr Lys Leu Glu Ile Lys
            100                 105

<210> SEQ ID NO 34
<211> LENGTH: 106
<212> TYPE: PRT
<213> ORGANISM: Artificial Sequence
<220> FEATURE:
<223> OTHER INFORMATION: Variant Vk3 light chain

<400> SEQUENCE: 34

Glu Ile Val Leu Thr Gln Ser Pro Ala Thr Leu Ser Leu Ser Pro Gly
1               5                   10                  15

Glu Arg Ala Thr Leu Ser Cys Arg Ala Asn Ser Ser Val Ser Tyr Met
                20                  25                  30

Ala Trp Tyr Gln Gln Lys Pro Gly Gln Ala Pro Arg Pro Trp Ile Tyr
            35                  40                  45

Leu Thr Ser Asn Arg Ala Thr Gly Val Pro Ala Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Phe Ala Thr Tyr Tyr Cys Gln Gln Trp Ser Ser Asn Pro Pro Thr
                85                  90                  95

Phe Gly Gln Gly Thr Lys Leu Glu Ile Lys
            100                 105

<210> SEQ ID NO 35
<211> LENGTH: 106
<212> TYPE: PRT
<213> ORGANISM: Artificial Sequence
<220> FEATURE:
<223> OTHER INFORMATION: Variant Vk4 light chain

<400> SEQUENCE: 35

Glu Ile Val Leu Thr Gln Ser Pro Ala Thr Leu Ser Leu Ser Pro Gly
1               5                   10                  15

Glu Arg Ala Thr Leu Ser Cys Arg Ala Asn Ser Ser Val Ser Tyr Met
                20                  25                  30

Tyr Trp Tyr Gln Gln Lys Pro Gly Gln Ala Pro Arg Pro Trp Ile Tyr
            35                  40                  45

Leu Thr Ser Asn Arg Ala Thr Gly Ile Pro Ala Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Phe Ala Thr Tyr Tyr Cys Gln Gln Trp Ser Ser Asn Pro Pro Thr
                85                  90                  95

Phe Gly Gln Gly Thr Lys Leu Glu Ile Lys
            100                 105

<210> SEQ ID NO 36
<211> LENGTH: 106
<212> TYPE: PRT
<213> ORGANISM: Artificial Sequence
<220> FEATURE:
<223> OTHER INFORMATION: Variant Vk5 light chain
```

```
<400> SEQUENCE: 36

Glu Ile Val Leu Thr Gln Ser Pro Ala Thr Leu Ser Leu Ser Pro Gly
1               5                   10                  15

Glu Arg Ala Thr Leu Ser Cys Arg Ala Asn Ser Ser Val Ser Tyr Met
                20                  25                  30

Ala Trp Tyr Gln Gln Lys Pro Gly Gln Ala Pro Arg Leu Leu Ile Tyr
            35                  40                  45

Leu Thr Ser Asn Arg Ala Thr Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Pro Thr
                85                  90                  95

Phe Gly Gln Gly Thr Lys Leu Glu Ile Lys
            100                 105

<210> SEQ ID NO 37
<211> LENGTH: 106
<212> TYPE: PRT
<213> ORGANISM: Artificial Sequence
<220> FEATURE:
<223> OTHER INFORMATION: Variant Vk6 light chain

<400> SEQUENCE: 37

Asp Ile Gln Leu Thr Gln Ser Pro Ser Phe Leu Ser Ala Ser Val Gly
1               5                   10                  15

Asp Arg Val Thr Ile Thr Cys Arg Ala Asn Ser Ser Val Ser Tyr Met
                20                  25                  30

Ala Trp Tyr Gln Gln Lys Pro Gly Lys Ala Pro Lys Leu Leu Ile Tyr
            35                  40                  45

Leu Thr Ser Asn Leu Gln Ser Gly Val Pro Ser Arg Phe Ser Gly Ser
        50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Pro Thr
                85                  90                  95

Phe Gly Gln Gly Thr Lys Leu Glu Ile Lys
            100                 105

<210> SEQ ID NO 38
<211> LENGTH: 106
<212> TYPE: PRT
<213> ORGANISM: Artificial Sequence
<220> FEATURE:
<223> OTHER INFORMATION: Variant Vk7 light chain

<400> SEQUENCE: 38

Glu Ile Val Leu Thr Gln Ser Pro Ala Thr Leu Ser Leu Ser Pro Gly
1               5                   10                  15

Glu Arg Ala Thr Leu Ser Cys Arg Ala Asn Ser Ser Val Ser Tyr Met
                20                  25                  30

Tyr Trp Tyr Gln Gln Lys Pro Gly Gln Ala Pro Arg Pro Trp Ile Tyr
            35                  40                  45

Leu Thr Ser Asn Arg Ala Thr Gly Val Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80
```

Asp Phe Ala Thr Tyr Tyr Cys Gln Gln Trp Ser Ser Asn Pro Pro Thr
                85                  90                  95

Phe Gly Gln Gly Thr Lys Leu Glu Ile Lys
            100                 105

<210> SEQ ID NO 39
<211> LENGTH: 106
<212> TYPE: PRT
<213> ORGANISM: Artificial Sequence
<220> FEATURE:
<223> OTHER INFORMATION: Variant Vk9 light chain

<400> SEQUENCE: 39

Glu Ile Val Leu Thr Gln Ser Pro Ala Thr Leu Ser Leu Ser Pro Gly
1               5                   10                  15

Glu Arg Ala Thr Leu Ser Cys Arg Ala Asn Ser Ser Val Ser Tyr Met
            20                  25                  30

Tyr Trp Tyr Gln Gln Lys Pro Gly Gln Ala Pro Arg Pro Leu Ile Tyr
        35                  40                  45

Leu Thr Ser Asn Arg Ala Thr Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Thr Tyr Tyr Cys Gln Gln Trp Ser Ser Asn Pro Pro Thr
                85                  90                  95

Phe Gly Gln Gly Thr Lys Leu Glu Ile Lys
            100                 105

<210> SEQ ID NO 40
<211> LENGTH: 106
<212> TYPE: PRT
<213> ORGANISM: Artificial Sequence
<220> FEATURE:
<223> OTHER INFORMATION: Variant Vk10 light chain

<400> SEQUENCE: 40

Glu Ile Val Leu Thr Gln Ser Pro Ala Thr Leu Ser Leu Ser Pro Gly
1               5                   10                  15

Glu Arg Ala Thr Leu Ser Cys Arg Ala Asn Ser Ser Val Ser Tyr Met
            20                  25                  30

Tyr Trp Tyr Gln Gln Lys Pro Gly Gln Ala Pro Arg Pro Trp Ile Tyr
        35                  40                  45

Leu Thr Ser Asn Arg Ala Thr Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Thr Tyr Tyr Cys Gln Gln Trp Ser Ser Asn Pro Pro Thr
                85                  90                  95

Phe Gly Gln Gly Thr Lys Leu Glu Ile Lys
            100                 105

<210> SEQ ID NO 41
<211> LENGTH: 106
<212> TYPE: PRT
<213> ORGANISM: Artificial Sequence
<220> FEATURE:
<223> OTHER INFORMATION: Variant Vk11 light chain

<400> SEQUENCE: 41

Glu Ile Val Leu Thr Gln Ser Pro Ala Thr Leu Ser Leu Ser Pro Gly

```
                1               5                      10                      15
            Glu Arg Ala Thr Leu Ser Cys Arg Ala Asn Ser Ser Val Ser Tyr Met
                           20                      25                      30

Tyr Trp Tyr Gln Gln Lys Pro Gly Gln Ala Pro Arg Pro Trp Ile Tyr
                       35                      40                      45

Leu Thr Ser Asn Arg Ala Thr Gly Ile Pro Ala Arg Phe Ser Gly Ser
                50                      55                      60

Gly Ser Gly Thr Asp Tyr Thr Leu Thr Ile Ser Ser Leu Glu Pro Glu
            65                      70                      75                      80

Asp Phe Ala Val Tyr Tyr Cys Gln Gln Trp Ser Ser Asn Pro Pro Thr
                               85                      90                      95

Phe Gly Gln Gly Thr Lys Leu Glu Ile Lys
                           100                     105
```

<210> SEQ ID NO 42
<211> LENGTH: 106
<212> TYPE: PRT
<213> ORGANISM: Artificial Sequence
<220> FEATURE:
<223> OTHER INFORMATION: Variant Vk12 light chain

<400> SEQUENCE: 42

```
            Glu Ile Val Leu Thr Gln Ser Pro Ala Thr Leu Ser Leu Ser Pro Gly
            1               5                      10                      15

Glu Arg Ala Thr Leu Ser Cys Arg Ala Asn Ser Ser Val Ser Tyr Met
                           20                      25                      30

Tyr Trp Tyr Gln Gln Lys Pro Gly Gln Ala Pro Arg Pro Leu Ile Tyr
                       35                      40                      45

Leu Thr Ser Asn Arg Ala Thr Gly Ile Pro Ala Arg Phe Ser Gly Ser
                50                      55                      60

Gly Ser Gly Thr Asp Tyr Thr Leu Thr Ile Ser Ser Leu Glu Pro Glu
            65                      70                      75                      80

Asp Phe Ala Thr Tyr Tyr Cys Gln Gln Trp Ser Ser Asn Pro Pro Thr
                               85                      90                      95

Phe Gly Gln Gly Thr Lys Leu Glu Ile Lys
                           100                     105
```

<210> SEQ ID NO 43
<211> LENGTH: 10
<212> TYPE: PRT
<213> ORGANISM: Artificial Sequence
<220> FEATURE:
<223> OTHER INFORMATION: heavy variable chain
<220> FEATURE:
<221> NAME/KEY: MISC_FEATURE
<222> LOCATION: (2)..(5)
<223> OTHER INFORMATION: any amino acid
<220> FEATURE:
<221> NAME/KEY: MISC_FEATURE
<222> LOCATION: (6)..(6)
<223> OTHER INFORMATION: A, D, N, or S
<220> FEATURE:
<221> NAME/KEY: MISC_FEATURE
<222> LOCATION: (8)..(8)
<223> OTHER INFORMATION: A or G
<220> FEATURE:
<221> NAME/KEY: MISC_FEATURE
<222> LOCATION: (9)..(9)
<223> OTHER INFORMATION: an amino acid with a hydrophobic side chain
      including I or M

<400> SEQUENCE: 43

Gly Xaa Xaa Xaa Xaa Xaa His Xaa Xaa Ser

```
1               5                   10

<210> SEQ ID NO 44
<211> LENGTH: 12
<212> TYPE: PRT
<213> ORGANISM: Artificial Sequence
<220> FEATURE:
<223> OTHER INFORMATION: CDR3H
<220> FEATURE:
<221> NAME/KEY: MISC_FEATURE
<222> LOCATION: (2)..(2)
<223> OTHER INFORMATION: D, G, or P
<220> FEATURE:
<221> NAME/KEY: MISC_FEATURE
<222> LOCATION: (3)..(3)
<223> OTHER INFORMATION: F or P
<220> FEATURE:
<221> NAME/KEY: MISC_FEATURE
<222> LOCATION: (8)..(8)
<223> OTHER INFORMATION: A or Y
<220> FEATURE:
<221> NAME/KEY: MISC_FEATURE
<222> LOCATION: (12)..(12)
<223> OTHER INFORMATION: L, H, or F

<400> SEQUENCE: 44

His Xaa Xaa Asp Tyr Phe Pro Xaa Trp Phe Ala Xaa
1               5                   10

<210> SEQ ID NO 45
<211> LENGTH: 12
<212> TYPE: PRT
<213> ORGANISM: Artificial Sequence
<220> FEATURE:
<223> OTHER INFORMATION: CDR3H
<220> FEATURE:
<221> NAME/KEY: MISC_FEATURE
<222> LOCATION: (2)..(2)
<223> OTHER INFORMATION: D, G, or P
<220> FEATURE:
<221> NAME/KEY: MISC_FEATURE
<222> LOCATION: (3)..(3)
<223> OTHER INFORMATION: F or P
<220> FEATURE:
<221> NAME/KEY: MISC_FEATURE
<222> LOCATION: (6)..(6)
<223> OTHER INFORMATION: D or F
<220> FEATURE:
<221> NAME/KEY: MISC_FEATURE
<222> LOCATION: (7)..(7)
<223> OTHER INFORMATION: P or A
<220> FEATURE:
<221> NAME/KEY: MISC_FEATURE
<222> LOCATION: (8)..(8)
<223> OTHER INFORMATION: A or Y
<220> FEATURE:
<221> NAME/KEY: MISC_FEATURE
<222> LOCATION: (12)..(12)
<223> OTHER INFORMATION: L, H, Y or F

<400> SEQUENCE: 45

His Xaa Xaa Asp Tyr Xaa Xaa Xaa Trp Phe Ala Xaa
1               5                   10

<210> SEQ ID NO 46
<211> LENGTH: 10
<212> TYPE: PRT
<213> ORGANISM: Artificial Sequence
<220> FEATURE:
<223> OTHER INFORMATION: CDR1H
<220> FEATURE:
<221> NAME/KEY: MISC_FEATURE
<222> LOCATION: (1)..(1)
<223> OTHER INFORMATION: G or E
```

```
<220> FEATURE:
<221> NAME/KEY: MISC_FEATURE
<222> LOCATION: (3)..(3)
<223> OTHER INFORMATION: T or I
<220> FEATURE:
<221> NAME/KEY: MISC_FEATURE
<222> LOCATION: (5)..(5)
<223> OTHER INFORMATION: N or S
<220> FEATURE:
<221> NAME/KEY: MISC_FEATURE
<222> LOCATION: (6)..(6)
<223> OTHER INFORMATION: A, D, or S
<220> FEATURE:
<221> NAME/KEY: MISC_FEATURE
<222> LOCATION: (8)..(8)
<223> OTHER INFORMATION: A or G
<220> FEATURE:
<221> NAME/KEY: MISC_FEATURE
<222> LOCATION: (9)..(9)
<223> OTHER INFORMATION: an amino acid with a hydrophobic side chain
      including I or M

<400> SEQUENCE: 46

Xaa Phe Xaa Phe Xaa Xaa His Xaa Xaa Ser
1               5                   10

<210> SEQ ID NO 47
<211> LENGTH: 12
<212> TYPE: PRT
<213> ORGANISM: Artificial Sequence
<220> FEATURE:
<223> OTHER INFORMATION: CDR3H
<220> FEATURE:
<221> NAME/KEY: MISC_FEATURE
<222> LOCATION: (2)..(2)
<223> OTHER INFORMATION: D or G
<220> FEATURE:
<221> NAME/KEY: MISC_FEATURE
<222> LOCATION: (6)..(6)
<223> OTHER INFORMATION: D or F
<220> FEATURE:
<221> NAME/KEY: MISC_FEATURE
<222> LOCATION: (7)..(7)
<223> OTHER INFORMATION: P or A
<220> FEATURE:
<221> NAME/KEY: MISC_FEATURE
<222> LOCATION: (8)..(8)
<223> OTHER INFORMATION: A or Y
<220> FEATURE:
<221> NAME/KEY: MISC_FEATURE
<222> LOCATION: (12)..(12)
<223> OTHER INFORMATION: H or Y

<400> SEQUENCE: 47

His Xaa Phe Asp Tyr Xaa Xaa Xaa Trp Phe Ala Xaa
1               5                   10

<210> SEQ ID NO 48
<211> LENGTH: 9
<212> TYPE: PRT
<213> ORGANISM: Artificial Sequence
<220> FEATURE:
<223> OTHER INFORMATION: CDR3L
<220> FEATURE:
<221> NAME/KEY: MISC_FEATURE
<222> LOCATION: (4)..(5)
<223> OTHER INFORMATION: S or T

<400> SEQUENCE: 48

Gln Gln Trp Xaa Xaa Asn Pro Pro Thr
1               5

<210> SEQ ID NO 49
```

```
<211> LENGTH: 10
<212> TYPE: PRT
<213> ORGANISM: Artificial Sequence
<220> FEATURE:
<223> OTHER INFORMATION: CDR1H
<220> FEATURE:
<221> NAME/KEY: MISC_FEATURE
<222> LOCATION: (1)..(1)
<223> OTHER INFORMATION: G or E
<220> FEATURE:
<221> NAME/KEY: MISC_FEATURE
<222> LOCATION: (5)..(5)
<223> OTHER INFORMATION: N or S
<220> FEATURE:
<221> NAME/KEY: MISC_FEATURE
<222> LOCATION: (6)..(6)
<223> OTHER INFORMATION: A or D
<220> FEATURE:
<221> NAME/KEY: MISC_FEATURE
<222> LOCATION: (9)..(9)
<223> OTHER INFORMATION: an amino acid with a hydrophobic side chain
      including I or M

<400> SEQUENCE: 49

Xaa Phe Thr Phe Xaa Xaa His Ala Xaa Ser
1               5                   10

<210> SEQ ID NO 50
<211> LENGTH: 363
<212> TYPE: DNA
<213> ORGANISM: Artificial Sequence
<220> FEATURE:
<223> OTHER INFORMATION: heavy variable chain VH1 (Fig. 3A)

<400> SEQUENCE: 50
gaggtgcagt tgttggagtc tgggggaggc ttggtgcagc ctggagggtc cctgagactc      60
tcctgtgcag cctctggatt catttcagt agccatggca tgtcttgggt tcgccaggct      120
ccagggaagg ggctggagtg ggtcgcaacc attagcagtg gtggtactta cacctactat     180
ccagacagtg tgaaggggcg attcaccata tccagagaca attccaaaaa cacccctgtac    240 ctgcaaatga acagtctgaa ggccgaggac acagccatgt attactgtgc aagacacgac     300
tttgattacg acgcggcctg gtttgcttac tggggccaag ggaccctggt caccgtctcc     360
tca                                                                   363

<210> SEQ ID NO 51
<211> LENGTH: 363
<212> TYPE: DNA
<213> ORGANISM: Artificial Sequence
<220> FEATURE:
<223> OTHER INFORMATION: heavy variable chain CP08H03 (Fig. 3B)

<400> SEQUENCE: 51
gaggtgcagt tgttggagtc tgggggaggc ttggtgcagc ctggagggtc cctgagactc      60
tcctgtgcag cctctggatt catttcagt agccatggca tgtcttgggt tcgccaggct      120
ccagggaagg ggctggagtg ggtcgcaacc attagcagtg gtggtactta cacctactat     180
ccagacagtg tgaaggggcg attcaccata tccagagaca attccaaaaa cacccctgtac    240 ctgcaaatga acagtctgaa ggccgaggac acagccatgt attactgtgc aagacacgac     300
tttgattacg acgcggcctg gtttgcttac tggggccaag ggaccctggt caccgtctcc     360
tca                                                                   363

<210> SEQ ID NO 52
<211> LENGTH: 318
```

```
<212> TYPE: DNA
<213> ORGANISM: Artificial Sequence
<220> FEATURE:
<223> OTHER INFORMATION: light variable chain V?8 S29A

<400> SEQUENCE: 52
gaaattgttc tcacccagtc tccagcaacc ctgtctttgt ctccagggga aagagccacc    60
ctctcctgca gggccaactc agctgtaagt tacatgtatt ggtatcaaca gaagccaggc   120
caggctccca ggccctggat ttatctcaca tccaacaggg ctactggagt ccctgctcgc   180
ttcagtggca gtgggtctgg gaccgactat actctcacaa tcagcagcct agagcctgaa   240
gattttgccg tttattactg ccagcagtgg agtagtaacc cacccacgtt cggccagggg   300
acaaagctgg agatcaaa                                                 318

<210> SEQ ID NO 53
<211> LENGTH: 15
<212> TYPE: PRT
<213> ORGANISM: Artificial Sequence
<220> FEATURE:
<223> OTHER INFORMATION: VH CDR1 - FIG-7
<220> FEATURE:
<221> NAME/KEY: MISC_FEATURE
<222> LOCATION: (5)..(14)
<223> OTHER INFORMATION: targeted positions

<400> SEQUENCE: 53

Cys Ala Ala Ser Gly Phe Ile Phe Ser Ser His Gly Met Glu Trp
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: VH CDR3 Block1 - FIG. 7
<220> FEATURE:
<221> NAME/KEY: MISC_FEATURE
<222> LOCATION: (3)..(9)
<223> OTHER INFORMATION: Targeted position

<400> SEQUENCE: 54

Cys Ala Arg His Asp Phe Asp Tyr Asp Ala Ala Trp Phe Ala Tyr Trp
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: VH CDR3 Block2 - FIG. 7
<220> FEATURE:
<221> NAME/KEY: misc_feature
<222> LOCATION: (9)..(15)
<223> OTHER INFORMATION: Targeted position

<400> SEQUENCE: 55

Cys Ala Arg His Asp Phe Asp Tyr Asp Ala Ala Trp Phe Ala Tyr Trp
1               5                   10                  15

<210> SEQ ID NO 56
<211> LENGTH: 11
<212> TYPE: PRT
<213> ORGANISM: Artificial Sequence
<220> FEATURE:
<223> OTHER INFORMATION: VL CDR3 - FIG. 7
<220> FEATURE:
<221> NAME/KEY: MISC_FEATURE
```

```
<222> LOCATION: (3)..(9)
<223> OTHER INFORMATION: Targeted position

<400> SEQUENCE: 56

Cys Gln Gln Trp Ser Ser Asn Pro Pro Thr Phe
1               5                   10

<210> SEQ ID NO 57
<211> LENGTH: 10
<212> TYPE: PRT
<213> ORGANISM: Artificial Sequence
<220> FEATURE:
<223> OTHER INFORMATION: CDR1H Variant CP09F03

<400> SEQUENCE: 57

Gly Phe Thr Phe Asn Asn His Gly Met Ser
1               5                   10

<210> SEQ ID NO 58
<211> LENGTH: 10
<212> TYPE: PRT
<213> ORGANISM: Artificial Sequence
<220> FEATURE:
<223> OTHER INFORMATION: CDR1H Variant CP09A04

<400> SEQUENCE: 58

Gly Phe Ser Phe Asn Ala His Ala Met Ser
1               5                   10

<210> SEQ ID NO 59
<211> LENGTH: 10
<212> TYPE: PRT
<213> ORGANISM: Artificial Sequence
<220> FEATURE:
<223> OTHER INFORMATION: CDR1H Variant CP09E03

<400> SEQUENCE: 59

Gly Phe Thr Phe Ser Ala His Ala Ile Ser
1               5                   10

<210> SEQ ID NO 60
<211> LENGTH: 10
<212> TYPE: PRT
<213> ORGANISM: Artificial Sequence
<220> FEATURE:
<223> OTHER INFORMATION: CDR1H Variant CP09D03

<400> SEQUENCE: 60

Gly Phe Thr Phe Ser Ser His Ala Ile Ser
1               5                   10

<210> SEQ ID NO 61
<211> LENGTH: 10
<212> TYPE: PRT
<213> ORGANISM: Artificial Sequence
<220> FEATURE:
<223> OTHER INFORMATION: CDR1H Variant CP09B02

<400> SEQUENCE: 61

Gly Phe Thr Phe Thr Ser His Ala Ile Ser
1               5                   10

<210> SEQ ID NO 62
<211> LENGTH: 10
<212> TYPE: PRT
<213> ORGANISM: Artificial Sequence
<220> FEATURE:
```

```
<223> OTHER INFORMATION: CDR1H Variant CP09C02

<400> SEQUENCE: 62

Glu Phe Thr Phe Ser Asp His Ala Met Ser
1               5                   10

<210> SEQ ID NO 63
<211> LENGTH: 10
<212> TYPE: PRT
<213> ORGANISM: Artificial Sequence
<220> FEATURE:
<223> OTHER INFORMATION: CDR1H Variant CP09B03

<400> SEQUENCE: 63

Gly Phe Thr Phe Asn Ala His Ala Ile Ser
1               5                   10

<210> SEQ ID NO 64
<211> LENGTH: 10
<212> TYPE: PRT
<213> ORGANISM: Artificial Sequence
<220> FEATURE:
<223> OTHER INFORMATION: CDR1H Variant CP09G03

<400> SEQUENCE: 64

Gly Phe Thr Phe Asn Ala His Ala Met Ser
1               5                   10

<210> SEQ ID NO 65
<211> LENGTH: 10
<212> TYPE: PRT
<213> ORGANISM: Artificial Sequence
<220> FEATURE:
<223> OTHER INFORMATION: CDR1H Variant CP08B01

<400> SEQUENCE: 65

Gly Phe Thr Phe Ser Ala His Ala Met Ser
1               5                   10

<210> SEQ ID NO 66
<211> LENGTH: 10
<212> TYPE: PRT
<213> ORGANISM: Artificial Sequence
<220> FEATURE:
<223> OTHER INFORMATION: CDR1H Variant CP08A08

<400> SEQUENCE: 66

Gly Phe Ile Phe Thr Asn His Gly Met Ser
1               5                   10

<210> SEQ ID NO 67
<211> LENGTH: 10
<212> TYPE: PRT
<213> ORGANISM: Artificial Sequence
<220> FEATURE:
<223> OTHER INFORMATION: CDR1H Variant CP08A03

<400> SEQUENCE: 67

Gly Phe Ile Phe Asn Asn His Ala Ile Ser
1               5                   10

<210> SEQ ID NO 68
<211> LENGTH: 10
<212> TYPE: PRT
<213> ORGANISM: Artificial Sequence
<220> FEATURE:
<223> OTHER INFORMATION: CDR1H Variant CP08B03
```

<400> SEQUENCE: 68

Gly Phe Thr Phe Thr Ala His Ala Ile Ser
1               5                   10

<210> SEQ ID NO 69
<211> LENGTH: 10
<212> TYPE: PRT
<213> ORGANISM: Artificial Sequence
<220> FEATURE:
<223> OTHER INFORMATION: CDR1H Variant CP08D11

<400> SEQUENCE: 69

Gly Tyr Ser Phe Ser Ala His Gly Met Ser
1               5                   10

<210> SEQ ID NO 70
<211> LENGTH: 10
<212> TYPE: PRT
<213> ORGANISM: Artificial Sequence
<220> FEATURE:
<223> OTHER INFORMATION: CDR1H Variant CP08B11

<400> SEQUENCE: 70

Gly Phe Thr Phe Thr Asn His Gly Met Ser
1               5                   10

<210> SEQ ID NO 71
<211> LENGTH: 10
<212> TYPE: PRT
<213> ORGANISM: Artificial Sequence
<220> FEATURE:
<223> OTHER INFORMATION: CDR1H Variant CP08C04

<400> SEQUENCE: 71

Gly Phe Thr Phe Ser Ser His Gly Met Ser
1               5                   10

<210> SEQ ID NO 72
<211> LENGTH: 10
<212> TYPE: PRT
<213> ORGANISM: Artificial Sequence
<220> FEATURE:
<223> OTHER INFORMATION: CDR1H Variant CP08B06

<400> SEQUENCE: 72

Gly Phe Ser Phe Asn Ser His Ala Ile Ser
1               5                   10

<210> SEQ ID NO 73
<211> LENGTH: 10
<212> TYPE: PRT
<213> ORGANISM: Artificial Sequence
<220> FEATURE:
<223> OTHER INFORMATION: CDR1H Variant CP08F07

<400> SEQUENCE: 73

Gly Phe Thr Phe Thr Asp His Ala Ile Ser
1               5                   10

<210> SEQ ID NO 74
<211> LENGTH: 10
<212> TYPE: PRT
<213> ORGANISM: Artificial Sequence
<220> FEATURE:
<223> OTHER INFORMATION: CDR1H Variant CP08C01

```
<400> SEQUENCE: 74

Gly Tyr Ser Phe Ser Asn His Gly Met Ser
1               5                   10

<210> SEQ ID NO 75
<211> LENGTH: 10
<212> TYPE: PRT
<213> ORGANISM: Artificial Sequence
<220> FEATURE:
<223> OTHER INFORMATION: CDR1H Variant CP08A06

<400> SEQUENCE: 75

Gly Tyr Ser Phe Ser Ser His Gly Met Ser
1               5                   10

<210> SEQ ID NO 76
<211> LENGTH: 10
<212> TYPE: PRT
<213> ORGANISM: Artificial Sequence
<220> FEATURE:
<223> OTHER INFORMATION: CDR1H Variant CP08D01

<400> SEQUENCE: 76

Gly Phe Thr Phe Asn Ala His Gly Met Ser
1               5                   10

<210> SEQ ID NO 77
<211> LENGTH: 7
<212> TYPE: PRT
<213> ORGANISM: Artificial Sequence
<220> FEATURE:
<223> OTHER INFORMATION: CDR3H (Block 1) variant V?8 S29A

<400> SEQUENCE: 77

Arg His Asp Phe Asp Tyr Asp
1               5

<210> SEQ ID NO 78
<211> LENGTH: 7
<212> TYPE: PRT
<213> ORGANISM: Artificial Sequence
<220> FEATURE:
<223> OTHER INFORMATION: CDR3H (Block 1) variant CP09E05

<400> SEQUENCE: 78

Arg His Gly Phe Asp Tyr Asp
1               5

<210> SEQ ID NO 79
<211> LENGTH: 7
<212> TYPE: PRT
<213> ORGANISM: Artificial Sequence
<220> FEATURE:
<223> OTHER INFORMATION: CDR3H (Block 1) variant CP09C02

<400> SEQUENCE: 79

Arg His Gly Phe Asp Tyr Asp
1               5

<210> SEQ ID NO 80
<211> LENGTH: 7
<212> TYPE: PRT
<213> ORGANISM: Artificial Sequence
<220> FEATURE:
<223> OTHER INFORMATION: CDR3H (Block 1) variant CP08H01

<400> SEQUENCE: 80
```

```
Lys His Pro Pro Asp Tyr Phe
1               5

<210> SEQ ID NO 81
<211> LENGTH: 7
<212> TYPE: PRT
<213> ORGANISM: Artificial Sequence
<220> FEATURE:
<223> OTHER INFORMATION: CDR3H (Block 2) variant V?8 S29A

<400> SEQUENCE: 81

Asp Ala Ala Trp Phe Ala Tyr
1               5

<210> SEQ ID NO 82
<211> LENGTH: 7
<212> TYPE: PRT
<213> ORGANISM: Artificial Sequence
<220> FEATURE:
<223> OTHER INFORMATION: CDR3H (Block 2) variant CP08B04

<400> SEQUENCE: 82

Phe Pro Ala Trp Phe Ala Leu
1               5

<210> SEQ ID NO 83
<211> LENGTH: 7
<212> TYPE: PRT
<213> ORGANISM: Artificial Sequence
<220> FEATURE:
<223> OTHER INFORMATION: CDR3H (Block 2) variant CP08H03

<400> SEQUENCE: 83

Phe Pro Tyr Trp Phe Ala His
1               5

<210> SEQ ID NO 84
<211> LENGTH: 7
<212> TYPE: PRT
<213> ORGANISM: Artificial Sequence
<220> FEATURE:
<223> OTHER INFORMATION: CDR3H (Block 2) variant CP08G10

<400> SEQUENCE: 84

Phe Pro Ala Trp Phe Ala Phe
1               5

<210> SEQ ID NO 85
<211> LENGTH: 7
<212> TYPE: PRT
<213> ORGANISM: Artificial Sequence
<220> FEATURE:
<223> OTHER INFORMATION: CDR3L variant Vk8 S29A

<400> SEQUENCE: 85

Gln Trp Ser Ser Asn Pro Pro
1               5

<210> SEQ ID NO 86
<211> LENGTH: 7
<212> TYPE: PRT
<213> ORGANISM: Artificial Sequence
<220> FEATURE:
<223> OTHER INFORMATION: CDR3L variant CP09F05

<400> SEQUENCE: 86
```

```
Gln Asn Thr Ala Leu Pro Phe
1               5

<210> SEQ ID NO 87
<211> LENGTH: 7
<212> TYPE: PRT
<213> ORGANISM: Artificial Sequence
<220> FEATURE:
<223> OTHER INFORMATION: CDR3L variant CP08G09

<400> SEQUENCE: 87

Gln Trp Thr Ala Phe Pro Pro
1               5

<210> SEQ ID NO 88
<211> LENGTH: 7
<212> TYPE: PRT
<213> ORGANISM: Artificial Sequence
<220> FEATURE:
<223> OTHER INFORMATION: CDR3L variant CP08D02

<400> SEQUENCE: 88

Gln Trp Thr Ser Phe Pro Pro
1               5

<210> SEQ ID NO 89
<211> LENGTH: 7
<212> TYPE: PRT
<213> ORGANISM: Artificial Sequence
<220> FEATURE:
<223> OTHER INFORMATION: CDR3L variant CP08G02

<400> SEQUENCE: 89

Gln Trp Thr Asn Asn Pro Pro
1               5

<210> SEQ ID NO 90
<211> LENGTH: 7
<212> TYPE: PRT
<213> ORGANISM: Artificial Sequence
<220> FEATURE:
<223> OTHER INFORMATION: CDR3L variant CP08C08

<400> SEQUENCE: 90

Gln Asn Thr Ser Leu Pro Phe
1               5

<210> SEQ ID NO 91
<211> LENGTH: 7
<212> TYPE: PRT
<213> ORGANISM: Artificial Sequence
<220> FEATURE:
<223> OTHER INFORMATION: CDR3L variant CP08F05

<400> SEQUENCE: 91

Gln Trp Thr Ser Asn Pro Pro
1               5

<210> SEQ ID NO 92
<211> LENGTH: 7
<212> TYPE: PRT
<213> ORGANISM: Artificial Sequence
<220> FEATURE:
<223> OTHER INFORMATION: CDR3L variant CP08E05

<400> SEQUENCE: 92

Gln Trp Thr Thr Asn Pro Pro
```

```
<210> SEQ ID NO 93
<211> LENGTH: 7
<212> TYPE: PRT
<213> ORGANISM: Artificial Sequence
<220> FEATURE:
<223> OTHER INFORMATION: CDR3L variant CP08G01

<400> SEQUENCE: 93

Gln Asn Thr Asn Leu Pro Phe
1               5

<210> SEQ ID NO 94
<211> LENGTH: 7
<212> TYPE: PRT
<213> ORGANISM: Artificial Sequence
<220> FEATURE:
<223> OTHER INFORMATION: CDR3L variant CP08E01

<400> SEQUENCE: 94

Gln Trp Thr Thr Phe Pro Pro
1               5

<210> SEQ ID NO 95
<211> LENGTH: 15
<212> TYPE: PRT
<213> ORGANISM: Artificial Sequence
<220> FEATURE:
<223> OTHER INFORMATION: VH CDR1

<400> SEQUENCE: 95

Cys Ala Ala Ser Gly Phe Ile Phe Ser Ser His Gly Met Ser Trp
1               5                   10                  15

<210> SEQ ID NO 96
<211> LENGTH: 7
<212> TYPE: PRT
<213> ORGANISM: Artificial Sequence
<220> FEATURE:
<223> OTHER INFORMATION: CDR3H B1

<400> SEQUENCE: 96

Arg His Gly Phe Asp Tyr Phe
1               5
```

HUMANIZED AND AFFINITY-MATURED ANTI-CEACAM1 ANTIBODIES

CROSS REFERENCE TO RELATED APPLICATIONS

This application is a national stage patent application of International Patent application No. PCT/US2019/065212, filed on Dec. 9, 2019, which claims priority to U.S. Provisional Application No. 62/776,877, filed on Dec. 7, 2018; both of which are hereby incorporated by reference in their entireties.

STATEMENT REGARDING FEDERALLY SPONSORED RESEARCH OR DEVELOPMENT

This invention was made with government support under DK0S 1362 awarded by the National Institutes of Health. The government has certain rights in the invention.

REFERENCE TO A SEQUENCE LISTING

This application contains a Sequence Listing, which has been submitted electronically in ASCII format and is hereby incorporated by reference in its entirety. Said file, created on Aug. 20, 2024, is named 199278-46601_Sequence-Listing_Updated.txt and is 52,236 bytes in size.

FIELD OF THE INVENTION

The present invention relates generally to the field of molecular biology and medicine. More particularly, the invention provides monoclonal antibodies and antigen-binding fragments that bind to CEACAM1 and therapeutic compositions thereof, as well as methods of using such antibodies, including the inhibition of homophilic and heterophilic interactions with CEACAM1, and methods for treating cancer and infectious diseases.

BACKGROUND

Carcinoembryonic antigen-related cell adhesion molecule 1 (CEACAM1) is a member of the carcinoembryonic antigen (CEA) family of immunoglobulin (Ig) like transmembrane glycoproteins. CEACAM family members are involved in cell-cell recognition and modulate cellular processes that range from the shaping of tissue architecture and neovascularization to the regulation of insulin homeostasis and T cell proliferation.

Various cellular activities have been attributed to the CEACAM1 protein, including roles in the differentiation and arrangement of tissue three-dimensional structure, angiogenesis, apoptosis, tumor suppression, metastasis, and the modulation of innate and adaptive immune responses. Further, several cell types express CEACAM1, including tumor cells, T cells, natural killer (NK) cells, and certain macrophages.

For instance, high CEACAM1 expression occurs in a variety of cancers such as melanoma, colorectal, gastric, pancreatic, bladder, and thyroid cancer and is associated with worse tumor progression, metastasis and poor clinical prognosis. Non-small cell lung cancers (NSCLC), for example, with high CEACAM1 expression exhibit high microvessel density, distant metastases, and shorter median overall survival and progression free survival. CEACAM1 expression has also been strongly correlated with distant metastasis of pancreatic adenocarcinoma. CEACAM1 expression on tumors promotes CEACAM1-mediated inhibition of T and NK cells. Consequently, inhibiting CEACAM1 activity can inhibit tumor cell metastasis and the formation of a cancer stem cell niche.

CEACAM1 is also expressed in certain immune system cells and plays a role in immune suppression and immune cell exhaustion. High CEACAM1 expression on tumor infiltrating lymphocytes (TILs) and other tumor infiltrating immune cells from gastric, lung, melanoma, colorectal cancer and glioma, for example, is associated with a poor prognosis. On T cells, CEACAM1 expression is mostly excluded from resting (naïve) T cells, while the protein is expressed at high levels on activated T cells. CEACAM1-L is the dominant isoform expressed in most T cells and acts as an inhibitory receptor downregulating T cell activation and suppressing T cell functions. As such, inhibition of CEACAM1 on T-cells can recover T cell activity and increase anti-tumor responses.

CEACAM1 is further expressed on NK cells, which are lymphocytes involved in innate immunity, participating in early control of viral infection and immune-surveillance of tumors. When NK cells encounter cells that express major histocompatibility complex (MHC) class I, an immune response against these cells is prevented by inhibitory signals through receptor-ligand interactions. However, when encountering cells in which MHC class I is downregulated, such as in virus-infected cells or cancer cells, NK cells are activated by the lack of inhibitory signals, which makes the "diseased" cells prone to NK cell-mediated killing. When CEACAM1 is present on the surface of both NK and melanoma cells, the CEACAM1:CEACAM1 interactions lead to an inhibition of NK-mediated killing, independent of MHC class I expression. As such, disruption of this homophilic CEACAM1 interaction can be beneficial for restoring the NK-mediated immune response.

CEACAM1 expression on subsets of macrophages is further associated with fibrosis in the tumor microenvironment. CEACAM1 also regulates other stromal cells in the tumor microenvironment such as the vascular endothelium. Therefore, inhibiting interactions of CEACAM1 with its binding partners can further inhibit fibrosis and angiogenesis.

CEACAM1 also mediates intercellular adhesion via the extracellular portion of CEACAM1 containing a IgV-like N-domain, which is involved in homophilic (CEACAM1:CEACAM1) and heterophilic interactions (e.g. with CEA, CEACAM5, CEACAM8, T cell-immunoglobulin and mucin-domain containing 3 (TIM-3) protein, *Helicobacter pylori* adhesin HopQ, *Neisseria gonorrhoeae/meningitidis* opacity proteins (OPA), *Moraxella* sp. Opa-like protein OlpA, *Haemophilus influenzae* outer membrane protein (OMP) P1, *Haemophilus aegyptius* OMP P1, *Candida albicans*, and influenza viruses such as H5N1). TIM-3 was identified as a Th1 specific cell surface protein that is expressed on activated T cells, subsets of dendritic cells and macrophages and NK cells. TIM-3 is an activation-induced inhibitory molecule that has been implicated in tolerance, and shown to induce T cell exhaustion in chronic viral infections and cancer. CEACAM1, which is also expressed on activated T cells, has been shown to interact with TIM-3, and this interaction is important for TIM-3-mediated T cell inhibition.

As indicated above, CEACAM1 also serves as cellular receptor on the apical membrane of mucosal cells for a variety of Gram-negative bacterial pathogens associated with the human mucosa, as well as with fungal pathogens such as *Candida albicans*. For instance, *N. gonorrhoeae, N.*

*meningitidis, Moraxella catarrhalis, H. influenza, H. aegyptius* and pathogenic *Escherichia coli* strains possess well-characterized CEACAM1-binding adhesins. CEACAM1 engagement with bacterial adhesins triggers endocytosis of the bacteria into epithelial cells and transcytosis of microorganisms through intact epithelial layers, thus allowing the microorganisms to exploit CEACAM1 during mucosal colonization. Additionally, CEACAM1 has been implicated in infection with influenza virus H5N1 and with filial nematodes such as *Wucheria bancrofti*.

SUMMARY OF THE INVENTION

Provided herein are antibodies and antigen-binding fragments thereof that bind to CEACAM1 and that block the interaction of CEACAM1 with one or more binding partners. Also provided are therapeutic compositions of such antibodies and antigen-binding fragments thereof, as well as methods of using these antibodies. By blocking the interaction of CEACAM1 with one or more binding partners, the antibodies and antigen-binding fragments thereof are useful for reducing, inhibiting, and/or reversing T cell tolerance and/or for enhancing T cell expansion. The CEACAM1 antibodies and antigen-binding fragments thereof are further useful for treating cancer, for reducing tumor growth, for reducing tumor metastasis, and/or for reducing cancer stemness in a subject in need thereof. The CEACAM1 antibodies and antigen-binding fragments thereof are also useful for treating patients that are resistant to checkpoint therapy. Further provided are methods of using the CEACAM1 antibodies and antigen-binding fragments thereof for reducing colonization of mammalian epithelia with bacteria expressing bacterial adhesins or *Candida albicans* or for reducing replication of an influenza virus or the release of pro-inflammatory cytokines or chemokines associated with influenza virus infection.

In one aspect, the invention relates to an antibody, or antigen-binding fragment thereof, which binds to CEACAM1, wherein the antibody or antigen-binding fragment comprises a heavy chain variable region and a light chain variable region, wherein each of the heavy chain and the light chain variable regions comprises a CDR1, CDR2, and CDR3, and wherein:
  the sequence of CDR1 of the heavy chain variable region (CDR1H) comprises the sequence $X_1HX_2X_3S$ (SEQ ID NO:1);
    wherein $X_1$ is A, D, N, or S;
    wherein $X_2$ is A or G; and
    wherein $X_3$ is an amino acid with a hydrophobic side chain including I or M;
  the sequence of CDR2 of the heavy chain variable region (CDR2H) comprises the sequence TISSGGTYTYYPDSVKG (SEQ ID NO:2);
  the sequence of CDR3 of the heavy chain variable region (CDR3H) comprises the sequence $HX_4X_5DYX_6PX_7WFAX_8$ (SEQ ID NO:3);
    wherein $X_4$ is D, G, or P;
    wherein $X_5$ is F or P;
    wherein $X_6$ is D or F;
    wherein $X_7$ is A or Y; and
    wherein $X_8$ is L, H, or F;
  the sequence of CDR1 of the light chain variable region (CDR1L) comprises the sequence RANSAVSYMY (SEQ ID NO:4);
  the sequence of CDR2 of the light chain variable region (CDR2L) comprises the sequence LTSNRAT (SEQ ID NO:5); and
  the sequence of CDR3 of the light chain variable region (CDR3L) comprises the sequence $QQX_9X_{10}X_{11}X_{12}PX_{13}T$ (SEQ ID NO:6);
    wherein $X_9$ is W or N;
    wherein $X_{10}$ is S or T;
    wherein $X_{11}$ is A or an amino acid with a neutral hydrophilic side chain including S, N, and T;
    wherein $X_{12}$ is L, F, or N; and
    wherein $X_{13}$ is P or F.

In one embodiment, the invention relates to an antibody, or antigen-binding fragment thereof, which binds to CEACAM1, wherein the antibody or antigen-binding fragment comprises a heavy chain variable region and a light chain variable region, wherein each of the heavy chain and the light chain variable regions comprises a CDR1, CDR2, and CDR3, and wherein:
  the sequence of the heavy variable chain comprises the sequence $GXXXXX_1HX_2X_3S$ (SEQ ID NO:43);
    wherein X is any amino acid;
    wherein $X_1$ is A, D, N, or S;
    wherein $X_2$ is A or G; and
    wherein $X_3$ is an amino acid with a hydrophobic side chain including I or M; and
  the sequence of CDR2 of the heavy chain variable region (CDR2H) comprises the sequence TISSGGTYTYYPDSVKG (SEQ ID NO:2);
  the sequence of CDR3H comprises the sequence $HX_4X_5DYFPX_7WFAX_8$ (SEQ ID NO: 44);
    wherein $X_4$ is D, G, or P;
    wherein $X_5$ is F or P;
    wherein $X_7$ is A or Y; and
    wherein $X_8$ L, H, or F;
  the sequence of CDR1 of the light chain variable region (CDR1L) comprises the sequence RANSAVSYMY (SEQ ID NO:4);
  the sequence of CDR2 of the light chain variable region (CDR2L) comprises the sequence LTSNRAT (SEQ ID NO:5); and
  the sequence of CDR3 of the light chain variable region (CDR3L) comprises the sequence $QQX_9X_{10}X_{11}X_{12}PX_{13}T$ (SEQ ID NO:6);
    wherein $X_9$ is W or N;
    wherein $X_{10}$ is S or T;
    wherein $X_{11}$ is A or an amino acid with a neutral hydrophilic side chain including S, N, and T;
    wherein $X_{12}$ is L, F, or N; and
    wherein $X_{13}$ is P or F.

In one embodiment, the invention relates to an antibody, or antigen-binding fragment thereof, which binds to CEACAM1, wherein the antibody or antigen-binding fragment comprises a heavy chain variable region and a light chain variable region, wherein each of the heavy chain and the light chain variable regions comprises a CDR1, CDR2, and CDR3, and wherein:
  the sequence of CDR1H comprises the sequence $X_1HX_2X_3S$ (SEQ ID NO:1);
    wherein $X_1$ is A, D, N, or S;
    wherein $X_2$ is A or G; and
    wherein $X_3$ is an amino acid with a hydrophobic side chain including I or M;
  the sequence of CDR2H comprises the sequence TISSGGTYTYYPDSVKG (SEQ ID NO:2);
  the sequence of CDR3H comprises the sequence $HX_4X_5DYFPYWFAX_8$ (SEQ ID NO: 7);
    wherein $X_4$ is D, G, or P;
    wherein $X_5$ is F or P; and
    wherein $X_8$ is L, H, or F;

the sequence of CDR1L comprises the sequence RANSAVSYMY (SEQ ID NO: 4);
the sequence of CDR2L comprises the sequence LTSNRAT (SEQ ID NO:5); and
the sequence of CDR3L comprises the sequence QQX$_9$SSX$_{12}$PX$_{13}$T (SEQ ID NO: 8);
wherein X$_9$ is W or N;
wherein X$_{12}$ is L, F, or N; and
wherein X$_{13}$ is P or F.

In one embodiment, the invention relates to an antibody, or antigen-binding fragment thereof, which binds to CEACAM1, wherein the antibody or antigen-binding fragment comprises a heavy chain variable region and a light chain variable region, wherein each of the heavy chain and the light chain variable regions comprises a CDR1, CDR2, and CDR3, and wherein the sequence of CDR1H comprises the sequence SHGMS (SEQ ID NO:9);
the sequence of CDR2H comprises the sequence TISSGGTYTYYPDSVKG (SEQ ID NO:2);
the sequence of CDR3H comprises the sequence HDFDYFPYWFAH (SEQ ID NO:10);
the sequence of CDR1L comprises the sequence RANSAVSYMY (SEQ ID NO:4);
the sequence of CDR2L comprises the sequence LTSNRAT (SEQ ID NO:5); and
the sequence of CDR3L comprises the sequence QQWSSNPPT (SEQ ID NO:11).

In one embodiment, the invention relates to an antibody, or antigen-binding fragment thereof, which binds to CEACAM1, wherein the antibody or antigen-binding fragment comprises a heavy chain variable region and a light chain variable region, wherein each of the heavy chain and the light chain variable regions comprises a CDR1, CDR2, and CDR3, and wherein the sequence of CDR1H comprises the sequence SHGMS (SEQ ID NO:9);
the sequence of CDR2H comprises the sequence TISSGGTYTYYPDSVKG (SEQ ID NO:2);
the sequence of CDR3H comprises the sequence HDFDYFPYWFAH (SEQ ID NO:10);
the sequence of CDR1L comprises the sequence RANSAVSYMY (SEQ ID NO:4);
the sequence of CDR2L comprises the sequence LTSNRAT (SEQ ID NO:5); and
the sequence of CDR3L comprises the sequence QQWTSNPPT (SEQ ID NO:12).

In one aspect, the invention provides an antibody or antigen-binding fragment thereof which binds to CEACAM1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO:13, and wherein the sequence of the light chain variable region comprises a sequence that is at least 90% identical to a light chain variable region amino acid sequence selected from the group consisting of SEQ ID NO: 14, SEQ ID NO: 15, and SEQ ID NO: 16.

In one embodiment, the invention provides an antibody or antigen-binding fragment thereof, which binds to CEACAM1, wherein the antibody or antigen-binding fragment comprises a heavy chain variable region and a light chain variable region, wherein the sequence of the heavy chain variable region comprises SEQ ID NO: 13, and wherein the sequence of the light chain variable region comprises a sequence selected from the group consisting of SEQ ID NO: 14, SEQ ID NO:15, and SEQ ID NO:16.

In another embodiment, the invention provides an antibody or antigen-binding fragment thereof which binds to CEACAM1, wherein the antibody or antigen-binding fragment comprises a heavy chain variable region and a light chain variable region, wherein the sequence of the heavy chain variable region comprises SEQ ID NO: 13, and wherein the sequence of the light chain variable region comprises SEQ ID NO:14.

In another embodiment, the invention provides an antibody or antigen-binding fragment thereof which binds to CEACAM1, wherein the sequence of the heavy chain variable region comprises SEQ ID NO:13, and wherein the sequence of the light chain variable region comprises SEQ ID NO:15.

In one aspect, the invention provides an antibody or antigen-binding fragment thereof which binds to CEACAM1, wherein the antibody or antigen-binding fragment comprises a heavy chain variable region and a light chain variable region;
wherein the sequence of the heavy chain variable region comprises a sequence that is at least 85% identical to the heavy chain variable region amino acid sequence of SEQ ID NO:13;
wherein the sequence of the light chain variable region comprises a sequence that is at least 85% identical to a light chain variable region amino acid sequence of SEQ ID NO: 14;
wherein the sequence of the heavy variable chain comprises the sequence GXXXXX$_1$HX$_2$X$_3$S (SEQ ID NO:43);
wherein X is any amino acid;
wherein X$_1$ is A, D, N, or S;
wherein X$_2$ is A or G; and
wherein X$_3$ is an amino acid with a hydrophobic side chain including I or M; and
wherein the sequence of CDR3H comprises the sequence HX$_4$X$_5$DYFPX-WFAX$_8$ (SEQ ID NO:44);
wherein X$_4$ is D, G, or P;
wherein X$_5$ is F or P;
wherein X$_7$ is A or Y; and
wherein X$_8$ is L, H, or F.

In one aspect, the invention provides an antibody or antigen-binding fragment thereof which binds to CEACAM1, wherein the antibody or antigen-binding fragment comprises a heavy chain variable region and a light chain variable region,
wherein the sequence of the heavy chain variable region comprises a sequence that is at least 85%, at least 90% or at least 95% identical to the heavy chain variable region amino acid sequence of SEQ ID NO:13,
wherein the sequence of the light chain variable region comprises a sequence that is at least 85%, at least 90% or at least 95% identical to a light chain variable region amino acid sequence of SEQ ID NO:14,
wherein each of the heavy chain and the light chain variable regions comprises a CDR1, CDR2, and CDR3; and
wherein:
the sequence of CDR2H comprises residues Y57 and Y59 of SEQ ID NO: 13,
the sequence of CDR3H comprises residues D102, Y103, F104, P105, and Y106 of SEQ ID NO: 13,
the sequence of CDR1L comprises residues A28, S30, and Y31 of SEQ ID NO: 14, the sequence of CDR2L comprises residues S51 and N52 of SEQ ID NO:14, and the sequence of CDR3L comprises residues S91 and S92 of SEQ ID NO: 14.

In one embodiment, the CEACAM1 antibody or antigen-binding fragment thereof provided by the invention is a chimeric antibody, a CDR-grafted antibody, or a humanized antibody or antigen-binding fragment thereof.

In one embodiment, the CEACAM1 antibody or antigen-binding fragment thereof provided by the invention is a multispecific or a bispecific antibody or antigen-binding fragment thereof. In one embodiment, the antibody or antigen-binding fragment is a bispecific antibody comprising a complementary region that binds to PD-1 or PD-L1.

In one embodiment, the CEACAM1 antibody or antigen-binding fragment thereof provided by the invention is an scFv, Fv, Fab', Fab, F(ab')2, or diabody.

In one embodiment, the CEACAM1 antibody or antigen-binding fragment thereof provided by the invention has isotype IgG4.

In one embodiment, the CEACAM1 antibody or antigen-binding fragment thereof provided by the invention contains a S241P substitution in the constant region of the heavy chain.

In one embodiment, the CEACAM1 antibody or antigen-binding fragment thereof provided by the invention is deglycosylated.

In one embodiment, the CEACAM1 antibody or antigen-binding fragment thereof provided by the invention is lacking a C-terminal lysine in the heavy chain.

In one embodiment, the CEACAM1 antibody or antigen-binding fragment thereof provided by the invention is conjugated to one ore more of a cytotoxin, a fluorescent label, and/or an imaging agent.

In another aspect, the invention provides CEACAM1 antibodies and antigen-binding fragments thereof that are characterized by the epitopes on CEACAM1 that they bind to. As described, such antibodies include, but are not limited to, the CEACAM1 antibodies and antigen-binding fragments thereof described by their structural features herein, including CDR motifs, CDR sequences, and heavy and light variable chain sequences. In some embodiments, the invention provides CEACAM1 antibodies and antigen-binding fragments thereof that bind to residues in the IgV-like N-domain of CEACAM1. In another embodiment, the antibodies and antigen-binding fragments thereof provided herein also bind selectively to CEACAM1 over one or more CEACAM family members. In one embodiment, the CEACAM1 antibody or antigen-binding fragment thereof does not exhibit significant binding to other CEACAM family members including to CEACAM3, CEACAM5, CEACAM6 and/or CEACAM8. In some embodiments, the invention provides CEACAM1 antibodies and antigen-binding fragments that bind an epitope on the N-domain of CEACAM1 that overlaps or at least partially overlaps with the CEACAM1:CEACAM1 dimer interface, thereby blocking CEACAM1 homophilic interactions. In some embodiments, the invention provides CEACAM1 antibodies and antigen-binding fragments that bind to CEACAM1 residues that are located in the binding site on CEACAM1 for heterologous interaction partners, including but not limited to, other CEACAM family members, TIM family members, bacterial adhesins (such as HopQ, OPA, OMP P1 and/or OlpA), *Candida albicans*, influenza viruses (such as H5N1) and/or filial nematodes such as *Wucheria bancrofti*.

In one embodiment, the contemplated CEACAM1 antibody or antigen-binding fragment thereof binds to the same epitope as an antibody or antigen-binding fragment with a heavy chain variable region and a light variable chain region, wherein the sequence of the heavy chain variable region comprises SEQ ID NO: 13 and wherein the sequence of the light chain variable region comprises SEQ ID NO:14.

In one aspect, the contemplated CEACAM1 antibody or antigen-binding fragment thereof binds to the IgV-like N-domain of CEACAM1 and binds to an epitope comprising one or more residues selected from the group consisting of residues F29, Y34, D40, G41, N42, T56, Q89, S93, D94, N97, and E99 of SEQ ID NO:17. In one embodiment, the epitope further comprises residue Q44 of SEQ ID NO:17. In one embodiment, the epitope further comprises one or more residues selected from the group consisting of residues S32, Q44, A49, I91, L95, and V96 of SEQ ID NO:17.

In one embodiment, the CEACAM1 antibody or antigen-binding fragment thereof binds to the IgV-like N-domain domain of CEACAM1.

In one embodiment, the CEACAM1 antibody or antigen-binding fragment thereof does not bind to one of more of CEACAM3, CEACAM5, CEACAM6, and CEACAM 8.

In one embodiment, the CEACAM1 antibody or antigen-binding fragment thereof binds at least partially binds to the binding site on CEACAM1 for TIM3.

In one embodiment, the CEACAM1 antibody or antigen-binding fragment thereof at least partially binds to the binding site on CEACAM1 for CEACAM1 during homodimerization.

In one aspect, the invention provides antibodies or antigen-binding fragments thereof which bind to CEACAM and which bind partially or fully to the binding site on CEACAM1 for bacterial adhesins including, but not limited to *Helicobacter pylori* adhesin HopQ, *Neisseria gonorrhoeae* Opa, *Neisseria meningitidis* Opa, *Haemophilus influenza* OMP P1, *Haemophilus aegyptius* OMP P1, and/or *Moraxella* sp. Opa-like protein OlpA. In one aspect, the CEACAM1 antibody or antigen-binding fragments thereof binds to an epitope comprising one or more residues selected from the group consisting of residues F29, Y34, N42, Q89, and N97 of SEQ ID NO: 17.

In one aspect, the CEACAM1 antibody or antigen-binding fragment thereof binds to an epitope comprising one or more residues selected from the group consisting of residues Y34, G41, N42, Q44, Q89, S93, D94, V96, and N97 of SEQ ID NO: 17. In one embodiment, the epitope further comprises residues F29, S32, D40, A49, T56, I91, L95, and E99 of SEQ ID NO: 17.

In one embodiment, the invention provides for nucleic acid molecules encoding the CEACAM1 antibodies or antigen-binding fragments thereof described herein, as well as vectors comprising such nucleic acid molecules. Also provided are cells comprising a vector encoding the CEACAM1 antibodies or antigen-binding fragments thereof described herein as well as cells expressing the CEACAM1 antibodies or antigen-binding fragments thereof described herein. Provided herein is further a chimeric antigen receptor T-cells comprising the CDRs of any of the antibodies or antigen-binding fragments disclosed herein.

In one embodiment, the invention provides compositions comprising the antibodies or antigen-binding fragments thereof described herein and a pharmaceutically acceptable excipient.

In one embodiment, the invention provides methods of using the CEACAM1 antibodies or antigen-binding fragments thereof described herein for inhibiting binding of CEACAM1 its interaction partners and/or for reducing CEACAM1 activity, the method comprising contacting CEACAM1 with a CEACAM1 antibody or antigen-binding fragment thereof described herein. For instance, embodiments of the inventions are useful for inhibiting the interaction between CEACAM1 and a member of the CEACAM family. In one embodiment, the CEACAM family member is CEACAM3, CEACAM5, CEACAM6, or CEACAM8. In some embodiments, the CEACAM family member is CEACAM1 itself.

In one embodiment, the invention provides methods of using the CEACAM1 antibodies or antigen-binding fragments thereof described herein for inhibiting binding of CEACAM1 to a member of the TIM family, the method comprising contacting CEACAM1 with a CEACAM1 antibody or antigen-binding fragment thereof described herein. In some embodiments, the TIM family member is TIM-3.

In one embodiment, the invention provides methods of using the CEACAM1 antibodies or antigen-binding fragments thereof described herein for inhibiting binding of CEACAM1 to bacterial adhesins, the method comprising contacting CEACAM1 with a CEACAM1 antibody or antigen-binding fragment thereof described herein. In some embodiments, the bacterial adhesin is *Helicobacter pylori* adhesin HopQ, *Neisseria gonorrhoeae* Opa, *Neisseria meningitidis* Opa, *Haemophilus influenza* OMP P1, *Haemophilus aegyptius* OMP P1, or *Moraxella* sp. adhesin OlpA. In one embodiment, the invention provides methods of using the CEACAM1 antibodies or antigen-binding fragments thereof described herein for inhibiting binding of CEACAM1 to *Candida albicans*, the method comprising contacting CEACAM1 with a CEACAM1 antibody or antigen-binding fragment thereof described herein. In one embodiment, the invention provides methods of using the CEACAM1 antibodies or antigen-binding fragments thereof described herein for inhibiting binding of CEACAM1 to an influenza virus, the method comprising contacting CEACAM1 with a CEACAM1 antibody or antigen-binding fragment thereof described herein. In one embodiment, the influenza virus is H5N1.

In one embodiment, the invention provides methods of using the CEACAM1 antibodies or antigen-binding fragments thereof described herein for reducing colonization of mammalian epithelia with bacteria expressing bacterial adhesins, the method comprising contacting CEACAM1 with a CEACAM1 antibody or antigen-binding fragment thereof described herein. In some embodiments, the bacterial adhesin is *Helicobacter pylori* adhesin HopQ, *Neisseria meningitidis* Opa, *Haemophilus influenza* OMP P1, *Haemophilus aegyptius* OMP P1, or *Moraxella* sp. adhesin OlpA.

In one embodiment, the invention provides methods of using the CEACAM1 antibodies or antigen-binding fragments thereof described herein for reducing colonization of mammalian epithelia with *Candida albicans*, the method comprising contacting CEACAM1 with a CEACAM1 antibody or antigen-binding fragment thereof described herein.

In one embodiment, the invention provides methods of reducing replication of an influenza virus, the method comprising contacting CEACAM1 with a CEACAM1 antibody or antigen-binding fragment thereof described herein. In one embodiment, the invention provides methods of reducing the release of pro-inflammatory cytokines or chemokines associated with an infection with an influenza virus, the method comprising contacting a cell population comprising epithelial cells with a CEACAM1 antibody or antigen-binding fragment thereof described herein. In some embodiments, the influenza virus is H5N1.

In one embodiment, the invention provides methods of using the CEACAM1 antibodies or antigen-binding fragments thereof described herein for reducing T cell tolerance, and/or for enhancing T cell expansion or activation. These methods are useful for in vitro and in vivo applications.

In one embodiment, the invention provides methods of using the CEACAM1 antibodies or antigen-binding fragments thereof described herein for reducing T cell tolerance and/or enhancing T cell expansion in a subject in need thereof, the method comprising administering to the subject an effective amount of the antibody or antigen-binding fragment thereof. In one embodiment, the invention provides methods of using the CEACAM1 antibodies or antigen-binding fragments thereof described herein for treating cancer in a subject in need thereof, the method comprising administering to the subject an effective amount of the antibody or antigen-binding fragment thereof. In some embodiments, the cancer is glioma, glioblastoma, thymoma, mesothelioma, sarcoma, uterine carcinosarcoma, chromophobe renal cell carcinoma, adenoid cystic carcinoma, acute myeloid leukemia, melanoma, uveal melanoma, papillary renal cell carcinoma, clear cell renal cell carcinoma, chloangiocarcinoma, lung adenocarcinoma, diffuse large B-cell lymphoma, pheochromocytoma and paraganglioma, pancreatic cancer, thyroid cancer, lung cancer, colorectal cancer, squamous cancer, breast cancer, prostate cancer, bladder cancer, gastric cancer, testicular germ cell cancer, ovarian cancer, head and neck cancer, uterine cancer, cervical cancer, or liver cancer. In embodiments, the invention provides methods of using the CEACAM1 antibodies or antigen-binding fragments thereof described herein for reducing tumor growth, reducing tumor metastasis, reducing tumor-associated fibrosis, and/or reducing cancer stemness in a subject in need thereof by administering to the subject an effective amount of the antibody or antigen-binding fragment. In some embodiments, the invention provides methods that further comprise administering a checkpoint inhibitor. In certain embodiments, the checkpoint inhibitor is a CTLA-4, a PD-1, a PD-L1, and a PD-L2 inhibitor. In some embodiments, the invention provides methods that further comprise administering one or more of an inhibitor of LAG3, TIGIT, LAP, Podoplanin, Protein C receptor, ICOS, GITR, CD226 or CD160. In some embodiments, the invention provides methods that further comprise administering a TIM-3 inhibitor. In some embodiments, the inhibitor is administered concurrently or consecutively with the antibody or antigen-binding fragment. In some embodiments, the inhibitor is administered separately or as a mixture with the antibody or antigen-binding fragment.

In one embodiment, the invention provides methods of using the CEACAM1 antibodies or antigen-binding fragments thereof described herein for reducing colonization of a subject's epithelia with bacteria expressing bacterial adhesins in a subject in need thereof, the method comprising administering to the subject an effective amount of the CEACAM1 antibodies or antigen-binding fragments thereof described herein. In some embodiments, the bacterial adhesin is *Helicobacter pylori* adhesin HopQ, *Neisseria meningitidis* Opa, *Haemophilus influenza* OMP P1, *Haemophilus aegyptius* OMP P1, or *Moraxella* sp. OlpA.

In one embodiment, the invention provides methods of using the CEACAM1 antibodies or antigen-binding fragments thereof described herein for reducing colonization of a subject's epithelia with *Candida albicans* in a subject in need thereof, the method comprising administering to the subject an effective amount of the CEACAM1 antibodies or antigen-binding fragments thereof described herein.

In one embodiment, the invention provides methods of using the CEACAM1 antibodies or antigen-binding fragments thereof described herein for reducing replication of an influenza virus in a subject in need thereof, the method comprising administering to the subject an effective amount of the CEACAM1 antibodies or antigen-binding fragments thereof described herein. In one embodiment, the invention provides methods of using the CEACAM1 antibodies or antigen-binding fragments thereof described herein for reducing the release of pro-inflammatory cytokines or chemokines associated with an infection with an influenza virus in a subject in need thereof, the method comprising administering to the subject an effective amount of the CEACAM1 antibodies or antigen-binding fragments thereof described herein. In some embodiments, the influenza virus in H5N1.

In one embodiment, the invention provides methods of using the CEACAM1 antibodies or antigen-binding fragments thereof described herein for treating a subject that does not respond to therapy with a checkpoint inhibitor therapy (primary resistance), as well as patients that initially respond to treatment, but later become resistant to checkpoint inhibitor blockade (secondary or acquired resistance). Such methods for treating comprise administering to said subject the CEACAM1 antibodies or antigen-binding fragments thereof described herein. In some embodiments, the subject has acquired resistance to therapy with one or more of a PD-1 inhibitor, a PD-L1 inhibitor, and a CTLA-4 inhibitor. Resistant cancer may also be referred to as refractory cancer.

BRIEF DESCRIPTION OF THE DRAWINGS

The patent or application file contains at least one drawing executed in color. Copies of this patent or patent application published with color drawing(s) will be provided by the Office upon request and payment of the necessary fee.

FIGS. 3A, 3B, and 3C show certain nucleotide and amino acid sequences. FIG. 3A. Nucleotide acid (SEQ ID NO:50) and amino acid (SEQ ID NO: 19) sequences of heavy variable chain V$_H$1. FIG. 3B. Nucleotide sequence of heavy variable chain V$_H$1 (SEQ ID NO:50) and amino acid sequence of heavy variable chain CP08H03 (SEQ ID NO:13). FIG. 3C. Nucleotide acid (SEQ ID NO:52) and amino acid (SEQ ID NO:14) sequence light variable chain V$_K$8 S29A. CDRs are shaded. Numbering of CDR residues according to Kabat and according to the primary amino acid sequence is indicated.

FIG. 7 provides an overview of the affinity maturation library design. CDRs (as defined by Kabat) are shown in bold. Sequences from top to bottom: SEQ ID NOs: 95, 54, 55, and 56. Positions targeted are designated with an X. Individual positions may contain all 20 amino acids or a subset thereof.

FIG. 9A: Selection campaign 1: Solid phase panning CEACAM5/CEACAM6 deselection was performed on library phage and prior to round 2, with rounds of selection carried out on decreasing concentrations of biotinylated soluble CEACAM1. FIG. 9B: Selection campaign 2: Panning selection using CEACAM1 was performed in round 1 followed by 2 rounds of panning CEACAM5/CEACAM6 deselection and selection using decreasing concentrations of biotinylated soluble CEACAM1.

FIG. 10 shows examples of scFv binding ELISA assays. A dilution series of purified parental scFv V$_H$1/V$_K$8 S29A or affinity matured scFv variants were added to plates coated with GST-CEACAM1. Binding was detected using an anti-HIS6-HRP antibody and TMB. All variable light chains contain a S29A mutation in CDR1L (Kabat numbering scheme, corresponding to a S28A mutation in the primary amino acid sequence of the variable light chain).

S29A, 8H3_9B3/CP08_E05, and 8H3_9C2/CPO08_F05, as well as data for CEACAM8 antibody 80H3 were omitted from the Fig. due to an unusually high background signal.

Figure 12A:
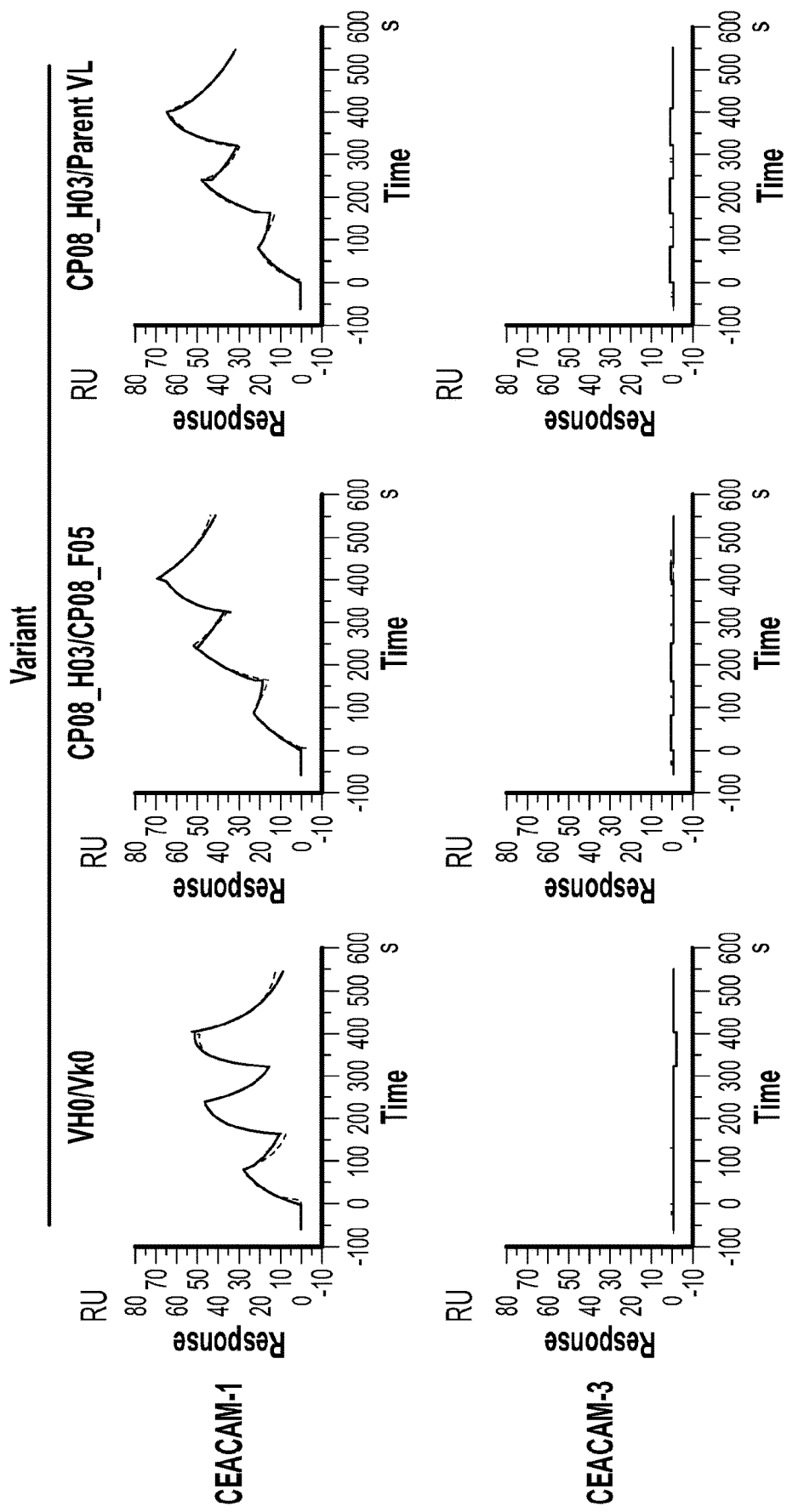
Figure 12A:
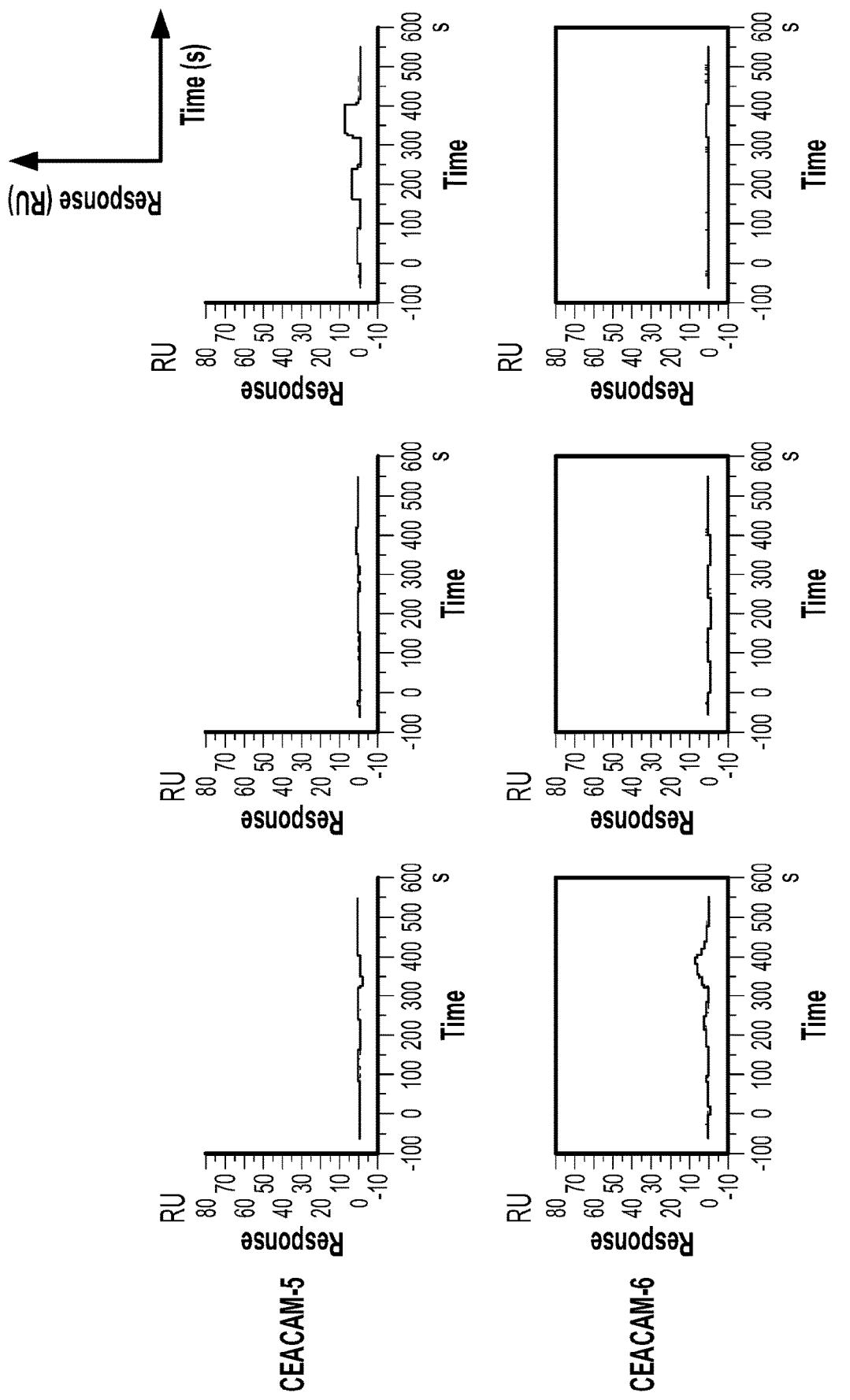
Figure 12B:
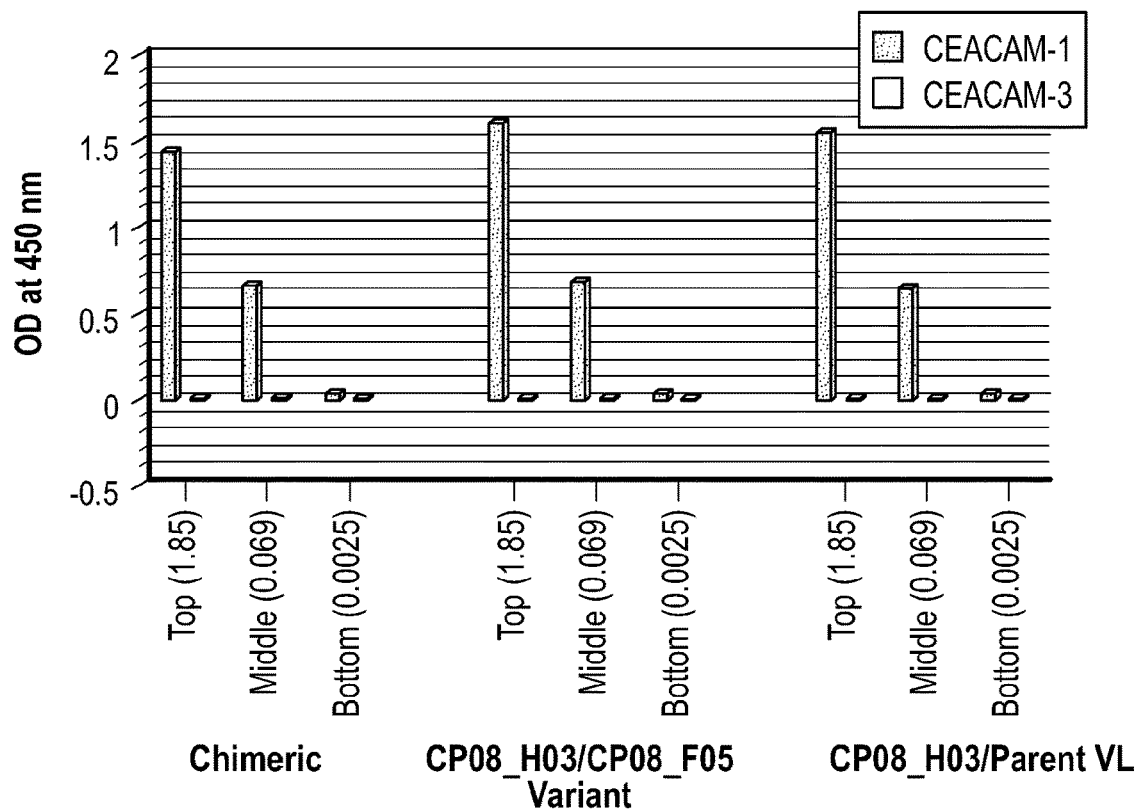
Figure 12C:
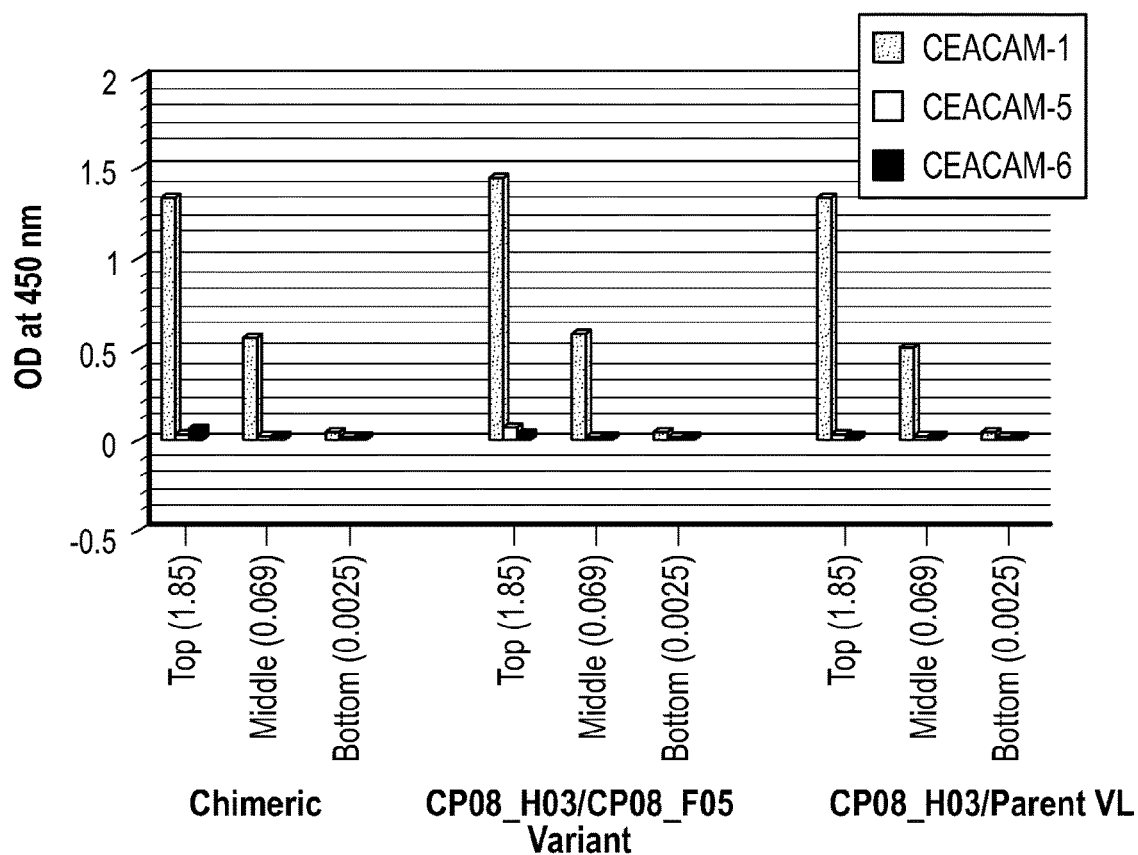

FIGS. 12A, 12B, and 12C illustrate that CEACAM antibodies CP08H03/$V_K$8 S29A (labeled "CP08_H03/Parent VL"), CP08H03/CP08_F05, and $V_H0/V_K0$ are selective for CEACAM1. CP08H03/$V_K$8 S29A and CP08H03/CP08F05 contain a S29A mutation in CDR1L (Kabat numbering scheme, corresponding to a S28A mutation in the primary amino acid sequence of the variable light chain). FIG. 12A shows single-cycle kinetics sensorgrams and fitted curves for the purified lead humanized and affinity-matured IgG4 variants. Increasing concentrations on different CEACAM family members were injected and a single off-rate was determined by single cycle kinetics (surface plasmon resonance, SPR). FIG. 12B shows three-point binding ELISA data for the binding of the chimeric antibody $V_H0/V_K0$ (labeled "chimeric'), purified lead humanized and affinity-matured IgG4 variants to CEACAM1 and CEACAM3 family members. A three-point (high, medium and low, with concentrations based on the binding of the chimeric antibody $V_H0/V_K0$ to CEACAM1) titration was performed and binding was detected using an anti-human kappa chain antibody and TMB substrate. FIG. 12C shows three-point binding ELISA data for the binding of the chimeric antibody $V_H0/V_K0$ (labeled "chimeric') and purified lead humanized and affinity-matured IgG4 variants to CEACAM1, 5 and 6 family members. A three-point (high, medium and low, with concentrations based on the binding of the chimeric antibody $V_H0/V_K0$ to CEACAM-1) titration was performed and binding was detected using an anti-human kappa chain antibody and TMB substrate.

Figures 13, 14:
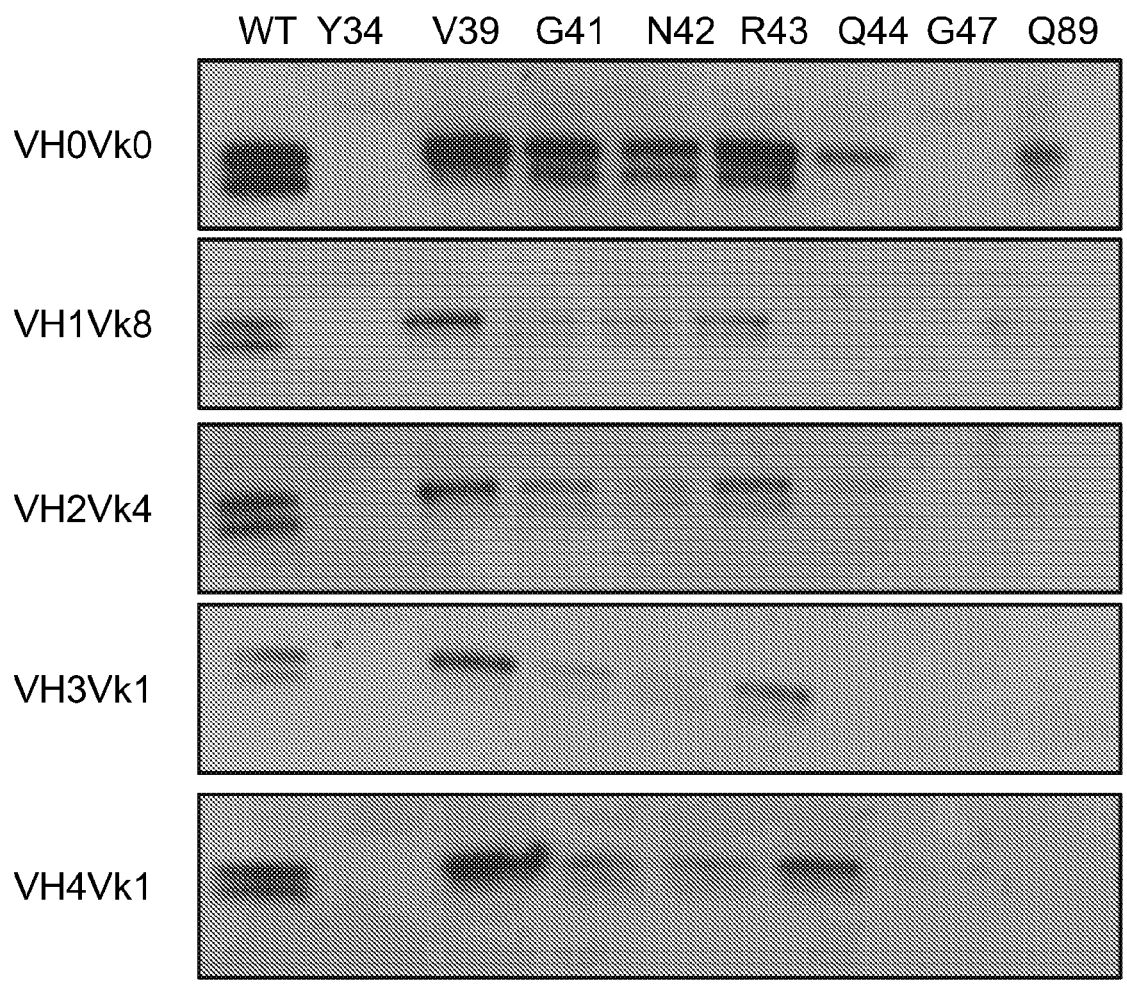

FIG. 13 shows the sequence homology among the N-domains of different CEACAM family members. CEACAM1 (C1, UniProtKB accession number P13688), CEACAM3 (C3, UniProtKB accession number P40198), CEACAM4 (C4, UniProtKB accession number O75871), CEACAM5 (C5, UniProtKB accession number P06731), CEACAM6 (C6, UniProtKB accession number P40199), CEACAM7 (C7, UniProtKB accession number Q14002), and CEACAM8 (C8, UniProtKB accession number P31997). The shown percent identity matrix was created using Clustal2.1. The specific residues analyzed for each CEACAM family member are indicated.

FIG. 14 shows the results of a CEACAM1 mutagenesis study aimed at identifying residues in CEACAM1 that are involved in binding to the indicated CEACAM1 antibodies. CEACAM1-FLAG was expressed in transfected human embryonic kidney (HEK) cells with CEACAM1 containing the indicated mutations (Y34C, V39A, G41A, N42A, R43A, Q44L, G47A, and Q89H), the proteins resolved by SDS-PAGE and then immunoblotted. The wild-type (WT) or mutant CEACAM1 proteins were detected using the indicated chimeric ($V_H0/V_K0$) and humanized CEACAM antibodies. Decreased detection indicates that the mutated residue is involved in binding to the respective antibody used for detection.

Figure 15:
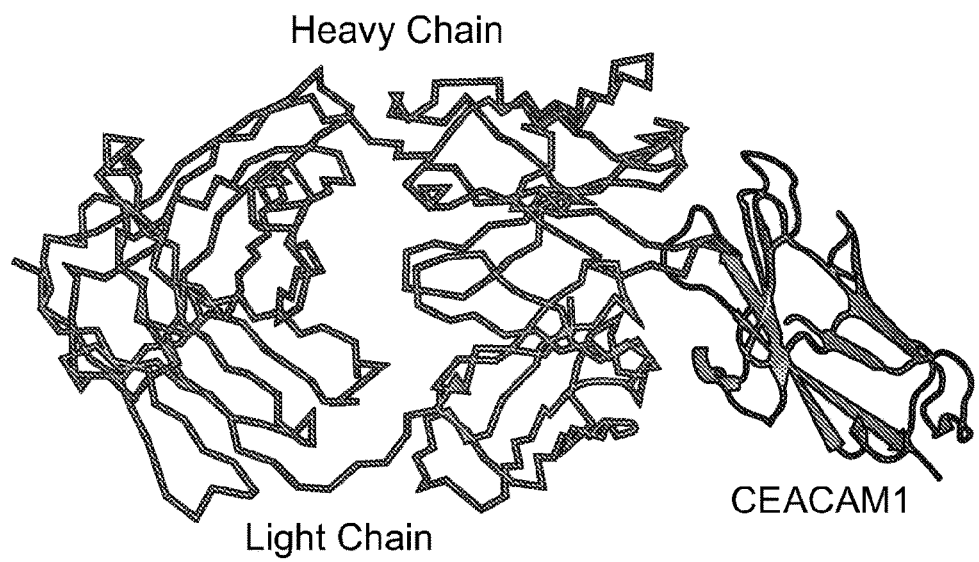

FIG. 15 shows the structure of the CEACAM1: CP08H03/$V_K$8 S29A Fab complex. In the structure of the complex, the Fab is shown as a Cα trace and the antigen is shown as a ribbon.

Figure 16:
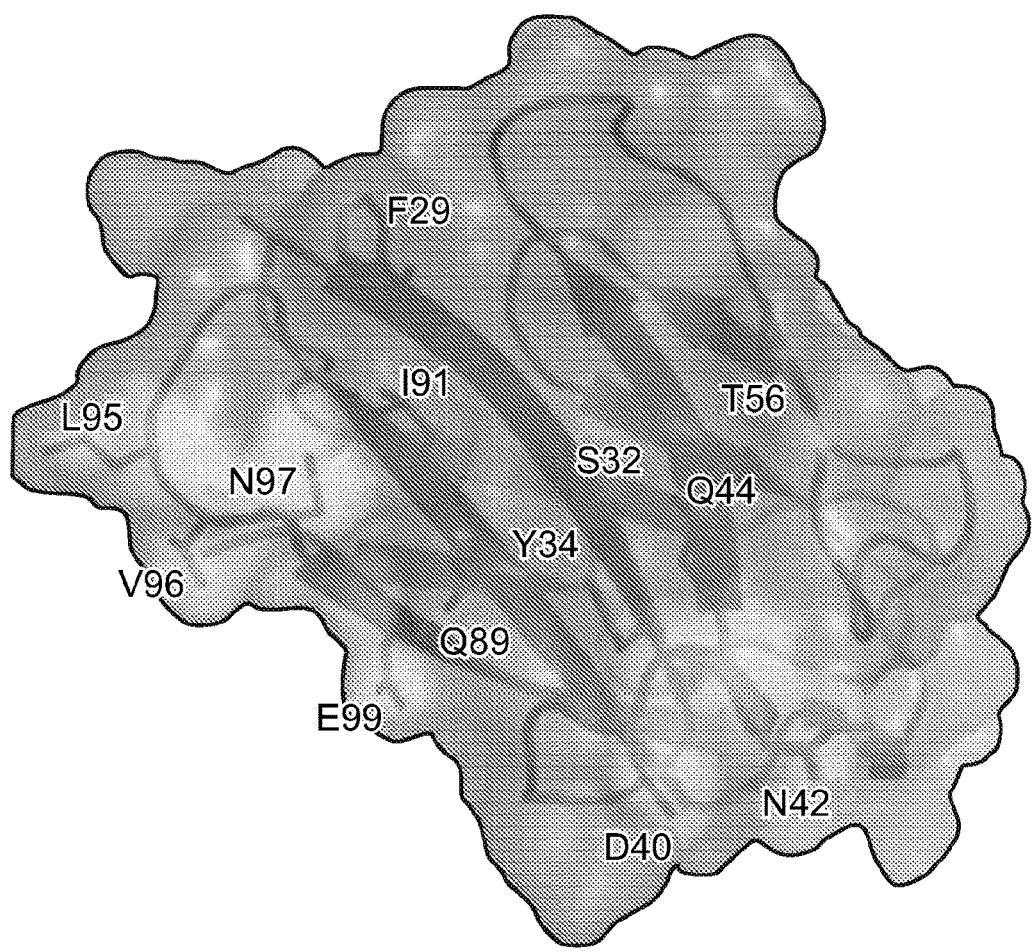

FIG. 16 shows a view of the antigen (CEACAM1) towards the dimer interface. CEACAM1 residues including D40, N42, L95, V96, N97, and E99, which are interacting with the CP08H03/$V_K$8 S29A Fab light chain (see FIG. 15), and CEACAM1 residues including F29, S32, Y34, Q44, T56, Q89, and I91, which are interacting with the CP08H03/$V_K$8 S29A Fab heavy chain, are labeled. The relevant side chains are drawn as sticks.

Figure 17:
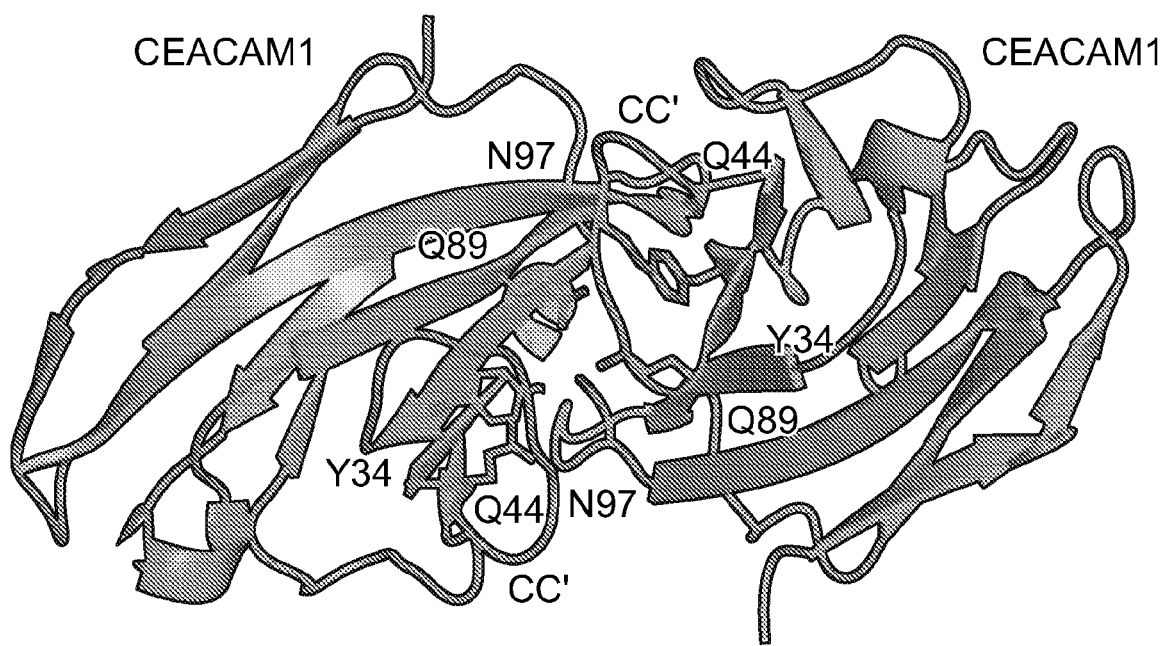

FIG. 17 shows a crystal structure illustrating the CEACAM1:CEACAM1 homodimer interface (PDB ID: 4QXW). One CEACAM1 monomer is shown in on the left, the other one on the right. Residues Y34, Q44, Q89, and N97 form a YQQN pocket.

FIG. 18 shows a stereo image of a close up view of the CP08H03/$V_K$8 S29A Fab-CEACAM1 interaction. CEACAM1 is drawn as a ribbon and Fab chains (light chain and heavy chain) are drawn as Cα traces. Regions of the Fab light chain residues (including S30, Y31, Y48, L49, S51, N52, W90, S91, and N93) and heavy chains residues S52, S53, T56, Y57, Y59, D102, Y103, F104, P105, Y106, which interact with CEACAM1 residues including F29, S32, Y34, D40, N42, Q44, A49, T56, Q89, I91, L95, V96, N97, and E99 are labeled. Side chains of interest are drawn as sticks and hydrogen bonds are drawn as black dashes. Residue numbering is based on the primary amino acid sequence of the antibody and CEACAM1.

Figure 19:
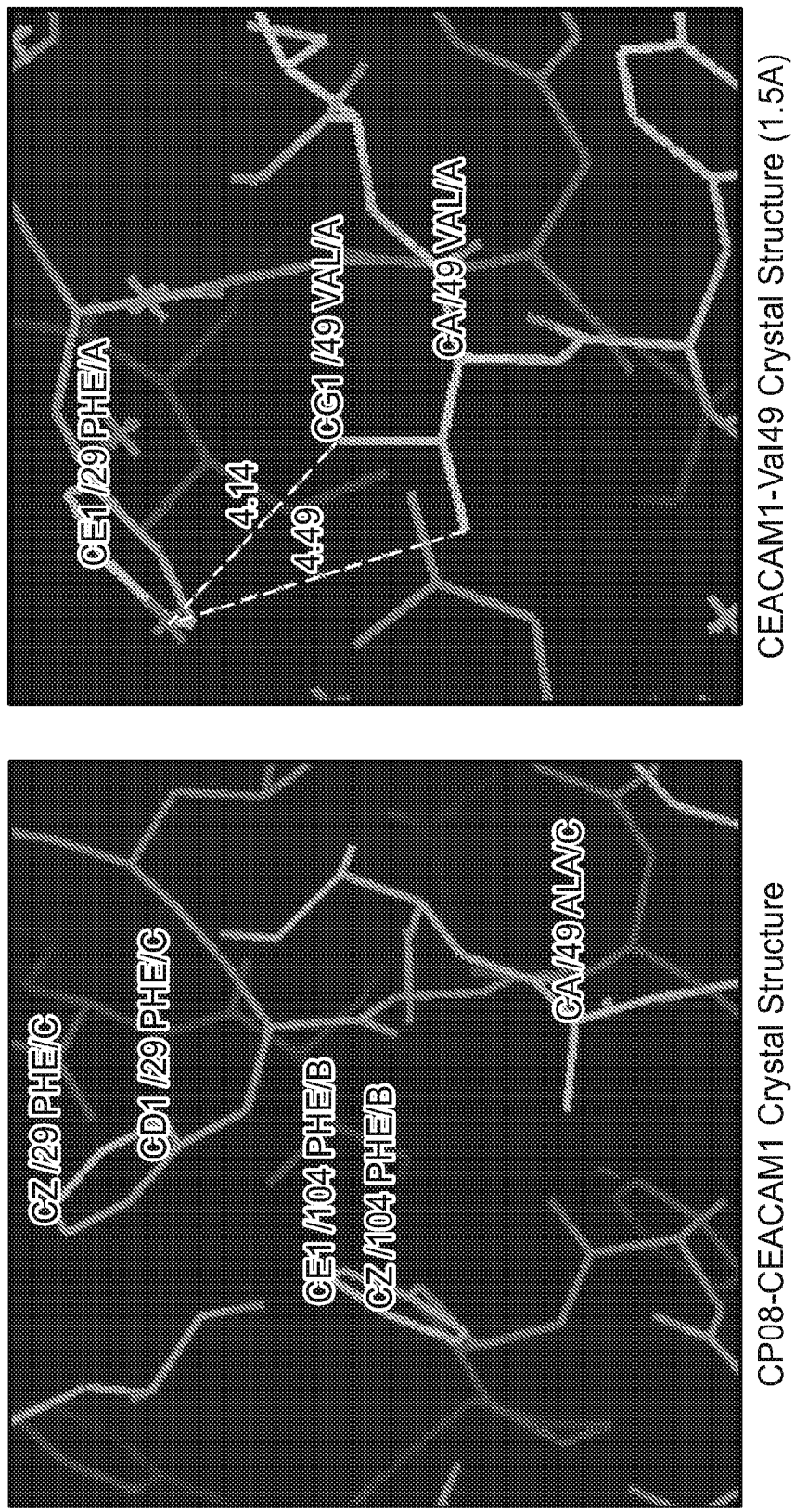

FIG. 19 shows a comparison of CEACAM1 F29 and V49 or A49 residues in CEACAM1 WT: CP08H03/$V_K$8 S29A antibody crystal structure (left) or CEACAM1 A49V/Q89H mutant crystal structure (right).

Figure 20A:
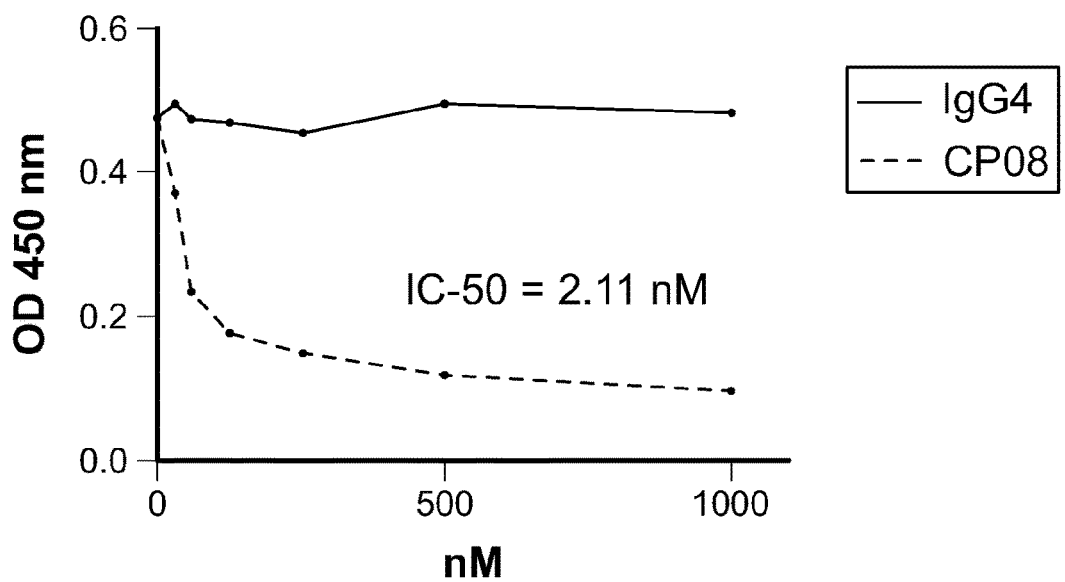
Figure 20B:
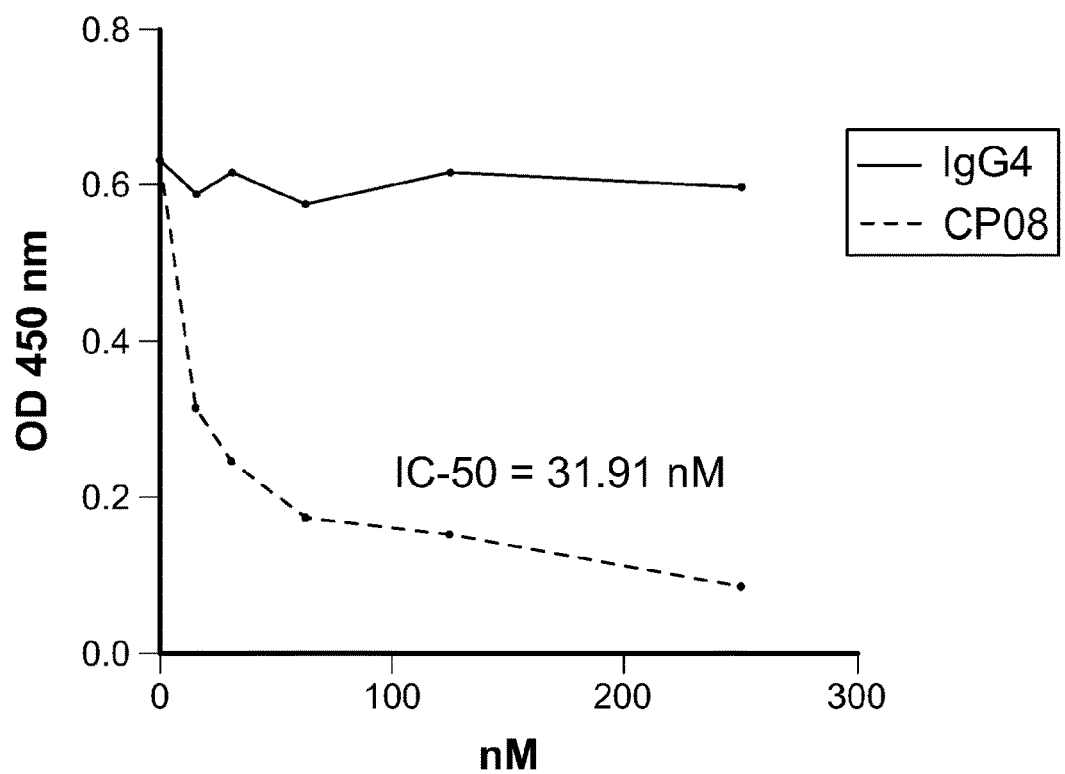

FIGS. 20A and 20B illustrate that the CEACAM1 antibody CP08H03/$V_K$8 S29A (labeled "CP08") blocks human CEACAM1:CEACAM1 (FIG. 20A) and CEACAM: human TIM-3 interactions (FIG. 20B). IgG4=control antibody.

Figure 21:
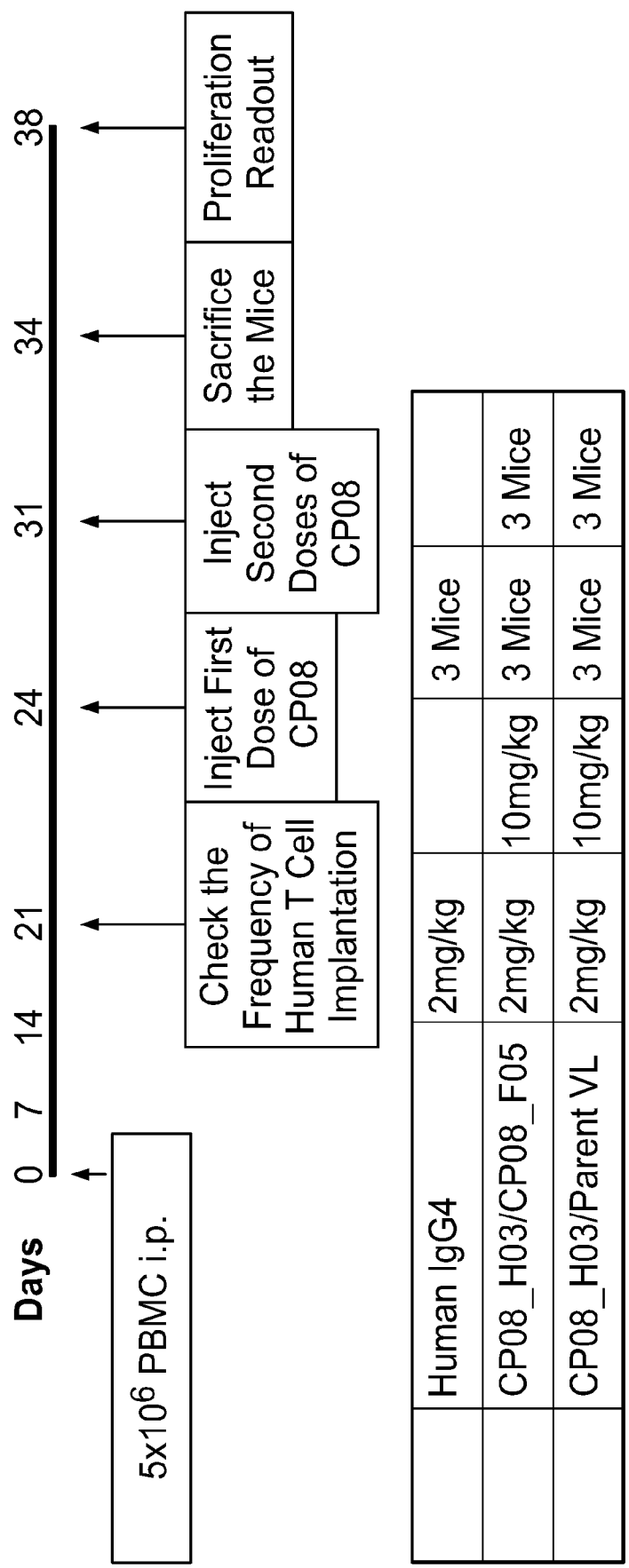

FIG. 21 shows the experimental setup for testing the ability of CEACAM1 antibodies to induce CD45$^+$ cell proliferation in humanized non-obese diabetic (NOD) scid gamma mice (NSG mice). Engraftment of human peripheral blood mononuclear cells (PBMC) adoptively transferred via intraperitoneal injection to NSG host mice was analyzed by fluorescence-activated cell sorter (FACS) for human CD45 and proliferation dye staining 38 days following injection. On day 24 following PBMC injection, mice were treated with a single injection of human IgG4 isotype control or the indicated concentration of CP08H03/$V_K$8 S29A (labeled "CP08_H03/Parent VL") or CP08H03/CP08F05 antibody. On day 31, mice were treated with the second injection. On day 38, mice were sacrificed for data acquisition.

Figure 22:
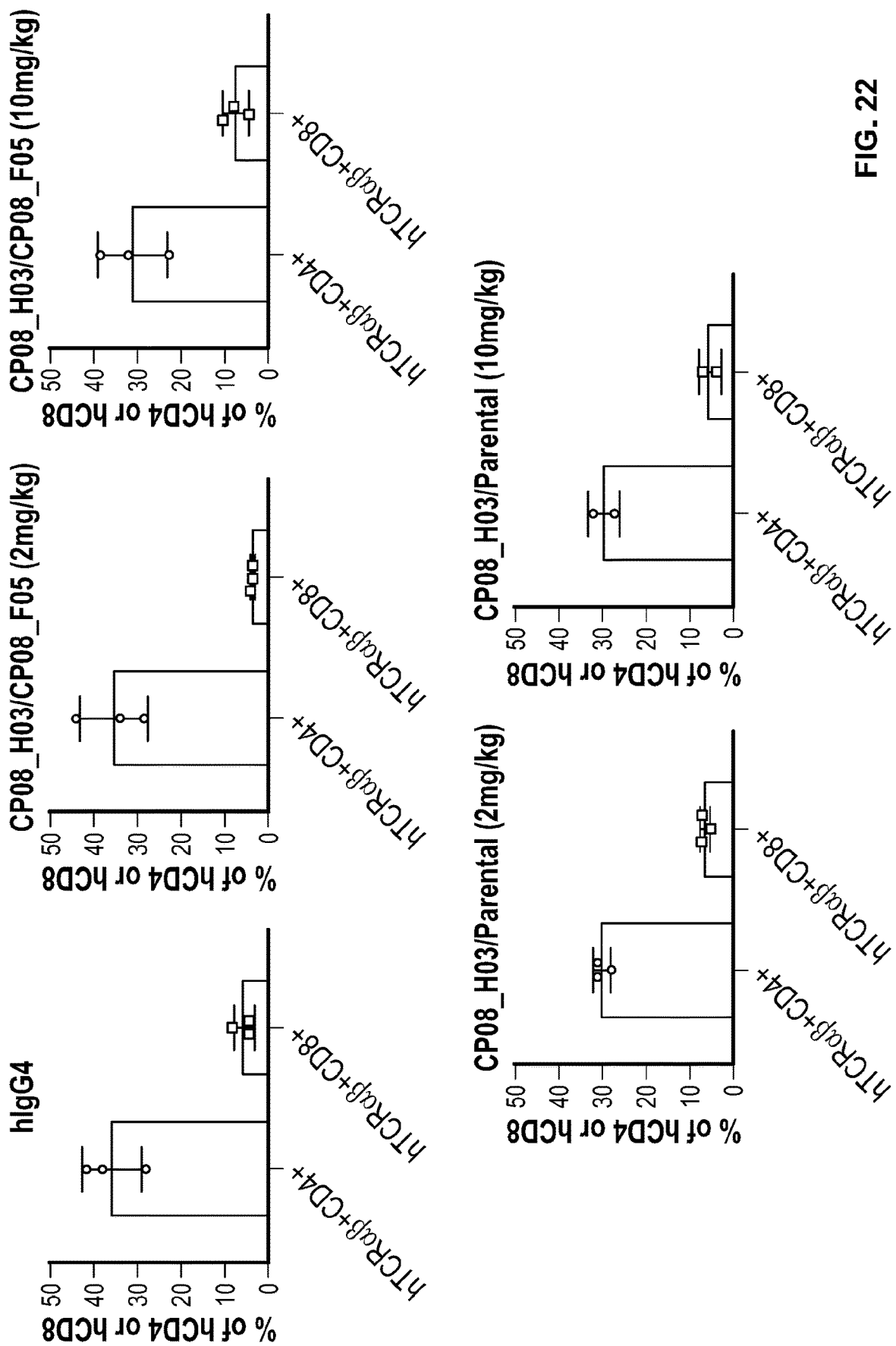

FIG. 22 shows that CEACAM1 antibodies CP08H03/$V_K$8 S29A (labeled "CP08_H03/Parental") and CP08H03/CP08F05 do not deplete the transplanted human cells in humanized NSG mice. Mean percentage of human CD4 and CD8 T lymphocytes was assessed at day 38. CP08H03/CP08F05 contains a S29A mutation in CDR1L (Kabat numbering scheme, corresponding to a S28A mutation in the primary amino acid sequence of the variable light chain).

Figure 23:
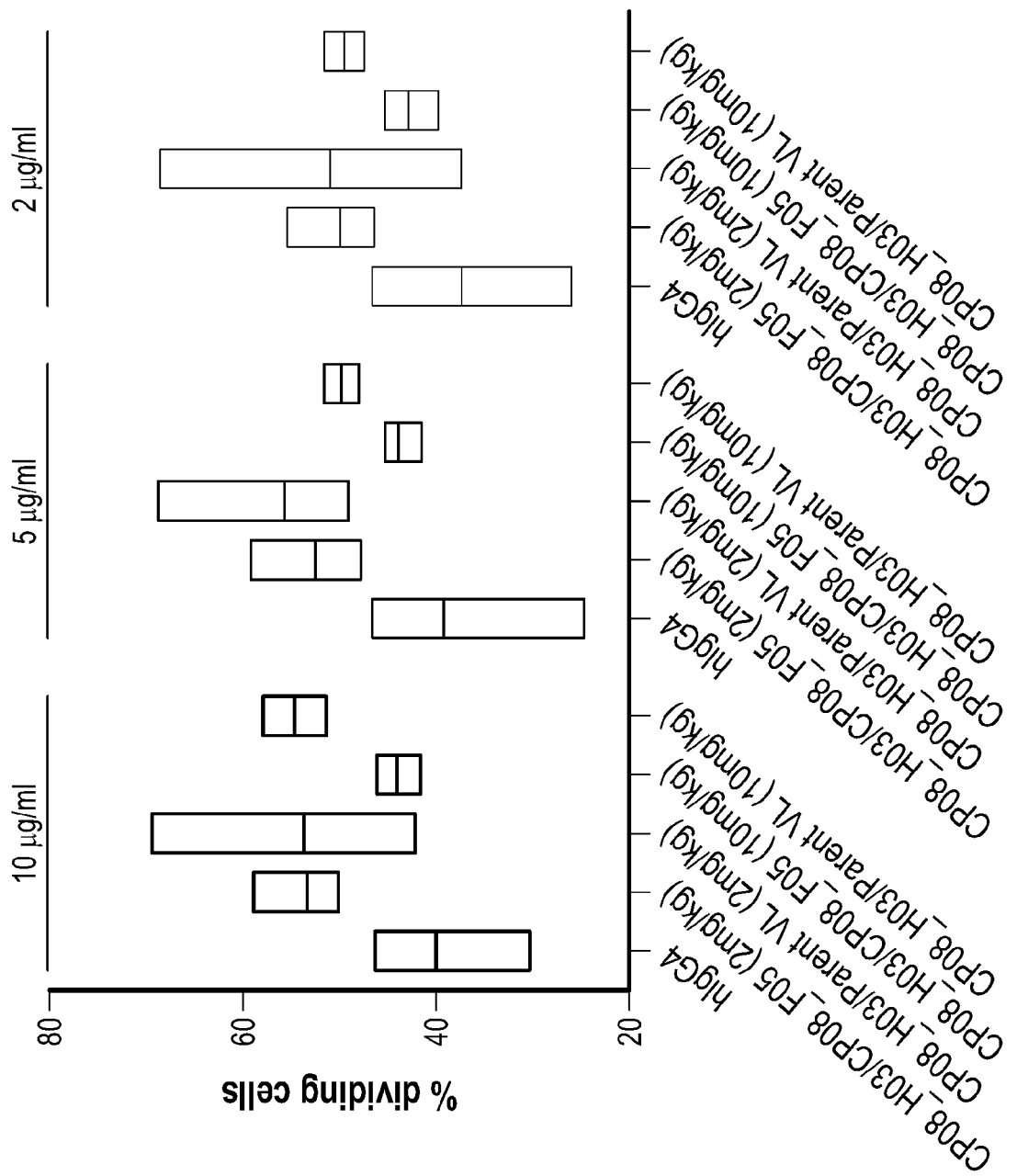

FIG. 23 illustrates that the administration of CEACAM1 antibody CP08H03/$V_K$8 S29A (labeled "CP08_H03/Parent VL") or CP08H03/CP08F05, respectively, leads to an increase in antibody induced human CD45 immune cell expansion in humanized NSG mice. CP08H03/$V_K$8 S29A induces expansion of human CD45 PBMC in vivo. On day 38, isotype hIgG4 control (10 mg/kg), CP08H03/$V_K$8 S29A (2 and 10 mg/kg) and CP08H03/CP08F05 (2 and 10 mg/kg) treated mice were sacrificed and solenocytes were isolated and collected for proliferation analyses. Proliferation ex vivo was carried out under T cell-stimulation condition, wherein cells were cultured under the soluble anti-CD3 (OKT3) (at indicated concentrations 10, 5, 2.5 μg/ml) and rIL-2 (40 units/ml) for 120 hours. The dilution of the proliferation dyes represents dividing cell/proliferation (when cells proliferate, duplex DNA was analyzed as diluted signal). CP08H03/CP08F05 contains a S29A mutation in CDR1L (Kabat numbering scheme, corresponding to a S28A mutation in the primary amino acid sequence of the variable light chain).

Figure 24A:
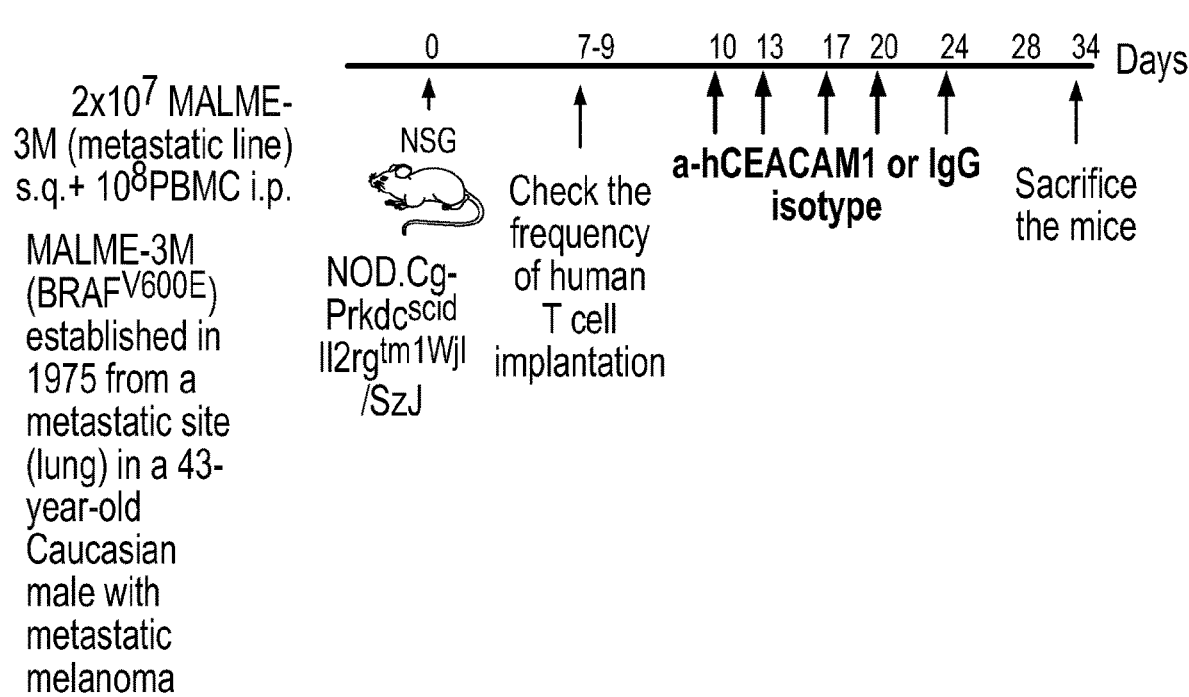
Figure 24B:
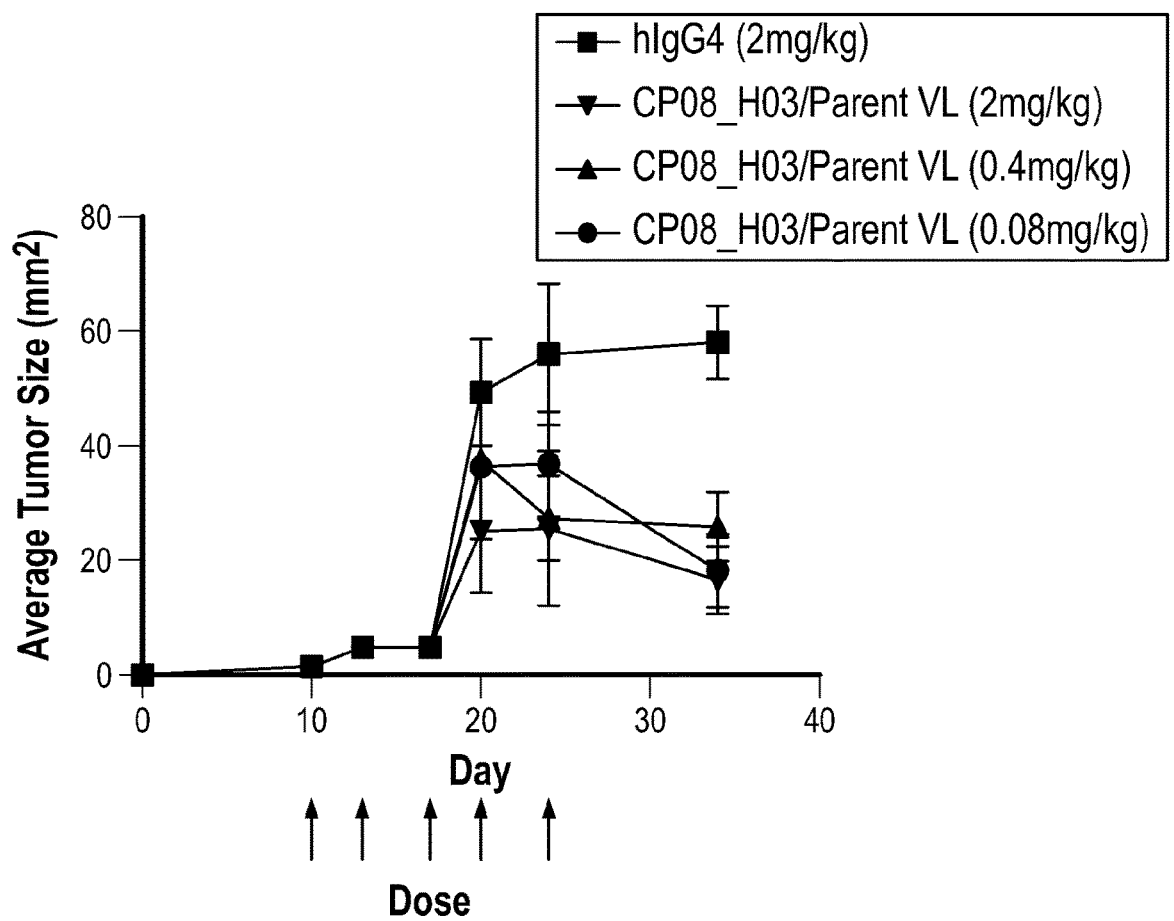
Figure 24C:
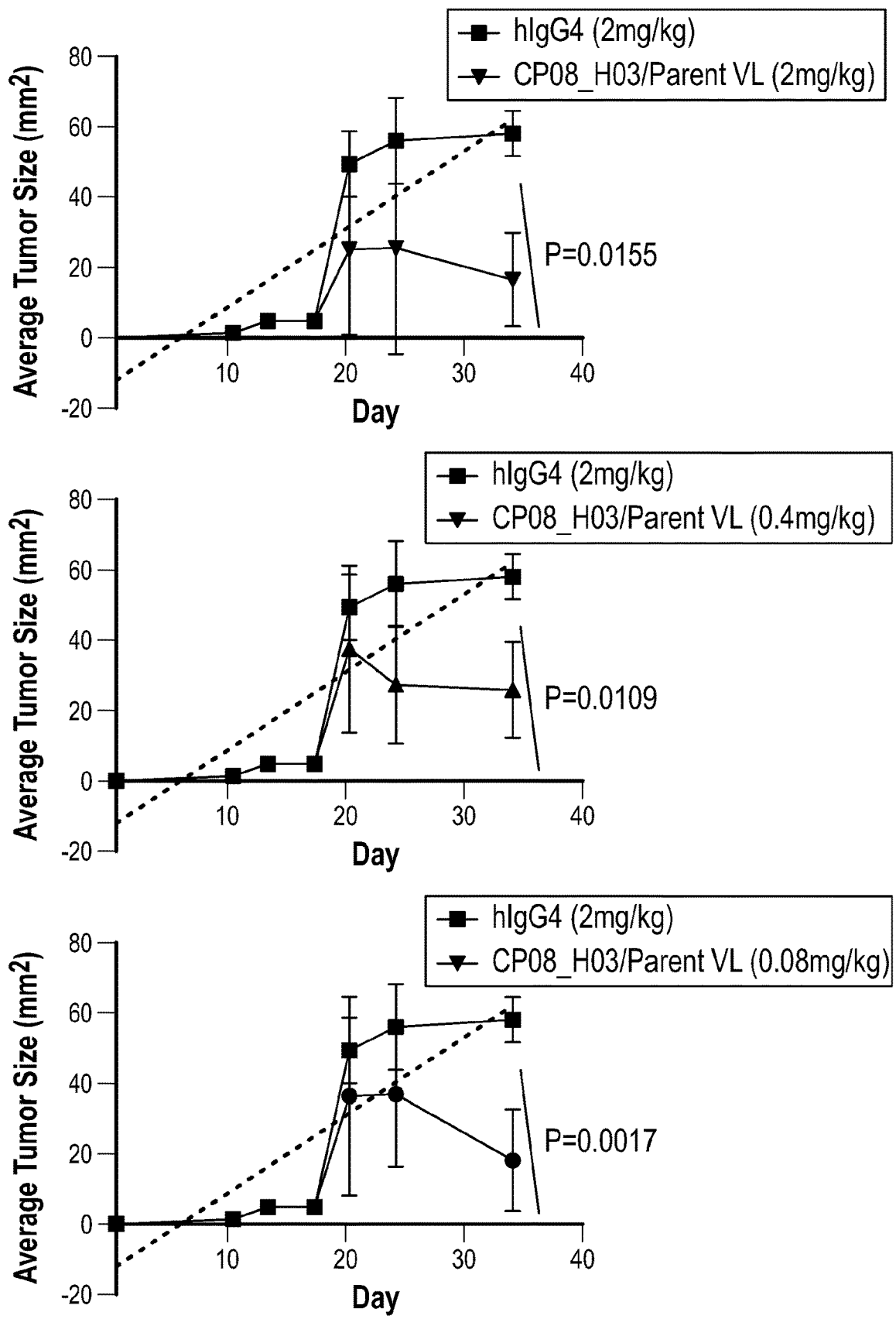

FIGS. 24A, 24B, and 24C illustrate that CEACAM1 antibody CP08H03/V$_\kappa$8 S29A (labeled "CP08_H03/Parent VL") reduces tumor growth in humanized mice. FIG. 24A provides a schematic for the experimental protocol resulting in FIG. 24B. FIG. 24B shows average tumor size after 1×10$^6$ MALME-3M (human melanoma) cells were injected subcutaneously into NSG, along with 5×10$^6$ human PBMC. After 10 days, palpable tumors were documented and the mice were randomized to treatment on days 10, 13, 17, 20 and 24 with the respective antibody concentrations intraperitoneally. FIG. 24C shows statistical comparisons by linear regression of the hIgG4 control treated group to the three different CP08H03/V$_\kappa$8 S29A groups (2 mg/kg, 0.4 mg/kg and 0.08 mg/kg).

Figure 25:
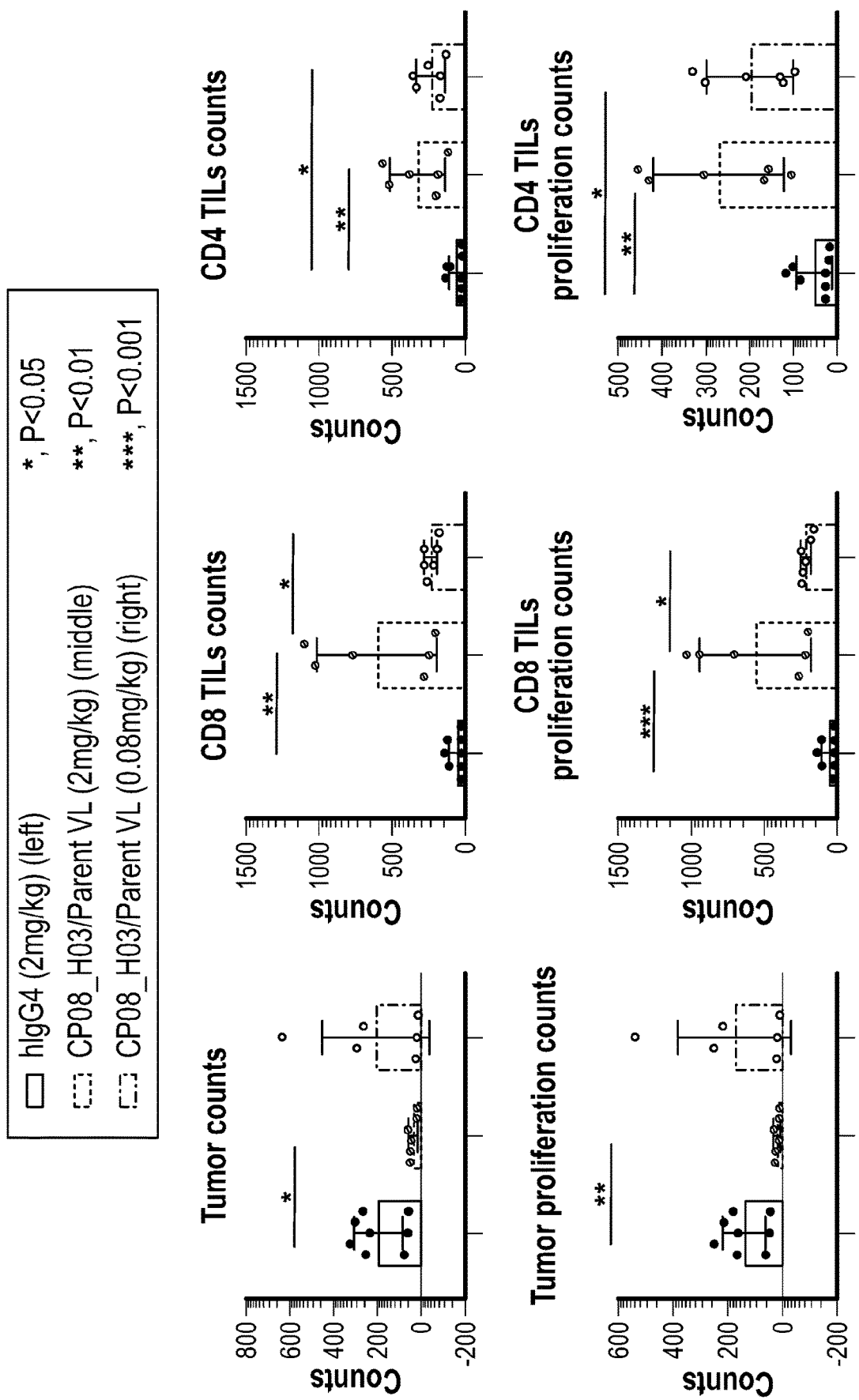

FIG. 25 illustrates that T cells from humanized mice engrafted with human melanoma cell line MALME-3M and treated with CEACAM1 antibody CP08H03/V$_\kappa$8 S29A (labeled "CP08_H03/Parent VL") as described in FIG. 24 exhibit decreased quantities of tumor cells with decreased proliferation and increased quantities of intratumoral CD8 and CD4 positive T cells. These T cells exhibit increased proliferation when examined ex vivo after stimulation with anti-CD3. On the day of sacrifice, isotype hIgG4 control (2 mg/kg), CP08H03/V$_\kappa$8 S29A (labeled "CP08_H03/Parent VL", 0.08 and 2 mg/kg) treated humanized NSG mice bearing melanoma tumors were sacrificed. Tumor cells as well as CD4 and CD8 tumor infiltrating lymphocytes were isolated and collected for proliferation analyses. Tumor cells were identified by being FSC$^{Hi}$SSC$^{Hi}$ cells, which were human CD45-negative, and proliferation quantified by dilution of a commercial dye that assesses proliferation (Becton-Dickinson). Human CD45$^+$CD4$^+$ and CD45$^+$CD8$^+$ T cells were identified by flow cytometry. Measurements of T cell proliferation ex vivo were carried out under T-cell-stimulation conditions wherein cells were cultured under the soluble anti-CD3 (2 μg/ml) and rIL-2 (40 units/ml) for 6 days.

Figure 26:
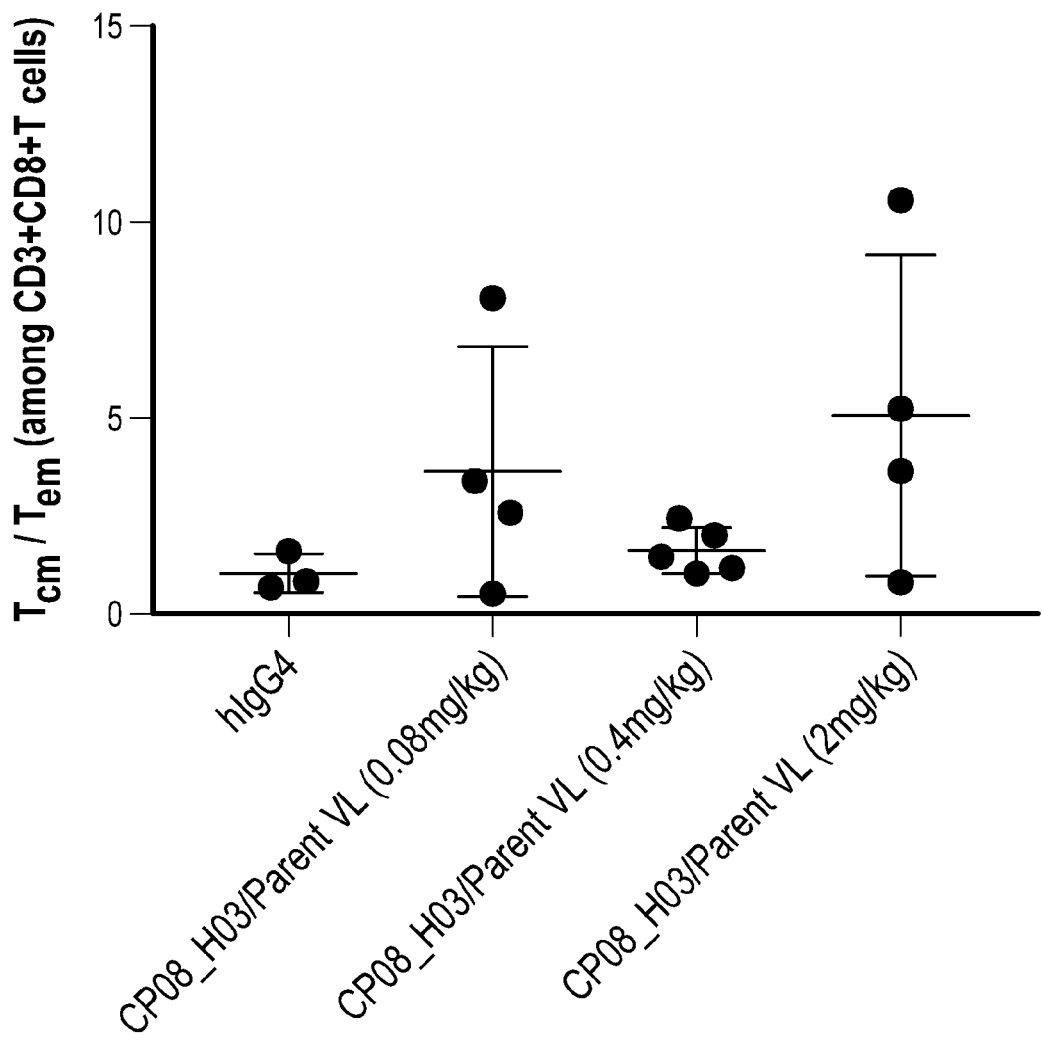

FIG. 26 illustrates phenotypic changes in intratumoral memory CD8 T cells upon blocking CEACAM1 with CEACAM1 antibody CP08H03/V$_\kappa$8 S29A (labeled "CP08_H03/Parent VL") as described in FIGS. 24-25. Flow cytometry analyses of tumor infiltrated CD3$^+$ CD8$^+$ T cells populations from humanized NSG mice bearing melanoma was conducted using CD62L and CD44 cell markers for the characterizations of the central memory (CD62L CD44) and effector memory (CD62L$^-$CD44$^+$ CD3$^+$ CD8$^+$) T cells populations. Treatment conditions were isotype hIgG4 control (2 mg/kg) and CP08H03/V$_\kappa$8 S29A (0.08, 0.4 and 2 mg/kg).

FIG. 27 shows that CEACAM1 is expressed on primary CD4$^+$ (top) and CD8$^+$ T (bottom) T cells in TILs from naïve (left) and PD-1 and/or CTLA-4 resistant (right) melanoma patients. A similar characterization of PD1 and TIM-3 expression is indicated as well.

Figure 28:
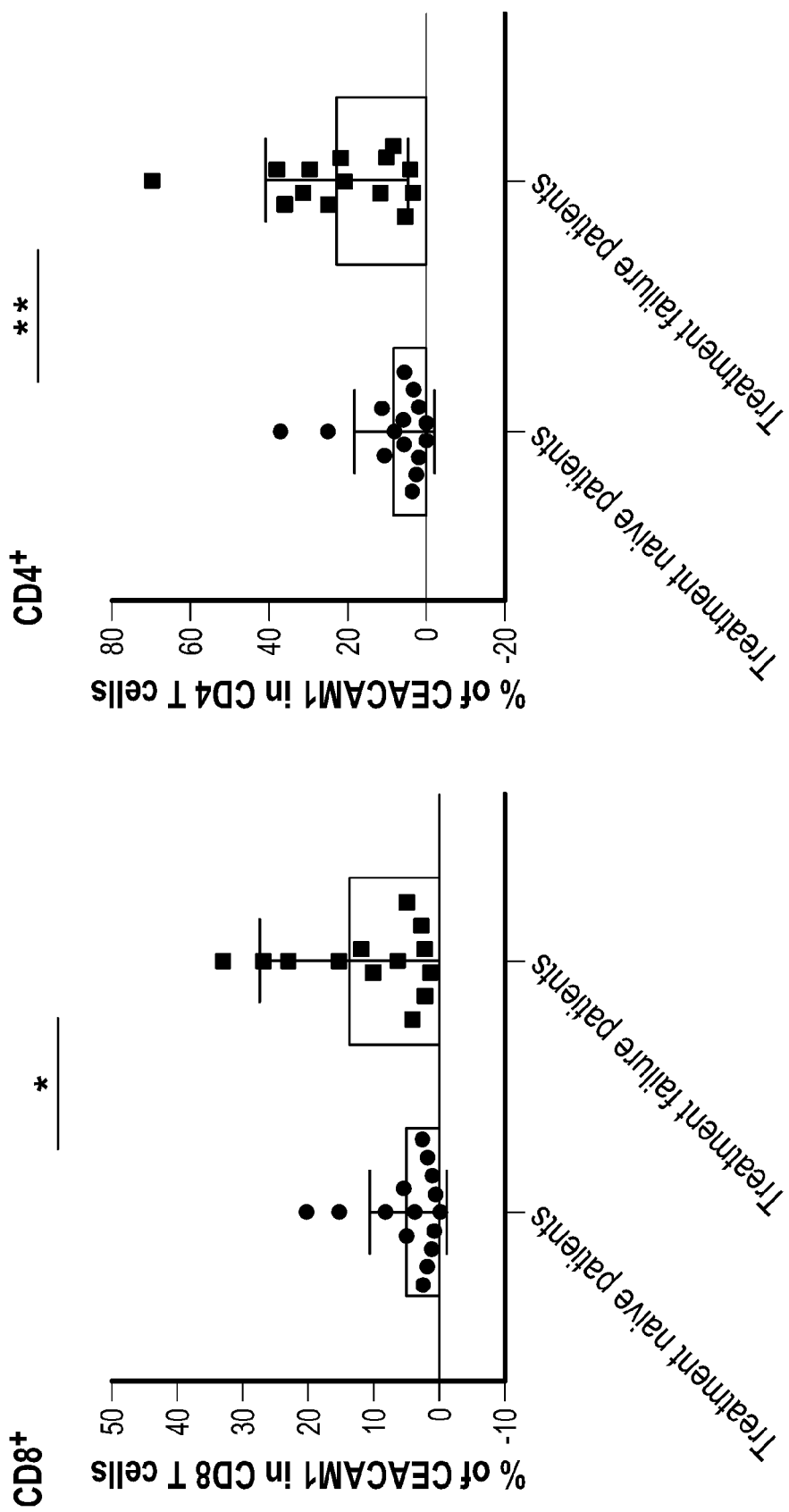

FIG. 28 shows that tumor associated cells (TACs) from patients that had acquired resistance to anti-PD-1 and/or anti-CTLA-4 therapy show significantly higher CEACAM1 expression as compared to TACs from patients that had no previous exposure to anti-PD-1 and/or anti-CTLA-4 therapy. TACs were obtained from melanoma patients who were naïve (no previous exposure to anti-PD-1 and/or anti-CTLA-4 therapy) or those that acquired resistance to anti-PD-1 and/or anti-CTLA-4 therapy (acquired resistance). TAC were obtained by culturing tumor tissue in DMEM medium and the floating cells removed from the supernatant and analyzed. The cells were stained for CD3, CD4 and CD8 and CEACAM1 expression on the CD3$^+$ CD4$^+$ cells and CD3$^+$ CD8$^+$ cells assessed. *, P=0.05; **, P<0.01.

Figure 29:
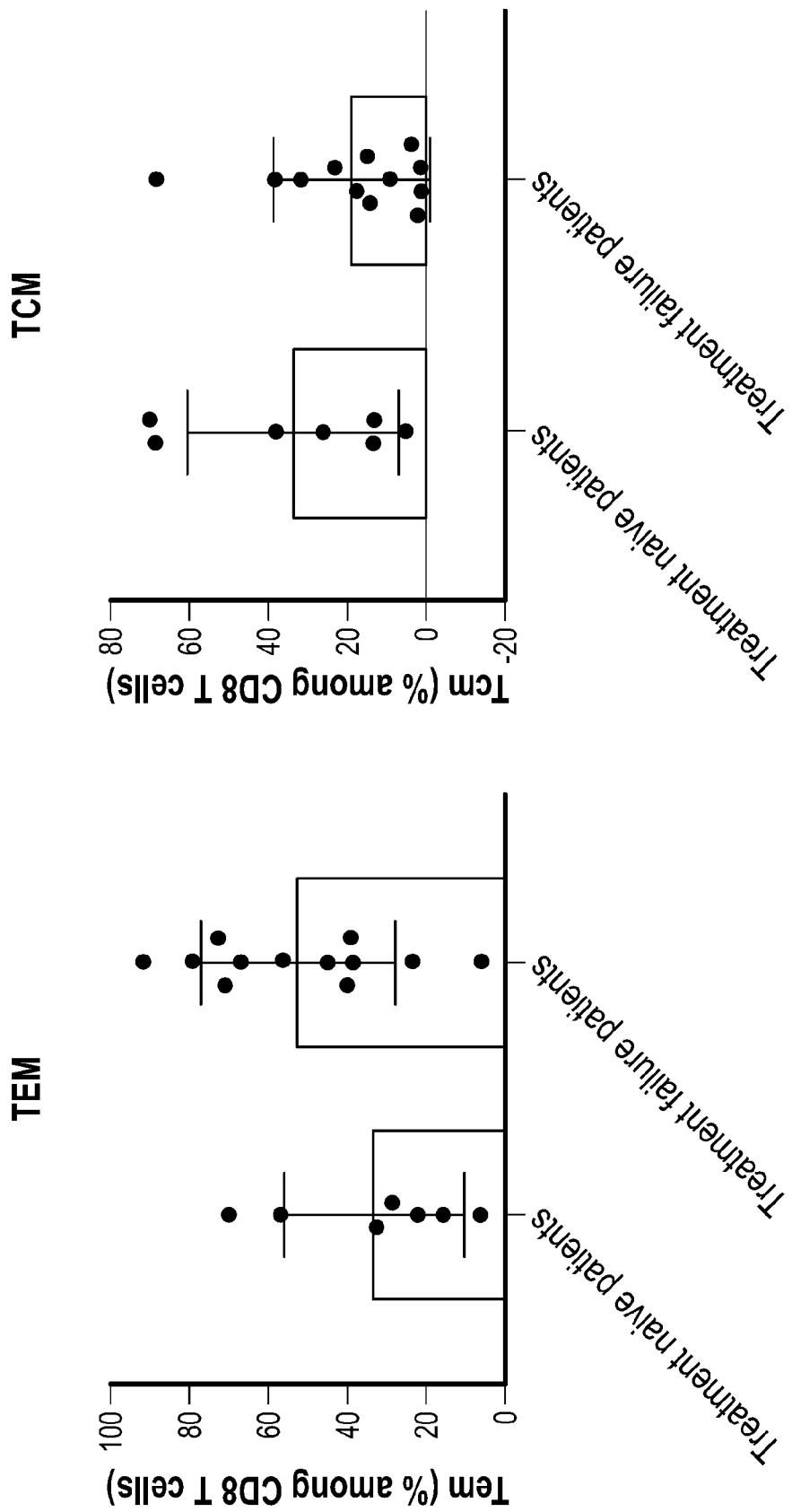

FIG. 29 illustrates a relative decrease in central memory ($T_{cm}$) relative to effector memory ($T_{em}$) cells among CD8$^+$ T cells isolated from patients resistant to anti-PD-1 and/or anti-CTLA-4 therapy as compared to CD8$^+$ T cells isolated from naïve patients. Tumor associated cells from naïve patients and those with acquired resistance were stained for central memory (CCR7$^+$ CD62L$^+$) and effector memory (CCR7$^-$ CD62L$^-$) markers in TACs derived from naïve and resistant patients.

Figure 30:
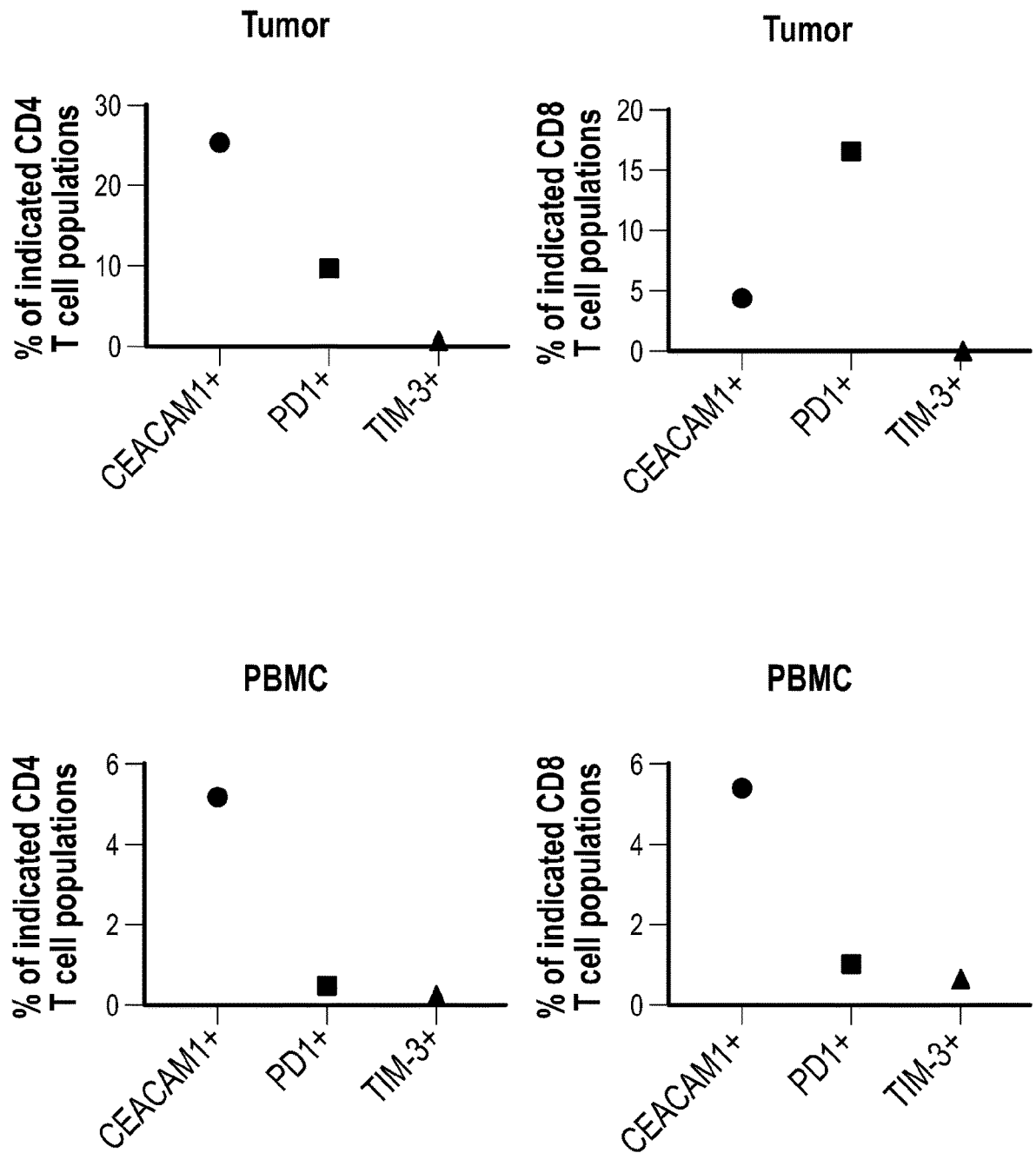
Figure 30:
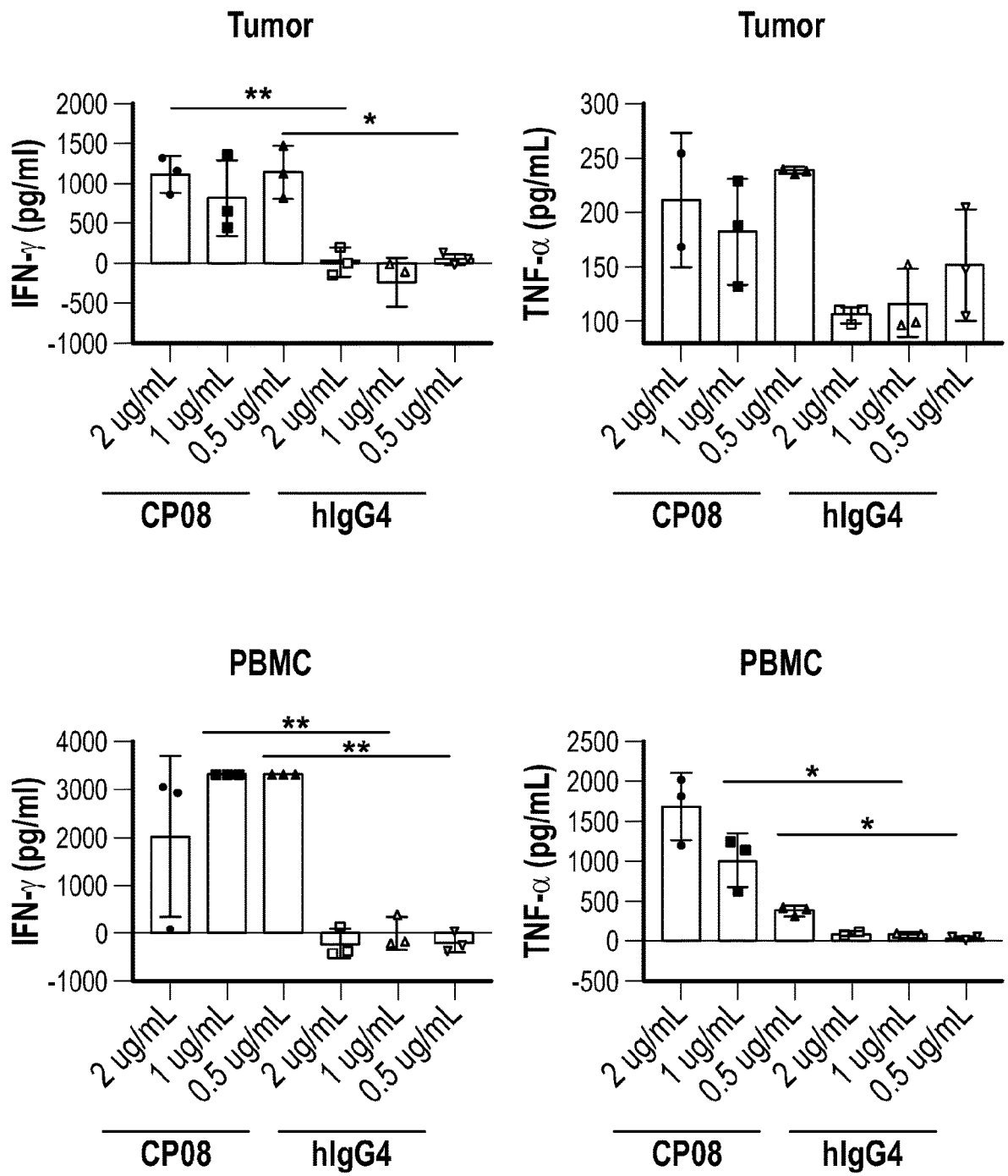

FIG. 30 illustrates that CEACAM1 antibody CP08H03/V$_\kappa$8 S29A (labeled "CP08") reverses T cell exhaustion in PD1/CTLA-4 resistant tumors. Tumor associated cells and PBMC were isolated from a melanoma patient with secondary resistance to Pembrolizumab, Ipilimumab+Nivolumab and Dabrafenib+Trametinib and Stage IV disease. Tumor associated cells and PBMC were stained for CEACAM1, PD1, or TIM-3 and the proportion of CD8$^+$ and CD4$^+$ T cells denoted that express these markers (left). PBMC or tumor-associated cells ("tumor") cultured with soluble anti-CD3 (2 μg/ml) and rIL-2 (40 units/ml) in the presence of CP08H03/V$_\kappa$8 S29A or hIgG4 control antibody are shown on the right. Release of IFNγ and TNFα, measures for the reversal of T cell tolerance, was determined by ELISA.

Figure 31A:
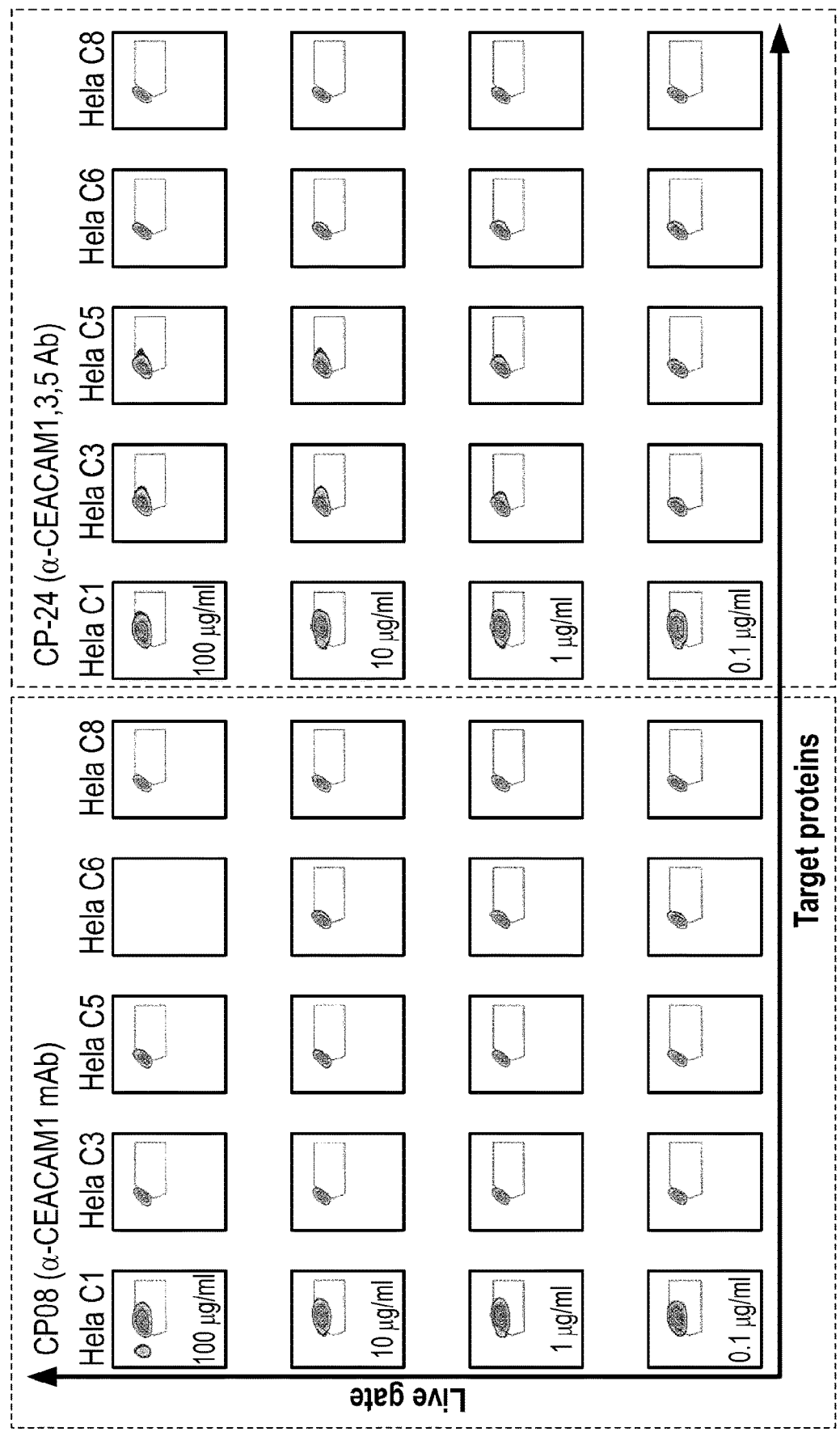
Figure 31B:
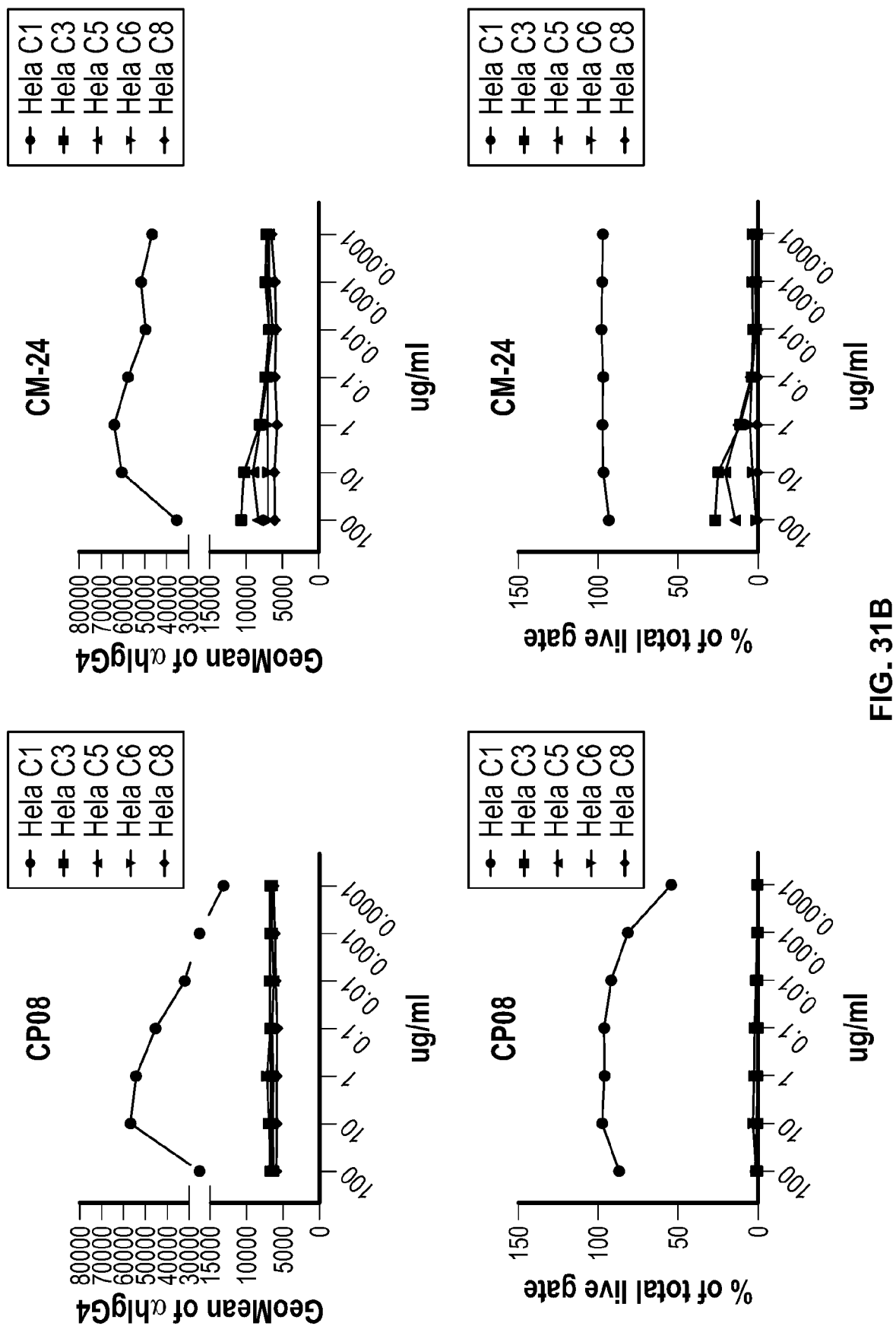

FIGS. 31A and 31B show flow cytometry analyses of stable HeLa CEACAM1 (HeLa C1) transfectant, stable HeLa CEACAM3 transfectant (HeLa C3), stable HeLa CEACAM5 transfectant (HeLa C5), stable HeLa CEACAM6 transfectant (HeLa C6), and stable HeLa CEACAM8 transfectant (HeLa C8). FIG. 31A: 5×10$^{\wedge}$4 indicated HeLa transfectants were washed with staining buffer and CP08H03/V$_\kappa$8 S29A (labeled "CP08", left) or CEACAM1 antibody CM-24 was incubated at room temperature for 30 min, washed twice with staining buffer, and stained for anti-human IgG4 Fluorescein isothiocyanate (FITC) conjugated secondary antibody at room temperature for 20 min. Fluorescence intensities were determined by flow cytometry. Live cells were determined by 4',6-diamidino-2-phenylindole (DAPI) staining as shown on the y-axis. Staining with the respective CEACAM1 antibody is shown on the x-axis. For CP08H03/V$_\kappa$8 S29A, note a positive signal in the gates is shown in only the HeLa CEACAM1 (C1) transfectants (left). In contrast, CM-24 (right panel) is not selective and cross-reacts with CEACAM1, CEACAM3, and CEACAM5. FIG. 31B shows a different representation of the data shown in FIG. 31A.

FIGS. 32A, 32B, and 32C illustrate that CEACAM1 antibody CP08H03/V$_\kappa$8 S29A (labeled "CP08") is more effective than CEACAM1 antibody CM-24 in reversing T cell tolerance in tumor associated cells. Tumor associated cells derived from a naïve Merkel cell carcinoma tumor were stained for CEACAM1, PD1 or TIM-3 and proportion of CD8 and CD4 T cell denoted (FIGS. 32A and 32B). Tumor associated cells were cultured with soluble anti-CD3 (2 μg/ml) and rIL-2 (40 units/ml) in presence of CP08H03/V$_\kappa$8 S29A, CM-24 or hIgG4 control, respectively. IFN-γ release, a measure for reversal of T cell tolerance, was determined (FIG. 32C). *, P=0.0138 comparing CP08 to hIgG4.

Figure 33C:
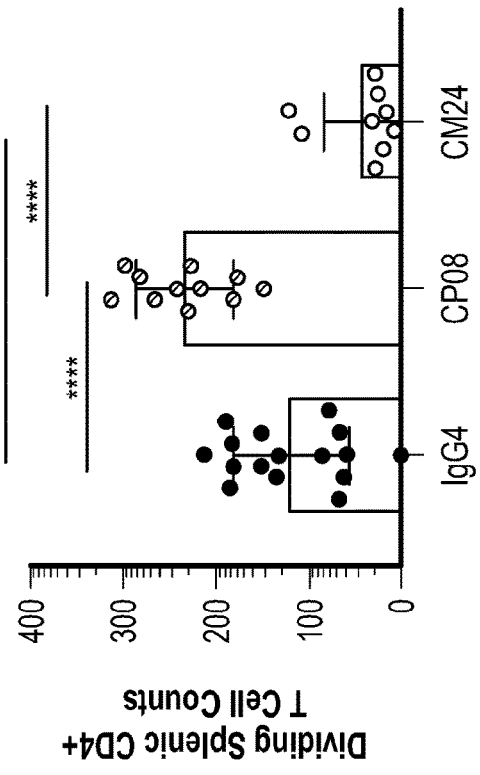
Figure 33A:
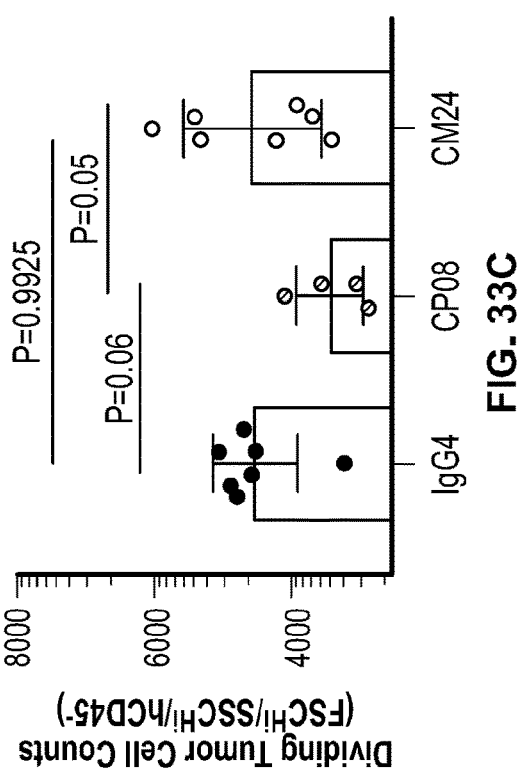
Figure 33D:
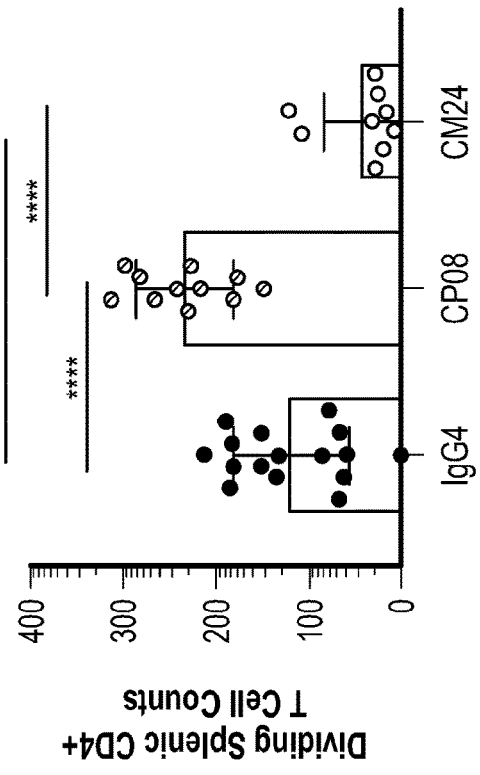
Figure 33B:
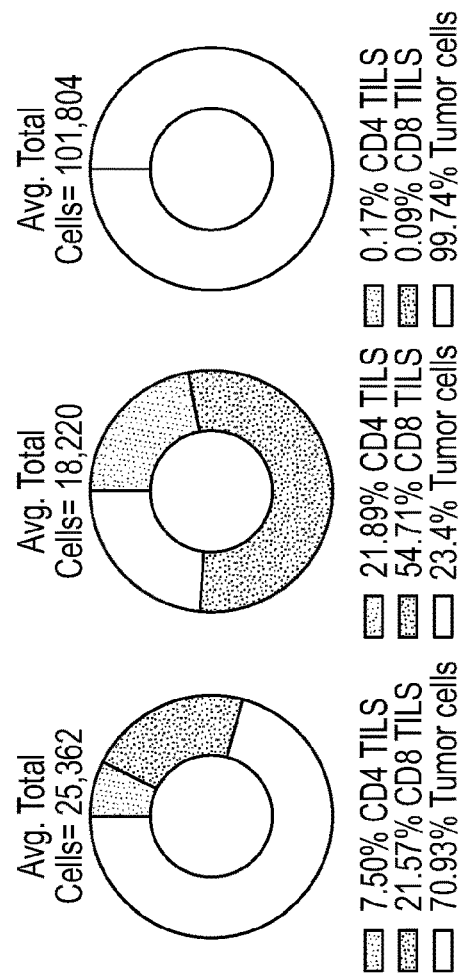

FIGS. 33A, 33B, 33C, and 33D illustrate that CM-24 treated metastatic melanoma in NSG mice exhibits deceased TILs and increased tumor cells in comparison to CP08H03/V$_\kappa$8 S29A (labeled "CP08") treated metastatic melanoma. FIG. 33A shows the experimental setup using a therapeutic tumor model in humanized NSG mice with human melanoma xenografts using four doses at 2 mg/kg of the respective antibodies including a hIgG4 control containing the identical stabilizing hinge mutation. FIG. 33B shows a pie chart display of the percentages of tumor infiltrating $CD4^+$ T lymphocytes (gray), $CD8^+$ T lymphocytes (black) and tumor cells (white) characterized by FSC/SCC High (FSC/$SCC^{Hi}$) and lack of the pan-leukocyte marker human CD45 (left: control antibody. middle: CEACAM1 antibody CP08H03/$V_κ$8 S29A. right: CEACAM1 antibody CM-24). FIG. 33C shows tumor cell proliferation for the IgG4 control, CP08H03/$V_κ$8 S29A, and CM-24, indicating inhibition of tumor proliferation by CP08H03/$V_κ$8 S29A but not by CM-24. FIG. 33D illustrates the increased proliferation of splenic $CD4^+$ T cells in CP08H03/$V_κ$8 S29A treated mice and decreased proliferation of splenic $CD4^+$ T cells in CM-24 treated mice.

Figure 34A:
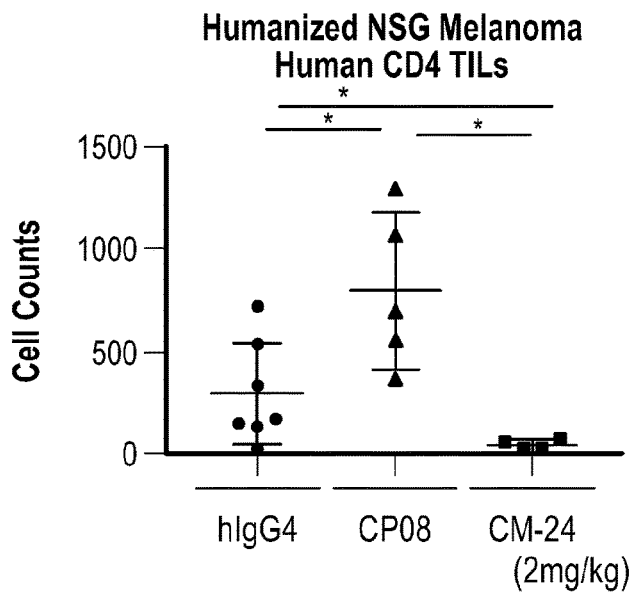
Figure 34B:
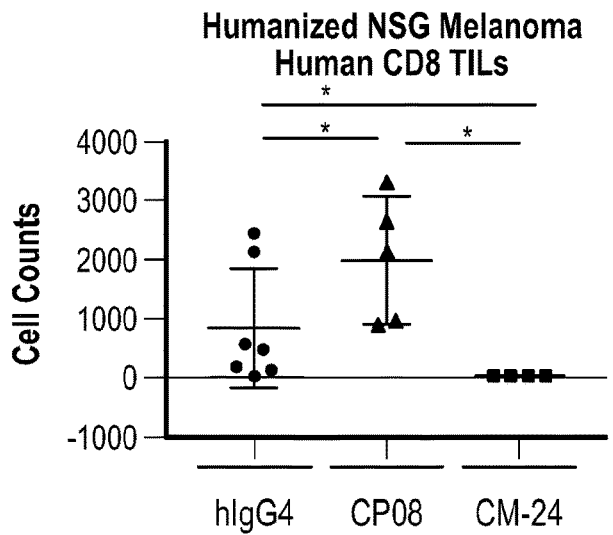
Figure 34C:
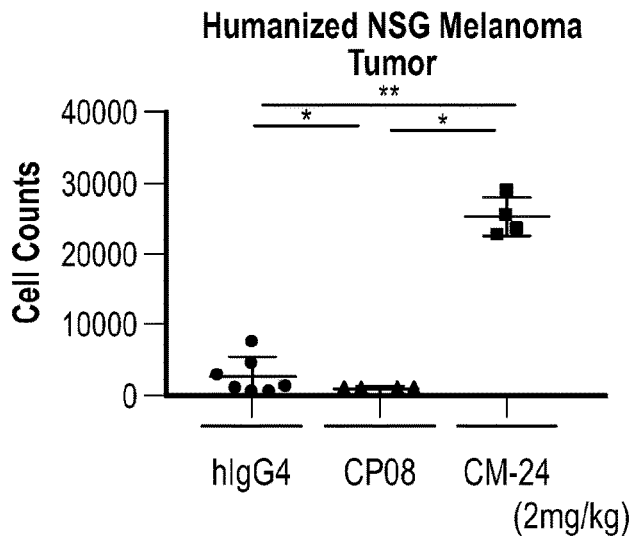

FIGS. 34A, 34B, and 34C show that CEACAM1 antibody CM-24 is an agonistic drug in a metastatic melanoma model. Shown are the absolute cell counts of tumor infiltrating CD4 T lymphocytes (FIG. 34A), $CD8^+$ T lymphocytes (FIG. 34B) and tumor cells characterized by forward/side scatter high (FSC/SCC Hi) (FIG. 34C) from metastatic melanomas. The values obtained for each group (n=9 for IgG4; n=8 for CP08; n=6 for CM-24) are shown. *P<0.05; **P<0.001. Statistical analysis refers to the data contained in FIG. 33B. Note the increased number of TILs (FIG. 34A and FIG. 34B) and decreased number of tumor cells (FIG. 34C) in the CP08H03/Vk8 S29A (labeled "CP08") treated mice vs. in the CM-24 treated mice. This data indicates that CP08H03/Vk8 S29A is an antagonistic and that CM-24 is an agonistic antibody.

Figure 35A:
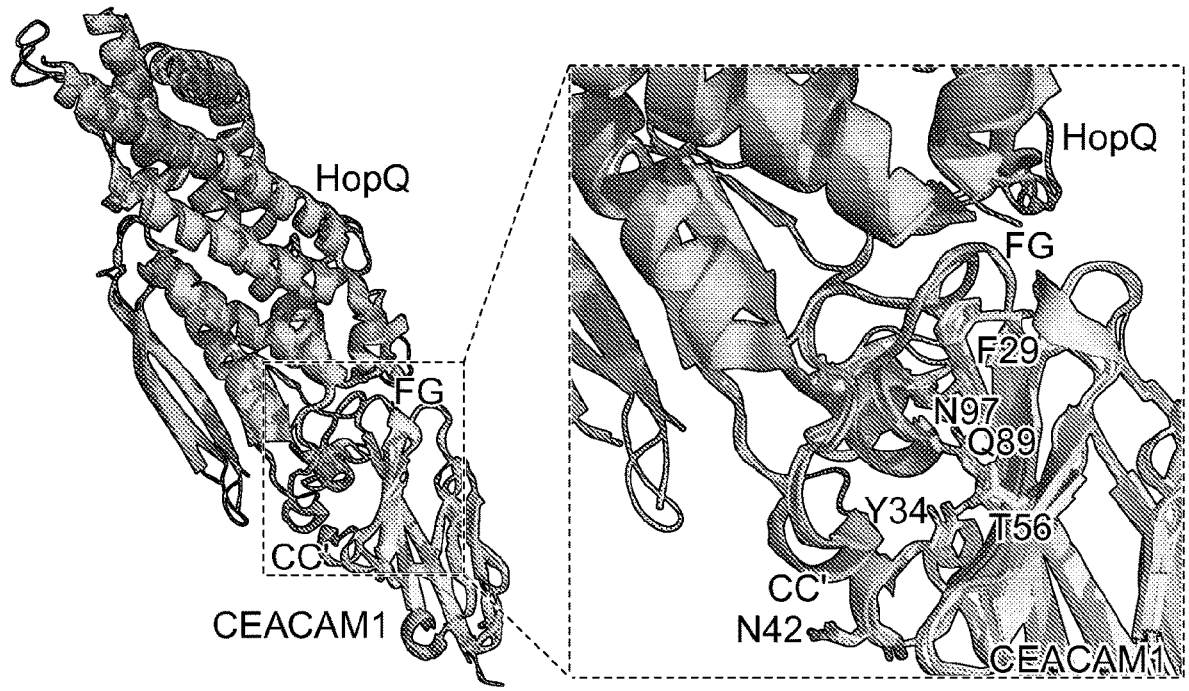
Figure 35B:
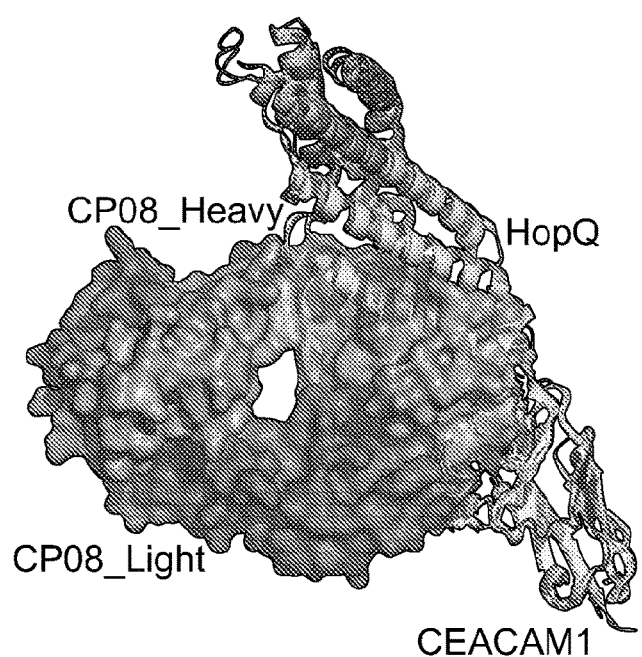

FIGS. 35A and 35B illustrate that CEACAM1 antibody CP08H03/$V_κ$8 S29A covers the CEACAM1:HopQ binding interface and is expected to block CEACAM1:HopQ or CEACAM1:Opa proteins interactions. FIG. 35A shows CEACAM1:HopQ binding interface based on the analysis of three crystal structures (PDB ID 6AW2, 6GBH and 6GBG). The CEACAM1 GFCC' face, which is formed by interactions of the CEACAM1 CC' and FG loops' (see Huang et al., Nature. 2015 Jan. 15; 517 (7534): 386-90) is involved in HopQ binding at CEACAM1 residues F29, Y34, N42, Q89, and N97 and makes various hydrogen bonded and hydrophobic interactions (Bonsor D, A. et. al. EMBO J. 2018 Jul. 2; 37 (13). pii: e98664; Moonens K et. al. EMBO J. 2018 Jul. 2; 37 (13). pii: e98665). FIG. 35B shows a superimposition of the CP08H03/$V_κ$8 S29A:CEACAM1 crystal structure and the CEACAM1:HopQ crystal structure. The CP08H03/$V_κ$8 S29A antibody light chain and heavy chain are shown in a surface representation. HopQ chains (three different crystal structures PDB ID 6AW2, 6GBH and 6GBG) and CEACAM1 from three different co-crystal structures with HopQ (PDB ID 6AW2, 6GBH, 6GBG), as well as CEACAM1 from co-crystal structure with CP08H03/$V_κ$8 S29A are shown in ribbon diagram to highlight superimposition of the CP08H03/$V_κ$8 S29A and HopQ binding epitopes.

Figure 36:
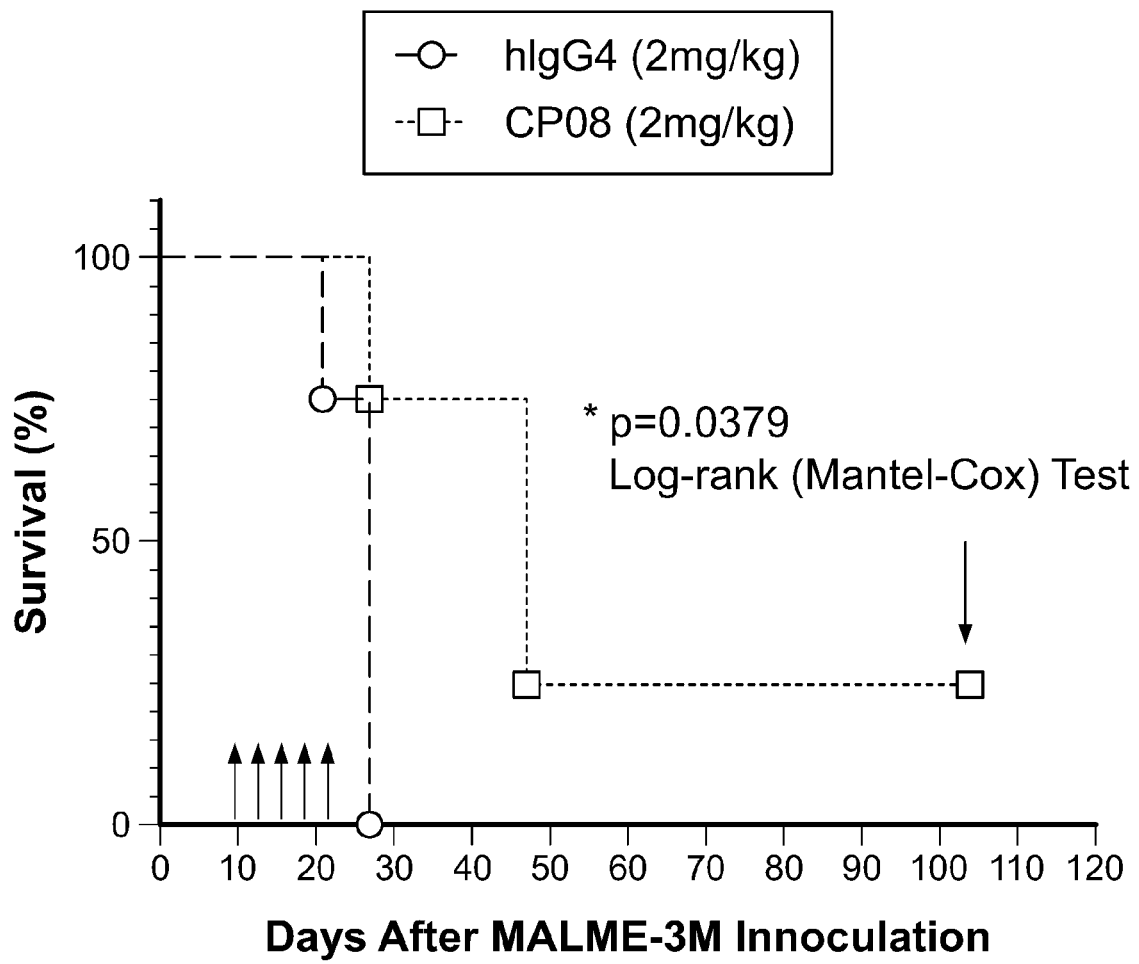

FIG. 36 illustrates that CEACAM1 antibody CP08H03/$V_κ$8 S29A increases survival in tumor-bearing mice. NSG mice were injected with MALME-3M (human melanoma) cells and human PBMCs. Treatment with CEACAM1 antibody CP08H03/$V_κ$8 S29A or the control human (h) IgG4 antibody, respectively, occurred on days 10, 13, 17, 20, and 24 (see arrows). Indicated is % survival. n=4/group.

Figure 37A:
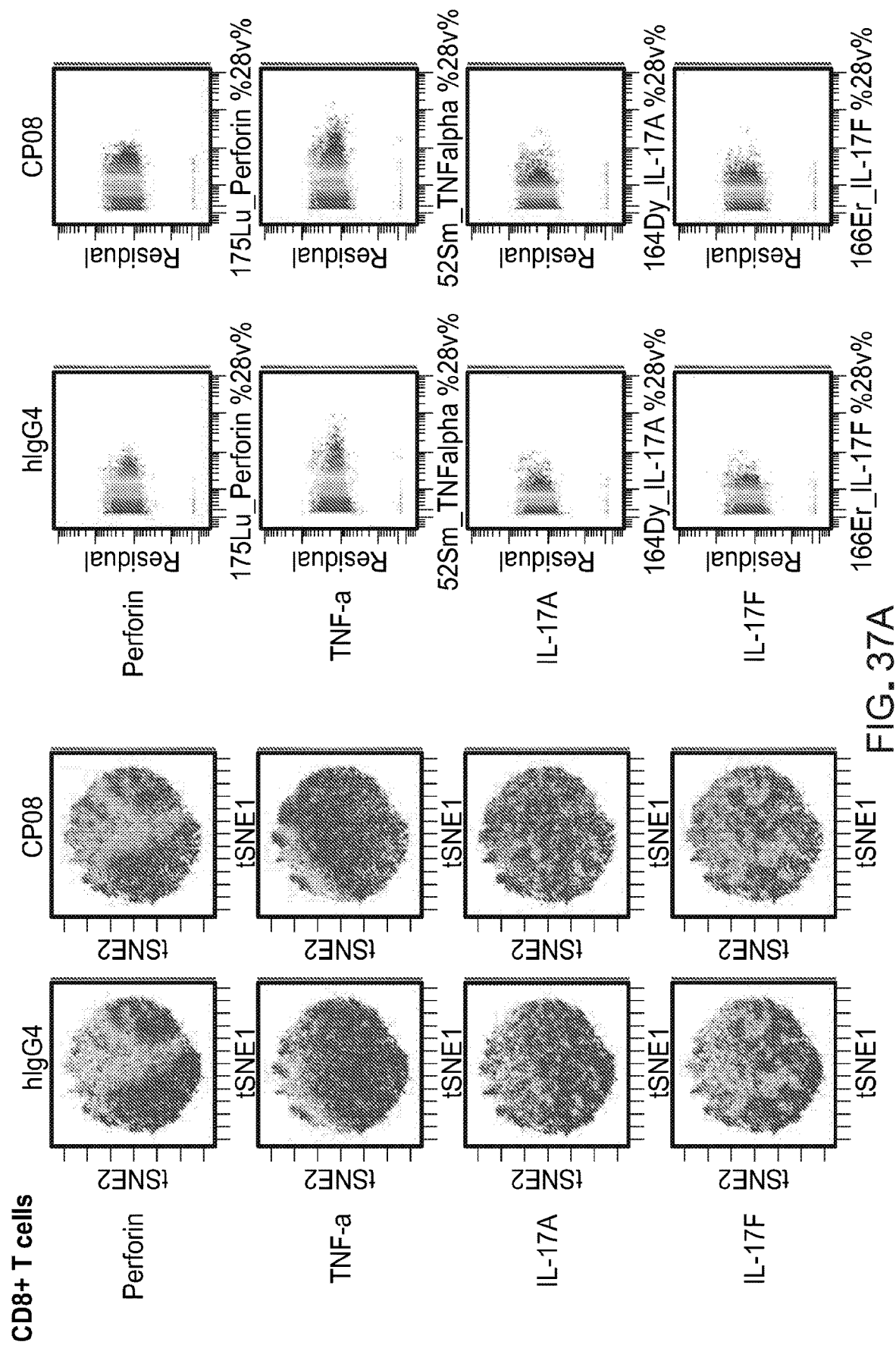
Figure 37A:
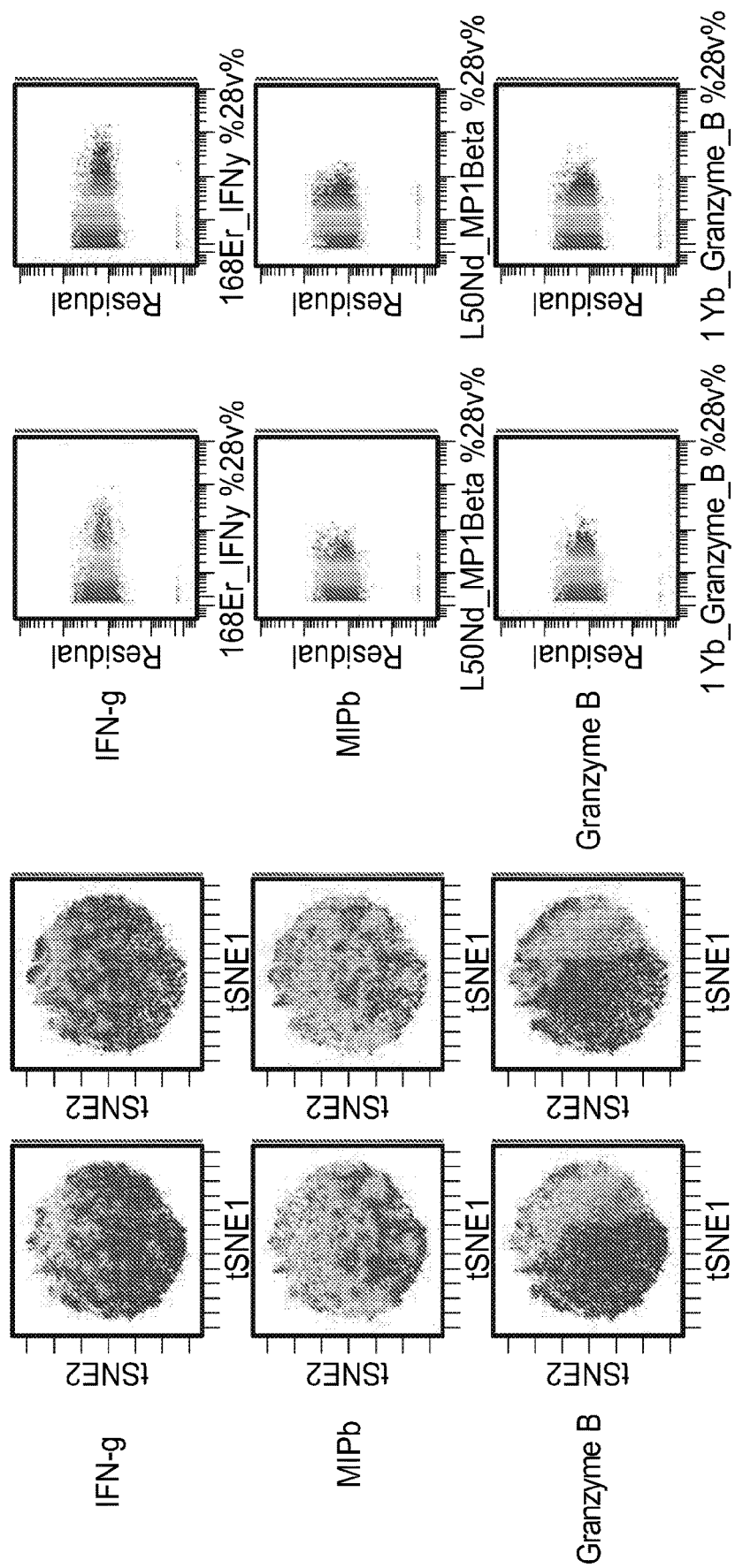
Figure 38A:
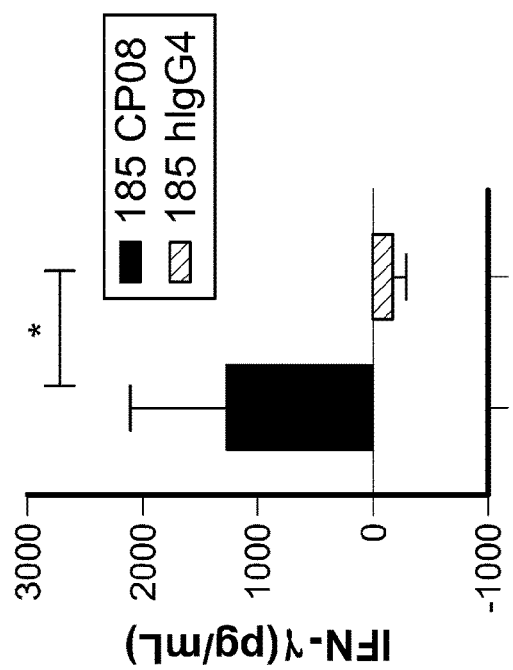
Figure 38B:
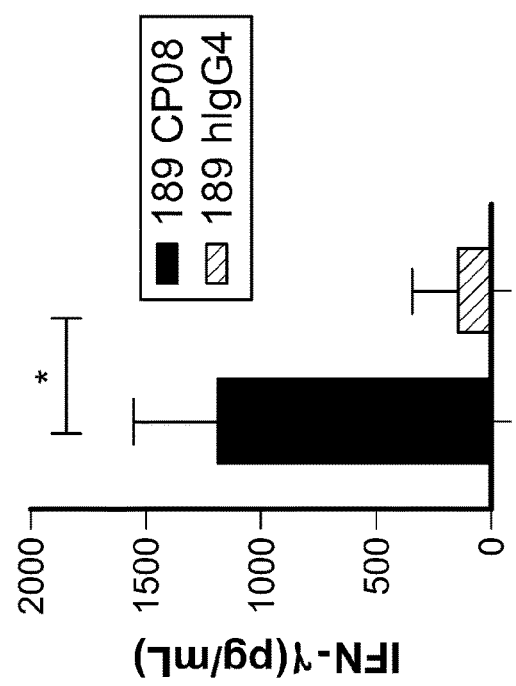
Figure 37B:
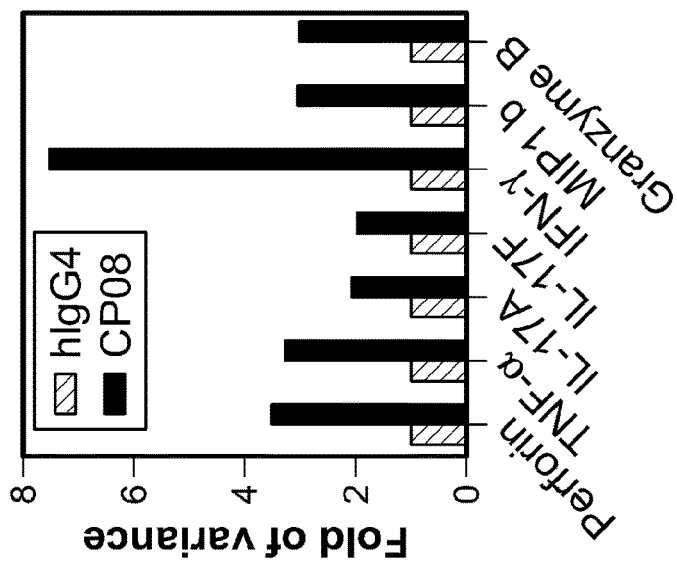

FIGS. 37A and 38B illustrate that CEACAM1 antibody CP08H03/$V_κ$8 S29A increases expression of a variety of factors involved in immune responses to cancers by $CD8^+$ T cells derived from a melanoma patient with secondary resistance to immunotherapy. FIG. 37A shows a series of viSNE (Visually-Distributed Stochastic Neighbor Embedding) maps rendered in Cytobank using the Barnes-Hut implementation of the t-SNE algorithm that describe the intracellular expression in $CD8^+$ T cells of the specific factors indicated as defined by mass cytometry on the left. The quantification of the heatmap levels for each indicated factor is shown on the right on the x-axis relative to the residuals associated with each factor as indicated on the y-axis. FIG. 37B shows the fold variance of the intracellular responses of the indicated factors described in FIG. 37A in response to CP08H03/$V_κ$8 S29A relative to the hIgG4 control antibody which is set as 1.0.

FIGS. 38A and 38B illustrate that CEACAM1 antibody CP08H03/$V_κ$8 S29A reinvigorates the ability of tumor dissociated cells from two melanoma patients with either no prior treatment (FIG. 38B, subject 189) or with secondary resistance to immunotherapy (FIG. 38A, subject 185) to secrete interferon-gamma (IFN-γ). In both cases tumor specimens were disrupted by mechanical dissociation (Miltenyi) and the tumor dissociated cells treated in vitro with only 2 μg/ml of the CP08H03/$V_κ$8 S29A or human IgG4 isotype control antibody. After 96 hours, significant levels of interferon-gamma were detected in the supernatants of the CP08H03/$V_κ$8 S29A but not the human IgG4 isotype control antibody treated samples. *P<0.05

DETAILED DESCRIPTION OF THE INVENTION

Antibodies

The term "antibody" is used in the broadest sense and includes monoclonal antibodies (including full length or intact monoclonal antibodies), polyclonal antibodies, multivalent antibodies, multispecific antibodies (e.g., bispecific antibodies), antibody fragments, and antigen-binding portions thereof (e.g., paratopes, CDRs), so long as they exhibit the desired biological activity and specificity.

As used herein, "antibody variable domain" refers to the portions of the light and heavy chains of antibody molecules that include amino acid sequences of Complementarity Determining Regions (CDRs; i.e., CDR1, CDR2, and CDR3), and Framework Regions (FRs). $V_H$ refers to the variable domain of the heavy chain. $V_L$ refers to the variable domain of the light chain. The amino acid positions assigned to CDRs and FRs may be defined according to Kabat or according to Chothia. The term "framework regions" (FR) refers to those variable domain residues other than the CDR residues.

As used herein, the term "Complementarity Determining Regions" (CDRs) refers to portions of an antibody variable domain that are (typically) involved in antigen binding. Each variable domain typically has three CDR regions identified as CDR1, CDR2 and CDR3. Each CDR can comprise amino acid residues from a CDR as defined by e.g. Kabat (i.e., about residues 24-34 (L1), 50-56 (L2) and 89-97 (L3) in the light chain variable domain and 31-35 (H1), 50-65 (H2) and 95-102 (H3) in the heavy chain variable domain (Kabat et al., Sequences of Proteins of Immunological Interest, 5th Ed. Public Health Service, National Institutes of Health, Bethesda, Md. (1987, 1991)). Each CDR can also comprise amino acid residues from a "hypervariable loop" (i.e., about residues 26-32 (L1), 50-52 (L2) and 91-96 (L3) in the light chain variable domain and 26-32 (H1), 53-55 (H2) and 96-101 (H3) in the heavy chain variable domain (Chothia & Lesk 196 J. Mol. Biol. 901 (1987)). In some instances, a CDR can include amino acids from both a CDR region defined according to Kabat and a hypervariable loop. The Kabat residue designations do not always correspond directly with the linear numbering of the amino acid residues (primary amino acid sequence). The actual linear amino acid sequence may contain fewer or additional amino acids than in the strict Kabat numbering corresponding to a shortening of, or insertion into, a structural component, whether framework or CDR, of the basic variable domain structure. The correct Kabat numbering of residues may be determined for a given antibody or antigen-binding fragment thereof by alignment of residues of homology in the sequence of the antibody or antigen-binding fragment thereof with a "standard" Kabat numbered sequence. An example of how the Kabat numbering relates to the primary amino acid sequence of an antibody can be seen in FIGS. 3A, 3B, and 3C. Alternatively, a CDR can be defined according to the ImMunoGeneTics (IMGT) system (Lefranc, M.-P. et al., Dev. Comp. Immunol., 27, 55-77 (2003))

In one embodiment, the CEACAM1 antibody or antigen-binding fragment thereof provided herein comprises six CDRs, wherein:
(i) the sequence of CDR1 of the heavy chain variable region comprises SEQ ID NO:9;
(ii) the sequence of CDR2 of the heavy chain variable region comprises SEQ ID NO:2;
(iii) the sequence of CDR3 of the heavy chain variable region comprises SEQ ID NO:10;
(iv) the sequence of CDR1 of the light chain variable region comprises SEQ ID NO:4;
(v) the sequence of CDR2 of the light chain variable region comprises SEQ ID NO:5; and
(vi) the sequence of CDR3 of the light chain variable region comprises SEQ ID NO:11.

In another embodiment, the CEACAM1 antibody or antigen-binding fragment thereof provided herein comprises six CDRs, wherein:
(i) the sequence of CDR1 of the heavy chain variable region comprises SEQ ID NO:9;
(ii) the sequence of CDR2 of the heavy chain variable region comprises SEQ ID NO:2;
(iii) the sequence of CDR3 of the heavy chain variable region comprises SEQ ID NO:10;
(iv) the sequence of CDR1 of the light chain variable region comprises SEQ ID NO:4;
(v) the sequence of CDR2 of the light chain variable region comprises SEQ ID NO:5; and
(vi) the sequence of CDR3 of the light chain variable region comprises SEQ ID NO: 12.

In one embodiment, the CEACAM1 antibody or antigen-binding fragment thereof comprises six CDRs, wherein:
(i) the sequence of CDR1 of the heavy chain variable region comprises SEQ ID NO:9
(ii) the sequence of CDR2 of the heavy chain variable region comprises SEQ ID NO:2;
(iii) the sequence of CDR3 of the heavy chain variable region comprises SEQ ID NO:10;
(iv) the sequence of CDR1 of the light chain variable region comprises SEQ ID NO:18;
(v) the sequence of CDR2 of the light chain variable region comprises SEQ ID NO:5; and
(vi) the sequence of CDR3 of the light chain variable region comprises SEQ ID NO:11.

As shown in the Examples below, affinity maturation of CDR1H, CDR3H and CDR3L of a humanized, aglycosylated CEACAM1 antibody led to variants that conferred substantial improvements in CEACAM1 binding affinity. Inspection of the variants that were obtained and comparison of these variants with the variability introduced into the affinity maturation libraries indicates certain CDR positions at which amino acids remained relatively unchanged and other CDR positions at which variation could be introduced, resulting in improved binding.

In one aspect, the invention provides CEACAM1 antibodies or antigen-binding fragments thereof that comprise a CDR1H, wherein the CDR1H comprises residues 31-35 of the CEACAM1 antibody (Kabat definition, corresponds, e.g., to residues 31 to 35 in the primary amino acid sequence of the heavy variable chain of SEQ ID NO:19, see FIG. 3A, or SEQ ID NO: 13, see FIG. 3B), and comprises the sequence $X_1HX_2X_3S$ (SEQ ID NO:1),
wherein $X_1$ of CDR1H is A, D, N, or S;
wherein $X_2$ of CDR1H is A or G; and
wherein $X_3$ of CDR1H is an amino acid with a hydrophobic side chain including I or M.

Alternatively, CDR1H can be defined using the IMGT definition, wherein CDR1H comprises residues 26-33 of the CEACAM1 antibody (corresponds, e.g., to residues 26 to 33 in the primary amino acid sequence of the heavy variable chain of SEQ ID NO: 19, see FIG. 3A, or SEQ ID NO: 13, see FIG. 3B,) and comprises the sequence $X_{14}X_{15}X_{16}FX_{17}X_1HX_2$ (SEQ ID NO: 20),
wherein $X_{14}$ of CDR1H is G or E;
wherein $X_{15}$ of CDR1H is an amino acid with an aromatic side chain including F or Y;
wherein $X_{16}$ of CDR1H is T, S, or I;
wherein $X_{17}$ of CDR1H is an amino acid with a polar uncharged side chain including S, T, or N;
wherein $X_1$ of CDR1H is A, D, N, or S; and
wherein $X_2$ of CDR1H is A or G.

In one embodiment, CDR1H (Kabat definition) of the CEACAM1 antibody or antigen-binding fragment thereof comprises sequence SHGMS (SEQ ID NO: 9).

In some embodiments, CDR1H (IMGT definition) comprises sequence GFIFSHG (SEQ ID NO: 21).

In one aspect, the invention provides CEACAM1 antibodies or antigen-binding fragments thereof that comprise a CDR1H region, wherein the CDR1H comprises residues 26-35 of the CEACAM1 antibody (Kabat definition, corresponds, e.g., to residues 26 to 35 in the primary amino acid sequence of the heavy variable chain of SEQ ID NO: 19, see FIG. 3A, or SEQ ID NO:13, see FIG. 3B) and comprises the sequence $X_{14}X_{15}X_{16}FX_{17}X_1HX_2X_3S$ (SEQ ID NO:22),
wherein $X_{14}$ is G or E;
wherein $X_{15}$ is an amino acid with an aromatic side chain including F or Y;
wherein $X_{16}$ is T, S, or I;
wherein $X_{17}$ is an amino acid with a polar uncharged side chain including S, T, or N; wherein $X_1$ is A, D, N, or S;
wherein $X_2$ is A or G; and wherein $X_3$ is an amino acid with a hydrophobic side chain including I or M.

In one embodiment, the CDR1H region comprises sequence GFIFSSHGMS (SEQ ID NO: 23).

In one aspect, the invention provides CEACAM1 antibodies or antigen-binding fragments thereof that comprise a CDR3H, wherein the CDR3H comprises residues 95-102 (Kabat definition, corresponds, e.g., to residues 99 to 110 in the primary amino acid sequence of the heavy variable chain of SEQ ID NO: 19, see FIG. 3A, or SEQ ID NO: 13, see FIG. 3B) and which comprises the sequence $HX_4X_5DYX_6PX_7WFAX_8$ (SEQ ID NO:3),
wherein $X_4$ of CDR3H is D, G, or P;
wherein $X_5$ of CDR3H is F or P;

wherein $X_6$ of CDR3H is D or F;
wherein $X_7$ of CDR3H is A or Y; and
wherein $X_8$ of CDR3H is L, H, or F.

In one embodiment, CDR3H comprises residues 95-102 (Kabat definition, corresponds, e.g., to residues 99 to 110 in the primary amino acid sequence of the heavy variable chain of SEQ ID NO: 19, see FIG. 3A, or SEQ ID NO: 13, see FIG. 3B) and comprises sequence $HX_4X_5DYFPYWFAX_8$ (SEQ ID NO:7);
wherein $X_4$ of CDR3H is D, G, or P;
wherein $X_5$ of CDR3H is F or P; and
wherein $X_8$ of CDR3H is L, H, or F.

In one embodiment, CDR3H comprises sequence HDFDYFPYWFAH (SEQ ID NO:10).

In one aspect, the invention provides CEACAM1 antibodies or antigen-binding fragments thereof that comprise a CDR3H region, wherein the CDR3H region comprises residues 94-102 (Kabat definition, corresponds, e.g., to residues 98 to 110 in the primary amino acid sequence of the heavy variable chain of SEQ ID NO: 19, see FIG. 3A, or SEQ ID NO: 13, see FIG. 3B) and comprises the sequence $X_{18}HX_4X_5DYX_6PX_7WFAX_8$ (SEQ ID NO:24),
wherein $X_{18}$ is R or K;
wherein $X_4$ is D, G, or P;
wherein $X_5$ is F or P;
wherein $X_6$ is D or F;
wherein $X_7$ is A or Y; and
wherein $X_8$ is L, H, or F.

In one aspect, the CDR3H region comprises sequence RHDFDYFPYWFAH (SEQ ID NO:25).

In one aspect, the invention provides CEACAM1 antibodies or antigen-binding fragments thereof that comprise a CDR3L, wherein the CDR3L comprises residues 89-97 (Kabat definition, corresponds, e.g., to residues 88 to 96 in the primary amino acid sequence of the heavy variable chain of SEQ ID NO:14, see FIG. 3C) and comprises the sequence $QQX_9X_{10}X_{11}X_{12}PX_{13}T$ (SEQ ID NO:6),
wherein $X_9$ is W or N;
wherein $X_{10}$ is S or T;
wherein $X_{11}$ is A or an amino acid with a neutral hydrophilic side chain including S, N, and T;
wherein $X_{12}$ is L, F, or N; and
wherein $X_{13}$ is P or F.

In one embodiment, CDR3L comprises residues 89-97 (Kabat definition, corresponds, e.g., to residues 88 to 96 in the primary amino acid sequence of the heavy variable chain of SEQ ID NO: 14, see FIG. 3C) and comprises sequence $QQX_9SSX_{12}PX_{13}T$ (SEQ ID NO:8),
wherein $X_9$ is W or N;
wherein $X_{12}$ is L, F, or N; and
wherein $X_{13}$ is P or F.

In one embodiment, CDR3L comprises sequence QQWSSNPPT (SEQ ID NO:11) or sequence QQWTSNPPT (SEQ ID NO:12).

In one aspect, the invention relates to an antibody, or antigen-binding fragment thereof, which binds to CEACAM1, wherein the antibody or antigen-binding fragment comprises a heavy chain variable region and a light chain variable region, wherein each of the heavy chain and the light chain variable regions comprises a CDR1, CDR2, and CDR3, and wherein:
the sequence of CDR1 of the heavy chain variable region (CDR1H) comprises the sequence $X_{14}X_{15}X_{16}FX_{17}X_1HX_2X_3S$ (SEQ ID NO:22);
wherein $X_{14}$ is G or E;
wherein $X_{15}$ is an amino acid with an aromatic side chain including F or Y;
wherein $X_{16}$ is T, S, or I;
wherein $X_{17}$ is an amino acid with a polar uncharged side chain including S, T, or N;
wherein $X_1$ is A, D, N, or S;
wherein $X_2$ is A or G; and
wherein $X_3$ is an amino acid with a hydrophobic side chain including I or M;
the sequence of CDR2 of the heavy chain variable region (CDR2H) comprises the sequence TISSGGTYTYYPDSVKG (SEQ ID NO:2);
the sequence of CDR3 of the heavy chain variable region (CDR3H) comprises the sequence $HX_4X_5DYX_6X_{19}X_7WFAX_{20}$ (SEQ ID NO:45);
wherein $X_4$ is D, G, or P;
wherein $X_5$ is F or P;
wherein $X_6$ is D or F;
wherein $X_{19}$ is P or A;
wherein $X_7$ is A or Y; and
wherein $X_{20}$ is L, H, Y or F;
the sequence of CDR1 of the light chain variable region (CDR1L) comprises the sequence RANSAVSYMY (SEQ ID NO:4);
the sequence of CDR2 of the light chain variable region (CDR2L) comprises the sequence LTSNRAT (SEQ ID NO:5); and
the sequence of CDR3 of the light chain variable region (CDR3L) comprises the sequence $QQX_9X_{10}X_{11}X_{12}PX_{13}T$ (SEQ ID NO:6);
wherein $X_9$ is W or N;
wherein $X_{10}$ is S or T;
wherein $X_{11}$ is A or an amino acid with a neutral hydrophilic side chain including S, N, and T;
wherein $X_{12}$ is L, F, or N; and
wherein $X_{13}$ is P or F; and
wherein
when $X_{19}$ is A and/or $X_{20}$ is Y, then $X_{10}$ is T, $X_4$ is G or P, $X_1$ is N, and/or $X_{16}$ is T or S.

In one aspect, the invention relates to an antibody, or antigen-binding fragment thereof, which binds to CEACAM1, wherein the antibody or antigen-binding fragment comprises a heavy chain variable region and a light chain variable region, wherein each of the heavy chain and the light chain variable regions comprises a CDR1, CDR2, and CDR3, and wherein:
the sequence of CDR1 of the heavy chain variable region (CDR1H) comprises the sequence $X_{14}FX_{21}FX_{22}X_{23}HX_2X_3S$ (SEQ ID NO:46);
wherein $X_{14}$ is G or E;
wherein $X_{21}$ is T or I;
wherein $X_{22}$ is N or S;
wherein $X_{23}$ is A, D, or S
wherein $X_2$ is A or G; and
wherein $X_3$ is an amino acid with a hydrophobic side chain including I or M;
the sequence of CDR2 of the heavy chain variable region (CDR2H) comprises the sequence TISSGGTYTYYPDSVKG (SEQ ID NO:2);
the sequence of CDR3 of the heavy chain variable region (CDR3H) comprises the sequence $HX_{24}FDYX_6X_{19}X_7WFAX_{25}$ (SEQ ID NO:47);
wherein $X_{24}$ is D or G;
wherein $X_6$ is D or F;
wherein $X_{19}$ is P or A;
wherein $X_7$ is A or Y; and
wherein $X_{25}$ is H or Y;

the sequence of CDR1 of the light chain variable region (CDR1L) comprises the sequence RANSAVSYMY (SEQ ID NO:4);

the sequence of CDR2 of the light chain variable region (CDR2L) comprises the sequence LTSNRAT (SEQ ID NO:5); and the sequence of CDR3 of the light chain variable region (CDR3L) comprises the sequence QQWX$_{10}$X$_{10}$NPPT (SEQ ID NO:48);

wherein X$_{10}$ is S or T;

wherein when X$_{21}$ is I, then X$_6$ is F, X$_{19}$ is P and/or X$_7$ is Y.

In one aspect, the invention relates to an antibody, or antigen-binding fragment thereof, which binds to CEACAM1, wherein the antibody or antigen-binding fragment comprises a heavy chain variable region and a light chain variable region, wherein each of the heavy chain and the light chain variable regions comprises a CDR1, CDR2, and CDR3, and wherein:

the sequence of CDR1 of the heavy chain variable region (CDR1H) comprises the sequence X$_{14}$FTFX$_{22}$X$_{26}$HAX$_3$S (SEQ ID NO:49);

wherein X$_{14}$ is G or E;

wherein X$_{17}$ is S or N;

wherein X$_{22}$ is N or S;

wherein X$_{26}$ is A or D and wherein X$_3$ is an amino acid with a hydrophobic side chain including I or M;

the sequence of CDR2 of the heavy chain variable region (CDR2H) comprises the sequence TISSGGTYTYYPDSVKG (SEQ ID NO:2);

the sequence of CDR3 of the heavy chain variable region (CDR3H) comprises the sequence HX$_{24}$FDYX$_6$X$_{19}$X$_7$WFAX$_{25}$ (SEQ ID NO:47);

wherein X$_{24}$ is D or G;

wherein X$_6$ is D or F;

wherein X$_{19}$ is P or A;

wherein X$_7$ is A or Y; and wherein X$_{25}$ is H or Y;

the sequence of CDR1 of the light chain variable region (CDR1L) comprises the sequence RANSAVSYMY (SEQ ID NO:4);

the sequence of CDR2 of the light chain variable region (CDR2L) comprises the sequence LTSNRAT (SEQ ID NO:5); and the sequence of CDR3 of the light chain variable region (CDR3L) comprises the sequence QQWX$_{10}$X$_{10}$NPPT (SEQ ID NO:48);

wherein X$_{10}$ is S or T.

In one aspect, the invention provides CEACAM1 antibodies or antigen-binding fragments thereof, the CEACAM1 antibodies or antigen-binding fragments thereof comprising a heavy chain variable region and a light chain variable region, wherein the chain variable region comprises a CDR1H, CDR2H, and CDR3H (Kabat definitions), wherein the light chain variable region comprises a CDR1L, CDR2L, and CDR3L (Kabat definitions), and wherein:

the sequence of CDR1H comprises the sequence X$_1$HX$_2$X$_3$S (SEQ ID NO:1), the sequence of CDR2H comprises the sequence TISSGGTYTYYPDSVKG (SEQ ID NO: 2), the sequence of CDR3H comprises the sequence HX$_4$X$_5$DYX$_6$PX$_7$WFAX$_8$ (SEQ ID NO: 3), the sequence of CDR1L comprises the sequence RANSAVSYMY (SEQ ID NO:4), the sequence of CDR2L comprises the sequence LTSNRAT (SEQ ID NO:5), and the sequence of CDR3L comprises the sequence QQX$_9$X$_{10}$X$_{11}$X$_{12}$PX$_{13}$T (SEQ ID NO:6). X$_1$-X$_{18}$ have been previously defined.

In one embodiment, the invention relates to an antibody, or antigen-binding fragment thereof, which binds to CEACAM1, wherein the antibody or antigen-binding fragment comprises a heavy chain variable region and a light chain variable region, wherein each of the heavy chain and the light chain variable regions comprises a CDR1, CDR2, and CDR3, and wherein:

the sequence of the heavy variable chain comprises the sequence GXXXXX$_1$HX$_2$X$_3$S (SEQ ID NO:43);

wherein X is any amino acid;

wherein X$_1$ is A, D, N, or S;

wherein X$_2$ is A or G; and wherein X$_3$ is an amino acid with a hydrophobic side chain including I or M; and the sequence of CDR2 of the heavy chain variable region (CDR2H) comprises the sequence TISSGGTYTYYPDSVKG (SEQ ID NO:2);

the sequence of CDR3H comprises the sequence HX$_4$X$_5$DYFPX$_7$WFAX$_8$ (SEQ ID NO: 44);

wherein X$_4$ is D, G, or P;

wherein X$_5$ is F or P;

wherein X$_7$ is A or Y; and wherein X$_8$ is L, H, or F;

the sequence of CDR1 of the light chain variable region (CDR1L) comprises the sequence RANSAVSYMY (SEQ ID NO:4);

the sequence of CDR2 of the light chain variable region (CDR2L) comprises the sequence LTSNRAT (SEQ ID NO:5); and the sequence of CDR3 of the light chain variable region (CDR3L) comprises the sequence QQX$_9$X$_{10}$X$_{11}$X$_{12}$PX$_{13}$T (SEQ ID NO:6);

wherein X$_9$ is W or N;

wherein X$_{10}$ is S or T;

wherein X$_{11}$ is A or an amino acid with a neutral hydrophilic side chain including S, N, and T;

wherein X$_{12}$ is L, F, or N; and wherein X$_{13}$ is P or F.

In one embodiment, the CEACAM1 antibodies or antigen-binding fragments thereof comprise a heavy chain variable region and a light chain variable region, wherein the chain variable region comprises a CDR1H, CDR2H, and CDR3H (Kabat definitions), wherein the light chain variable region comprises a CDR1L, CDR2L, and CDR3L (Kabat definitions), and wherein:

the sequence of CDR1H comprises the sequence X$_1$HX$_2$X$_3$S (SEQ ID NO:1), the sequence of CDR2H comprises the sequence TISSGGTYTYYPDSVKG (SEQ ID NO: 2), the sequence of CDR3H comprises the sequence HX$_4$X$_5$DYFPYWFAX$_8$ (SEQ ID NO:7), the sequence of CDR1L comprises the sequence RANSAVSYMY (SEQ ID NO:4), the sequence of CDR2L comprises the sequence LTSNRAT (SEQ ID NO:5), and the sequence of CDR3L comprises the sequence QQX$_9$SSX$_{12}$PX$_{13}$T (SEQ ID NO:8). X$_1$-X$_{18}$ have been previously defined.

According to certain embodiments, the contemplated antibodies and antigen-binding fragments thereof also feature humanized frameworks for reduced immunogenicity. In certain embodiments, the CDRs of the contemplated antibody or antigen-binding fragment thereof are located in frameworks obtained from a human antibody or antigen-binding fragment thereof. In other embodiments, surface-exposed framework residues of the contemplated antibody or antigen-binding fragment thereof are replaced with framework residues of a human antibody or antigen-binding fragment thereof. The CDRs may also be located in murine or humanized frameworks linked to human constant regions (i.e., chimeric antibodies). In a preferred embodiment, the CDRs of a contemplated antibody or antigen-binding fragment thereof are located in frameworks that are a composite of two or more human antibodies. In such embodiments, the contemplated antibodies or antigen-binding fragments thereof comprise two or more sequence segments ("composites") derived from V-regions of unrelated human antibodies that are selected to maintain monoclonal antibody sequences important for antigen binding of the starting precursor anti-human CEACAM1 monoclonal antibody, and which have all been filtered for the presence of potential T cell epitopes using "in silico tools" (Holgate & Baker, IDrugs. 2009 April; 12 (4): 233-7). The close fit of human sequence segments with all sections of the starting antibody V regions and the elimination of $CD4^+$ T cell epitopes prior to synthesis of the antibody or antigen-binding fragment thereof allow this technology to circumvent immunogenicity while maintaining optimal affinity and specificity through the prior analysis of sequences necessary for antigen-specificity (Holgate & Baker, 2009).

Also provided herein variable heavy chain and variable light chain sequences as well as pairing thereof that are similar, but not identical to the variable heavy chain and variable light chains disclosed in SEQ ID NOs: 13-16 and pairings thereof.

In some embodiments, the CEACAM1 antibody or antigen-binding fragment thereof comprises a variable heavy chain amino acid sequence comprising SEQ ID NO:13.

In some embodiments, the antibody or antigen-binding fragment thereof comprises a variable light chain amino acid sequence comprising SEQ ID NO:16. In other embodiments, the antibody or antigen-binding fragment thereof comprises a variable light chain amino acid sequence comprising SEQ ID NO: 14. In other embodiments, the antibody or antigen-binding fragment thereof comprises a variable light chain amino acid sequence comprising SEQ ID NO: 15.

In some embodiments, the CEACAM1 antibody or antigen-binding fragment thereof comprises a variable heavy chain amino acid sequence comprising SEQ ID NO:13 and a variable light chain amino acid sequence comprising SEQ ID NO:14.

In some embodiments, the CEACAM1 antibody or antigen-binding fragment thereof comprises a variable heavy chain amino acid sequence comprising SEQ ID NO: 13 and a variable light chain amino acid sequence comprising SEQ ID NO:15.

In some embodiments, the CEACAM1 antibody or antigen-binding fragment thereof comprises a variable heavy chain amino acid sequence comprising SEQ ID NO:13 and a variable light chain amino acid sequence comprising SEQ ID NO:16.

As used herein, the term "identity" refers to sequence identity between two nucleic acid molecules or polypeptides. Identity can be determined by comparing a position in each sequence which may be aligned for purposes of comparison. For example, when a position in the compared nucleotide sequence is occupied by the same base, then the molecules are identical at that position. A degree of identity between nucleic acid or amino acid sequences is a function of the number of identical or matching nucleotides or amino acids at shared positions. For example, polypeptides having at least 85%, 90%, 95%, 98%, or 99% identity to specific polypeptides described herein and preferably exhibiting substantially the same functions, as well as polynucleotides encoding such polypeptides, are contemplated. Methods and computer programs for determining both sequence identity and similarity are publicly available, including, but not limited to, the GCG program package (Devereux et al., Nucleic Acids Research 12:387, 1984), BLASTP, BLASTN, FASTA (Altschul et al., J. Mol. Biol. 215:403 (1990), and the ALIGN program (version 2.0). The well-known Smith Waterman algorithm may also be used to determine similarity. The BLAST program is publicly available from NCBI and other sources (BLAST Manual, Altschul, et al., NCBI NLM NIH, Bethesda, Md. 20894; BLAST 2.0. In comparing sequences, these methods account for various substitutions, deletions, and other modifications.

In another aspect, the CEACAM1 antibody or antigen-binding fragment thereof comprises
  (i) a heavy chain variable domain comprising a sequence that is at least 90%, at least 95%, at least 96%, at least 97%, at least 98%, or at least 99% identical to a heavy chain variable domain sequence of SEQ ID NO: 13; and/or
  (ii) a light chain variable domain comprising a sequence that is at least 90%, at least 95%, at least 96%, at least 97%, at least 98%, or at least 99% identical to the light chain variable domain sequence of SEQ ID NO: 14.

In another aspect, the CEACAM1 antibody or antigen-binding fragment thereof comprises
  (i) a heavy chain variable domain comprising a sequence that is at least 85%, at least 90%, at least 95%, at least 96%, at least 97%, at least 98%, or at least 99% identical to a heavy chain variable domain sequence of SEQ ID NO: 13;
  (ii) a light chain variable domain comprising a sequence that is at least 85%, at least 90%, at least 95%, at least 96%, at least 97%, at least 98%, or at least 99% identical to the light chain variable domain sequence of SEQ ID NO:14
  (iii) and wherein:
  the sequence of CDR2H comprises residues Y57 and Y59 of SEQ ID NO: 13,
  the sequence of CDR3H comprises residues D102, Y103, F104, P105, and Y106 of SEQ ID NO: 13,
  the sequence of CDR1L comprises residues A28, S30, and Y31 of SEQ ID NO: 14,
  the sequence of CDR2L comprises residues S51 and N52 of SEQ ID NO: 14, and
    the sequence of CDR3L comprises residues S91 and S92 of SEQ ID NO: 14.
    Numbering of residues is based on the primary amino acid sequence of the antibody, see FIGS. 3A, 3B, and 3C for example heavy and light chain sequences.

In another aspect, the CEACAM1 antibody or antigen-binding fragment thereof comprises
  (i) a heavy chain variable domain comprising a sequence that is at least 85%, at least 90%, at least 95%, at least 96%, at least 97%, at least 98%, or at least 99% identical to a heavy chain variable domain sequence of SEQ ID NO:13;
  (ii) a light chain variable domain comprising a sequence that is at least 85%, at least 90%, at least 95%, at least 96%, at least 97%, at least 98%, or at least 99% identical to the light chain variable domain sequence of SEQ ID NO: 14; and (iii) six CDRs, wherein:
  a. the sequence of CDR1 of the heavy chain variable region comprises SEQ ID NO:9;
  b. the sequence of CDR2 of the heavy chain variable region comprises SEQ ID NO:2;
  c. the sequence of CDR3 of the heavy chain variable region comprises SEQ ID NO: 10;
  d. the sequence of CDR1 of the light chain variable region comprises SEQ ID NO:4;
  e. the sequence of CDR2 of the light chain variable region comprises SEQ ID NO:5; and
  f. the sequence of CDR3 of the light chain variable region comprises SEQ ID NO:11.

In one aspect, the invention provides an antibody or antigen-binding fragment thereof which binds to CEACAM1, wherein the antibody or antigen-binding fragment comprises a heavy chain variable region and a light chain variable region;
  wherein the sequence of the heavy chain variable region comprises a sequence that is at least 85% identical to the heavy chain variable region amino acid sequence of SEQ ID NO:13;
  wherein the sequence of the light chain variable region comprises a sequence that is at least 85% identical to a light chain variable region amino acid sequence of SEQ ID NO: 14;
  wherein the sequence of the heavy variable chain comprises the sequence $GXXXXX_1HX_2X_3S$ (SEQ ID NO:43);
    wherein X is any amino acid;
    wherein $X_1$ is A, D, N, or S;
    wherein $X_2$ is A or G; and
    wherein $X_3$ is an amino acid with a hydrophobic side chain including I or M; and
  wherein the sequence of CDR3H comprises the sequence $HX_4X_5DYFPX_7WFAX_8$ (SEQ ID NO:44);
    wherein $X_4$ is D, G, or P;
    wherein $X_5$ is F or P;
    wherein $X_7$ is A or Y; and
    wherein $X_8$ is L, H, or F.

In another aspect, the CEACAM1 antibody or antigen-binding fragment thereof comprises
  (i) a heavy chain variable domain comprising a sequence that is at least 90%, at least 95%, at least 96%, at least 97%, at least 98%, or at least 99% identical to a heavy chain variable domain sequence of SEQ ID NO: 13; and/or
  (ii) a light chain variable domain comprising a sequence that is at least 90%, at least 95%, at least 96%, at least 97%, at least 98%, or at least 99% identical to the light chain variable domain sequence of SEQ ID NO:15.

In another aspect, the CEACAM1 antibody or antigen-binding fragment thereof comprises
  (i) a heavy chain variable domain comprising a sequence that is at least 85%, at least 90%, at least 95%, at least 96%, at least 97%, at least 98%, or at least 99% identical to a heavy chain variable domain sequence of SEQ ID NO:13;
  (ii) a light chain variable domain comprising a sequence that is at least 85%, at least 90%, at least 95%, at least 96%, at least 97%, at least 98%, or at least 99% identical to the light chain variable domain sequence of SEQ ID NO: 15;
  (iii) and wherein:
    the sequence of CDR2H comprises residues Y57 and Y59 of SEQ ID NO: 13, the sequence of CDR3H comprises residues D102, Y103, F104, P105, and Y106 of SEQ ID NO: 13,
    the sequence of CDR1L comprises residues A28, S30, and Y31 of SEQ ID NO: 15,
      the sequence of CDR2L comprises residues S51 and N52 of SEQ ID NO: 15, and
      the sequence of CDR3L comprises residue S92 of SEQ ID NO: 15.
      Numbering of residues is based on the primary amino acid sequence of the antibody, see FIGS. 3A, 3B, and 3C for example heavy and light chain sequences.

In another aspect, the CEACAM1 antibody or antigen-binding fragment thereof comprises
  (iv) a heavy chain variable domain comprising a sequence that is at least 85%, at least 90%, at least 95%, at least 96%, at least 97%, at least 98%, or at least 99% identical to a heavy chain variable domain sequence of SEQ ID NO:13;
  (v) a light chain variable domain comprising a sequence that is at least 85%, at least 90%, at least 95%, at least 96%, at least 97%, at least 98%, or at least 99% identical to the light chain variable domain sequence of SEQ ID NO: 15; and
  (vi) six CDRs, wherein:
    a. the sequence of CDR1 of the heavy chain variable region comprises SEQ ID NO:9;
    b. the sequence of CDR2 of the heavy chain variable region comprises SEQ ID NO:2;
    c. the sequence of CDR3 of the heavy chain variable region comprises SEQ ID NO:10;
    d. the sequence of CDR1 of the light chain variable region comprises SEQ ID NO:4;
    e. the sequence of CDR2 of the light chain variable region comprises SEQ ID NO:5; and
    f. the sequence of CDR3 of the light chain variable region comprises SEQ ID NO:12.

In another aspect, the CEACAM1 antibody or antigen-binding fragment thereof comprises
  (i) a heavy chain variable domain comprising a sequence that is at least 90%, at least 95%, at least 96%, at least 97%, at least 98%, or at least 99% identical to a heavy chain variable domain sequence of SEQ ID NO: 13; and/or
  (ii) a light chain variable domain comprising a sequence that is at least 90%, at least 95%, at least 96%, at least 97%, at least 98%, or at least 99% identical to the light chain variable domain sequence of SEQ ID NO: 16.

In another aspect, the CEACAM1 antibody or antigen-binding fragment thereof comprises
  (i) a heavy chain variable domain comprising a sequence that is at least 85%, at least 90%, at least 95%, at least 96%, at least 97%, at least 98%, or at least 99% identical to a heavy chain variable domain sequence of SEQ ID NO:13;
  (ii) a light chain variable domain comprising a sequence that at least 85%, at least 90%, at least 95%, at least 96%, at least 97%, at least 98%, or at least 99% identical to the light chain variable domain sequence of SEQ ID NO: 16;
  (iii) and wherein:
    the sequence of CDR2H comprises residues Y57 and Y59 of SEQ ID NO:13,
    the sequence of CDR3H comprises residues D102, Y103, F104, P105, and Y106 of SEQ ID NO: 13, the sequence of CDR1L comprises residues S30 and Y31 of SEQ ID NO: 16, the sequence of CDR2L comprises residues S51 and N52 of SEQ ID NO: 16, and the sequence of CDR3L comprises residues S91 and S92 of SEQ ID NO:16.

Numbering of residues is based on the primary amino acid sequence of the antibody, see FIGS. 3A, 3B, and 3C for example heavy and light chain sequences.

In another aspect, the CEACAM1 antibody or antigen-binding fragment thereof comprises (vii) a heavy chain variable domain comprising a sequence that is at least 85%, at least 90%, at least 95%, at least 96%, at least 97%, at least 98%, or at least 99% identical to a heavy chain variable domain sequence of SEQ ID NO: 13;

(viii) a light chain variable domain comprising a sequence that is at least 85%, at least 90%, at least 95%, at least 96%, at least 97%, at least 98%, or at least 99% identical to the light chain variable domain sequence of SEQ ID NO: 16; and (ix) six CDRs, wherein:
  a. the sequence of CDR1 of the heavy chain variable region comprises SEQ ID NO:9;
  b. the sequence of CDR2 of the heavy chain variable region comprises SEQ ID NO:2;
  c. the sequence of CDR3 of the heavy chain variable region comprises SEQ ID NO: 10;
  d. the sequence of CDR1 of the light chain variable region comprises SEQ ID NO: 18;
  e. the sequence of CDR2 of the light chain variable region comprises SEQ ID NO:5; and
  f. the sequence of CDR3 of the light chain variable region comprises SEQ ID NO:11.

It will be evident that any of the frameworks described herein can be utilized in combination with any of the CDRs and CDR motifs described herein. In some embodiments, the CEACAM1 antibody or antigen-binding fragment thereof utilizes a framework described in Table 1.

In some embodiments of the aspects described herein, amino acid sequence modification(s) of the antibodies or antigen-binding fragments thereof that bind to CEACAM1 described herein are contemplated. Amino acid sequence variants of the antibody or antigen-binding fragment thereof are prepared by introducing appropriate nucleotide changes into the nucleic acid encoding the antibody or antigen-binding fragment thereof, or by peptide synthesis. Such modifications include, for example, deletions from, and/or insertions into and/or substitutions of, residues within the amino acid sequences of the antibody or antigen-binding fragment thereof. Any combination of deletion, insertion, and substitution is made to arrive at the final construct, provided that the final construct possesses the desired characteristics, e.g., binding specificity, inhibition of biological activity.

One type of variant is a conservative amino acid substitution variant. These variants have at least one amino acid residue in the antibody or antigen-binding fragment thereof replaced by a different residue that has similar side chain properties. Amino acids can be grouped according to similarities in the properties of their side chains (see Lehninger, BIOCHEMISTRY (2nd ed., Worth Publishers, New York, 1975):

(1) non-polar: Ala (A), Val (V), Leu (L), Ile (I), Pro (P), Phe (F), Trp (W), Met (M);

(2) uncharged polar: Gly (G), Ser(S), Thr (T), Cys (C), Tyr (Y), Asn (N), Gln (Q);

(3) acidic: Asp (D), Glu (E);

(4) basic: Lys (K), Arg (R), His (H).

As such, a non-limiting example for a conservative amino acid substitution is one that replaces a non-polar amino acid with another non-polar amino acid.

Alternatively, naturally occurring residues can be divided into groups based on common side-chain properties:

(1) hydrophobic: Ala (A), Val (V), Leu (L), Ile (I), Met (M);

(2) neutral hydrophilic: Ser(S), Thr (T), Cys (C), Asn (N), Gln (Q);

(3) acidic: Asp (D), Glu (E);

(4) basic: Lys (K), Arg (R), His (H);

(5) residues that influence chain orientation: Gly (G), Pro (P);

(6) aromatic: Phe (F), Trp (W), Tyr (Y).

As such, a non-limiting example for a conservative amino acid substitution is one that replaces a hydrophobic amino acid with another hydrophobic amino acid.

Further contemplated are amino acid sequence insertions, which can include amino- and/or carboxyl-terminal fusions ranging in length from one residue to polypeptides containing a hundred or more residues, as well as intrasequence insertions of single or multiple amino acid residues. Examples of terminal insertions include an antibody or antigen-binding fragment thereof with an N-terminal methionyl residue or the antibody or antigen-binding fragment thereof fused to a cytotoxic polypeptide. Other insertional variants of the antibody or antigen-binding fragment thereof include the fusion to the N- or C-terminus of the antibody or antigen-binding fragment thereof to an enzyme or a polypeptide which increases the serum half-life of the antibody or antigen-binding fragment thereof, such as, for example, biotin.

Any cysteine residue not involved in maintaining the proper conformation of the antibodies or antigen-binding fragments thereof that bind to CEACAM1 also can be substituted, for example with a serine or an alanine, to improve the oxidative stability of the molecule and prevent aberrant crosslinking.

Conversely, cysteine bond(s) can be added to the antibody or antigen-binding fragment thereof to improve its stability (particularly where the antibody or antigen-binding fragment thereof is an antibody fragment such as an Fv fragment).

In some embodiments, the antibodies or antigen-binding fragments thereof describes have amino acid alterations that alter the original glycosylation pattern of the antibody or antigen-binding fragment thereof. By "altering the original glycosylation pattern" is meant deleting one or more carbohydrate moieties found in the antibody or antigen-binding fragment thereof, and/or adding one or more glycosylation sites that are not present in the antibody or antigen-binding fragment thereof. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, wherein X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine can also be used. Addition of glycosylation sites to the antibodies or antigen-binding fragments thereof that bind to CEACAM1 is accomplished by altering the amino acid sequence such that it contains one or more of the above-described tripeptide sequences (for N-linked glycosylation sites). The alteration can also be made by the addition of, or substitution by, one or more serine or threonine residues to the sequence of the original antibody or antigen-binding fragment thereof (for O-linked glycosylation sites).

In some embodiments, the CEACAM1 antibodies or antigen-binding fragments thereof provided herein are deglycosylated or aglycosylated. In some embodiments, the contemplated CEACAM1 antibody or antigen-binding fragment thereof lacks a C-terminal lysine in the heavy chain and/or contains a S241P substitution in the constant region of the heavy chain. In some embodiments, the CEACAM1 antibody or antigen-binding fragment thereof lacks a glycosylation site in the CDR1 of the variable light chain. In some embodiments, the CEACAM1 antibody or antigen-binding fragment thereof lacks an N—X—S/T consensus sequence in the CDR1 of the variable light chain. In some embodiments, the CEACAM1 antibody or antigen-binding fragment thereof has a mutation in CDR residues 26 and/or 29 (Kabat numbering) of the CDR1 of the variable light chain. Where the antibody or antigen-binding fragment thereof comprises an Fc region, the carbohydrate(s) attached thereto can be altered. For example, antibodies with a mature carbohydrate structure that lacks fucose attached to an Fc region of the antibody or antigen-binding fragment thereof are described. See, e.g., U.S. Patent Pubs. No. 2003/0157108; No. 2004/0093621. Antibodies with a bisecting N-acetylglucosamine (GlcNAc) in the carbohydrate attached to an Fc region of the antibody or antigen-binding fragment thereof are referenced in WO 03/011878; U.S. Pat. No. 6,602,684. Antibodies with at least one galactose residue in the oligosaccharide attached to an Fc region of the antibody or antigen-binding fragment thereof are reported in WO 97/30087. See also WO 98/58964; WO 99/22764 concerning antibodies with altered carbohydrate attached to the Fc region thereof.

In some embodiments, it can be desirable to modify the antibodies or antigen-binding fragment thereof that bind to CEACAM1 described herein with respect to effector function, e.g., so as to enhance antigen-dependent cell-mediated cytotoxicity (ADCC) and/or complement dependent cytotoxicity (CDC) of the antibody or antigen-binding fragment thereof. This can be achieved by introducing one or more amino acid substitutions in an Fc region of the antibody or antigen-binding fragment thereof. Alternatively or additionally, one or more cysteine residues can be introduced in the Fc region, thereby allowing interchain disulfide bond formation in this region. The homodimeric antibody or antigen-binding fragment thereof thus generated can have improved internalization capability and/or increased complement-mediated cell killing and antibody-dependent cellular cytotoxicity (ADCC). See Caron et al., 176 J. Exp. Med. 1191 (1992); Shopes, 148 J. Immunol. 2918 (1992). Homodimeric antibodies with enhanced anti-tumor activity can also be prepared using heterobifunctional cross-linkers as described in Wolff et al., 53 Cancer Res. 2560 (1993). Alternatively, an antibody or antigen-binding fragment thereof can be engineered which has dual Fc regions and can thereby have enhanced complement lysis and ADCC capabilities. See Stevenson et al., 3 Anti-Cancer Drug Design 219 (1989).

For example, WO 00/42072 describes antibodies with improved ADCC function in the presence of human effector cells, where the antibodies comprise amino acid substitutions in the Fc region thereof. Preferably, the antibody or antigen-binding fragment thereof with improved ADCC comprises substitutions at positions 298, 333, and/or 334 of the Fc region (Eu numbering of residues). Typically, the altered Fc region is a human IgG1 Fc region comprising or consisting of substitutions at one, two or three of these positions. Such substitutions are optionally combined with substitution(s) which increase Clq binding and/or CDC. Substitutions include an Asn297Ala mutation in IgG1 Fc.

Antibodies with altered Clq binding and/or complement dependent cytotoxicity (CDC) are described in WO 99/51642, U.S. Pat. Nos. 6,194,551, 6,242,195, 6,528,624, and 6,538,124. The antibodies comprise an amino acid substitution at one or more of amino acid positions 270, 322, 326, 327, 329, 313, 333 and/or 334 of the Fc region thereof (Eu numbering of residues).

Antibodies with improved binding to the neonatal Fc receptor (FcRn), and increased half-lives, are described in WO 00/42072 and U.S. Patent Pub. No. 2005/0014934. These antibodies comprise an Fc region with one or more substitutions therein which improve binding of the Fc region to CEACAM1. For example, the Fc region can have substitutions at one or more of positions 238, 250, 256, 265, 272, 286, 303, 305, 307, 311, 312, 314, 317, 340, 356, 360, 362, 376, 378, 380, 382, 413, 424, 428 or 434 (Eu numbering of residues). The preferred Fc region-comprising an antibody variant with improved CEACAM1 binding comprises amino acid substitutions at one, two or three of positions 307, 380 and 434 of the Fc region thereof (Eu numbering of residues). In one embodiment, the antibody or antigen-binding fragment thereof has 307/434 mutations. Engineered antibodies that bind to CEACAM1 with three or more (e.g., four) functional antigen binding sites are also contemplated. See, e.g., U.S. Patent Pub. No. US 2002/0004587.

Antibody Fragments and Types

In some embodiments of the aspects described herein, the CEACAM1 antibody fragment is a Fab fragment, which comprises or consist essentially a variable ($V_L$) and constant ($C_L$) domain of the light chain and a variable domain ($V_H$) and the first constant domain ($C_H1$) of the heavy chain.

In some embodiments of the aspects described herein, the CEACAM1 antibody fragment is a Fab' fragment, which refers to a Fab fragment having one or more cysteine residues at the C-terminus of the CHI domain.

In some embodiments of the aspects described herein, the CEACAM1 antibody fragment is an Fd fragment comprising or consisting essentially of $V_H$ and $C_H1$ domains.

In some embodiments of the aspects described herein, the CEACAM1 antibody portion is an Fd' fragment comprising $V_H$ and $C_H1$ domains and one or more cysteine residues at the C-terminus of the $C_H1$ domain.

Single-chain Fv or scFv antibody fragments comprise or consist essentially of the $V_H$ and $V_L$ domains of antibody, such that these domains are present in a single polypeptide chain. Generally, an Fv polypeptide further comprises a polypeptide linker between the $V_H$ and $V_L$ domains, which allows the scFv to form the desired structure for antigen binding. See, for example, Pluckthun, 113 Pharmacology Monoclonal Antibodies 269 (Rosenburg & Moore, eds., Springer-Verlag, New York, 1994). Accordingly, in some embodiments of the aspects described herein, the CEACAM1 antibody fragment is a Fv fragment comprising or consisting essentially of the $V_L$ and $V_H$ domains of a single arm of an antibody.

In some embodiments of the aspects described herein, the CEACAM1 antibody portion is a diabody comprising two antigen binding sites, comprising a heavy chain variable domain ($V_H$) connected to a light chain variable domain ($V_L$) in the same polypeptide chain.

In some embodiments of the aspects described herein, the CEACAM1 antibody portion is a dAb fragment comprising or consisting essentially of a $V_H$ domain.

In some embodiments of the aspects described herein, the CEACAM1 antibody portion is a F(ab')2 fragment, which comprises a bivalent fragment comprising two Fab' fragments linked by a disulfide bridge at the hinge region.

Linear antibodies refers to the antibodies as described in Zapata et al., Protein Engin., 8 (10): 1057-1062 (1995). Briefly, these antibodies comprise a pair of tandem Fd segments ($V_H$—$C_H$1-$V_H$—$C_H$1), which, together with complementary light chain polypeptides, form a pair of antigen binding regions. Linear antibodies can be bispecific or monospecific. In some embodiments of the aspects described herein, the CEACAM1 antibody fragment is a linear antibody comprising a pair of tandem Fd segments ($V_H$—$C_H$1-$V_H$—$C_H$1) which, together with complementary light chain polypeptides, form a pair of antigen binding regions.

Various techniques have been developed and are available for the production of antibody fragments. Traditionally, these fragments were derived via proteolytic digestion of intact antibodies. See, e.g., Morimoto et al., 24 J. Biochem. Biophys. Meths. 107 (1992); Brennan et al., 229 Science 81 (1985). However, these fragments can now be produced directly by recombinant host cells. For example, antibody fragments can be isolated from the antibody phage libraries discussed herein. Alternatively, Fab'-SH fragments can be directly recovered from E. coli and chemically coupled to form F(ab')2 fragments (Carter et al., 1992). According to another approach, F(ab')2 fragments can be isolated directly from recombinant host cell culture. Other techniques for the production of antibody fragments will be apparent to the skilled practitioner. In other embodiments, the antibody fragment of choice is a single chain Fv fragment (scFv). See, for example, WO 93/16185.

In one embodiment, the antibody is a bispecific antibody comprising a complementary region that binds to CEACAM1 and a complementary region that binds to PD-1.

In one embodiment, the antibody is a bispecific antibody comprising a complementary region that binds to CEACAM1 and a complementary region that binds to PD-L1.

Contemplated antibodies or antigen-binding fragments may have all types of constant regions, including IgM, IgG, IgD, and IgE, and any isotype, including IgG1, IgG2, IgG3, and IgG4. In one embodiment, the human isotype IgG1 is used. In another embodiment, the human isotype IgG4 is used. Light chain constant regions can be λ or κ. The antibody or antigen-binding fragment thereof may comprise sequences from more than one class or isotype.

Also disclosed herein are chimeric antigen receptor T-cells (CAR T-cells) that bind to CEACAM1. In one embodiment, one or more of the CDRs of an anti-CEACAM antibody disclosed herein are grafted onto a chimeric antigen receptor (CAR) on a T-cell. Such a genetically modified T-cell utilizes the CAR, also known as a chimeric T cell receptor, to target antigens expressed on tumor cells in a human leukocyte antigen-independent manner.

Antibody Binding

The human CEACAM1 gene produces 11 isoforms by alternative splicing. Each isoform has one variable (V)-like Ig domain at the amino (N) end of the protein. With the exception of CEACAM1-1L and CEACAM1-1S isoforms, the various isoforms also have 2 or 3 constant C2-like Ig domains. Eight CEACAM1 isoforms are anchored to the cellular membrane via a transmembrane domain and three CEACAM1 isoforms (CEACAM1-4C1, -3 and -3C2) lack the transmembrane domain and are secreted. Two isoforms (CEACAM1-3AL and -3AS) have an Alu family repeat sequence (A) between the constant C2-like Ig domains and the transmembrane domain. The transmembrane CEACAM1 isoforms also possess a long (L) or short(S) cytoplasmic domain determined by inclusion or exclusion of CEACAM1 exon 7 in the message. The CEACAM1 L cytoplasmic domain has two ITIM motifs, which are unique to CEACAM1 among the CEACAM family members. In one aspect, the invention provides CEACAM1 antibodies or antigen-binding fragments thereof, including the antibodies described herein by their structural characteristics, that bind to the extracellular, variable (V)-like Ig domain at the amino (N) end of the protein (N-domain) of CEACAM1, a domain that is common to all isoforms of CEACAM1, including CEACAM1 isoforms 1L, 1S, 3L, 3S, 4L, 4S, 3Al, 3AS, 3, 4C1, and 4C2. In some embodiments, the provided antibodies and antigen-binding fragments thereof bind to human CEACAM1. In some embodiments, the provided antibodies and antigen-binding fragments thereof bind to mammalian CEACAM1. The sequence of the full-length form of CEACAM1 (NCBI Reference Sequence NP_001703.2; UNIPROT ID P13688) is provided as SEQ ID NO:26 (signal sequence: residues 1-34 of SEQ ID NO:26; Ig-V N domain: residues 35-142 of SEQ ID NO:26. The mature form of CEACAM1 (without signal sequence) is provided as SEQ ID NO:17.

As used herein, "binding" of an antibody or antigen binding fragment thereof to CEACAM1, an epitope on CEACAM1, or, in certain embodiments described below, particular residues on CEACAM1, includes the selective interaction of the antibody or antigen binding fragment thereof with CEACAM1. Binding therefore includes, e.g., primary and secondary interactions including hydrogen bonds, ionic interactions, salt bridges, as well as hydrophilic and hydrophobic interactions.

In certain embodiments, the CEACAM1 antibodies or antigen-binding fragments thereof described herein bind to CEACAM1 with a $K_D$ of $10^{-5}$ to $10^{-12}$ mol/l, $10^{-6}$ to $10^{-12}$ mol/l, $10^{-7}$ to $10^{-12}$ mol/l, $10^{-8}$ to $10^{-12}$ mol/l, $10^{-9}$ to $10^{-12}$ mol/l, $10^{-10}$ to $10^{-12}$ mol/l, or $10^{-11}$ to $10^{-12}$ mol/l. In other embodiments, the CEACAM1 antibodies or antigen-binding fragments thereof described herein bind to CEACAM1 with a $K_D$ of $10^{-5}$ to $10^{-11}$ mol/l, $10^{-6}$ to $10^{-11}$ mol/l, $10^{-7}$ to $10^{-11}$ mol/l, $10^{-8}$ to $10^{-11}$ mol/l, $10^{-9}$ to $10^{-11}$ mol/l, or $10^{-10}$ to $10^{-11}$ mol/l. In other embodiments, the CEACAM1 antibodies or antigen-binding fragments thereof described herein bind to CEACAM1 with a $K_D$ of $10^{-5}$ to $10^{-10}$ mol/l, $10^{-6}$ to $10^{-10}$ mol/l, $10^{-7}$ to $10^{-10}$ mol/l, $10^{-8}$ to $10^{-10}$ mol/l, or $10^{-9}$ to $10^{-10}$ mol/l. In other embodiments, the CEACAM1 antibodies or antigen-binding fragments thereof described herein bind to CEACAM1 with a $K_D$ of $10^{-5}$ to $10^{-8}$ mol/l, $10^{-6}$ to $10^{-8}$ mol/l, or $10^{-7}$ to $10^{-8}$ mol/l.

The term "specificity" herein refers to the ability of an antibody or antigen-binding fragment thereof, such as an anti-CEACAM1 antibody or antigen-binding fragment thereof, to recognize an epitope within CEACAM1, while only having little or no detectable reactivity with other portions of CEACAM1. Specificity can be relatively determined by competition assays or by epitope identification/characterization techniques described herein or their equivalents known in the art.

As used herein, an "epitope" can be formed both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a particular spatial conformation. An "epitope" includes the unit of structure conventionally bound by an immunoglobulin $V_H/V_L$ pair. Epitopes define the minimum binding site for an antibody or antigen-binding fragment thereof, and thus represent the target of specificity of an antibody or antigen-binding fragment thereof. In the case of a single domain antibody, an epitope represents the unit of structure bound by a variable domain in isolation.

In a particular embodiment, the contemplated antibody or antigen-binding fragment specifically binds to the same epitope as antibody CP08H03/Vk8 S29A. In another embodiment, the contemplated antibody or antigen-binding fragment binds to the same epitope as CP08H03/CP08F05.

In one aspect, the invention provides antibodies and antigen-binding fragments thereof, including the antibodies described herein by their structural characteristics, wherein the antibodies and antigen-binding fragments thereof specifically bind to at least part of the homophilic binding domain on CEACAM1 (i.e. in portion of the CEACAM1 protein that is involved in formation of a CEACAM1:CEACAM1 homodimer), thereby blocking CEACAM1 homophilic interactions. In certain embodiments, the provided antibody or antigen-binding fragment thereof specifically binds to one or more of CEACAM1 residues that are contained in the CC' and FG loops of CEACAM1 and that include a YQQN pocket at the CEACAM1:CEACAM1 dimer interface (i.e., Y34, Q44, Q89, N97 of SEQ ID NO:17), see Huang et al., Nature. 2015 Jan. 15; 517 (7534): 386-90.

As used herein, a "blocking" antibody or an antibody "antagonist" is one that inhibits or reduces biological activity of the antigen to which it binds. For example, in some embodiments, a CEACAM1 antagonist antibody or antigen-binding fragment thereof binds CEACAM1 and inhibits activity of CEACAM1 and/or binding of CEACAM1 to heterologous binding partners such as other CEACAM proteins or TIM-3. Inhibition of activity and inhibition of binding includes partial inhibition. Methods for the identification of CEACAM1 antibodies that block CEACAM1 homophilic and heterophilic interactions are described herein and are known to the ones skilled in the art. For instance, competing, cross-blocking, and cross-blocked antibodies can be identified using any suitable method known in the art, including competition ELISAs or BIACORE® assays where binding of the competing or cross-blocking antibody to human CEACAM1 prevents the binding of an antibody disclosed herein or vice versa.

In one embodiment, the heavy chain of the contemplated antibody or antigen-binding fragment thereof specifically binds to CEACAM1 at residues F29, Y34, T56, Q89, S93, and/or D94 of SEQ ID NO: 17. In another embodiment, the heavy chain of the contemplated antibody or antigen-binding fragment thereof further specifically binds to CEACAM1 at residues S32, Q44, A49, and/or I91 of SEQ ID NO: 17.

In one embodiment, the light chain of the contemplated antibody or antigen-binding fragment thereof specifically binds to CEACAM1 at residues D40, G41, N42, N97, and/or E99 of SEQ ID NO:17. In another embodiment, the light chain of the contemplated antibody or antigen-binding fragment thereof further specifically binds to CEACAM1 at residues L95, and/or V96 of SEQ ID NO: 17.

In another embodiment, the CEACAM1 antibody or antigen-binding fragment thereof specifically binds to CEACAM1 at residues F29, Y34, D40, G41, N42, T56, Q89, S93, D94, N97, and/or E99 of SEQ ID NO: 17. In another preferred embodiment, the CEACAM1 antibody or antigen-binding fragment thereof further specifically binds to CEACAM1 at residues S32, Q44, A49, I91, L95, and/or V96 of SEQ ID NO: 17.

In another embodiment, the CEACAM1 antibody or antigen-binding fragment thereof specifically binds to CEACAM1 at residues F29, Y34, D40, G41, N42, T56, Q89, S93, D94, N97, and E99 of SEQ ID NO: 17.

In another embodiment, the CEACAM1 antibody or antigen-binding fragment thereof specifically binds to CEACAM1 at residues F29, S32, Y34, D40, G41, N42, Q44, A49, T56, Q89, I91, S93, D94, L95, V96, N97, and E99 of SEQ ID NO: 17.

In certain embodiments, not all CDRs are directly involved in binding to the antigen. In one embodiment, four out of six CDRs of the CEACAM1 antibody or antigen-binding fragment thereof make contact with the antigen. In one embodiment, five out of six CDRs of the CEACAM1 antibody or antigen-binding fragment thereof make contact with the antigen. In one embodiment, six out of six CDRs of the CEACAM1 antibody or antigen-binding fragment thereof make contact with the antigen. In one embodiment, CDR2H, CDR3H, CDR1L, CDR2L, and CDR3L of the CEACAM1 antibody or antigen-binding fragment thereof are directly involved in binding to the antigen.

In one embodiment, the antibodies and antigen-binding fragments thereof provided herein specifically bind to an epitope of CEACAM1 located on the N-domain of CEACAM1. In one embodiment, the antibody or antigen-binding fragment thereof specifically binds a CEACAM1 epitope comprising one or more CEACAM1 residues selected from F29, S32, D40, A49, and T56 of SEQ ID NO:17. In a further embodiment, the CEACAM1 antibody specifically binds a CEACAM1 epitope comprising residues F29, S32, D40, A49, T56, and I91 of SEQ ID NO: 17.

In one embodiment, the antibodies and antigen-binding fragments thereof provided herein specifically bind to an epitope of CEACAM1 located on the N-domain of CEACAM1. In one embodiment, the antibody or antigen-binding fragment thereof specifically binds a CEACAM1 epitope comprising one or more CEACAM1 residues selected from S32, D40, A49, and I91 of SEQ ID NO:17. In a further embodiment, the CEACAM1 antibody specifically binds a CEACAM1 epitope comprising residues S32, D40, A49, and I91 of SEQ ID NO:17.

In one embodiment, the CEACAM1 antibody or antigen-binding fragment thereof provided herein binds to CEACAM1, wherein
CDR2H residue Y57 binds to CEACAM1 at residue F29,
CDR2H residue Y59 binds to CEACAM1 at residue S93,
CDR3H residue D102 binds to CEACAM1 at residue T56,
CDR3H residue Y103 binds to CEACAM1 at residues Y34 and/or Q89,
CDR3H residue F104 binds to CEACAM1 at residue F29, CDR3H residue Y106 binds to CEACAM1 at residue D94,
CDR1L residue S30 binds to CEACAM1 at residue E99,
CDR1L residue Y31 binds to CEACAM1 at residue N97,
CDR2L residue S51 binds to CEACAM1 at residue D40, and/or CDR2L residue N52 binds to CEACAM1 at residues G41 and/or N42.

Numbering of CDR residues is based on the primary amino acid sequence of the antibody, see FIGS. 3A, 3B, and 3C for example heavy and light chain sequences. CEACAM1 residues are numbered according to SEQ ID NO:17.

In one embodiment, the CEACAM1 antibody or antigen-binding fragment thereof provided herein binds to CEACAM1, wherein
CDR2H residue Y57 binds to CEACAM1 at residue F29,
CDR2H residue Y59 binds to CEACAM1 at residue S93,
CDR3H residue D102 binds to CEACAM1 at residue T56,
CDR3H residue Y103 binds to CEACAM1 at residues S32, Y34, Q44, and/or Q89,
CDR3H residue F104 binds to CEACAM1 at residues F29 and/or A49,
CDR3H residue P105 binds to CEACAM1 at residue I91,
CDR3H residue Y106 binds to CEACAM1 at residue D94,
CDR1L residue S30 binds to CEACAM1 at residue E99,
CDR1L residue Y31 binds to CEACAM1 at residue N97,
CDR2L residue S51 binds to CEACAM1 at residue D40,
CDR2L residue N52 binds to CEACAM1 at residues G41 and/or N42,
CDR3L residue S91 binds to CEACAM1 at residue L95, and/or
CDR3L residue S92 binds to CEACAM1 at residue V96.

Numbering of residues is based on the primary amino acid sequence of the antibody, see FIGS. 3A, 3B, and 3C for example heavy and light chain sequences. CEACAM1 residues are numbered according to SEQ ID NO:17.

In one embodiment, the CEACAM1 antibody or antigen-binding fragment thereof provided herein binds to CEACAM1, wherein
CDR2H residue Y57 binds to CEACAM1 at residue F29,
CDR2H residue Y59 binds to CEACAM1 at residue S93,
CDR3H residue D102 binds to CEACAM1 at residue T56,
CDR3H residue Y103 binds to CEACAM1 at residues S32, Y34, Q44, and Q89,
CDR3H residue F104 binds to CEACAM1 at residues F29 and A49,
CDR3H residue P105 binds to CEACAM1 at residue I91,
CDR3H residue Y106 binds to CEACAM1 at residue D94,
CDR1L residue S30 binds to CEACAM1 at residue E99,
CDR1L residue Y31 binds to CEACAM1 at residue N97,
CDR2L residue S51 binds to CEACAM1 at residue D40,
CDR2L residue N52 binds to CEACAM1 at residues G41 and N42,
CDR3L residue S91 binds to CEACAM1 at residue L95, and
CDR3L residue S92 binds to CEACAM1 at residue V96.

Numbering of residues is based on the primary amino acid sequence of the antibody, see FIGS. 3A, 3B, and 3C for example heavy and light chain sequences. CEACAM1 residues are numbered according to SEQ ID NO: 17.

CEACAM family members are expressed widely on a variety of cell types (especially leukocytes), affecting a magnitude of cellular functions. For instance, CEACAM1 is expressed on epithelial cells, endothelial cells, lymphocytes, and myeloid cells, CEACAM3 is expressed on granulocytes and neutrophils, CEACAM5 expressed on epithelial cells, and CEACAM6 is expressed on epithelial cells and granulocytes. However, the N-domain of CEACAM1 is about 90% similar to the N-domains of CEACAM family members 3, 5, and 6, making it difficult to target CEACAM1 selectively.

Despite the high similarity of N-domains among CEACAM family members, in some embodiments, antibodies or antigen-binding fragments thereof provided herein, including the antibodies described herein by their structural characteristics, are selective for CEACAM1. By selectively targeting CEACAM1, embodiments of the invention may avoid undesired interfering e.g. with the broad activating function of CEACAM3.

The terms "selective" and "selectivity" herein refer to the preferential binding of an antibody or antigen-binding fragment thereof (i.e., a CEACAM1 antibody or antigen-binding fragment thereof), for a particular region, target, or peptide; typically a region or epitope in CEACAM1, as opposed to one or more other biological molecules, including other CEACAM family members.

In some embodiments, the contemplated CEACAM1 antibody or antigen-binding fragment thereof does not exhibit significant binding to CEACAM3, CEACAM5, CEACAM6 and/or CEACAM8. In some embodiments, the contemplated CEACAM1 antibody or antigen-binding fragment thereof does not exhibit detectable binding to CEACAM3, CEACAM5, CEACAM6 and/or CEACAM8. In some embodiments, the contemplated CEACAM1 antibody or antigen-binding fragment thereof binds CEACAM1 with an affinity that is at least 10 times, such as at least 100 times, and at least 1000 times, and up to 10,000 times or more stronger than the affinity with which the contemplated CEACAM1 antibody or antigen-binding fragment thereof binds to another target or polypeptide.

As used herein, "affinity", represented by the equilibrium constant for the dissociation ($K_D$)) of an antigen with an antigen-binding protein, is a measure of the binding strength between an antigenic determinant and an antigen-binding site on the antigen-binding protein, such as an antibody or antibody fragment thereof. The smaller the value of the $K_D$, the stronger the binding strength between an antigenic determinant and the antigen-binding molecule. Alternatively, the affinity can also be expressed as the affinity constant ($K_A$), which is $1/K_D$). As will be clear to the skilled person, affinity can be determined in a manner known per se, depending on the specific antigen of interest.

In one aspect, the invention provides antibodies and antigen-binding fragments thereof, including the antibodies described herein by their structural characteristics, wherein the antibodies and antigen-binding fragments thereof specifically bind to at least part of the binding site on CEACAM1 for one or more other members of the CEACAM family, thereby blocking CEACAM1 interactions with the one or more other members of the CEACAM family. These CEACAM family members include, but are not limited to, CEACAM3, CEACAM5, CEACAM6, and CEACAM8 (Ramani et al, Anal. Biochem. Jan. 15, 2012; 420 (2); 127-38; Scheffrahn et al, J. Immunol. May 15, 2002; 168 (10); 5139-46).

In one aspect, the invention provides antibodies and antigen-binding fragments thereof, including the antibodies described herein by their structural characteristics, wherein the antibodies and antigen-binding fragments thereof specifically bind to at least part of the binding site on CEACAM1 for a member of the TIM family, thereby blocking CEACAM1 interaction with the TIM family member. In some embodiments, this TIM family member is TIM-1, TIM-3, or TIM-4. In some embodiments, the CEACAM1 antibody or antigen-binding fragment thereof specifically binds to one or more of CEACAM1 residues Y34, G41, N42, Q44, Q89, S93, D94, V96, and/or N97 of SEQ ID NO: 17, residues which have been indicated to be involved in CEACAM1 binding to TIM-3 (Huang et al., Nature. 2015 Jan. 15; 517 (7534): 386-90).

In one aspect, the invention provides antibodies and antigen-binding fragments thereof, including the antibodies described herein by their structural characteristics, wherein the antibodies and antigen-binding fragments thereof specifically bind to at least part of the binding site on CEACAM1 for a bacterial adhesive surface protein (adhesin), thereby blocking the interaction between CEACAM1 and the adhesin. In certain embodiments, the adhesin is expressed on the surface of a CEACAM1-binding pathogenic bacterium including, but not limited to, *Escherichia coli*, particularly Diffusively Adhering *Escherichia coli* (DAEC), *Neisseria gonorrhoeae, N. meningitidis*, commensal *Neisseria, Moraxella catarrhalis, Haemophilus influenza, Haemophilus aegyptius, Helicobacter pylori*, and or *Salmonella* sp.

In one embodiment, the CEACAM1 antibody or antigen-binding fragment thereof disrupts the interaction between CEACAM1 and HopQ expressed on the surface of *Helicobacter pylori*. In one embodiment, the CEACAM1 antibody or antigen-binding fragment specifically binds to one or more of CEACAM1 residues F29, Y34, N42, Q89, and N97, which have been predicted to be involved in CEACAM1 binding to HopQ.

In another embodiment, the CEACAM1 antibody or antigen-binding fragment thereof disrupts the interaction between CEACAM1 and an opacity-associated (Opa) adhesin protein expressed on the surface of *Neisseria* sp, including, but not limited to, $Opa_{52}$, $Opa_{65}$, $Opa_{68}$, $Opa_{70}$, $Opa_{72}$, $Opa_{73}$, $Opa_{74}$, and $Opa_{75}$. In one embodiment, the CEACAM1 antibody or antigen-binding fragment specifically binds to one or more of CEACAM1 residues Q44 and A49, which have been predicted to be involved in CEACAM1 binding to neisserial Opa proteins.

In another embodiment, the CEACAM1 antibody or antigen-binding fragment thereof disrupts the interaction between CEACAM1 and Opa-like protein OlpA expressed on the surface of *Moraxella* sp.

In one embodiment, the CEACAM1 antibody or antigen-binding fragment thereof disrupts the interaction between CEACAM1 and *Haemophilus influenza* OMP P1. In one embodiment, the CEACAM1 antibody or antigen-binding fragment specifically binds to one or more of CEACAM1 residues Q44 and A49, which have been predicted to be involved in CEACAM1 binding to *Haemophilus influenza* OMP P1.

In another embodiment, the CEACAM1 antibody or antigen-binding fragment thereof disrupts the interaction between CEACAM1 and *Haemophilus aegyptius* OMP P1. In one embodiment, the CEACAM1 antibody or antigen-binding fragment specifically binds to CEACAM1 residue F29, which has been predicted to be involved in CEACAM1 binding to *Haemophilus aegyptius* OMP P1.

In another embodiment, the CEACAM1 antibody or antigen-binding fragment thereof disrupts the interaction between CEACAM1 and *C. albicans*.

In another embodiment, the CEACAM1 antibody or antigen-binding fragment thereof disrupts the interaction between CEACAM1 and an influenza virus, including but not limited to H5N1.

In another embodiment, the invention provides methods of using the CEACAM1 antibodies or antigen-binding fragments thereof described herein for inhibiting binding of CEACAM1 to a filial nematode, the method comprising contacting CEACAM1 with a CEACAM1 antibody or antigen-binding fragment thereof described herein. In one embodiment, the filial nematode is *Wucheria bancrofti*.

Antibody Conjugates

In some embodiments of the aspects described herein, the antibody or antigen-binding fragment thereof that bind to CEACAM1 are conjugated to a functional moiety. Examples of useful functional moieties include, but are not limited to, a blocking moiety, a detectable moiety, a diagnostic moiety, a targeting, and a therapeutic moiety.

Exemplary blocking moieties include moieties of sufficient steric bulk and/or charge such that reduced glycosylation occurs, for example, by blocking the ability of a glycosidase to glycosylate the antibody or antigen-binding fragment thereof. The blocking moiety may additionally or alternatively, reduce effector function, for example, by inhibiting the ability of the Fc region to bind a receptor or complement protein. Preferred blocking moieties include cysteine adducts and PEG moieties.

In a preferred embodiment, the blocking moiety is a cysteine, preferably a cysteine that has associated with a free cysteine, e.g., during or subsequent to the translation of the Fc containing polypeptide, e.g., in cell culture. Other blocking cysteine adducts include cystine, mixed disulfide adducts, or disulfide linkages.

In another preferred embodiment, the blocking moiety is a polyalkylene glycol moiety, for example, a PEG moiety and preferably a PEG-maleimide moiety. Preferred pegylation moieties (or related polymers) can be, for example, polyethylene glycol ("PEG"), polypropylene glycol ("PPG"), polyoxyethylated glycerol ("POG") and other polyoxyethylated polyols, polyvinyl alcohol ("PVA") and other polyalkylene oxides, polyoxyethylated sorbitol, or polyoxyethylated glucose. The polymer can be a homopolymer, a random or block copolymer, a terpolymer based on the monomers listed above, straight chain or branched, substituted or unsubstituted as long as it has at least one active sulfone moiety. The polymeric portion can be of any length or molecular weight but these characteristics can affect the biological properties. Polymer average molecular weights particularly useful for decreasing clearance rates in pharmaceutical applications are in the range of 2,000 to 35,000 Daltons. In addition, if two groups are linked to the polymer, one at each end, the length of the polymer can impact upon the effective distance, and other spatial relationships, between the two groups. Thus, one skilled in the art can vary the length of the polymer to optimize or confer the desired biological activity. PEG is useful in biological applications for several reasons. PEG typically is clear, colorless, odorless, soluble in water, stable to heat, inert to many chemical agents, does not hydrolyze, and is nontoxic. Pegylation can improve pharmacokinetic performance of a molecule by increasing the molecule's apparent molecular weight. The increased apparent molecular weight reduces the rate of clearance from the body following subcutaneous or systemic administration. In many cases, pegylation can decrease antigenicity and immunogenicity. In addition, pegylation can increase the solubility of a biologically-active molecule.

Examples of detectable moieties which are useful in the methods and antibodies and antigen-binding fragments thereof contemplated by the invention include fluorescent moieties or labels, imaging agents, radioisotopic moieties, radiopaque moieties, and the like, e.g. detectable labels such as biotin, fluorophores, chromophores, spin resonance probes, or radiolabels. Exemplary fluorophores include fluorescent dyes (e.g. fluorescein, rhodamine, and the like) and other luminescent molecules (e.g. luminal). A fluorophore may be environmentally-sensitive such that its fluorescence changes if it is located close to one or more residues in the modified protein that undergo structural changes upon binding a substrate (e.g. dansyl probes). Exemplary radiolabels include small molecules containing atoms with one or more low sensitivity nuclei ($^{13}C$, $^{15}N$, $^{2}H$, $^{125}I$, $^{123}I$, $^{99}Tc$, $^{43}K$, $^{52}Fe$, $^{67}Ga$, $^{68}Ga$, $^{111}In$ and the like). Other useful moieties are known in the art.

Examples of diagnostic moieties which are useful in the methods and antibodies and antigen-binding fragments thereof contemplated by the invention include detectable moieties suitable for revealing the presence of a disease or disorder. Typically a diagnostic moiety allows for determining the presence, absence, or level of a molecule, for example, a target peptide, protein, or proteins, that is associated with a disease or disorder. Such diagnostics are also suitable for prognosing and/or diagnosing a disease or disorder and its progression.

Examples of therapeutic moieties which are useful in the methods and antibodies and antigen-binding fragments thereof contemplated by the invention include, for example, anti-inflammatory agents, anti-cancer agents, anti-neurodegenerative agents, anti-infective agents, or generally a therapeutic. The functional moiety may also have one or more of the above-mentioned functions.

Exemplary therapeutic moieties include radionuclides with high-energy ionizing radiation that are capable of causing multiple strand breaks in nuclear DNA, and therefore suitable for inducing cell death (e.g., of a cancer). Exemplary high-energy radionuclides include: $^{90}Y$, $^{125}I$, $^{131}I$, $^{123}I$, $^{111}In$, $^{105}Rh$, $^{153}Sm$, $^{67}Cu$, $^{67}Ga$, $^{166}Ho$, $^{177}Lu$, $^{186}Re$ and $^{188}Re$. These isotopes typically produce high-energy α- or β-particles which have a short path length. Such radionuclides kill cells to which they are in close proximity, for example neoplastic cells to which the conjugate has attached or has entered. They have little or no effect on non-localized cells and are essentially non-immunogenic.

Exemplary therapeutic moieties also include cytotoxic agents such as cytostatics (e.g. alkylating agents, DNA synthesis inhibitors, DNA-intercalators or cross-linkers, or DNA-RNA transcription regulators), enzyme inhibitors, gene regulators, cytotoxic nucleosides, tubulin binding agents, hormones and hormone antagonists, anti-angiogenesis agents, and the like.

Exemplary therapeutic moieties also include alkylating agents such as the anthracycline family of drugs (e.g., adriamycin, carminomycin, cyclosporin-A, chloroquine, methopterin, mithramycin, porfiromycin, streptonigrin, anthracenediones, and aziridines). In another embodiment, the chemotherapeutic moiety is a cytostatic agent such as a DNA synthesis inhibitor. Examples of DNA synthesis inhibitors include, but are not limited to, methotrexate and dichloromethotrexate, 3-amino-1,2,4-benzotriazine 1,4-dioxide, aminopterin, cytosine β-D-arabinofuranoside, 5-fluoro-5'-deoxyuridine, 5-fluorouracil, ganciclovir, hydroxyurea, actinomycin-D, and mitomycin C. Exemplary DNA-intercalators or cross-linkers include, but are not limited to, bleomycin, carboplatin, carmustine, chlorambucil, cyclophosphamide, cis-diammineplatinum (II) dichloride (cisplatin), melphalan, mitoxantrone, and oxaliplatin.

Exemplary therapeutic moieties also include transcription regulators such as actinomycin D, daunorubicin, doxorubicin, homoharringtonine, and idarubicin. Other exemplary cytostatic agents that are compatible with the present invention include ansamycin benzoquinones, quinonoid derivatives (e.g. quinolones, genistein, bactacyclin), busulfan, ifosfamide, mechlorethamine, triaziquone, diaziquone, carbazilquinone, indoloquinone EO9, diaziridinyl-benzoquinone methyl DZQ, triethylenephosphoramide, and nitrosourea compounds (e.g. carmustine, lomustine, semustine).

Exemplary therapeutic moieties also include cytotoxic nucleosides such as, for example, adenosine arabinoside, cytarabine, cytosine arabinoside, 5-fluorouracil, fludarabine, floxuridine, ftorafur, and 6-mercaptopurine; tubulin binding agents such as taxoids (e.g. paclitaxel, docetaxel, taxane), nocodazole, rhizoxin, dolastatins (e.g. Dolastatin-10, -11, or -15), colchicine and colchicinoids (e.g. ZD6126), combretastatins (e.g. Combretastatin A-4, AVE-6032), and vinca alkaloids (e.g. vinblastine, vincristine, vindesine, and vinorelbine (navelbine)); anti-angiogenesis compounds such as Angiostatin K1-3, DL-α-difluoromethyl-ornithine, endostatin, fumagillin, genistein, minocycline, staurosporine, and (+)-thalidomide.

Exemplary therapeutic moieties also include hormones and hormone antagonists, such as corticosteroids (e.g. prednisone), progestins (e.g. hydroxyprogesterone or medroprogesterone), estrogens, (e.g. diethylstilbestrol), antiestrogens (e.g. tamoxifen), androgens (e.g. testosterone), aromatase inhibitors (e.g. aminogluthetimide), 17-(allylamino)-17-demethoxygeldanamycin, 4-amino-1,8-naphthalimide, apigenin, brefeldin A, cimetidine, dichloromethylene-diphosphonic acid, leuprolide (leuprorelin), luteinizing hormone-releasing hormone, pifithrin-α, rapamycin, sex hormone-binding globulin, and thapsigargin.

Exemplary therapeutic moieties also include enzyme inhibitors such as, S(+)-camptothecin, curcumin, (−)-deguelin, 5,6-dichlorobenz-imidazole 1-β-D-ribofuranoside, etoposide, formestane, fostriecin, hispidin, 2-imino-1-imidazolidineacetic acid (cyclocreatine), mevinolin, trichostatin A, tyrphostin AG 34, and tyrphostin AG 879.

Exemplary therapeutic moieties also include gene regulators such as 5-aza-2'-deoxycytidine, 5-azacytidine, cholecalciferol (vitamin D3), 4-hydroxytamoxifen, melatonin, mifepristone, raloxifene, trans-retinal (vitamin A aldehydes), retinoic acid, vitamin A acid, 9-cis-retinoic acid, 13-cis-retinoic acid, retinol (vitamin A), tamoxifen, and troglitazone.

Exemplary therapeutic moieties also include cytotoxic agents such as, for example, the pteridine family of drugs, diynenes, and the podophyllotoxins. Particularly useful members of those classes include, for example, methopterin, podophyllotoxin, or podophyllotoxin derivatives such as etoposide or etoposide phosphate, leurosidine, vindesine, leurosine and the like.

Still other cytotoxins that are compatible with the teachings herein include auristatins (e.g. auristatin E and monomethylauristan E), calicheamicin, gramicidin D, maytansanoids (e.g. maytansine), neocarzinostatin, topotecan, taxanes, cytochalasin B, ethidium bromide, emetine, tenoposide, colchicin, dihydroxy anthracindione, mitoxantrone, procaine, tetracaine, lidocaine, propranolol, puromycin, and analogs or homologs thereof.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

To increase the half-life of the antibodies or polypeptide containing the amino acid sequences described herein, one can attach a salvage receptor binding epitope to the antibody or antigen-binding fragment thereof (especially an antibody fragment), as described, e.g., in U.S. Pat. No. 5,739,277. The term "salvage receptor binding epitope" may refer to an epitope of the Fc region of an IgG molecule (e.g., IgG1, IgG2, IgG3, or IgG4) that is responsible for increasing the in vivo serum half-life of the IgG molecule (e.g., Ghetie et al., 18 Ann. Rev. Immunol. 739 (2000). Antibodies with substitutions in an Fc region thereof and increased serum half-lives are also described in WO 00/42072, WO 02/060919; Shields et al., 276 J. Biol. Chem. 6591 (2001); Hinton, 279 J. Biol. Chem. 6213-6216 (2004). For example, a nucleic acid molecule encoding the salvage receptor binding epitope can be linked in frame to a nucleic acid encoding a polypeptide sequence described herein so that the fusion protein expressed by the engineered nucleic acid molecule comprises the salvage receptor binding epitope and a polypeptide sequence described herein. In another embodiment, the serum half-life can also be increased, for example, by attaching other polypeptide sequences. For example, antibodies or antigen-binding fragments thereof useful in the methods of the invention can be attached to serum albumin or a portion of serum albumin that binds to the CEACAM1 receptor or a serum albumin binding peptide so that serum albumin binds to the antibody or antigen-binding fragment thereof, e.g., such polypeptide sequences are disclosed in WO 01/45746. In one embodiment, the half-life of a Fab is increased by these methods. See also, Dennis et al., 277 J. Biol. Chem. 35035 (2002), for additional serum albumin binding peptide sequences.

Other types of functional moieties are known in the art and can be readily used in the methods and compositions of the present invention based on the teachings contained herein.

Nucleic Acids

Also provided herein are nucleic acids encoding CEACAM1 antibodies and antigen-binding fragments thereof, as well as vectors, host cells, and expression systems. The term "nucleic acid" as used herein refers to a polymeric form of nucleotides of any length, either ribonucleotides or desoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases.

The nucleic acids encoding CEACAM1 antibodies and antigen-binding fragments thereof may be, e.g., DNA, cDNA, RNA, synthetically produced DNA or RNA, or a recombinantly produced chimeric nucleic acid molecule comprising any of those polynucleotides either alone or in combination. For example, provided is an expression vector comprising a polynucleotide sequence encoding a CEACAM1 antibody or antigen-binding fragment thereof described herein operably linked to expression control sequences suitable for expression in a eukaryotic and/or prokaryotic host cell.

The term "vector" refers to a nucleic acid molecule capable of transporting another nucleic acid to which it has been linked. A "vector" includes, but is not limited to, a viral vector, a plasmid, a RNA vector or a linear or circular DNA or RNA molecule which may consists of a chromosomal, non-chromosomal, semi-synthetic or synthetic nucleic acids. In some embodiments, the employed vectors are those capable of autonomous replication (episomal vector) and/or expression of nucleic acids to which they are linked (expression vectors). Large numbers of suitable vectors are known to those of skill in the art and commercially available. Viral vectors include retrovirus, adenovirus, parvovirus (e.g., adeno associated viruses, AAV), coronavirus, negative strand RNA viruses such as orthomyxovirus (e.g., influenza virus), rhabdovirus (e. g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, and spumavirus.

A variety of expression vectors have been developed for the efficient synthesis of antibodies and antigen-binding fragments thereof in prokaryotic cells such as bacteria and in eukaryotic systems, including but not limited to yeast and mammalian cell culture systems have been developed. The vectors can comprise segments of chromosomal, non-chromosomal and synthetic DNA sequences. Also provided are cells comprising expression vectors for the expression of the contemplated CEACAM1 antibodies or antigen-binding fragments thereof.

Antibody Preparation and Expression Systems

The antibodies or antigen-binding fragments thereof of the invention are typically produced by recombinant expression. Nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the cross-reacting antibodies.

These expression vectors are typically replicable in the host organisms either as episomes or as an integral part of the host chromosomal DNA. Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362).

The expression of the antibodies and antigen-binding fragments contemplated by the invention can occur in either prokaryotic or eukaryotic cells. Suitable hosts include bacterial or eukaryotic hosts, including yeast, insects, fungi, bird and mammalian cells either in vivo, or in situ, or host cells of mammalian, insect, bird or yeast origin. The mammalian cell or tissue can be of human, primate, hamster, rabbit, rodent, cow, pig, sheep, horse, goat, dog or cat origin, but any other mammalian cell may be used.

E. coli is one prokaryotic host particularly useful for cloning the polynucleotides (e.g., DNA sequences) of the present invention. Other microbial hosts suitable for use include bacilli, such as Bacillus subtilus, and other enterobacteriaceae, such as Salmonella, Serratia, and various Pseudomonas species.

Other microbes, such as yeast, are also useful for expression. Saccharomyces and Pichia are exemplary yeast hosts, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for methanol, maltose, and galactose utilization.

Further, by use of, for example, the yeast ubiquitin hydrolase system, in vivo synthesis of ubiquitin-transmembrane polypeptide fusion proteins can be accomplished. The fusion proteins so produced can be processed in vivo or purified and processed in vitro, allowing synthesis of a CEACAM1 antibody or antigen-binding fragment thereof of the present invention with a specified amino terminus sequence. Moreover, problems associated with retention of initiation codon-derived methionine residues in direct yeast (or bacterial) expression maybe avoided. Sabin et al., 7 Bio/Technol. 705 (1989); Miller et al., 7 Bio/Technol. 698 (1989).

Any of a series of yeast gene expression systems incorporating promoter and termination elements from the actively expressed genes coding for glycolytic enzymes produced in large quantities when yeast are grown in mediums rich in glucose can be utilized to obtain recombinant CEACAM1 antibodies or peptides of the present invention. Known glycolytic genes can also provide very efficient transcriptional control signals. For example, the promoter and terminator signals of the phosphoglycerate kinase gene can be utilized.

Production of CEACAM1 antibodies or antigen-binding fragments thereof in insects can be achieved. For example, by infecting the insect host with a baculovirus engineered to express a transmembrane polypeptide by methods known to those of skill. See Ausubel et al., 1987, 1993.

In addition to microorganisms, mammalian tissue culture may also be used to express and produce the antibodies or antigen-binding fragments thereof of the present invention (e.g., polynucleotides encoding immunoglobulins or fragments thereof). See Winnacker, From Genes to Clones, VCH Publishers, N.Y., N.Y. (1987). Eukaryotic cells are actually preferred, because a number of suitable host cell lines capable of secreting heterologous proteins (e.g., intact immunoglobulins) have been developed in the art, and include CHO cell lines, various COS cell lines, HeLa cells, 293 cells, myeloma cell lines, transformed B-cells, and hybridomas. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. See Co et al., J. Immunol. 148:1149 (1992).

Alternatively, nucleotide sequences encoding antibodies or antigen-binding fragments thereof can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for light and/or heavy chains in operable linkage with a promoter and enhancer from a mammary gland specific gene, such as casein or beta lactoglobulin.

Additionally, plants have emerged as a convenient, safe and economical alternative main-stream expression systems for recombinant antibody production, which are based on large scale culture of microbes or animal cells. Antibodies or antigen-binding fragments thereof can be expressed in plant cell culture, or plants grown conventionally. The expression in plants may be systemic, limited to sub-cellular plastids, or limited to seeds (endosperms). See, e.g., U.S. Patent Pub. No. 2003/0167531; U.S. Pat. Nos. 6,080,560 and 6,512,162; and WO 0129242. Several plant-derived antibodies have reached advanced stages of development, including clinical trials (see, e.g., Biolex, NC).

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., Molecular Cloning: A Laboratory Manual (Cold Spring Harbor Press, 2nd ed., 1989). Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

The antibodies and antigen-binding fragments thereof of the invention can be expressed using a single vector or two vectors. When the antibody heavy and light chains are cloned on separate expression vectors, the vectors are co-transfected to obtain expression and assembly of intact immunoglobulins. Once expressed, the whole antibodies, their dimers, individual light and heavy chains, or other immunoglobulin forms of the present invention can be purified according to standard procedures of the art, including ammonium sulfate precipitation, affinity columns, column chromatography, HPLC purification, gel electrophoresis and the like (see generally Scopes, Protein Purification (Springer-Verlag, N.Y., (1982)). Substantially pure immunoglobulins of at least about 90 to 95% homogeneity are preferred, and 98 to 99% or more homogeneity most preferred, for pharmaceutical uses.

Methods for Modulating CEACAM1 Activity

In one aspect, the invention provides methods of using the antibodies and antigen-binding fragments thereof described herein for decreasing the interaction between CEACAM1 and another member of the CEACAM family, including, but not limited to, CEACAM1, CEACAM3, CEACAM5, CEACAM6, and CEACAM8. In some embodiments, the antibody or antigen-binding fragment thereof disrupts the homophilic interaction between CEACAM1 monomers.

In another aspect, the invention provides methods of using the antibodies and antigen-binding fragments thereof of the invention for decreasing the interaction between CEACAM1 and a member of the TIM family, including but not limited to TIM-1, TIM-3, and TIM-4. In some embodiments, the antibody or antigen-binding fragment thereof disrupts the heterophilic interaction between CEACAM1 and TIM-3. Disruption of the interaction between CEACAM1 and TIM-3 by using the antibodies and antigen-binding fragments thereof contemplated by the invention may reverse CEACAM1 inhibitory functions while maintain TIM-3 activating functions.

The embodiments of the invention are useful for reducing immunosuppression, e.g., T cell tolerance. By "reducing" is meant the ability to cause an overall decrease of about 20% or greater, 30% or greater, 40% or greater, 45% or greater, 50% or greater, of 55% or greater, of 60% or greater, of 65% or greater, of 70% or greater, or 75%, 80%, 85%, 90%, 95%, or greater, as compared to a control that is not treated. Immunosuppression can be mediated by immune inhibitory receptors expressed on the surface of an immune cell, and their interactions with their ligands. For example, cytotoxic CD8 T cells can enter a state of "functional exhaustion," or "unresponsiveness" whereby they express inhibitory receptors that prevent antigen-specific responses, such as proliferation and cytokine production. Accordingly, by inhibiting the activity and/or expression of such inhibitory receptors, an immune response to a cancer or tumor that is suppressed, inhibited, or unresponsive, can be enhanced or uninhibited. Such enhancements or reversal of inhibition of the immune response can lead to greater T cell activity, responsiveness, and/or ability or receptiveness with regards to activation.

Methods of measuring T cell activity are known in the art. By way of non-limiting example, T cell tolerance can be induced by contacting T cells with recall antigen, anti-CD3 in the absence of costimulation, and/or ionomycin. Levels of, e.g., IL-27, LDH-A, RAB10, and/or ZAP70 (both intracellular or secreted) can be monitored, for example, to determine the extent of T cell tolerogenesis (with levels of IL-2, interferon-γ and TNF correlating with increased T cell tolerance). The response of cells pre-treated with, e.g. ionomycin, to an antigen can also be measured in order to determine the extent of T cell tolerance in a cell or population of cells, e.g., by monitoring the level of secreted and/or intracellular IL-2 and/or TNF-α (see, e.g., Macian et al. Cell 2002 109:719-731). Other characteristics of T cells having undergone adaptive tolerance include increased levels of Fyn and ZAP-70/Syk, Cbl-b, GRAIL, Ikaros, CREM (CAMP response element modulator), B lymphocyte-induced maturation protein-1 (Blimp-1), PD1, CD5, and SHP2; increased phosphorylation of ZAP-70/Syk, LAT, PLCyl/2, ERK, PKC-Θ/IKBA; increased activation of intracellular calcium levels; decreased histone acetylation or hypoacetylation and/or increased CpG methylation at the IL-2 locus. Thus, in some embodiments, one or more of any of these parameters can be assayed to determine whether the antibodies or antigen-binding fragments thereof disclosed herein that inhibit CEACAM1 decrease immune tolerance.

Reduction of T cell tolerance can also be assessed by examination of tumor infiltrating lymphocytes or T lymphocytes within lymph nodes that drain from an established tumor. Such T cells exhibit features of "exhaustion" through expression of cell surface molecules such as PD1, TIM-3 or LAG-3, for example, and decreased secretion of cytokines such as interferon-γ. Accordingly, evidence that T cell tolerance has been reduced in the presence of a CEACAM1 antibodies or antigen-binding fragments thereof includes, e.g., increased quantities of T cells with (a) antigen specificity for tumor associated antigens (e.g., as determined by major histocompatibility complex class I or class II tetramers which contain tumor associated peptides) and (b) the capability of secreting high levels of interferon-γ and cytolytic effector molecules such as granzyme-B, relative to that observed in the absence of the inhibitory agent.

The CEACAM1 antibodies and antigen-binding fragments thereof are further useful for enhancing T cell expansion, activation, and proliferation.

In another aspect, the invention provides methods of using the antibodies and antigen-binding fragments thereof of the invention for decreasing the interaction between CEACAM1 and bacterial adhesins. In some embodiments, the antibodies and antigen-binding fragments thereof of the invention are effective in reducing and/or preventing the colonization of mammalian epithelia. In some embodiments, the adhesins are expressed by *Escherichia coli*, particularly Diffusively Adhering *Escherichia coli* (DAEC), *Neisseria gonorrhoeae*, *N. meningitidis*, commensal *Neisseria*, *Moraxella catarrhalis*, *Haemophilus influenza*, *Haemophilus aegyptius*, *Helicobacter pylori*, and/or *Salmonella* sp. In one embodiment, the CEACAM1 antibody or antigen-binding fragment thereof disrupts the interaction between CEACAM1 and HopQ expressed on the surface of *Helicobacter pylori*. In another embodiment, the CEACAM1 antibody or antigen-binding fragment thereof disrupts the interaction between CEACAM1 and opacity-associated (Opa) adhesin proteins expressed on the surface of *Neisseria* sp. In another embodiment, the CEACAM1 antibody or antigen-binding fragment thereof disrupts the interaction between CEACAM1 and OMP adhesin proteins expressed on the surface of *Haemophilus* sp.

In one embodiment, the CEACAM1 antibody or antigen-binding fragment thereof disrupts the interaction between CEACAM1 and *C. albicans*. In one embodiment, the CEACAM1 antibody or antigen-binding fragment thereof disrupts the interaction between CEACAM1 and influenza virus, including but not limited to H5N1. In one embodiment, the invention provides methods of using the CEACAM1 antibodies or antigen-binding fragments thereof described herein for inhibiting binding of CEACAM1 to a filial nematode. In one embodiment, the filial nematode is *Wucheria bancrofti*.

Methods of Treatment

In one aspect, the invention provides for CEACAM1 antibodies and antigen-binding fragments thereof that are also useful for the treatment of subjects in need thereof.

In the methods described herein, a therapeutically effective amount of an antibody or antigen-binding portions thereof set forth herein is administered to a mammal in need thereof. Although antibodies or antigen-binding portions thereof set forth herein are particularly useful for administration to humans, they may be administered to other mammals as well. The term "mammal" as used herein is intended to include, but is not limited to, humans, laboratory animals, domestic pets and farm animals. "Therapeutically effective amount" means an amount of antibody or antigen-binding portions thereof set forth herein that, when administered to a mammal, is effective in producing the desired therapeutic effect.

In some aspects, the antibody or antigen-binding fragment thereof binds to CEACAM1 expressed by an exhausted T cell or natural killer (NK) cells, thereby recovering T cell and NK cell activity and leading to increased anti-tumor responses. In other aspects, the antibody or antigen-binding fragment thereof binds to CEACAM1 expressed by a tumor cell, thereby inhibiting tumor cell metastasis and the formation of a cancer stem cell niche. In yet another aspects, the antibody or antigen-binding fragment thereof binds to CEACAM1 expressed by macrophage associated with fibrosis in the tumor environment thereby inhibiting fibrosis. In another aspects, the antibody or antigen-binding fragment thereof binds to CEACAM1 expressed by other stromal cells in the tumor microenvironment such as vascular endothelium cells, thereby inhibiting angiogenesis.

As such, also provided herein are methods of treating a subject having a cancer or tumor and/or reducing tumor growth, comprising administering an effective amount of a CEACAM1-antibody or antigen-binding fragment thereof provided herein. "Reducing" includes inhibiting and/or reversing and can refer to, for example, the symptoms of the disorder being treated, the presence or size of metastases or micrometastases, the size of the primary tumor, the presence or the size of the dormant tumor.

The term "cancer" refers to or describes the physiological condition in mammals that is typically characterized by unregulated cell growth. Included in this definition are benign and malignant cancers, as well as dormant tumors or micrometastases. Accordingly, the term "cancer" as used herein refers to an uncontrolled growth of cells, which interferes with the normal functioning of the bodily organs and systems, including cancer stem cells and tumor vascular niches. A subject that has a cancer is a subject having objectively measurable cancer cells present in the subject's body. Included in this definition are benign and malignant cancers, as well as dormant tumors or micrometastases. Cancers that migrate from their original location and seed vital organs can eventually lead to the death of the subject through the functional deterioration of the affected organs. Hematopoietic cancers, such as leukemia, are able to out-compete the normal hematopoietic compartments in a subject, thereby leading to hematopoietic failure (in the form of anemia, thrombocytopenia and neutropenia) ultimately causing death.

By "subject" is meant a mammal, including, but not limited to, a human or non-human mammal, such as a bovine, equine, canine, ovine, or feline, etc. Individuals and patients are also subjects herein.

The terms "treat," "treated," "treating," or "treatment" as used herein refer to therapeutic treatment, wherein the object is to slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. The terms "prevent", "prevention", and the like refer to acting prior to overt disease or disorder onset, to prevent the disease or disorder from developing or to minimize the extent of the disease or disorder, or slow its course of development.

The embodiments of the invention may be used for treating metastasis, which relates to the spreading of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant. Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Also contemplated are methods of reducing cancer stemness comprising the administration of the CEACAM1 antibodies or antigen-binding fragments thereof disclosed herein. Cancer stemness may refer to the ability of a cell to self-renew and to generate an additional, phenotypically distinct cell type. Cancer stem cells (CSCs) are cancer cells that exhibit stem-cell like properties. CSCs often exhibit at least one hallmark of cancer, and is capable of generating at least one additional, phenotypically distinct cell type. Furthermore, cancer stem cells are capable of both asymmetric and symmetric replication. It is appreciated that a cancer stem cell may result from differentiated cancer cells that acquire stemness traits and/or stem cells that acquire phenotypes associated with cancer cells. Alternatively, cancer stem cells can reconstitute non-stromal cell types within a tumor.

CEACAM1 is expressed by many tumor types and CEACAM1 may regulate the growth and metastatic behavior of the tumor. In another embodiment, CEACAM1 inhibition will decrease tumor growth and metastasis.

CEACAM1 expression on subsets of macrophages is associated with fibrosis during carcinogenesis. In a further embodiment, CEACAM1 inhibition will decrease tumor-associated fibrosis.

Cancers that may be treated by the compositions and methods contemplated by the invention include tumors that are not vascularized, or not yet substantially vascularized, as well as vascularized tumors. The cancers may comprise nonsolid tumors (such as hematological tumors, for example, leukemias and lymphomas) or may comprise solid tumors. Types of cancers to be treated include, but are not limited to benign and malignant tumors, and malignancies e.g., sarcomas, carcinomas, and melanomas. Adult tumors/cancers and pediatric tumors/cancers are also included. Examples of cancer include but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglubinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. A patient can have more than one type of cancer.

The efficacy of the treatment methods for cancer comprising therapeutic formulations of the compositions comprising the antibodies and antigen-binding fragments thereof described herein can be measured by various endpoints commonly used in evaluating cancer treatments, including but not limited to, tumor regression, tumor weight or size shrinkage, time to progression, duration of survival, progression free survival, overall response rate, duration of response, and quality of life. In the case of cancers, the therapeutically effective amount of the recombinant CEACAM1-antibody or antigen-binding fragment thereof can reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. In cases where a patient has more than one type of cancer, the therapeutically effective amount of the recombinant CEACAM1-antibody or antigen-binding fragment thereof is an amount effective in treating at least one of the cancers. To the extent the recombinant CEACAM1-antibody or antigen binding-fragment thereof acts to prevent growth and/or kill existing cancer cells, it can be cytostatic and/or cytotoxic. For cancer therapy, efficacy in vivo can, for example, be measured by assessing the duration of survival, duration of progression free survival (PFS), the response rates (RR), duration of response, and/or quality of life.

Checkpoint proteins interact with specific ligands that send a signal into the T cell and switch off or inhibit T cell function. By expressing high levels of checkpoint proteins on their surface, cancer cells can control the function of T cells that enter the tumor microenvironment, thus suppressing the anticancer immune response. The immune checkpoint protein Programmed Death-1 (PD-1) is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to downregulate T cell activation and cytokine secretion upon binding to PD-1 (Freeman et al., 2000; Latchman et al., 2001). Inhibition of the PD-1/PD-L1 interaction can promote potent antitumor activity. Examples of PD-1 inhibitors include, but are not limited to, Pembrolizumab (MK-3475), Nivolumab (MDX-1106), Cemiplimab-rwlc (REGN2810), Pidilizumab (CT-011), Spartalizumab (PDR001), tislelizumab (BGB-A317), PF-06801591, AK105, BCD-100, BI 754091, JS001, LZM009, MEDI0680, MGA012, Sym021, TSR-042. Examples of PD-L1 inhibitors include, but are not limited to, Atezolizumab (MPDL3280A), Durvalumab (MEDI4736), Avelumab (MSB0010718C), BGB-A333, CK-301, CS1001, FAZ053, KN035, MDX-1105, MSB2311, SHR-1316.

However, there is a significant population of cancer patients receiving checkpoint inhibitor therapy that (1) fail to respond to this type of therapy (innate or primary resistance) or that (2) initially respond but eventually develop disease progression (secondary or acquired resistance). Resistant cancer may also be referred to as refractory cancer. As shown in the Examples below, tumor associated cells isolated from patients with acquired resistance to PD-1/PD-L1 inhibitors upregulate CEACAM1 expression relative tumor associated cells isolated from naïve patients, that had not been exposed to PD-1 inhibitors. When CEACAM1 is expressed in the setting of acquired resistance, the CEACAM1 bearing cells are more like likely to be effector memory rather than central memory cells, consistent with a reduction of an anti-cancer response in the resistant patients.

As such, also provided herein are methods of using CEACAM1 antibodies and antigen-binding fragments thereof, including, but not limited to the specific CEACAM1 antibodies and antigen-binding fragments thereof provided herein, for the treatment of patients with resistance to checkpoint inhibitors such as inhibitors of PD-1, PD-L1, and/or CTLA-4. In some embodiments, the CEACAM1 antibody used in the treatment of patients with resistance to inhibitors of PD-1, PD-L1, and/or CTLA-4 is CP08H03/Vk8 S29A or CP08H03/CP08F05. In some embodiments, the resistance is innate or primary resistance. In some embodiments, the resistance is secondary or acquired resistance. In some embodiments, the administered CEACAM1 antibodies, including, but not limited to the CEACAM1 antibodies and antigen-binding fragments thereof provided herein, reverse T cell exhaustion in patients resistant to checkpoint inhibitor therapy. Any cancer exhibiting PD-1, PDL-1 and/or CTLA-4 resistance is suitable for treatment with the methods of the invention. In some embodiments, the CEACAM1 antibody or antigen-binding fragment is administered to a patient that has not previously receive checkpoint inhibitor therapy.

In another aspect, the invention provides for the use of the CEACAM1 antibodies and antigen-binding fragments provided herein in the treatment of patients with resistance to therapy with other checkpoint inhibitors, including but not limited to, inhibitors of PD-L2, B7-H3, B7-H4, BTLA, HVEM, GAL9, LAG3, TIM-3, VISTA, KIR, 2B4 (belongs to the CD2 family of molecules and is expressed on all NK, γδ, and memory CD8$^+$ (αβ) T cells), CD160 (also referred to as BY55), CGEN-15049, CHK1 and CHK2 kinases, A2aR and various B-7 family ligands (including, but are not limited to, B7-1, B7-2, B7-DC, B7-H1, B7-H2, B7-H3, B7-H4, B7-H5, B7-H6 and B7-H7).

In another aspect, the invention provides methods of using the CEACAM1 antibodies and antigen-binding fragments thereof disclosed herein for the treatment of a subject in need of reducing and/or preventing the colonization of mammalian epithelia with *Candida albicans* and/or bacteria expressing bacterial adhesins (including, but not limited to, *Escherichia coli*, particularly Diffusively Adhering *Escherichia coli* (DAEC), *Neisseria gonorrhoeae, N. meningitidis*, commensal *Neisseria, Moraxella catarrhalis, Haemophilus influenza, Haemophilus aegyptius, Helicobacter pylori*, and/or *Salmonella* sp,). In another aspect, the invention provides methods of using the CEACAM1 antibodies and antigen-binding fragments thereof disclosed herein for reducing replication of an influenza virus and/or for reducing the release of pro-inflammatory cytokines or chemokines associated with an infection with an influenza virus. In some embodiments, the influenza virus is H5N1. In another aspect, the invention provides methods of using the CEACAM1 antibodies and antigen-binding fragments thereof disclosed herein for the treatment of a subject in need of reducing and/or preventing the infection with a filial nematode such as *Wucheria bancrofti*. In another aspect, the invention provides methods of using the CEACAM1 antibodies and antigen-binding fragments thereof disclosed herein for the treatment of a subject in need of reducing and/or preventing the development of lymphedema and/or hydrocele associated with an infection with a filial nematode such as *Wucheria bancrofti*. In one embodiment, the invention provides methods of using the CEACAM1 antibodies or antigen-binding fragments thereof described herein for reducing invasion of a subject's lymphatic system with a filarial worm in a subject in need thereof. In one embodiment, the filial nematode is *Wucheria bancrofti*. A subject may be infected with more than one of a bacterium expressing a bacterial adhesin, *Candida albicans*, an influenza virus and/or a filial nematode.

In another embodiment, the invention provides methods of using the CEACAM1 antibodies or antigen-binding fragments thereof described herein for reducing the invasion of a subject's lymphatic system with cancer cells in a subject in need thereof.

Screening Methods

Provided herein are also methods of identifying patent populations who are likely to respond to treatment with the CEACAM1 antibodies and antibody-fragments provided herein, including but not limited to, CP08H03/Vk8 S29A and CP08H03/CP08F05.

In some embodiments, a cancer patient is screened for CEACAM1 expression on certain cell types, including T cells, NK cells, tumor cells, or other cells in the tumor microenvironment such as macrophages. In some embodiments, cancer patients that show an increased expression of CEACAM1 on certain cell types as compared to a control are selected for treatment with the CEACAM1 antibodies and antibody-fragments provided herein. A "control" level of CEACAM1 expression can refer to the level of CEACAM1 expression in one or more individuals to do not have cancer. The level may be measured on an individual-by-individual basis, or on an aggregate basis such as an average. In some embodiments, the control level of CEACAM1 expression from the same individual whose condition is being monitored, but is obtained at a different time. In certain embodiments, a "control" level can refer to a level obtained from the same patient at an earlier time, e.g., weeks, months, or years earlier. In some embodiment, the control level is obtained from a patient before the patient received any cancer therapy. In some embodiment, the control level is obtained from a patient before the patient received treatment with a checkpoint inhibitor.

In some embodiments, CEACAM1 expression is determined for patients resistant to checkpoint inhibitor therapy, including, but not limited to therapy with PD-1/PD-L1/CTLA-4 inhibitors. In some embodiments, patients that are resistant to checkpoint inhibitor therapy and that show an increased expression of CEACAM1 on certain cell types as compared to a control are selected for treatment with the CEACAM1 antibodies and antibody-fragments provided herein, including but not limited to, CP08H03/Vk8 S29A and CP08H03/CP08F05.

In some embodiments, a patient is assayed for an allelic variant of human CEACAM1. Based on which allelic variant of human CEACAM1 the patient expresses, more or less anti-CEACAM1 antibody may be administered to the patient as compared to a patient expressing the wildtype variant of CEACAM1. In some embodiments, the patient is assayed for the presence of a Y34C, a Q44L, and/or a Q89H allelic variant of CEACAM1. In some embodiments, a patient that is found to express a Y34C, a Q44L, and/or a Q89H allelic variant of CEACAM1 is administered a higher and/or a more frequent dose of an anti-CEACAM1 antibody as compared to a patient expressing the wildtype variant of CEACAM1.

Pharmaceutical Compositions

In another aspect, the present invention provides pharmaceutically acceptable compositions that comprise a therapeutically effective amount of a CEACAM1 antibody or antigen-binding fragment thereof is described herein formulated together with one or more pharmaceutically acceptable excipients.

The dosage of active agent(s) may vary, depending on the reason for use, the individual subject, and the mode of administration. The dosage may be adjusted based on the subject's weight, the age and health of the subject, and tolerance for the compound(s) or composition. For example, depending on the disease, for an antibody or antigen-binding fragment thereof, this may require 0.1, 1.0, 3.0, 6.0, or 10.0 mg/Kg. For an IgG having a molecular mass of 150,000 g/mole (two binding sites), these doses correspond to approximately 18 nM, 180 nM, 540 nM, 1.08 µM, and 1.8 UM of binding sites for a 5 L blood volume.

The active agent and excipient(s) may be formulated into compositions and dosage forms according to methods known in the art. The pharmaceutical compositions of the present invention may be specially formulated in solid or liquid form, including those adapted for parenteral administration, for example, by subcutaneous, intratumoral, intramuscular or intravenous injection as, for example, a sterile solution or suspension.

Therapeutic compositions comprising antibodies or antigen-binding fragments thereof that bind to CEACAM1 may formulated with one or more pharmaceutically-acceptable excipients, which can be a pharmaceutically-acceptable material, composition or vehicle, such as a liquid or solid filler, diluent, carrier, manufacturing aid (e.g., lubricant, talc magnesium, calcium or zinc stearate, or steric acid), solvent or encapsulating material, involved in carrying or transporting the therapeutic compound for administration to the subject, bulking agent, salt, surfactant and/or a preservative. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; gelatin; talc; waxes; oils, such as peanut oil, cottonseed oil, safflower oil, sesame oil, olive oil, corn oil and soybean oil; glycols, such as ethylene glycol and propylene glycol; polyols, such as glycerin, sorbitol, mannitol and polyethylene glycol; esters, such as ethyl oleate and ethyl laurate; agar; buffering agents; water; isotonic saline; pH buffered solutions; and other non-toxic compatible substances employed in pharmaceutical formulations.

A bulking agent is a compound which adds mass to a pharmaceutical formulation and contributes to the physical structure of the formulation in lyophilized form. Suitable bulking agents according to the present invention include mannitol, glycine, polyethylene glycol and sorbitol.

The use of a surfactant can reduce aggregation of the reconstituted protein and/or reduce the formation of particulates in the reconstituted formulation. The amount of surfactant added is such that it reduces aggregation of the reconstituted protein and minimizes the formation of particulates after reconstitution. Suitable surfactants according to the present invention include polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and polyethyl glycol, polypropyl glycol, and copolymers of ethylene and propylene glycol (e.g. Pluronics, PF68, etc.).

Preservatives may be used in formulations of invention. Suitable preservatives for use in the formulation of the invention include octadecyldimethylbenzyl ammonium chloride, hexamethonium chloride, benzalkonium chloride (a mixture of alkylbenzyl-dimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. Other suitable excipients can be found in standard pharmaceutical texts, e.g. in "Remington's Pharmaceutical Sciences", The Science and Practice of Pharmacy, 19th Ed. Mack Publishing Company, Easton, Pa., (1995).

The compositions comprising an antibody or antigen-binding fragment thereof and a pharmaceutically acceptable carrier may comprise the CEACAM1 antibodies or antigen-binding portions thereof set forth herein at various concentrations. For example, the compositions may comprise an antibody or antigen-binding fragment thereof at 10 mg/ml to 200 mg/ml, 25 mg/ml to 130 mg/ml, 50 mg/ml to 125 mg/ml, 75 mg/ml to 110 mg/ml, or 80 mg/ml to 100 mg/ml. The compositions also may comprise an antibody or antigen-binding fragment thereof at about 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 110 mg/ml, 120 mg/ml, 130 mg/ml, 140 mg/ml, or 150 mg/ml.

In some embodiments, the compositions comprising the antibody or antigen-binding fragment thereof and the pharmaceutically acceptable carrier are lyophilized and provided in a composition for reconstitution prior to administration.

Methods of Administration

Therapeutic compositions comprising the contemplated antibody or antigen-binding fragment thereof may be administered in any convenient manner, including by injection, transfusion, implantation or transplantation. The compositions described herein may be administered to a patient subcutaneously, intradermally, intratumorally, intranodally, intramedullary, intramuscularly, intracranially, by intravenous or intralymphatic injection, or intraperitoneally. In one embodiment, the cell compositions of the present invention are preferably administered by intravenous injection.

In certain embodiments, the antibody or antigen-binding fragment thereof is administered to the mammal by intravenous infusion, i.e., introduction of the antibody or antigen-binding fragment thereof into the vein of a mammal over a certain period of time. In certain embodiments, the period of time is about 5 minutes, about 10 minutes, about 30 minutes, about 1 hour, about 2 hours, about 4 hours, or about 8 hours.

In certain embodiments, a dose of a compound or a composition is administered to a subject every day, every other day, every couple of days, every third day, once a week, twice a week, three times a week, once every two weeks, or once a month. In other embodiments, two, three or four doses of a compound or a composition is administered to a subject every day, every couple of days, every third day, once a week, once every two weeks or once a month. In some embodiments, a dose(s) of a compound or a composition is administered for 2 days, 3 days, 5 days, 7 days, 14 days, 21 days or 28 days. In certain embodiments, a dose of a compound or a composition is administered for 1 month, 1.5 months, 2 months, 2.5 months, 3 months, 4 months, 5 months, 6 months or more.

Combination Therapies

In one aspect, the invention provides CEACAM1 antibodies or antigen-binding fragments thereof that are administered with an additional therapeutic agent. Such additional agents include, but are not limited to, cytotoxic agents, chemotherapeutic agents, growth inhibitory agents, anti-inflammatory agents, anti-cancer agents, anti-neurodegenerative agents, and anti-infective agents. Agents that are used in such combination therapies may fall into one or more of the preceding categories. The administration of the antibody or antigen-binding fragment thereof and the additional therapeutic agent may be concurrently or consecutively. The administration of the antibody or antigen-binding fragment thereof and the additional therapeutic agent may be separately or as a mixture. Further, the methods of treatment contemplated by the invention can relate to a treatment in combination with one or more cancer therapies selected from the group of antibody therapy, chemotherapy, cytokine therapy, dendritic cell therapy, gene therapy, hormone therapy, laser light therapy, and radiation therapy.

Exemplary additional therapeutic agents also include radionuclides with high-energy ionizing radiation that are capable of causing multiple strand breaks in nuclear DNA, and therefore suitable for inducing cell death (e.g., of a cancer). Exemplary high-energy radionuclides include: $^{90}Y$, $^{125}I$, $^{131}I$, $^{123}I$, $^{111}In$, $^{105}Rh$, $^{153}Sm$, $^{67}Cu$, $^{67}Ga$, $^{166}Ho$, $^{177}Lu$, $^{186}Re$ and $^{188}Re$. These isotopes typically produce high energy $\alpha$- or $\beta$-particles which have a short path length. Such radionuclides kill cells to which they are in close proximity, for example neoplastic cells to which the conjugate has attached or has entered. They have little or no effect on non-localized cells and are essentially non-immunogenic.

Exemplary additional therapeutic agents also include cytotoxic agents such as cytostatics (e.g. alkylating agents, DNA synthesis inhibitors, DNA-intercalators or cross-linkers, or DNA-RNA transcription regulators), enzyme inhibitors, gene regulators, cytotoxic nucleosides, tubulin binding agents, hormones and hormone antagonists, anti-angiogenesis agents, and the like.

Exemplary additional therapeutic agents also include alkylating agents such as the anthracycline family of drugs (e.g. adriamycin, carminomycin, cyclosporin-A, chloroquine, methopterin, mithramycin, porfiromycin, streptonigrin, anthracenediones, and aziridines). In another embodiment, the chemotherapeutic moiety is a cytostatic agent such as a DNA synthesis inhibitor. Examples of DNA synthesis inhibitors include, but are not limited to, methotrexate and dichloromethotrexate, 3-amino-1,2,4-benzotriazine 1,4-dioxide, aminopterin, cytosine β-D-arabinofuranoside, 5-fluoro-5'-deoxyuridine, 5-fluorouracil, ganciclovir, hydroxyurea, actinomycin-D, and mitomycin C. Exemplary DNA-intercalators or cross-linkers include, but are not limited to, bleomycin, carboplatin, carmustine, chlorambucil, cyclophosphamide, cis-diammineplatinum (II) dichloride (cisplatin), melphalan, mitoxantrone, and oxaliplatin.

Exemplary additional therapeutic agents also include transcription regulators such as actinomycin D, daunorubicin, doxorubicin, homoharringtonine, and idarubicin. Other exemplary cytostatic agents that are compatible with the present invention include ansamycin benzoquinones, quinonoid derivatives (e.g. quinolones, genistein, bactacyclin), busulfan, ifosfamide, mechlorethamine, triaziquone, diaziquone, carbazilquinone, indoloquinone EO9, diaziridinylbenzoquinone methyl DZQ, triethylenephosphoramide, and nitrosourea compounds (e.g. carmustine, lomustine, semustine).

Exemplary additional therapeutic agents also include cytotoxic nucleosides such as, for example, adenosine arabinoside, cytarabine, cytosine arabinoside, 5-fluorouracil, fludarabine, floxuridine, ftorafur, and 6-mercaptopurine; tubulin binding agents such as taxoids (e.g. paclitaxel, docetaxel, taxane), nocodazole, rhizoxin, dolastatins (e.g., Dolastatin-10, -11, or -15), colchicine and colchicinoids (e.g., ZD6126), combretastatins (e.g., Combretastatin A-4, AVE-6032), and vinca alkaloids (e.g., vinblastine, vincristine, vindesine, and vinorelbine (navelbine)); anti-angiogenesis compounds such as Angiostatin K1-3, DL-α-difluoromethyl-ornithine, endostatin, fumagillin, genistein, minocycline, staurosporine, and (±)-thalidomide.

Exemplary additional therapeutic agents also include hormones and hormone antagonists, such as corticosteroids (e.g., prednisone), progestins (e.g., hydroxyprogesterone or medroprogesterone), estrogens, (e.g., diethylstilbestrol), antiestrogens (e.g., tamoxifen), androgens (e.g., testosterone), aromatase inhibitors (e.g., aminogluthetimide), 17-(allylamino)-17-demethoxygeldanamycin, 4-amino-1,8-naphthalimide, apigenin, brefeldin A, cimetidine, dichloromethylene-diphosphonic acid, leuprolide (leuprorelin), luteinizing hormone-releasing hormone, pifithrin-α, rapamycin, sex hormone-binding globulin, and thapsigargin.

Exemplary additional therapeutic agents also include enzyme inhibitors such as, S(+)-camptothecin, curcumin, (−)-deguelin, 5,6-dichlorobenz-imidazole 1-β-D-ribofuranoside, etoposide, formestane, fostriecin, hispidin, 2-imino-1-imidazolidineacetic acid (cyclocreatine), mevinolin, trichostatin A, tyrphostin AG 34, and tyrphostin AG 879.

Exemplary additional therapeutic agents also include gene regulators such as 5-aza-2'-deoxycytidine, 5-azacytidine, cholecalciferol (vitamin D3), 4-hydroxytamoxifen, melatonin, mifepristone, raloxifene, trans-retinal (vitamin A aldehydes), retinoic acid, vitamin A acid, 9-cis-retinoic acid, 13-cis-retinoic acid, retinol (vitamin A), tamoxifen, and troglitazone.

Exemplary additional therapeutic agents also include cytotoxic agents such as, for example, the pteridine family of drugs, diynenes, and the podophyllotoxins. Particularly useful members of those classes include, for example, methopterin, podophyllotoxin, or podophyllotoxin derivatives such as etoposide or etoposide phosphate, leurosidine, vindesine, leurosine and the like.

Still other additional therapeutic agents that are compatible with the teachings herein include auristatins (e.g. auristatin E and monomethylauristan E), calicheamicin, gramicidin D, maytansanoids (e.g. maytansine), neocarzinostatin, topotecan, taxanes, cytochalasin B, ethidium bromide, emetine, tenoposide, colchicin, dihydroxy anthracindione, mitoxantrone, procaine, tetracaine, lidocaine, propranolol, puromycin, and analogs or homologs thereof.

In one embodiment, the CEACAM antibody or antigen-binding fragment thereof is administered in combination with an agent that is a checkpoint inhibitor. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM-3, VISTA, KIR, 2B4 (belongs to the CD2 family of molecules and is expressed on all NK, γδ, and memory $CD8^+$ (αβ) T cells), CD160 (also referred to as BY55), CGEN-15049, CHK1 and CHK2 kinases, A2aR and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics or small molecules, that bind to and block or inhibit the activity of one or more of CTLA-4, PDL1, PDL2, PD1, BTLA, HVEM, TIM-3, GAL9, LAG3, VISTA, KIR, 2B4, CD160 and CGEN-15049. Illustrative immune checkpoint inhibitors include Tremelimumab (CTLA-4 blocking antibody), anti-OX40, and Yervoy/ipilimumab (anti-CTLA-4 checkpoint inhibitor), as well as the PD-1 and PD-L1 inhibitors described above. Checkpoint protein ligands include, but are not limited to PD-L1, PD-L2, B7-H3, B7-H4, CD28, CD86 and TIM-3.

In some embodiments, the CEACAM1 antibodies and antigen-binding fragments thereof described herein are administered with a TIGIT, LAP, Podoplanin, Protein C receptor, ICOS, GITR, CD226 or a CD160 inhibiting agent.

In some embodiments, the CEACAM1 antibodies and antigen-binding fragments thereof described herein are administered with a CTLA-4, a PD-1, a PD-L1, or a PD-L2 inhibiting agent. In some embodiments, the CEACAM1 antibodies and antigen-binding fragments thereof described herein are administered with a TIM-3 inhibiting agent.

It is to be understood that this invention is not limited to the particular molecules, compositions, methodologies, or protocols described, as these may vary. Any methods and materials similar or equivalent to those described herein can be used in the practice or testing of embodiments of the present invention. It is further to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes those possibilities).

All other referenced patents and applications are incorporated herein by reference in their entirety. Furthermore, where a definition or use of a term in a reference, which is incorporated by reference herein is inconsistent or contrary to the definition of that term provided herein, the definition of that term provided herein applies and the definition of that term in the reference does not apply.

To facilitate a better understanding of the present invention, the following examples of specific embodiments are given. The following examples should not be read to limit or define the entire scope of the invention.

EXAMPLES

Example 1: Generation of Fully Humanized CEACAM1 Antibodies

1. Generation of Humanized Antibody Variants
Design of Composite Human Antibody Variable Region Sequences and Expression of Antibodies First, structural models of the parental, murine CEACAM1 antibody's V regions were produced using Swiss PDB and analyzed in order to identify potential "constraining" amino acids in the V regions that were likely to contribute to the binding properties of the antibody. For regions outside of, and flanking the CDRs, a wide selection of human sequence segments were identified as possible components of the novel humanized V regions.

Based upon the structural analysis, a large preliminary set of sequence segments that could be used to create humanized CEACAM antibody variants were selected and analyzed using iTope™ technology for in silico analysis of peptide binding to human MHC class II alleles (Perry et al, 2008. Drugs RD 9 (6): 385-396), and using the TCED™ of known antibody sequence-related T cell epitopes (Bryson et al 2010, Biodrugs 21 (1): 1-8). Sequence segments that were identified as significant non-human germline binders to human MHC class II or that scored significant hits against the TCED™ were discarded. This analysis resulted in a reduced set of segments, and combinations of these were again analyzed, as above, to ensure that the junctions between segments did not contain potential T cell epitopes. Selected sequence segments were assembled into complete V region sequences that were devoid of significant T cell epitopes. The heavy and light chains chosen for gene synthesis, expression in mammalian cells, and testing for activity are listed in Table 1. Some of the heavy and light chains in Table 1 contained variations at positions to be considered part of a CDR according to the Kabat CDR definition, but not according to the IMGT CDR definition.

TABLE 1

Heavy and light chains chosen for gene synthesis.

| Heavy chain | | Light chain | |
|---|---|---|---|
| Variant | SEQ ID No: | Variant | SEQ ID No: |
| $V_H0$ | 27 | $V\kappa0$ | 31 |
| $V_H1$ | 19 | $V\kappa1$ | 32 |
| $V_H2$ | 28 | $V\kappa2$ | 33 |
| $V_H3$ | 29 | $V\kappa3$ | 34 |
| $V_H4$ | 30 | $V\kappa4$ | 35 |
| | | $V\kappa5$ | 36 |
| | | $V\kappa6$ | 37 |
| | | $V\kappa7$ | 38 |
| | | $V\kappa8$ | 16 |
| | | $V\kappa9$ | 39 |
| | | $V\kappa10$ | 40 |
| | | $V\kappa11$ | 41 |
| | | $V\kappa12$ | 42 |

Figure 1:
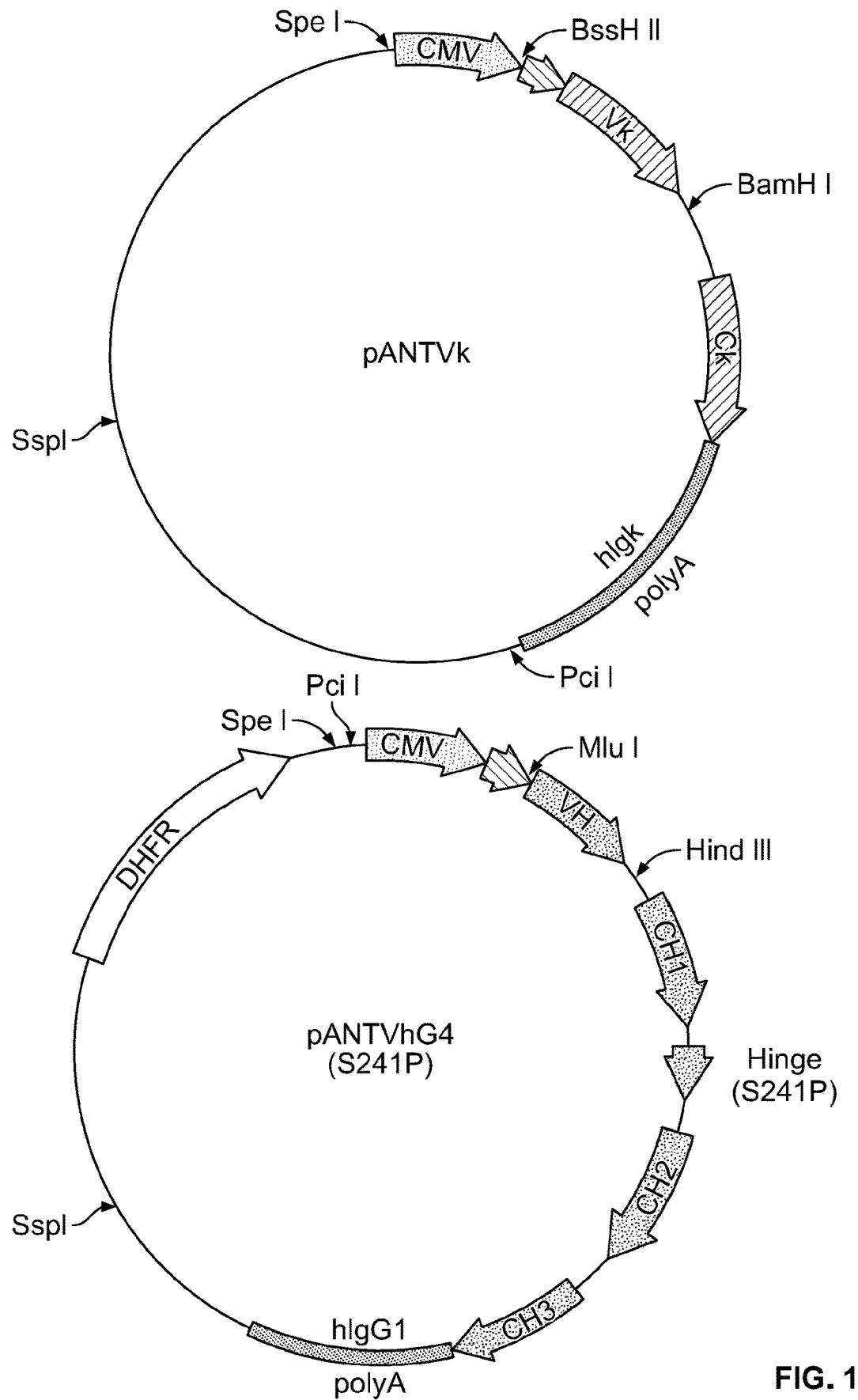
FIG. 1 shows plasmid maps for light chain expression vector pANTV$_K$ and heavy chain expression vector pANTVhG4 (S241P). Both V$_H$ and V$_K$ vectors contain genomic DNA fragments incorporating introns and polyA sequences. Expression of both chains is driven by a CMV promoter.

Next, the $V_H$ and $V_\kappa$ sequences of the parental, murine CEACAM1 antibody and the humanized CEACAM antibody variants were synthesized with flanking restriction enzyme sites for cloning into the pANT expression vector system for IgG4 (S241P) heavy and κ light chain (FIG. 1). The $V_H$ regions were cloned between the MluI and HindIII restriction sites, and the $V_\kappa$ regions were cloned between the BssHII and BamHI restriction sites. All constructs were confirmed by sequencing.

Thirty-nine heavy and light chain pairings were transiently transfected into HEK EBNA adherent cells using a PEI transfection method and incubated for 5-7 days post-transfection. These 39 pairings included three controls: (1) the chimeric antibody $V_H0/V_\kappa0$ (consisting of the murine $V_H$ region ($V_H0$) fused to the constant heavy region of human IgG4, and the murine $V_\kappa$ region ($V_\kappa0$) fused to the constant light region of human IgG4); (2) the pairing of the chimeric $V_H$ heavy chain ($V_H0$) with the light chain variant $V_\kappa1$; and (3) the pairing of the $V_H1$ heavy chain with the chimeric $V_\kappa$ light chain variant ($V_\kappa0$). The other 36 were combinations of the composite IgG4 $V_H$ and the $V_\kappa$ variants: $V_H1$ was paired with $V_\kappa1$ through $V_\kappa12$, $V_H2$ was paired with $V_\kappa1$ through $V_\kappa12$, $V_H3$ was paired with $V_\kappa1$ through $V_\kappa6$, and $V_H4$ was paired with $V_\kappa1$ through $V_\kappa6$.

Antibodies were purified from cell culture supernatants on Protein A sepharose columns, buffer exchanged into PBS pH 7.4 and quantified by OD 280 nm using an extinction coefficient based on the predicted amino acid sequence. 1 μg of each antibody was analyzed by SDS-PAGE and bands corresponding to the profile of a typical antibody were observed. The size of the light chain and the presence of a faint band at 25 kDa indicates that the glycosylation motif identified in the light chain is substantially utilized.

Competition ELISA Analysis of Humanized Variants Binding to CEACAM1

The binding of the purified antibodies to human CEACAM1 was assessed in a competition ELISA assay. Nunc Immuno MaxiSorp 96 well flat bottom microtitre plates were pre-coated with 1 μg/ml of GST-CEACAM1 in 1×PBS, overnight at 4° C. The following day the plates were blocked for 1 hour at room temperature ("RT") with 2% BSA/PBS before washing 3× with PBST pH 7.4. A 3-fold dilution series of the chimeric antibody chimeric antibody $V_H0/V_\kappa0$, an irrelevant IgG4 antibody, and the humanized CEACAM1 antibodies from 100 μg/ml to 0.07 or 0.002 μg/ml were pre-mixed with a constant concentration of parental murine antibody (0.45 μg/ml final concentration), added to the plate and incubated for 1 hour at room temperature. Following 3×PBST washes, the binding of the parental murine CEACAM1 antibody was detected with an anti-mouse-HRP and TMB substrate. The reaction was stopped with 3 M HCl, absorbance read at 450 nm on a Dynex Technologies MRX TC II plate reader and the binding curves plotted. The binding of the humanized CEACAM antibody variants to CEACAM1 was compared to the chimeric antibody ($V_H0/V_\kappa 0$), which was included on each plate. Twelve of the 36 humanized CEACAM antibody variants showed no binding to CEACAM1 (those including $V_\kappa 3$, $V_\kappa 4$, and $V_\kappa 5$). Variants that bound CEACAM1 showed a range of relative IC50 values from 0.9 to 5.2 compared to the chimeric antibody $V_H0/V_\kappa 0$. Data are summarized in Table 2.

TABLE 2

Summary of humanized CEACAM antibody variants and control antibody titers and binding data. Antibody expression titers (µg/ml) are from static HEK EBNA transient transfections. IC50 values obtained in competition assays were normalized to the chimeric antibody $V_H0/V\kappa 0$ on the same plate. Antibodies that did not bind are not included in the table. Antibodies indicated in bold were taken forward for multi-cycle kinetic analysis.

| Variant | Expression titer (µg/ml) | Average relative IC50 values | Number of experiments |
|---|---|---|---|
| $V_H0/V\kappa 0$ (control) | 22.9 | 1 | 4 |
| $V_H0/V\kappa 1$ (control) | 21.3 | 1.6 | 4 |
| $V_H1/V\kappa 0$ (control) | 30.5 | 0.9 | 4 |
| $V_H1/V\kappa 1$ | 20.6 | 2.5 | 4 |
| $V_H1/V\kappa 2$ | 23.1 | 1.8 | 4 |
| $V_H1/V\kappa 4$ | 27.2 | 2.7 | 4 |
| $V_H1/V\kappa 7$ | 34.6 | 1.6 | 2 |
| $V_H1/V\kappa 8$ | 33.3 | 1.7 | 2 |
| $V_H1/V\kappa 9$ | 39.2 | 1.5 | 2 |
| $V_H1/V\kappa 10$ | 35.4 | 1.6 | 2 |
| $V_H1/V\kappa 11$ | 38.0 | 2.2 | 2 |
| $V_H1/V\kappa 12$ | 44.5 | 1.4 | 2 |
| $V_H2/V\kappa 1$ | 10.6 | 2.8 | 4 |
| $V_H2/V\kappa 2$ | 43.9 | 2.0 | 4 |
| $V_H2/V\kappa 4$ | 30.2 | 3.0 | 4 |
| $V_H2/V\kappa 7$ | 41.7 | 1.3 | 2 |
| $V_H2/V\kappa 8$ | 44.9 | 1.6 | 2 |
| $V_H2/V\kappa 9$ | 39.6 | 1.7 | 2 |
| $V_H2/V\kappa 10$ | 35.6 | 1.4 | 2 |
| $V_H2/V\kappa 11$ | 32.0 | 1.4 | 2 |
| $V_H2/V\kappa 12$ | 40.9 | 1.5 | 2 |
| $V_H3/V\kappa 1$ | 17.1 | 3.5 | 4 |
| $V_H3/V\kappa 2$ | 17.0 | 2.5 | 4 |
| $V_H3/V\kappa 4$ | 21.0 | 5.2 | 4 |
| $V_H4/V\kappa 1$ | 13.7 | 4.0 | 4 |
| $V_H4/V\kappa 2$ | 29.7 | 3.3 | 4 |
| $V_H4/V\kappa 4$ | 30.1 | 4.0 | 4 |

Kinetic Analysis of Humanized Variants Binding to CEACAM1

As an alternative approach to assess the binding of the 36 antibody combinations and the three control antibodies to CEACAM1, a kinetic analysis was performed on a Biacore T200 (serial no. 1909913) running Biacore T200 Evaluation Software V2.0.1 (Uppsala, Sweden). All experiments were run at 25° C. with HBS-P+ running buffer (pH 7.4) (GE Healthcare, cat. no. BR100671). All kinetic experiments were performed using His-tagged CEACAM1 as the analyte. For all experiments, antibodies were immobilized onto a Series S Protein A sensor chip surface. For kinetic experiments, the amount of immobilized/captured ligand was limited to avoid mass transfer effects at the surface of the chip with the surface ideally having an analyte binding level ($R_{max}$) of 50-150 RUs. Using a MW of 45 kDa for the CEACAM1 analyte, 150 kDa for the antibody ligand (estimated value for IgG), 50 RU for Rmax and the stoichiometry (Sm) as 2 due to the ability of each antibody to bind 2 target molecules, a target response level of ~75 RUs was set for capture of all the sample antibodies.

Single cycle analysis of the 36 antibody combinations and the three control antibodies was performed on purified antibodies ($V_\kappa 1$ to $V_\kappa 6$ variants) or on the supernatants of the transiently transfected HEK EBNA cells ($V_\kappa 7$ to $V_\kappa 12$ variants). In some instances, where supernatant was not available, purified chimeric antibody $V_H0/V_\kappa 0$ was spiked into HEK EBNA culture medium to use as a positive control. Antibodies were diluted in HBS-P+ to a concentration of 1 µg/ml (as determined by an IgG quantitation ELISA). At the start of each cycle, antibodies were loaded onto Fc2, Fc3 and Fc4 of a protein A chip and IgG captured at a flow rate of 8 µl/min to give an RU of ~75. The surface was then allowed to stabilize. Single cycle kinetic data was obtained at a flow rate of 50 µl/min to minimize any potential mass transfer effects. Multiple repeats of the chimeric antibody $V_H0/V_\kappa 0$ were performed to check the stability of the surface and analyte over the kinetic cycles. The signal from the reference channel Fc1 (no antibody) was subtracted from that of Fc2, Fc3 and Fc4 to correct for differences in non-specific binding to a reference surface. A 5 point 2-fold dilution range from 3.125 to 50 nM CEACAM1 without regeneration between each concentration was used. The association phase for the 5 injections of increasing concentrations of CEACAM1 was monitored for 100 seconds and a single dissociation phase was measured for 150 seconds following the last injection of CEACAM1. Regeneration of the Protein A surface was conducted using 2 injections of 10 mM glycine-HCl pH 1.5 followed by a stabilization period of 500 seconds. The signal from each antibody blank run (no CEACAM1) was subtracted to correct for differences in surface stability. Single cycle kinetics (Table 3) demonstrated that 24 humanized variants bound to CEACAM1 while 12 variants did not bind. The light chains of $V_\kappa 3$, $V_\kappa 5$ and $V_\kappa 6$ abolished CEACAM1 binding when combined with any humanized heavy chain. These data are consistent with the competition ELISA data (Table 2).

TABLE 3

Single cycle kinetic parameters for humanized CEACAM antibody variants and control antibodies binding to CEACAM1-HIS as determined using the Biacore T200. The relative $K_D$ compared to chimeric antibody $V_H0/V\kappa 0$ was calculated by dividing the $K_D$ of the humanized CEACAM1 antibody variants by that of the chimeric antibody $V_H0/V\kappa 0$ assayed in the same experiment. Antibodies indicated in bold were taken forward for multi-cycle kinetic analysis.

| Variant | Antibody source | $K_D$ (nM) | Relative $K_D$ to chimeric antibody $V_H0/V\kappa 0$ |
|---|---|---|---|
| $V_H0/V\kappa 0$ (control) | Purified | 42 | 1.0 |
| $V_H0/V\kappa 1$ (control) | Purified | 49 | 1.2 |
| $V_H1/V\kappa 0$ (control) | Purified | 64 | 1.5 |
| $V_H1/V\kappa 1$ | Purified | 85 | 2.0 |
| $V_H1/V\kappa 2$ | Purified | 134 | 3.2 |
| $V_H1/V\kappa 4$ | Purified | 131 | 3.1 |
| $V_H1/V\kappa 7$ | S/N | 109 | 2.6 |
| $V_H1/V\kappa 8$ | S/N | 131 | 3.2 |
| $V_H1/V\kappa 9$ | S/N | 142 | 3.4 |
| $V_H1/V\kappa 10$ | S/N | 146 | 3.5 |
| $V_H1/V\kappa 11$ | S/N | 143 | 3.5 |
| $V_H1/V\kappa 12$ | S/N | 143 | 3.5 |
| $V_H2/V\kappa 1$ | Purified | 113 | 2.7 |
| $V_H2/V\kappa 2$ | Purified | 98 | 2.3 |
| $V_H2/V\kappa 4$ | Purified | 103 | 2.5 |
| $V_H2/V\kappa 7$ | S/N | 152 | 3.7 |
| $V_H2/V\kappa 8$ | S/N | 125 | 3.0 |
| $V_H2/V\kappa 9$ | S/N | 110 | 2.7 |

TABLE 3-continued

Single cycle kinetic parameters for humanized CEACAM antibody variants and control antibodies binding to CEACAM1-HIS as determined using the Biacore T200. The relative $K_D$ compared to chimeric antibody $V_H0/V\kappa0$ was calculated by dividing the $K_D$ of the humanized CEACAM1 antibody variants by that of the chimeric antibody $V_H0/V\kappa0$ assayed in the same experiment. Antibodies indicated in bold were taken forward for multi-cycle kinetic analysis.

| Variant | Antibody source | $K_D$ (nM) | Relative $K_D$ to chimeric antibody $V_H0/V\kappa0$ |
|---|---|---|---|
| $V_H2/V\kappa10$ | S/N | 131 | 3.2 |
| $V_H2/V\kappa11$ | S/N | 122 | 3.0 |
| $V_H2/V\kappa12$ | S/N | 145 | 3.5 |
| $V_H3/V\kappa1$ | Purified | 135 | 3.2 |
| $V_H3/V\kappa2$ | Purified | 103 | 2.5 |
| $V_H3/V\kappa4$ | Purified | 81 | 1.9 |
| $V_H4/V\kappa1$ | Purified | 99 | 2.4 |
| $V_H4/V\kappa2$ | Purified | 74 | 1.8 |
| $V_H4/V\kappa4$ | Purified | 120 | 2.9 |

S/N, Supernatant. Non-binding variants were not included in the table.

Of the 24 antibodies that bound to CEACAM1, the antibody variants that showed binding within 2-fold of the chimeric antibody $V_H0/V_\kappa0$ with relative IC50s ranging from 0.9 to 1.8 were taken forward for multi-cycle kinetics analysis using Biacore: $V_H1/V_\kappa2$, $V_H1/V_\kappa7$, $V_H1/V_\kappa8$, $V_H1/V_\kappa9$, $V_H1/V_\kappa10$, $V_H1/V_\kappa12$, $V_H2/V_\kappa7$, $V_H2/V_\kappa8$, $V_H2/V_\kappa9$, $V_H2/V_\kappa10$, $V_H2/V_\kappa11$ and $V_H2/V_\kappa12$ (see Table 2 and Table 3, highlighted in bold).

For multi-cycle kinetic analysis, purified antibody was immobilized at a protein concentration of 1 μg/ml in HBS-P+. At the start of each cycle, antibody was captured on Protein A to give an RU of ~75 and the surface allowed to stabilize. Kinetic data was obtained at a flow rate of 80 μl/min to minimize any potential mass transfer effects. Multiple repeats of the blank (no CEACAM1) and a repeat of a single concentration of the analyte were programmed into the kinetic run in order to check the stability of both the surface and analyte over the kinetic cycles. For kinetic analysis, a 2-fold dilution range was selected from either 200 to 3.125 nM or 100 to 1.5625 nM CEACAM1. The association phase of CEACAM1 was monitored for 50 or 150 seconds and the dissociation phase was measured for 100 seconds. Regeneration of the Protein A surface was conducted using two injections of 10 mM glycine-HCL pH 1.5 at the end of each cycle.

The signal from the reference channel Fc1 was subtracted from that of Fc2, Fc3 and Fc4 to correct for differences in non-specific binding to a reference surface, a global Rmax parameter was used in the 1-to-1 binding model. The relative $K_D$ compared to $V_H1/V_\kappa0$ was calculated by dividing the $K_D$ of the humanized CEACAM antibody variants by that of the chimeric antibody $V_H0/V_\kappa0$ on the same chip. The kinetic parameters measured for the interaction of CEACAM1 with humanized CEACAM antibody variants are shown in Table 4. A summary of the averaged relative $K_D$ obtained for the 12 antibody combinations analyzed using multi cycle kinetics can be found in Table 5.

Selectivity Analysis of Humanized Variants Binding to CEACAM1

Figure 2:
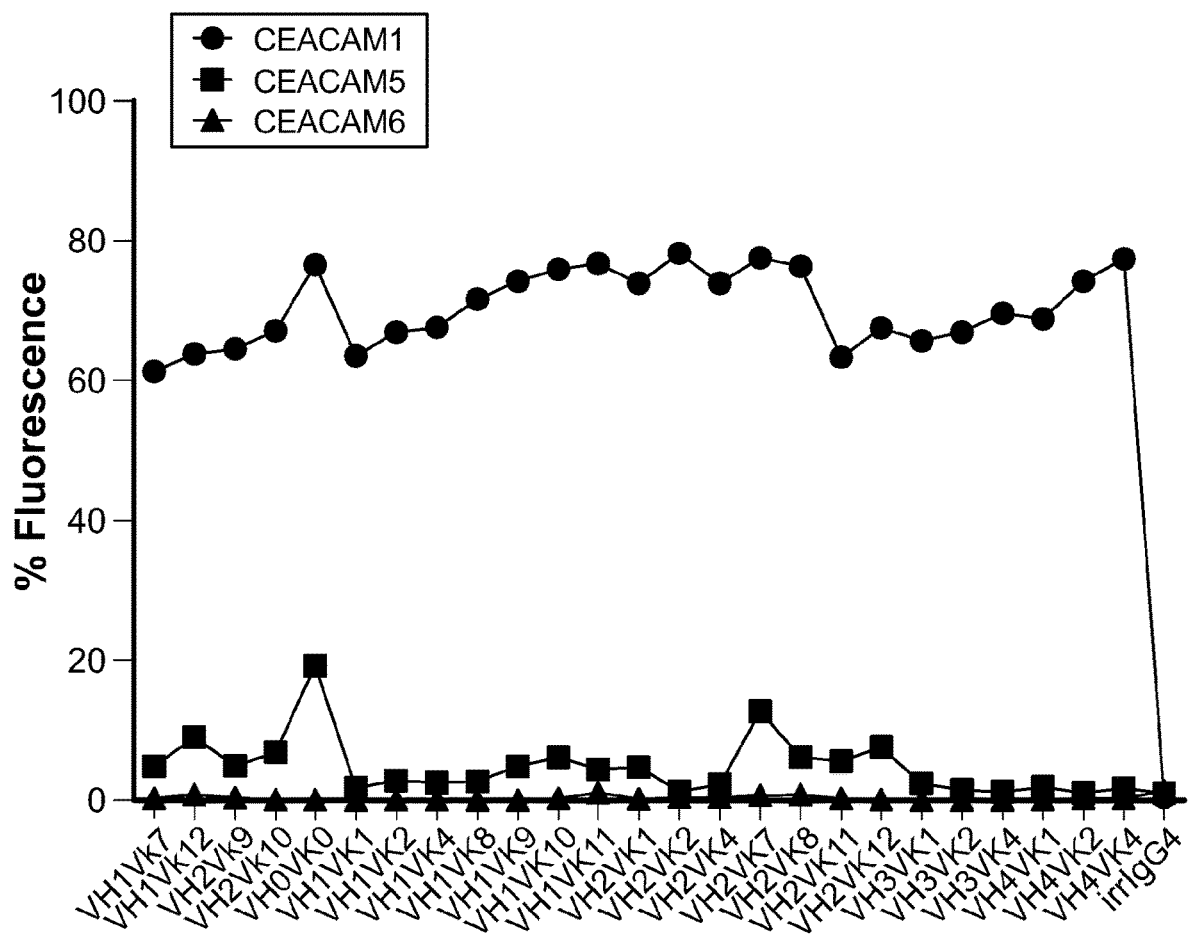
FIG. 2 shows selectivity of CEACAM1 antibody variants. Humanized variant intermediates were examined by flow cytometry on HeLa cells transfected with CEACAM1, 3, 5, 6 and 8. The proportion of cells that were positive based on irrelevant hIgG4 staining is shown. There was no evidence of any staining of the HeLa-CEACAM3 or HeLa-CEACAM8 transfectants so these data are not reported.

Binding selectivity for CEACAM1 was tested for the 24 humanized antibody variants that bound to CEACAM1 (see Table 3), as well as the chimeric control antibody $V_H0/V_\kappa0$, by flow cytometry on HeLa cells transfected with CEACAM1, 3, 5, 6 and 8. As shown in FIG. 2, the majority of variants are highly selective for CEACAM1 and show very little or no binding to CEACAM3, 5, 6, or 8. All 24 variants showed decreased binding to CEACAM5 as compared to the chimeric control antibody $V_H0/V_\kappa0$. There was no evidence of any staining of the HeLa-CEACAM3 or HeLa-CEACAM8 transfectants. As such, this data was not reported. Due to its favorable affinity to and selectivity for CEACAM1 as well as its favorable expression level, $V_H1/V_\kappa8$ was chosen as the framework for affinity maturation.

TABLE 4

Multi cycle kinetic data (n = 1) for composite human antibody variants binding to CEACAM1-HIS as determined using the Biacore T200. The relative $K_D$ compared to chimeric antibody $V_H0/V\kappa0$ was calculated by dividing the $K_D$ of the humanized CEACAM antibody variants by that of the chimeric antibody $V_H0/V\kappa0$ assayed on the same chip.

| Variant | $k_a$ (M$^{-1}$s$^{-1}$) | $k_d$ (s$^{-1}$) | $K_D$ (nM) | $R_{max}$ (RU) | Chi$^2$ (RU$^2$) | Relative $K_D$ compared to chimeric antibody $V_H0/V\kappa0$ |
|---|---|---|---|---|---|---|
| $V_H0/V\kappa0$ | 5.10 × 10$^5$ | 1.64 × 10$^{-2}$ | 32 | 69.2 | 0.139 | 1.0 |
| $V_H1/V\kappa7$ | 5.10 × 10$^5$ | 3.52 × 10$^{-2}$ | 69 | 39.2 | 0.057 | 2.1 |
| $V_H2/V\kappa9$ | 5.59 × 10$^5$ | 4.17 × 10$^{-2}$ | 75 | 41.80 | 0.075 | 2.3 |
| $V_H0/V\kappa0$ | 5.17 × 10$^5$ | 1.52 × 10$^{-2}$ | 29 | 66.3 | 0.184 | 1.0 |
| $V_H1/V\kappa12$ | 4.11 × 10$^5$ | 2.68 × 10$^{-2}$ | 65 | 33.2 | 0.077 | 2.2 |
| $V_H2/V\kappa10$ | 4.07 × 10$^5$ | 2.46 × 10$^{-2}$ | 61 | 36.6 | 0.095 | 2.1 |
| $V_H0/V\kappa0$ | 6.46 × 10$^5$ | 1.97 × 10$^{-2}$ | 30 | 67.8 | 0.201 | 1.0 |
| $V_H2/V\kappa7$ | 3.62 × 10$^5$ | 2.58 × 10$^{-2}$ | 71 | 36.3 | 0.062 | 2.4 |
| $V_H2/V\kappa11$ | 3.75 × 10$^5$ | 2.89 × 10$^{-2}$ | 77 | 37.2 | 0.086 | 2.5 |
| $V_H0/V\kappa0$ | 4.33 × 10$^5$ | 2.44 × 10$^{-2}$ | 56 | 63.6 | 0.022 | 1.0 |
| $V_H1/V\kappa2$ | 2.65 × 10$^5$ | 5.03 × 10$^{-2}$ | 190 | 45.8 | 0.008 | 3.4 |
| $V_H1/V\kappa10$ | 2.84 × 10$^5$ | 5.11 × 10$^{-2}$ | 180 | 55.2 | 0.012 | 3.2 |
| $V_H0/V\kappa0$ | 5.53 × 10$^5$ | 3.05 × 10$^{-2}$ | 55 | 64.8 | 0.018 | 1.0 |
| $V_H1/V\kappa7$ | 4.15 × 10$^5$ | 4.92 × 10$^{-2}$ | 119 | 36.9 | 0.007 | 2.2 |
| $V_H2/V\kappa8$ | 3.34 × 10$^5$ | 4.17 × 10$^{-2}$ | 125 | 42.6 | 0.012 | 2.3 |
| $V_H0/V\kappa0$ | 5.91 × 10$^5$ | 3.12 × 10$^{-2}$ | 53 | 64.3 | 0.023 | 1.0 |
| $V_H1/V\kappa8$ | 4.30 × 10$^5$ | 4.06 × 10$^{-2}$ | 95 | 28.2 | 0.016 | 1.8 |
| $V_H2/V\kappa9$ | 2.19 × 10$^6$ | 2.11 × 10$^{-1}$ | 96 | 33.4 | 0.015 | 1.8 |
| $V_H0/V\kappa0$ | 5.76 × 10$^5$ | 3.20 × 10$^{-2}$ | 56 | 68.1 | 0.037 | 1.0 |
| $V_H1/V\kappa9$ | 2.29 × 10$^5$ | 5.04 × 10$^{-2}$ | 220 | 53.1 | 0.014 | 4.0 |
| $V_H2/V\kappa12$ | 3.02 × 10$^5$ | 4.58 × 10$^{-2}$ | 152 | 44.5 | 0.024 | 2.7 |

TABLE 5

Summary of relative $K_D$ to chimeric antibody $V_H0/V\kappa0$ for all humanized CEACAM antibody variants, obtained from multi cycle kinetics as determined using the Biacore T200. The fold difference in $K_D$ compared to chimeric antibody $V_H0/V\kappa0$ was calculated by dividing the $K_D$ of the test antibody variant by that of the chimeric antibody $V_H0/V\kappa0$ tested on each chip. The number of independent experiments is shown for each variant.

| Variant | Average of relative $K_D$ compared to chimeric antibody $V_H0/V\kappa0$ | Number of experiments |
|---|---|---|
| $V_H1/V\kappa2$ | 3.4 | 1 |
| $V_H1/V\kappa7$ | 2.0 | 3 |
| $V_H1/V\kappa8$ | 1.8 | 1 |
| $V_H1/V\kappa9$ | 4.0 | 1 |
| $V_H1/V\kappa10$ | 3.2 | 1 |
| $V_H1/V\kappa12$ | 2.2 | 1 |
| $V_H2/V\kappa7$ | 2.3 | 1 |
| $V_H2/V\kappa8$ | 2.3 | 2 |
| $V_H2/V\kappa9$ | 1.9 | 3 |
| $V_H2/V\kappa10$ | 2.1 | 1 |
| $V_H2/V\kappa11$ | 2.7 | 2 |
| $V_H2/V\kappa12$ | 2.7 | 1 |

2. Removal of N-Linked/HEK-Derived Glycosylation

Figure 4:
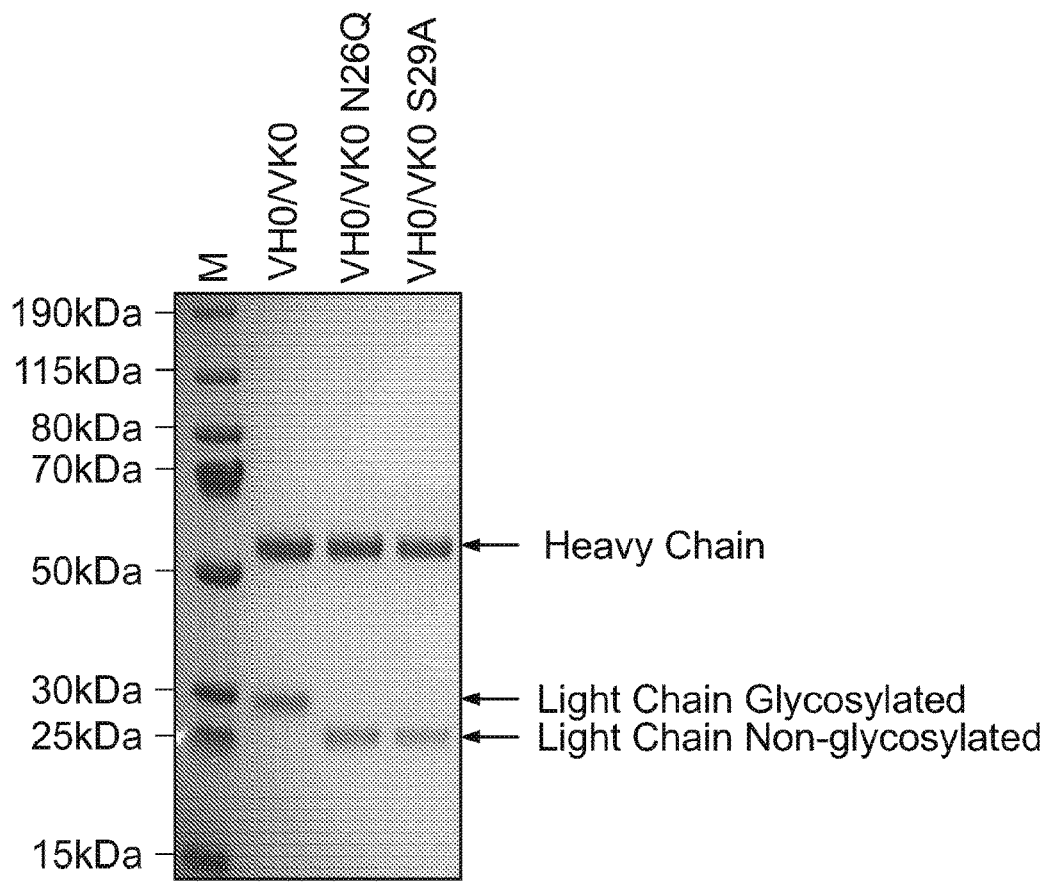
FIG. 4 illustrates that the chimeric CEACAM1 antibody V$_H$0/V$_K$0 is glycosylated in CDR1L. Introduction of mutations N26Q and S29A abrogates this glycosylation. Proteins were separated on a SDS-PAGE under denaturing conditions. The molecular weights of the heavy chain, the glycosylated light chain, and the aglycosylated light chain are indicated. Residues N26 and S29 are numbered using the Kabat numbering scheme.

Sequence analysis revealed a potential N-linked glycosylation motif in the original mouse hybridoma light chain CDR1. CDR1L of the parental, murine antibody contains an N—X—S/T consensus sequence (N26 and S29 according to Kabat numbering, correspond to residues 26 and 28 in the primary amino acid sequence of the light variable chain, see FIG. 3C), which makes the N26 residue a target for N-linked glycosylation. To reduce potential glycosylation related immunogenicity, two CDR mutations were designed to remove N—X—S/T consensus sequence (glycosylation site): N26Q and S29A (Kabat numbering scheme). Mutation of either residue abrogates glycosylation, as shown in FIG. 4.

Competition ELISA experiments (see Table 6), multi-cycle kinetic analysis (see Table 7), and selectivity analysis (see Table 8) were performed to confirm binding of the mutant chimerics to CEACAM1. Compared to antibody mutant N26Q, antibody mutant S29A (Kabat numbering scheme) exhibited higher expression levels and $K_D$ more similar to the un-mutated antibody (see Table 9), while maintaining a high selectivity for CEACAM1. As such, the S29A mutation (Kabat numbering scheme) was incorporated into the CEACAM1 lead antibodies during further development.

TABLE 6

Results from competition ELISA experiment using aglycosylated chimeric antibodies. CDR1L residues are numbered according to the Kabat numbering scheme.

| Experiment 1 | | Experiment 2 | |
|---|---|---|---|
| Variant | Relative IC50 | Variant | Relative IC50 |
| Chimeric $V_H0/V\kappa0$ | 1.00 | Chimeric $V_H0/V\kappa0$ | 1.00 |
| $V_H0/V\kappa0$ N26Q | 0.90 | $V_H0/V\kappa0$ N26Q | 0.97 |
| $V_H0/V\kappa0$ S29A | 0.96 | $V_H0/V\kappa0$ S29A | 0.72 |
| Irrelevant IgG4 | No binding observed | Irrelevant IgG4 | No binding observed |

TABLE 7

Multi-cycle kinetic analysis using aglycosylated chimeric antibodies. CDR1L residues are numbered according to the Kabat numbering scheme.

| Variant | $k_a$ (M$^{-1}$s$^{-1}$) | $k_d$ (s$^{-1}$) | $K_D$ (M) | Relative $K_D$ | Chi$^2$ (RU$^2$) |
|---|---|---|---|---|---|
| $V_H0/V\kappa0$ | 2.46E+05 | 2.58E−02 | 1.05E−07 | 1.0 | 0.0853 |
| $V_H0/V\kappa0$ N26Q | 1.51E+05 | 2.99E−02 | 1.98E−07 | 1.89 | 0.175 |
| $V_H0/V\kappa0$ S29A | 2.51E+05 | 2.77E−02 | 1.10E−07 | 1.05 | 0.0822 |

TABLE 8

Selectivity analysis of aglycosylated humanized variants. CDR1L residues are numbered according to the Kabat numbering scheme. Binding selectivity of antibody variants was assessed by flow cytometry using HeLa cells transfected with vectors expressing CEACAM1, CEACAM5, and CEACAM6, respectively. Indicated is the relative amount of cells expressing the respective antigen that the indicated antibody bound to.

| Variant | CEACAM1 | CEACAM5 | CEACAM6 |
|---|---|---|---|
| $V_H0/V\kappa0$ | 78.00 | 8.81 | 0.30 |
| $V_H0/V\kappa0$ N26Q | 79.90 | 15.50 | 0.18 |
| $V_H0/V\kappa0$ S29A | 77.90 | 9.82 | 0.00 |
| Control IgG4 | 0.37 | 1.02 | 1.39 |

TABLE 9

Summary of experiments with aglycosylated chimeric antibodies. CDR1L residues are numbered according to the Kabat numbering scheme.

| Variant | Expression level (µg/ml) | Multi-cycle kinetic analysis: Relative $K_D$ compared to $V_H0/V\kappa0$ | Competition ELISA: Average relative IC50 compared to $V_H0/V\kappa0$ |
|---|---|---|---|
| $V_H0/V\kappa0$ | 30.43 | 1.0 | 1.00 |
| $V_H0/V\kappa0$ N26Q | 3.75 | 1.89 | 0.94 |
| $V_H0/V\kappa0$ S29A | 7.25 | 1.05 | 0.84 |

Figure 5:
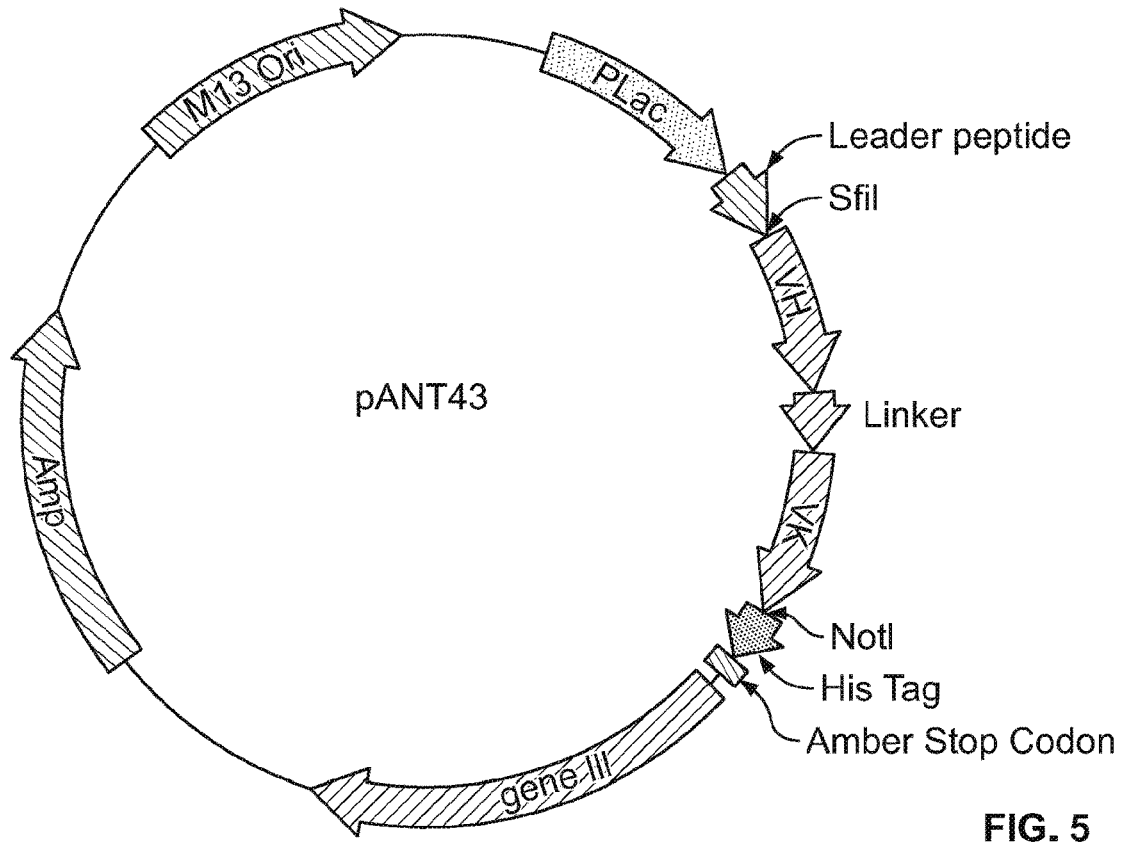
FIG. 5 shows a plasmid map for the phagemid expression vector pANT43. V$_H$ and V$_K$ domains are linked via a flexible glycine-serine (G4S) linker and are fused in frame to the M13 gene III phage coat protein. Expression of the single-chain variable fragment (scFv) is driven by a Lac promoter.
Figure 6:
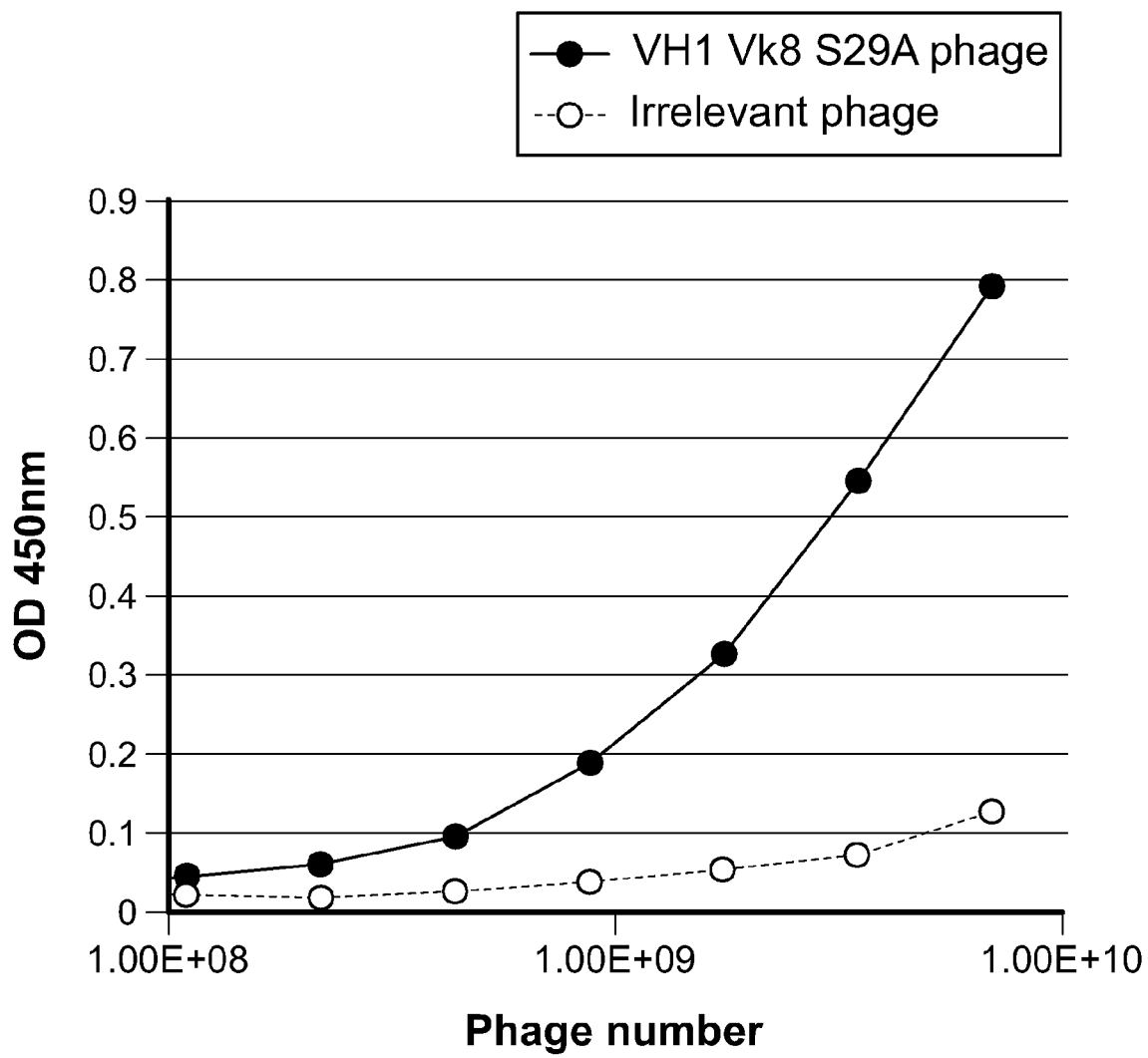
FIG. 6 illustrates the binding of phage to CEACAM1 antigen. Phage prepared from either the parent V$_H$1/V$_K$8 S29A scFv or an irrelevant scFv were serially diluted and incubated with plate bound GST-CEACAM1. Phage binding to CEACAM1 was detected using an anti-M13 Horseradish peroxidase (HRP) conjugate and 3,3',5,5'-Tetramethylbenzidine (TMB) substrate.

3. Affinity Maturation of the Aglycosylated CEACAM1 Antibody $V_H1/V_\kappa8$ S29A Phage Vector Construction and Testing of Binding of Parent $V_H1/V_\kappa8$ S29A scFv For the affinity maturation of one of the lead antibodies, $V_H1/V_\kappa8$, genes encoding the $V_H1$ and $V_\kappa8$ were constructed and converted to a scFv format using overlapping PCR where the heavy chain was linked to the light chain via a 15 amino acid (G4S) 3 linker. CDR1L residue S29 is numbered according to the Kabat numbering scheme and corresponds to residue 28 in the primary amino acid sequence of the light variable chain (FIG. 3C). The scFv sequence was then cloned into the phagemid vector pANT43 using the restriction enzymes Sfi I and Not I, allowing for display of scFv on the phage surface as a gene III fusion protein (FIG. 5). The cloned scFv was transformed into E. coli (TG1) and all constructs were confirmed by sequencing. Phage containing either the parent $V_H1/V_\kappa8$ S29A scFv or an irrelevant scFv were prepared and tested for binding to GST-CEACAM1 (FIG. 6). Phage derived from the parent $V_H1/V_\kappa8$ S29A sequence bound specifically to the antigen, since no binding was observed with the irrelevant phage.

Mutagenesis and Library Construction

For the construction of an affinity maturation library, specific amino acids within the CDR1H, CDR3H and CDR3L of the aglycosylated, humanized antibody $V_H1/V_\kappa8$ S29A were targeted for "hotspot" mutagenesis using semi-randomized codons. Sequence positions were analyzed for likely contact residues and ranked in order within each block. This information was used together with the amino acid preferences at any given position within the CDR3 and the crystal structure of the parental murine antibody. Where possible, priority was given to the highest ranked contact residue within each block.

Four different libraries were generated: one library for the mutation of CDR1H (HC), two libraries for the mutation of CDR3H, and one library for the mutation of CDR3L (see FIG. 7).

CDR1H was identified as being five amino acids (S31 to S35) in length (Kabat definition, corresponds to residues 31-35 of the primary amino acid sequence of the heavy variable chain, see FIG. 3A) with the IMGT CDR1H definition (G26 to G33) covering a more extended region. Taken together and with the crystal data of the parental murine antibody, G26 to S35 was covered in a single library with a subset of amino acids included at each position.

CDR3H was identified as being 12 amino acids in length (H95-Y102 according to Kabat definition, corresponds to residues 99-110 of the primary amino acid sequence of the heavy variable chain, see FIG. 3A). For the mutagenesis, CDR3H was split into two libraries overlapping at D100 (according to Kabat definition, corresponds to residue 104 of the primary amino acid sequence of the heavy variable chain, see FIGS. 3A and 3B): Block 1 (R94 to D100 according to Kabat definition, corresponds to residues 98 to 104 in the primary amino acid sequence of the heavy variable chain, see FIGS. 3A and 3B) and Block 2 (D100 to Y102 according to Kabat definition, corresponds to residues 104 to 110 of the primary amino acid sequence of the heavy variable chain, see FIGS. 3A and 3B), with each containing a subset of amino acids in all positions. Position R94 (according to Kabat definition, corresponds to residue 98 of the primary amino acid sequence of the heavy variable chain, see FIGS. 3A and 3B) (Block 1) was included to allow more diversity in the germline residue anchoring the CDR.

CDR3L was identified as being 9 amino acids (Q89-T97) (according to Kabat definition, corresponds to residues 88 to 96 of the primary amino acid sequence of the light variable chain, see FIG. 3C) in length. The region Q90 to P96 (according to Kabat definition, corresponds to residues 89 to 97 of the primary amino acid sequence of the light variable chain, see FIG. 3C) was covered in a single library with a subset of amino acids included at each position. Kabat numbering is used for all protein sequence coordinates.

Figure 8A:
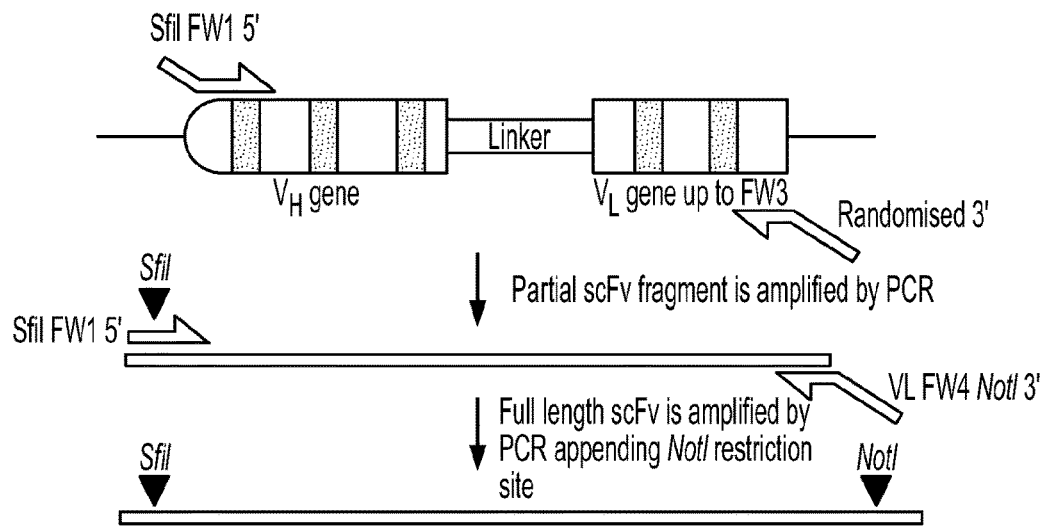
FIGS. 8A, 8B, and 8C provide an overview of the library construction process to generate randomized phage libraries. Light chain CDR3 library (FIG. 8A), heavy chain CDR1 library (FIG. 8B), and heavy chain CDR3 libraries (FIG. 8C).
Figure 8B:
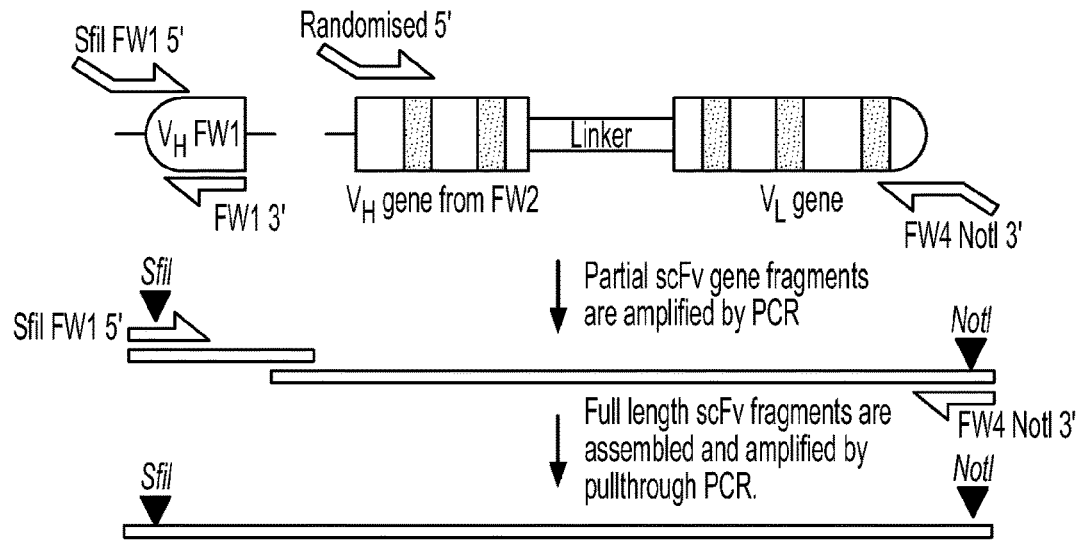
Figure 8C:
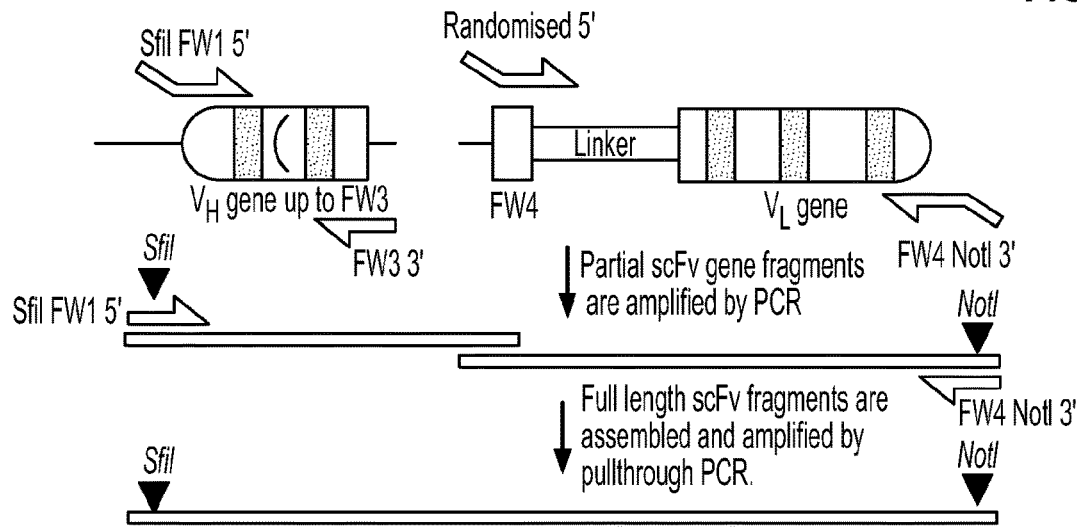

An overview of library construction is shown in FIGS. 8A, 8B, and 8C. Non-expressing plasmids were prepared containing truncated fragments of $V_H1/V_\kappa8$ S29A parental scFv as well as two sequential stop codons in the region to be randomized. The purpose of this step was to reduce the likelihood of parental scFv being produced and dominating selections (as is occasionally observed during affinity maturation), such that only recombined antibody fragments generated by PCR are able to form functional scFvs in a phagemid vector.

For the CDR3L library, randomization of the CDR3L was carried out by performing two PCRs. In the first PCR, a randomized 3' primer and a $V_H$ FW1 specific 5' primer containing a Sfi I restriction site were used to amplify the majority of the scFv gene and introduce mutations into the $V_\kappa$ CDR3. The second PCR added the remainder of the scFv and appended a restriction site (Not I) for subcloning of the fragment.

For the $V_H$ libraries, the PCR for the $V_H$ repertoire was carried out by performing two PCRs using two templates containing portions of the full-length parent scFv. Initially, the $V_H$ was amplified with the randomized 5' library primer and a 3' primer specific for the $V_\kappa$ light chain FW4. In a separate PCR, the remainder of the $V_H$ was amplified with a 5' primer based in the heavy chain FW1 region plus a 3' primer that was complementary to a portion of the $V_H$ CDR randomized primer. The full length $V_H$ CDR randomized scFv libraries were then constructed by annealing of the two amplified fragments and re-amplification of the scFv by PCR with primers that appended two restriction sites (either Sfi I or Not I) for subcloning of the fragment.

To assess the diversity of the generated libraries, purified, amplified DNA for all four libraries was then digested using Sfi I and Not I and ligated into the similarly cut phagemid vector (pANT43). Ligated DNA was precipitated, resuspended in nuclease-free water and transformed by electroporation into freshly prepared electrocompetent TG1 cells. The following day, colonies were counted, plates scraped and glycerol stocks prepared. Libraries were electroporated multiple times in order to sufficiently cover the theoretical library diversity. In all cases, a coverage of 4.0-fold or greater was obtained. Individual colonies from each of the four libraries were sequenced to confirm that the appropriate CDR block had been mutated.

Bacteria from each library were inoculated into 150 ml 2TYCG (2%) cultures using inocula at least 10× the observed library diversity. The cultures were grown to mid-log phase ($OD_{600\ nm} \approx 0.5$-$0.6$) and the total number of cells estimated (based on an $OD_{600\ nm}$ of $1 \approx 5 \times 10^8$ cells/ml). Helper phage were added and incubated for 1 hour, then centrifuged, resuspended in 2TYCK media and grown overnight at 30° C. The following day, phage were harvested by recovering the culture supernatant by centrifugation followed by precipitation using $4/10^{th} \times$ volume of chilled 20% PEG/2.5 M NaCl. After 1 hour incubation on ice, precipitated phage were recovered by centrifugation and the pellet resuspended in 1×PBS pH 7.4. The supernatant was re-centrifuged to remove any cellular debris, following which the supernatant was re-precipitated as described above. The precipitated phage were resuspended in 1×PBS pH 7.4 and filter sterilized. To increase the chances of obtaining scFvs with increased affinity, multivalent hyperphage M13 K07ΔpIII helper phage were used at a multiplicity of infection of 20 for library rescue due to the relatively low affinity of the starting antibody. Following the first round of selection, monovalent M13K07 helper phage at a multiplicity of infection of 10 were used as a result of an expected enrichment of antigen binders.

Affinity Improved Phage Selection

Two separate selection strategies were implemented to increase the probability of obtaining affinity improved phage. CEACAM1 was used throughout the selections either biotinylated (for soluble selections) or unbiotinylated (for solid phase panning). Soluble selections (Campaign 1) or solid phase panning selections (Campaign 2) were used at round 1 in the different selection cascades to enrich for functional binding phage and diversity. Deselection using the closely related family members CEACAM5 and CEACAM6 was performed by separate panning of each protein at 1 μg/ml in order to try and reduce cross reactivity. This was performed twice during each campaign, either by deselecting prior to any rounds of selection and prior to round 2 (Campaign 1) or prior to both the second and third rounds of selection (Campaign 2). For both campaigns the four libraries were kept separate at all stages.

For soluble selections, each of the libraries were pre-blocked with PBSB following which the phage was incubated with decreasing concentrations of biotinylated CEACAM1 antigen for up to three hours. Following incubation, streptavidin paramagnetic beads (pre-blocked as above) were added to each selection and rotated turning end-over-end for 15 minutes. Streptavidin-antigen-phage complexes were washed using increasing numbers of washes with PBST at each successive round of selection followed by a PBS wash, capturing with a magnet between each step. Phage were eluted from the beads by the addition of 50 mM HCl following which the solution was neutralized by the addition of 1 M Tris-HCl pH 9.0.

Figure 9A:
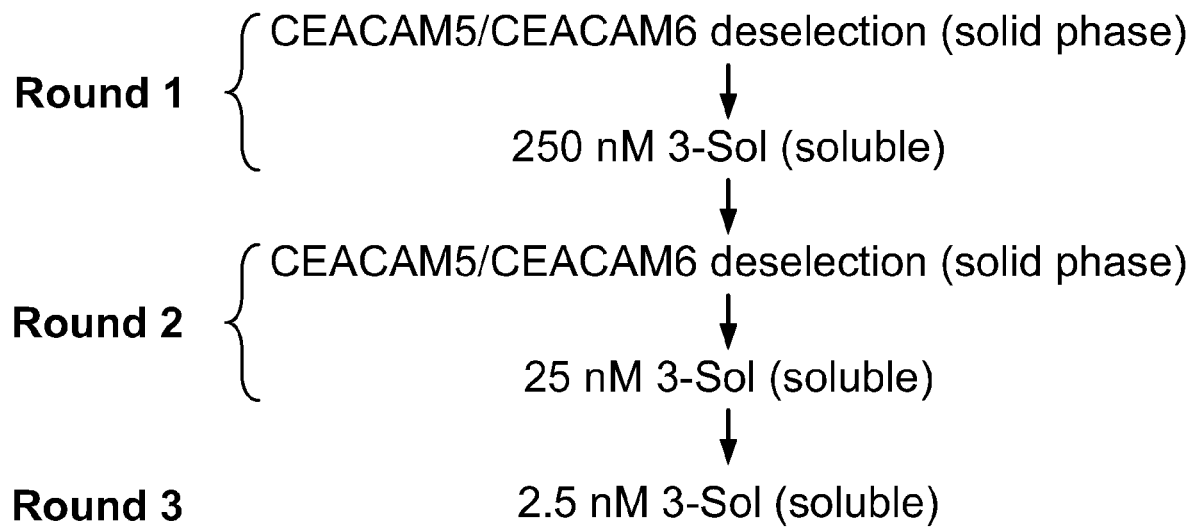
FIGS. 9A and 9B provide an overview of the two different selection campaigns employed during the affinity maturation of CEACAM1 antibodies.
Figure 9B:
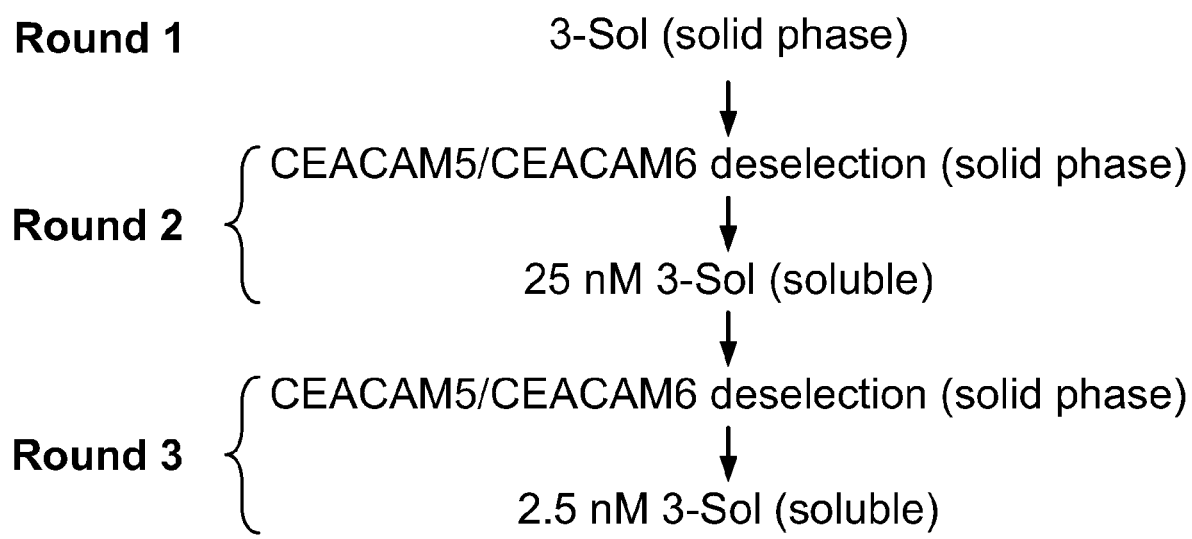

Solid-phase panning selections and all deselections were performed on Nunc Immuno MaxiSorp 96 well flat bottom microtitre plates coated with antigen overnight at 4° C. then blocked with PBSB. For deselections, pre-blocked phage was incubated with CEACAM5 followed by CEACAM6 before unbound phage were removed and used for subsequent selections. For CEACAM1 panning selections pre-blocked phage were incubated with 8 µg/ml antigen before plates were washed with 3×PBST and 2×PBS. Bound phage were eluted with 50 mM HCl as with the soluble selection. For both soluble and panning selections, eluted phage were added to mid-log E. coli TG1 and allowed to infect the cells for 1 hour at 37° C. before plating out on 2TYCG (2%) plates and growing overnight at 37° C. The following day, colonies were picked for screening or, alternatively, plates were scraped, and the phage rescued as described above. An overview of the different selection strategies used is shown in FIGS. 9A and 9B.

Expression and Initial Testing of scFv

Soluble scFv were initially expressed and tested as crude periplasmic extracts. Individual colonies were picked into 1 ml 2TYCG (0.1%) media and grown by shaking at 37° C. for 5 hours. Cultures were induced by adding IPTG to a final concentration of 1 mM and then grown overnight, with shaking, at 30° C. The following day, cultures were centrifuged and the supernatant discarded. Bacterial pellets were resuspended in Tris(hydroxymethyl)methyl-2-aminoethane-sulfonic acid (TES) buffer pH 7.4 and incubated on ice for 30 minutes. The cells were then centrifuged and the supernatant discarded. The pellet was resuspended in ice cold 5 mM $MgSO_4$. The plate was then centrifuged and the scFv-containing supernatant transferred to a fresh plate for assay.

Periplasmic extracts of colonies from different rounds of selection were screened in a single point binding assay for their ability to bind GST-CEACAM1. The parental scFv ($V_H1/V_\kappa 8$ S29A) and an irrelevant scFv were included on each assay plate for comparison. Periplasmic extracts were blocked by diluting 1:1 with PBSB before incubating for 1 hour at room temperature on a Nunc Immuno MaxiSorp 96 well flat bottom microtitre plate pre-coated with GST-CEACAM1 at 1.0 µg/ml. Plates were subsequently washed and the binding of scFv was detected with an anti-HIS6-HRP antibody and TMB substrate. The reaction was stopped with 1 M HCl, absorbance read at 450 nm on a Dynex Technologies MRX TC II plate reader and the binding data plotted.

Improved clones were identified on the basis of activity in the binding ELISA relative to the parental scFv $V_H1/V_\kappa 8$ S29A (which contains the mouse CDRs) and the irrelevant scFv assayed on the same plate. Greater than 4400 periplasmic extracts were analyzed and 34 leads with binding at least 1.5 greater than parent in two separate experiments were sequenced and unique clones identified. Examination of the sequences obtained showed that in several positions the parental amino acid was found but was encoded by a different codon from the parent. This indicates that selection had occurred as expected but that the parent amino acid was the preferred amino acid at this position. Based upon this sequence analysis, 19 unique CDR1H, three CDR3H block 1, three CDR3H block 2 and 9 unique CDR3L clones were taken forward for large scale scFv expression. A summary of the 34 leads that were selected for further analysis as purified scFvs is shown in Table 10, together with the CDR mutations of these mutants.

Table 11, Table 12, and Table 13 highlight the conservation/variability of affinity matured CDRs in scFv variant leads identified using the GST-CEACAM1 binding ELISA.

TABLE 10

Summary of the 34 scFv variant leads identified using the GST-CEACAM1 binding ELISA. Summarized is the library the scFvs were derived from and deselection rounds the scFvs were subjected to. The parent (Vκ8 S29A) CDR is shown at the top of the table. The mutations differing from the parent sequence within CDR1H, CDR3H B1, CDR3H B2, and CDR3L are highlighted in bold. All variable light chains contain a S29A mutation in CDR1L (Kabat numbering scheme, corresponding to a S28A mutation in the primary amino acid sequence of the variable light chain).

| Variant | CDR1H | CDR3H (Block 1) | CDR3H (Block 2) | CDR3L |
|---|---|---|---|---|
| Parent | GFIFSSHGMS (SEQ ID NO: 23) | RHDFDYD (SEQ ID NO: 77) | DAAWFAY (SEQ ID NO: 81) | QWSSNPP (SEQ ID NO: 85) |
| CP09E05 | | RHGFDYD (SEQ ID NO: 79) | | |
| CP09F05 | | | | QNTALPF (SEQ ID NO: 86) |
| CP09F03 | GFTFNNHGMS (SEQ ID NO: 57) | | | |
| CP09A04 | GFSFNAHAMS (SEQ ID NO: 58) | | | |
| CP09E03 | GFTFSAHAIS (SEQ ID NO: 59) | | | |
| CP09D03 | GFTFSSHAIS (SEQ ID NO: 60) | | | |
| CP09B02 | GFTFTSHAIS (SEQ ID NO: 61) | | | |
| CP09C02 | EFTFSDHAMS (SEQ ID NO: 62) | RHGFDYD (SEQ ID NO: 79) | | |
| CP09B03 | GFTFNAHAIS (SEQ ID NO: 63) | | | |
| CP09G03 | GFTFNAHAMS (SEQ ID NO: 64) | | | |

TABLE 10-continued

Summary of the 34 scFv variant leads identified using the GST-CEACAM1 binding ELISA. Summarized is the library the scFvs were derived from and deselection rounds the scFvs were subjected to. The parent (Vκ8 S29A) CDR is shown at the top of the table. The mutations differing from the parent sequence within CDR1H, CDR3H B1, CDR3H B2, and CDR3L are highlighted in bold. All variable light chains contain a S29A mutation in CDR1L (Kabat numbering scheme, corresponding to a S28A mutation in the primary amino acid sequence of the variable light chain).

| Variant | CDR1H | CDR3H (Block 1) | CDR3H (Block 2) | CDR3L |
|---|---|---|---|---|
| CP08G09 | | | | QWTAFPP (SEQ ID NO: 87) |
| CP08D02 | | | | QWTSFPP (SEQ ID NO: 88) |
| CP08G02 | | | | QWTNNPP (SEQ ID NO: 89) |
| CP08C08 | | | | QNTSLPF (SEQ ID NO: 90) |
| CP08F05 | | | | QWTSNPP (SEQ ID NO: 91) |
| CP08E05 | | | | QWTTNPP (SEQ ID NO: 92) |
| CP08G01 | | | | QNTNLPF (SEQ ID NO: 93) |
| CP08E01 | | | | QWTTFPP (SEQ ID NO: 94) |
| CP08B04 | | | FPAWFAL (SEQ ID NO: 82) | |
| CP08H03 | | | FPYWFAH (SEQ ID NO: 83) | |
| CP08G10 | | | FPAWFAF (SEQ ID NO: 84) | |
| CP08H01 | | KHPPDYF (SEQ ID NO: 80) | | |
| CP08B01 | GFTFSAHAMS (SEQ ID NO: 65) | | | |
| CP08A08 | GFIFTNHGMS (SEQ ID NO: 66) | | | |
| CP08A03 | GFIFNNHAIS (SEQ ID NO: 67) | | | |
| CP08B03 | GFTFTAHAIS (SEQ ID NO: 68) | | | |
| CP08D11 | GYSFSAHGMS (SEQ ID NO: 69) | | | |
| CP08B11 | GFTFTNHGMS (SEQ ID NO: 70) | | | |
| CP08C04 | GFTFSSHGMS (SEQ ID NO: 71) | | | |
| CP08B06 | GFSFNSHAIS (SEQ ID NO: 72) | | | |
| CP08F07 | GFTFTDHAIS (SEQ ID NO: 73) | | | |
| CP08C01 | GYSFSNHGMS (SEQ ID NO: 74) | | | |
| CP08A06 | GYSFSSHGMS (SEQ ID NO: 75) | | | |
| CP08D01 | GFTFNAHGMS (SEQ ID NO: 76) | | | |

TABLE 11

CDR motif for heavy chain CDR1 in scFv variant leads
identified using the GST-CEACAM1 binding ELISA.

| | | | | | CDR1H CDR residues CDR residue (Kabat)$ | | | | |
|---|---|---|---|---|---|---|---|---|---|
| 26 | 27 | 28 | 29 | 30 | 31 | 32 | 33 | 34 | 35 |
| | | | | | HC residue* | | | | |
| 26 | 27 | 28 | 29 | 30 | 31 | 32 | 33 | 34 | 35 |
| Motif G (19/20) | F (17/20) | T (13/20) | F | S (8/20) | A (8/20) | H | A (12/20) | M (12/20) | S |
| E (1/20) | Y (3/20) | S (5/20) | | N (7/20) | N (5/20) | | G (8/20) | I (8/20) | |
| | | I (2/20) | | T (5/20) | S (5/20) | | | | |
| | | | | | D (2/20) | | | | |

$Numbering of residues based on Kabat numbering scheme.
*Numbering of residues based on primary amino acid sequence of the heavy variable chain. CDR1H comprises residues 31-35 according to the Kabat CDR definition and residues 26-33 according to the IMGT definition.

TABLE 12

CDR motif for heavy chain CDR3 in scFv variant leads
identified using the GST-CEACAM1 binding ELISA.

| | | | | | | CDR3H CDR residue CDR residue (Kabat)$ | | | | | |
|---|---|---|---|---|---|---|---|---|---|---|---|
| 94# | 95 | 96 | 97 | 98 | 99 | 100 | 100A | 100B | 100C | 100D | 101 | 102 |
| | | | | | | HC residue* | | | | | | |
| 98# | 99 | 100 | 101 | 102 | 103 | 104 | 105 | 106 | 107 | 108 | 109 | 110 |
| Block 1 R# (2/3) | H | G (2/3) | F (2/3) | D | Y | D (2/3) | | | | | | |
| K# (1/3) | | P (1/3) | P (1/3) | | | F (1/3) | | | | | | |
| Block 2 | | | | | | F | P | A (2/3) | W | F | A | L (1/3) |
| | | | | | | | | Y (1/3) | | | | H (1/3) |
| | | | | | | | | | | | | F (1/3) |

$Numbering of residues based on Kabat numbering scheme.
*Numbering of residues based on primary amino acid sequence of the heavy variable chain.
Not part of the CDR according to Kabat definition. Residue was included in mutagenesis to allow for more diversity in the germline residue anchoring the CDR.

TABLE 13

CDR motif for light chain CDR3 in scFv variant leads
identified using the GST-CEACAM1 binding ELISA.

| | | | | | CDR3L CDR residue CDR residue (Kabat)$ | | | |
|---|---|---|---|---|---|---|---|---|
| 89 | 90 | 91 | 92 | 93 | 94 | 95 | 96 | 97 |
| | | | | | LC residue* | | | |
| 88 | 89 | 90 | 91 | 92 | 93 | 94 | 95 | 96 |
| VL CDR3 Q# | Q | W (6/9) | T | S (3/9) | L (3/9) | P | P (6/9) | T# |
| | | N (3/9) | | A (2/9) | F (3/9) | | F (3/9) | |
| | | | | N (2/9) | N (3/9) | | | |
| | | | | T (2/9) | | | | |

$Numbering of residues based on Kabat numbering scheme.
*Numbering of residues based on primary amino acid sequence of the light variable chain.
Residue was not mutated during affinity maturation.

Large Scale ScFv Expression and Purification

Selected clones were expressed, purified and quantified in order to accurately test the scFv by binding ELISA. Briefly, individual colonies were picked into 15 ml 2TYCG (2%) media and grown overnight by shaking at 30° C. The starter culture was used to inoculate 500 ml 2TYCG (0.1%) and grown at 30° C. until $OD_{600\,nm}$=~0.8. Cultures were induced by adding IPTG to a final concentration of 1 mM and then grown overnight with shaking at 30° C. The following day, cultures were centrifuged and the supernatant discarded. The bacterial pellets were resuspended in 15 ml TES and incubated on ice for 15 minutes. 22.5 ml of TES (diluted 1 in 5 in cold water) was then added and incubated on ice for a further 30 minutes. The cells were then centrifuged and the scFv-containing supernatant transferred to a fresh tube, following which $MgCl_2$, NaCl and imidazole were added to final concentrations of 1 mM, 300 mM and 20 mM respectively to reduce non-specific binding. Ni-agarose beads were added and scFv allowed to bind by incubating with rotation at 4° C. for 2 hours. Beads were pelleted by centrifugation and washed twice with wash buffer (25 mM Tris pH 7.4, 300 mM NaCl, 20 mM imidazole) before scFv were eluted from the beads using elution buffer (25 mM Tris pH 7.4, 300 mM NaCl, 400 mM imidazole). Samples were quantified by measuring the OD 280 nm and using an extinction coefficient based on the predicted amino acid sequences. Approximately 1 μg of each scFv was analyzed by SDS-PAGE. Bands corresponding to the profiles of typical scFv were observed.

Assessment of scFv Binding to GST-CEACAM1 as Determined by ELISA

The binding of affinity matured purified scFv to human CEACAM1 was analyzed using GST-CEACAM1. A Nunc Immuno MaxiSorp 96 well flat bottom microtitre plate was pre-coated with 1.0 µg/ml GST-CEACAM1 overnight at 4° C. The following day a two-fold dilution series of $V_H1/V_\kappa 8$ S29A parent scFv or test scFv (50 µg/ml to 0.8 µg/ml) in PBSB was incubated for 2 hours at RT on pre-coated ELISA plates. The binding of scFv was detected with an anti-HIS6-HRP antibody and TMB substrate. The reaction was stopped with 3 M HCl, absorbance read at 450 nm on a Dynex Technologies MRX TC II plate reader and the binding curves plotted. Example binding assay data is shown in FIG. 10. Parent scFv ($V_H1/V_\kappa 8$ S29A scFv) was included on each ELISA plate as a reference. An irrelevant scFv was included on at least one plate as a negative control. It was observed that a number of scFvs had improved binding to CEACAM1 compared to the parental $V_H1/V_\kappa 8$ S29A scFv. Improved binding was seen with scFv derived from both $V_H$ and $V_\kappa$ libraries. All 34 scFv variants were reformatted to whole IgG to provide greater accuracy with regard to purity and quantitation. The reformatting further allowed for an analysis of the avidity component of antibody binding, which is influenced by the bivalent nature of IgGs. As used herein, "avidity" is the measure of the strength of binding between an antigen-binding molecule (such as an antibody or antibody fragment thereof described herein) and the pertinent antigen.

Construction and Testing of Affinity Matured Whole Antibodies

Reformatting of scFvs to Whole IgG

The 34 variants identified by scFv screening were PCR amplified using primers that introduced flanking restriction enzyme sites for cloning into a IgG4 S241P PANTVhG4 vector and k light chain pANTVK vector. 25 affinity matured $V_H$ variants were subcloned into the IgG4 S241P pANTVhG4 vector using Mlu I and Hind III restriction sites. Similarly, 9 affinity matured $V_\kappa$ sequences were subcloned into the k light chain pANTVK vector using BssH II and BamH I restriction sites. All constructs were confirmed by sequencing.

For expression, the 25 lead humanized affinity matured IgG4 $V_H$ variants were combined with the parent humanized, aglycosylated light chain ($V_\kappa 8$ S29A). The 9 lead humanized affinity matured K light chains were combined with the parent humanized heavy chain ($V_H1$). These combinations were transiently transfected into HEK EBNA adherent cells (in 6-well plates using a PEI transfection method. Five to seven days post-transfection, the supernatants were harvested, quantified by ELISA and filtered for Biacore single-cycle kinetics analysis.

Single-Cycle Kinetics Analysis of Humanized and Affinity Matured Lead IgGs Binding to CEACAM1

In order to assess the binding of the humanized, affinity matured reformatted lead IgGs, single-cycle kinetics analysis was performed on crude supernatants using a Biacore T200 running Biacore T200 Control Software V2.0.1 and Biacore T200 Evaluation Software V3.0. Antibodies were diluted in HBS-P+ to a final concentration of 0.5 µg/ml. At the start of each cycle, antibodies were loaded onto Fc2, Fc3 and Fc4 of the Protein A chip. IgGs were captured at a flow rate of 10 µl/min to give an immobilisation level (RL) of ~100 RU (a level calculated to obtain a $R_{max}$ of ~50-150 RU once the analyte is bound). The surface was then allowed to stabilize. Single-cycle kinetics data was obtained with CEACAM1 as the analyte at a flow rate of 80 µl/min to minimize any potential mass transfer effects. Multiple repeats with the parent ($V_H1/V_\kappa 8$ S29A) antibody were performed to check the stability of the surface and analyte over the kinetic cycles. The signal from the reference channel Fc1 (no antibody) was subtracted from that of Fc2, Fc3 and Fc4 to correct for differences in non-specific binding to the reference surface. A three point, two-fold dilution range from 70 nM to 280 nM CEACAM1 without regeneration between each concentration was used. The signal from each antibody blank run (no CEACAM1) was subtracted to correct for differences in surface stability. The association phase for the three injections of increasing concentrations of CEACAM1 was monitored for 80 seconds each time and a single dissociation phase was measured for 150 seconds following the last injection of CEACAM1. Regeneration of the Protein A surface was conducted using two injections of 10 mM glycine-HCL pH 1.5 followed by a stabilization period of 250 seconds.

Single-cycle kinetic constants (Table 14) demonstrated that all but one humanized, affinity matured antibody bound to CEACAM1.

TABLE 14

Single-cycle kinetics constants for humanized and affinity matured variants and parent ($V_H1/V_\kappa 8$ S29A) antibody binding to CEACAM1. The relative $K_D$ compared to parent IgG was calculated by dividing the $K_D$ of the humanized and affinity matured variants by that of the parent assayed multiple times in the same experiment. Variants progressed are outlined in bold. The CDRs containing the mutations are indicated with "+". All variable light chains contain a S29A mutation in CDR1L (Kabat numbering scheme, corresponding to a S28A mutation in the primary amino acid sequence of the variable light chain). Indicated in bold the variants with relative $K_D$s > two-fold compared to parent $V_H1/V_\kappa 8$ S29A.

| Heavy chain variant | Light chain variant | $V_H$ CDR1 | $V_H$ CDR3 B1 | $V_H$ CDR3 B2 | VL CDR 3 | $k_a$ ($M^{-1}s^{-1}$) | $k_d$ ($s^{-1}$) | $K_D$ (M) | Relative $K_D$ to parent |
|---|---|---|---|---|---|---|---|---|---|
| $V_H1$ | Vκ8 S29A | | | | | $9.5 \times 10^4$ | $5.7 \times 10^{-2}$ | $5.9 \times 10^{-7}$ | 1 |
| | CP09F05 | | | | + | $3.5 \times 10^4$ | $5.5 \times 10^{-2}$ | $1.6 \times 10^{-6}$ | 0.4 |
| CP09F03 | | + | | | | $7.4 \times 10^4$ | $7.6 \times 10^{-2}$ | $1.0 \times 10^{-6}$ | 0.5 |
| CP09A04 | | + | | | | $9.0 \times 10^4$ | $3.6 \times 10^{-2}$ | $4.0 \times 10^{-7}$ | 1.4 |
| CP09E03 | | + | | | | $1.1 \times 10^5$ | $3.7 \times 10^{-2}$ | $4.0 \times 10^{-7}$ | 1.6 |
| CP09D03 | | + | | | | $1.1 \times 10^5$ | $3.3 \times 10^{-2}$ | $3.1 \times 10^{-7}$ | 1.8 |
| CP09B02 | | + | | | | $1.2 \times 10^5$ | $4.0 \times 10^{-2}$ | $3.4 \times 10^{-7}$ | 1.6 |
| CP09C02 | | + | + | | | $2.0 \times 10^5$ | $1.7 \times 10^{-2}$ | $8.8 \times 10^{-8}$ | 7.1 |
| CP09B03 | | + | | | | $1.5 \times 10^5$ | $3.9 \times 10^{-2}$ | $2.6 \times 10^{-7}$ | 2.4 |
| CP09G03 | | + | | | | $1.1 \times 10^5$ | $3.8 \times 10^{-2}$ | $3.5 \times 10^7$ | 1.5 |
| CP09E05 | | | | + | | $1.2 \times 10^5$ | $3.7 \times 10^{-2}$ | $3.2 \times 10^{-7}$ | 1.4 |
| | CP08G09 | | | | + | $4.7 \times 10^5$ | $4.9 \times 10^{-2}$ | $1.1 \times 10^{-7}$ | 5.9 |
| | CP08D02 | | | | + | $4.3 \times 10^5$ | $4.3 \times 10^{-2}$ | $1.0 \times 10^{-7}$ | 6.2 |
| | CP08G02 | | | | + | $2.3 \times 10^4$ | $5.2 \times 10^{-2}$ | $2.3 \times 10^{-6}$ | 0.3 |

TABLE 14-continued

Single-cycle kinetics constants for humanized and affinity matured variants and parent ($V_H1/V\kappa8$ S29A) antibody binding to CEACAM1. The relative $K_D$ compared to parent IgG was calculated by dividing the $K_D$ of the humanized and affinity matured variants by that of the parent assayed multiple times in the same experiment. Variants progressed are outlined in bold. The CDRs containing the mutations are indicated with "+". All variable light chains contain a S29A mutation in CDR1L (Kabat numbering scheme, corresponding to a S28A mutation in the primary amino acid sequence of the variable light chain). Indicated in bold the variants with relative $K_D$s > two-fold compared to parent $V_H1/V\kappa8$ S29A.

| Heavy chain variant | Light chain variant | $V_H$ CDR1 | $V_H$ CDR3 B1 | $V_H$ CDR3 B2 | VL CDR 3 | $k_a$ ($M^{-1}s^{-1}$) | $k_d$ ($s^{-1}$) | $K_D$ (M) | Relative $K_D$ to parent |
|---|---|---|---|---|---|---|---|---|---|
| | CP08C08 | | | | + | No binding observed | | | |
| | CP08F05 | | | | + | 4.0 × 10⁵ | 1.1 × 10⁻¹ | 2.8 × 10⁻⁷ | 2.2 |
| | CP08E05 | | | | + | 2.4 × 10⁵ | 3.4 × 10⁻² | 1.4 × 10⁻⁷ | 4.4 |
| | CP08G01 | | | | + | 1.2 × 10⁵ | 4.7 × 10⁻² | 4.0 × 10⁻⁷ | 1.5 |
| | CP08E01 | | | | + | 3.3 × 10⁵ | 5.4 × 10⁻² | 1.7 × 10⁻⁷ | 3.7 |
| CP08B04 | | | | + | | 1.2 × 10⁵ | 4.9 × 10⁻² | 4.1 × 10⁻⁷ | 1.4 |
| CP08H03 | | | | + | | 1.8 × 10⁵ | 7.6 × 10⁻³ | 4.5 × 10⁻⁸ | 13.7 |
| CP08G10 | | | | + | | 8.7 × 10⁴ | 5.5 × 10⁻² | 6.3 × 10⁻⁷ | 0.9 |
| CP08H01 | | | + | | | 2.1 × 10⁵ | 8.7 × 10⁻² | 4.2 × 10⁻⁷ | 1.3 |
| CP08B01 | | + | | | | 7.2 × 10⁴ | 4.4 × 10⁻² | 6.1 × 10⁻⁷ | 0.9 |
| CP08A08 | | + | | | | 5.7 × 10⁴ | 7.3 × 10⁻² | 1.3 × 10⁻⁶ | 0.4 |
| CP08A03 | | + | | | | 9.3 × 10⁴ | 3.9 × 10⁻² | 4.3 × 10⁻⁷ | 1.3 |
| CP08B03 | | + | | | | 2.0 × 10⁵ | 6.9 × 10⁻² | 3.6 × 10⁻⁷ | 1.6 |
| CP08D11 | | + | | | | 8.6 × 10⁴ | 1.7 × 10⁻¹ | 2.0 × 10⁻⁶ | 0.3 |
| CP08B11 | | + | | | | 9.6 × 10⁴ | 5.9 × 10⁻² | 6.1 × 10⁻⁷ | 0.9 |
| CP08C04 | | + | | | | 2.2 × 10⁵ | 2.6 × 10⁻¹ | 1.2 × 10⁻⁶ | 0.5 |
| CP08B06 | | + | | | | 1.1 × 10⁵ | 4.4 × 10⁻² | 4.2 × 10⁻⁷ | 1.3 |
| CP08F07 | | + | | | | 1.7 × 10⁵ | 8.1 × 10⁻² | 4.7 × 10⁻⁷ | 1.2 |
| CP08C01 | | + | | | | 8.2 × 10⁴ | 1.0 × 10⁻¹ | 1.2 × 10⁻⁶ | 0.5 |
| CP08A06 | | + | | | | 1.7 × 10⁵ | 7.5 × 10⁻² | 4.4 × 10⁻⁷ | 1.3 |
| CP08D01 | | + | | | | 1.4 × 10⁵ | 4.3 × 10⁻² | 3.0 × 10⁻⁷ | 1.9 |

Eight humanized and affinity matured heavy and light chain variants were identified that demonstrated relative $K_D$s>two-fold compared to parent (highlighted in bold in Table 14. These included three $V_H$ variants (CP08H03, CP09B03 and CP09C02) and five k light chain variants (CP08E01, CP08E05, CP08F05, CP08D02, and CP08G09).

CP09C02 (which originated from the CDR1H library) contained an additional point mutation in CDR3H B1 (D96G), which most likely had been introduced through PCR at the library construction stage (see section "Example 1, 1. Generation of humanized antibody variants"). Therefore, an additional heavy chain clone CP09E05 was also taken forward as it was identified as having only this single point mutation in $V_H$ CDR3 B1 and thus could potentially help to identify which region was involved in the observed affinity gain. The four $V_H$ and five $V_\kappa$ variants were subsequently taken forward to determine whether there could be improved effects from recombining affinity matured heavy and light chains.

Expression of Combined Lead Heavy and Light Chain Antibodies

Each of the four humanized affinity matured IgG4 $V_H$ variants (CP08H03, CP09B03, CP09C02, and CP09E05) identified following expression with parent light chain were combined with the five lead humanized affinity matured K light chains (CP08E01, CP08E05, CP08F05, CP08D02, and CP08G09) (i.e. a total of 20 pairings, see Table 15). As controls, the humanized affinity matured IgG4 $V_H$ variants were combined with the parent light chain ($V_\kappa8$ S29A) and the five lead humanized affinity matured K light chains were combined with the parent heavy chain ($V_H1$) (i.e. a total of 10 control antibodies, see Table 15). As described above, combinations were transiently transfected into HEK EBNA adherent cells in 6-well plates using a PEI transfection method and incubated for 5-7 days post-transfection. The supernatants were harvested, quantified by ELISA and filtered for single-cycle kinetics analysis on the Biacore.

TABLE 15

Combinations of parent $V_H$ or lead humanized affinity matured IgG4 $V_H$ variants with parent V$\kappa$ or lead humanized affinity matured V$\kappa$ light chains. Transfected antibodies with recombined affinity matured heavy and light chains (black), affinity matured antibodies expressed with either the parent heavy or light chain and parent antibody. All variable light chains contain a S29A mutation in CDR1L (Kabat numbering scheme, corresponding to a S28A mutation in the primary amino acid sequence of the variable light chain).

| | | $V_H$ | | | | |
|---|---|---|---|---|---|---|
| | | CP08H03 | CP09B03 | CP09C02 | CP09E05 | Parent |
| $V_L$ | CP08E01 | + | + | + | + | + |
| | CP08E05 | + | + | + | + | + |
| | CP08F05 | + | + | + | + | + |
| | CP08D02 | + | + | + | + | + |
| | CP08G09 | + | + | + | + | + |
| | Parent | + | + | + | + | |

Single-Cycle Kinetics Analysis of Combined Lead Heavy and Light Chain Antibodies Single-cycle kinetics using transient HEK supernatant was performed as described previously. The fitted data for the single-cycle kinetics are shown in Table 16. Fifteen heavy and light chain combinations had relative $K_D$s at least two-fold better than parent. Of these, six combinations (CP08H03/CP08E05, CP08H03/CP08F05, CP08H03/$V_\kappa8$ S29A, CP09B03/CP08E05, CP09C02/CP08E05, and CP09C02/CP08F05) achieved $K_D$s greater than four-fold better than parent (highlighted in bold in Table 16). These six variants were taken forward for larger scale production and Protein A purification for further analysis. Single-cycle kinetics also revealed that three variants were found to be non-functional when combined.

TABLE 16

Single cycle kinetic constants for lead $V_H$ and Vκ combination antibodies and parent antibody binding to CEACAM1. The relative $K_D$ compared to parent was calculated by dividing the $K_D$ of the lead $V_H$ and Vκ combination variants by that of the parent assayed in the same experiment. Variants highlighted in bold were the lead combinations with $K_D$s > four-fold better than parent. The CDRs containing the mutations are indicated with "+". All variable light chains contain a S29A mutation in CDR1L (Kabat numbering scheme, corresponding to a S28A mutation in the primary amino acid sequence of the variable light chain).

| | $V_H$ CDR1 | $V_H$ CDR3 B1 | $V_H$ CDR3 B2 | VL CDR3 | ka (1/Ms) | kd (1/s) | $K_D$ (M) | Relative $K_D$ to parent |
|---|---|---|---|---|---|---|---|---|
| Parent ($V_H$1/Vκ8 S29A) | | | | | $9.6 \times 10^4$ | $5.3 \times 10^{-2}$ | $5.5 \times 10^{-7}$ | 1.0 |
| CP08H03/CP08E01 | | | + | + | No binding observed | | | |
| CP08H03/CP08E05 | | | + | + | $\mathbf{7.1 \times 10^4}$ | $\mathbf{8.5 \times 10^{-3}}$ | $\mathbf{1.2 \times 10^{-7}}$ | 4.6 |
| CP08H03/CP08F05 | | | + | + | $\mathbf{7.0 \times 10^4}$ | $\mathbf{7.4 \times 10^{-3}}$ | $\mathbf{1.1 \times 10^{-7}}$ | 5.2 |
| CP08H03/CP08D02 | | | + | + | No binding observed | | | |
| CP08H03/CP08G09 | | | + | + | No binding observed | | | |
| CP08H03/Vκ8 S29A | | | + | | $\mathbf{6.5 \times 10^4}$ | $\mathbf{8.5 \times 10^{-3}}$ | $\mathbf{1.3 \times 10^{-7}}$ | 4.2 |
| CP09B03/CP08E01 | + | | | + | $1.8 \times 10^5$ | $4.6 \times 10^{-2}$ | $2.5 \times 10^{-7}$ | 2.2 |
| CP09B03/CP08E05 | + | | | + | $\mathbf{1.1 \times 10^5}$ | $\mathbf{1.0 \times 10^{-2}}$ | $\mathbf{9.7 \times 10^{-8}}$ | 5.7 |
| CP09B03/CP08F05 | + | | | + | $1.1 \times 10^5$ | $1.7 \times 10^{-2}$ | $1.5 \times 10^{-7}$ | 3.6 |
| CP09B03/CP08D02 | + | | | + | $2.1 \times 10^5$ | $5.9 \times 10^{-2}$ | $2.9 \times 10^{-7}$ | 1.9 |
| CP09B03/CP08G09 | + | | | + | $1.3 \times 10^5$ | $3.7 \times 10^{-2}$ | $3.0 \times 10^{-7}$ | 1.9 |
| CP09B03/Vκ8 S29A | + | | | | $1.7 \times 10^5$ | $5.2 \times 10^{-2}$ | $3.0 \times 10^{-7}$ | 1.8 |
| CP09C02/CP08E01 | + | + | | + | $1.4 \times 10^5$ | $2.0 \times 10^{-2}$ | $1.4 \times 10^{-7}$ | 3.9 |
| CP09C02/CP08E05 | + | + | | + | $\mathbf{9.6 \times 10^4}$ | $\mathbf{7.5 \times 10^{-2}}$ | $\mathbf{7.8 \times 10^{-8}}$ | 7.1 |
| CP09C02/CP08F05 | + | + | | + | $\mathbf{1.1 \times 10^5}$ | $\mathbf{1.1 \times 10^{-2}}$ | $\mathbf{1.0 \times 10^{-7}}$ | 5.5 |
| CP09C02/CP08D02 | + | + | | + | $1.6 \times 10^5$ | $2.2 \times 10^{-2}$ | $1.4 \times 10^{-7}$ | 4.0 |
| CP09C02/CP08G09 | + | + | | + | $1.3 \times 10^5$ | $1.8 \times 10^{-2}$ | $1.4 \times 10^{-7}$ | 3.9 |
| CP09C02/Vκ8 S29A | + | + | | | $1.1 \times 10^5$ | $1.9 \times 10^{-2}$ | $1.7 \times 10^{-7}$ | 3.3 |
| CP09E05/CP08E01 | + | | | + | $1.3 \times 10^5$ | $4.1 \times 10^{-2}$ | $3.2 \times 10^{-7}$ | 1.7 |
| CP09E05/CP08E05 | + | | | + | $1.0 \times 10^5$ | $2.0 \times 10^{-2}$ | $2.0 \times 10^{-7}$ | 2.8 |
| CP09E05/CP08F05 | + | | | + | $1.4 \times 10^5$ | $3.4 \times 10^{-2}$ | $2.5 \times 10^{-7}$ | 2.2 |
| CP09E05/CP08D02 | + | | | + | $2.3 \times 10^5$ | $7.4 \times 10^{-2}$ | $3.3 \times 10^{-7}$ | 1.7 |
| CP09E05/CP08G09 | + | | | + | $1.4 \times 10^5$ | $4.3 \times 10^{-2}$ | $3.2 \times 10^{-7}$ | 1.8 |
| CP09E05/Vκ8 S29A | + | | | | $1.2 \times 10^5$ | $3.5 \times 10^{-2}$ | $3.0 \times 10^{-7}$ | 1.8 |
| Parent $V_H$/CP08E01 | | | | + | $1.2 \times 10^5$ | $5.3 \times 10^{-2}$ | $4.5 \times 10^{-7}$ | 1.2 |
| Parent $V_H$/CP08E05 | | | | + | $1.5 \times 10^5$ | $3.4 \times 10^{-2}$ | $2.3 \times 10^{-7}$ | 2.4 |
| Parent $V_H$/CP08F05 | | | | + | $1.0 \times 10^5$ | $2.9 \times 10^{-2}$ | $2.8 \times 10^{-7}$ | 2.0 |
| Parent $V_H$/CP08D02 | | | | + | $1.3 \times 10^5$ | $5.7 \times 10^{-2}$ | $4.5 \times 10^{-7}$ | 1.2 |
| Parent $V_H$/CP08G09 | | | | + | $1.2 \times 10^5$ | $5.7 \times 10^{-2}$ | $4.8 \times 10^{-7}$ | 1.2 |

Recombination of Four Affinity Maturated Heavy Chain CDRs to Create Six Additional Heavy Chain Variants The six combinations with greater than four-fold improvements comprised three unique heavy chains with mutations in four different $V_H$ CDRs: CP08H03 (CDRH3 B2); CP09B03 (CDR1H) and CP09C02 (CDR3H B2 and a single mutation in CDR3H B1 which is also uniquely present in CP08E05), see Table 17. In order to determine whether further improvements could be gained, recombinations of the four mutated $V_H$ CDRs were performed (Table 18). Using scFv specific primers individual $V_H$ CDRs were recombined using pull through PCR and subsequently cloned into IgG4 S241P heavy chain expression vectors using Mlu I and Hind III restriction sites to generate six new $V_H$ variants (8H3_9B3, 8H3_9C2, 8H3_9E5, 9B3_9E5, 8H3_9C2 (CDR1) and 9B3_9E5_8H3).

TABLE 17

$V_H$ CDRs used for recombination.

| | Mutation location | | |
|---|---|---|---|
| Variant | CDR1H | CDR3H B1 | CDR3H B2 |
| Parent ($V_H$1/Vκ8 S29A) | GFIFSSHGMS (SEQ ID NO: 23) | RHDFDYD (SEQ ID NO: 77) | DAAWFAY (SEQ ID NO: 81) |
| CP09E05 | GFIFSSHGMS (Parent) (SEQ ID NO: 23) | RHGFDYD (SEQ ID NO: 79) | DAAWFAY (Parent) (SEQ ID NO: 81) |
| CP09C02 | EFTFSDHAMS (SEQ ID NO: 62) | RHGFDYD (SEQ ID NO: 79) | DAAWFAY (Parent) (SEQ ID NO: 81) |
| CP09B03 | GFTFNAHAIS (SEQ ID NO: 63) | RHDFDYD (Parent) (SEQ ID NO: 77) | DAAWFAY (Parent) (SEQ ID NO: 81) |
| CP08H03 | GFIFSSHGMS (Parent) (SEQ ID NO: 23) | RHDFDYD (Parent) (SEQ ID NO: 77) | FPYWFAH (SEQ ID NO: 83) |

TABLE 18

Recombined heavy chain clones. Individual CDRs from the four lead V_H clones were recombined to generate six recombined affinity matured heavy chains. The mutations differing from the parent sequence within CDR1H, CDR3H B1, and CDR3H B2 are highlighted in bold.
*Residue 104 was chosen based on sequence selected for CDR3H B2.

| Variant | $V_H$ CDR1 | $V_H$ CDR3 B1 | $V_H$ CDR3 B2 | $V_H$ CDR1 | $V_H$ CDR3 B1 | $V_H$ CDR3 B2 |
|---|---|---|---|---|---|---|
| 8H3_9B3 | $V_H$ CDR1 of CP09B03 | parent | $V_H$ CDR3 B2 of CP08H03 | GFTFNAHAIS (SEQ ID NO: 63) | parent | FPYWFAH (SEQ ID NO: 83) |
| 8H3_9C2 | $V_H$ CDR1 of CP09C02 | $V_H$ CDR3 B1 of CP09C02* | $V_H$ CDR3 B2 of CP08H03 | EFTFSDHAMS (SEQ ID NO: 62) | RHGFDYF (SEQ ID NO: 96) | FPYWFAH (SEQ ID NO: 83) |
| 8H3_9E5 | parent | $V_H$ CDR3 B1 of CP09C05* | $V_H$ CDR3 B2 of CP08H03 | parent | RHGFDYF (SEQ ID NO: 96) | FPYWFAH (SEQ ID NO: 83) |
| 9B3_9E5 | $V_H$ CDR1 of CP09B03 | $V_H$ CDR3 B1 of CP09C05 | parent | GFTFNAHAIS (SEQ ID NO: 63) | RHGFDYD (SEQ ID NO: 79) | parent |
| 8H3_9C2(CDR1) | $V_H$ CDR1 of CP09C02 | parent | $V_H$ CDR3 B2 of CP08H03 | EFTFSDHAMS (SEQ ID NO: 62) | parent | FPYWFAH (SEQ ID NO: 83) |
| 9B3_9E5_8H3 | $V_H$ CDR1 of CP09B03 | $V_H$ CDR3 B1 of CP09C05* | $V_H$ CDR3 B2 of CP08H03 | GFTFNAHAIS (SEQ ID NO: 63) | RHGFDYF (SEQ ID NO: 96) | FPYWFAH (SEQ ID NO: 83) |

Expression of Recombined $V_H$ CDR1 and CDR3 Heavy Chains with Lead Light Chains:

The six recombined $V_H$ CDR1 and CDR3 variants (see Table 18) were combined with the (1) parent light chain ($V_\kappa 8$ S29A), (2) light chain CP08E05, or (3) light chain CP08F05. The latter two light chains previously gave an improved effect when combined with affinity matured heavy chains (see Table 16). The resulting 18 combinations are summarized in Table 19. These combinations were transiently transfected in 6-well plates into HEK EBNA adherent cells using a PEI transfection method and incubated for 5-7 days post-transfection. The supernatants were harvested, quantified by ELISA and filtered for single-cycle kinetics analysis on the Biacore.

TABLE 19

Combinations of the recombined $V_H$ CDR1 and CDR3 lead humanized affinity matured IgG4 $V_H$ variants with either parent Vκ or the two lead humanized affinity matured κ light chains. Combinations with the two affinity matured light chains are indicated with "AM", combinations with the parental light chain are indicated with "P". All variable light chains contain a S29A mutation in CDR1L (Kabat numbering scheme, corresponding to a S28A mutation in the primary amino acid sequence of the variable light chain).

| | | $V_H$ | | | | | |
|---|---|---|---|---|---|---|---|
| | | 8H3_9B3 (CDR1) | 8H3_9C2 | 8H3_9E5 | 9B3_9E5 | 9C2_8H3 | 9B3_9E5 |
| VL | CP08E05 | AM | AM | AM | AM | AM | AM |
| | CP08F0 | AM | AM | AM | AM | AM | AM |
| | Parent ($V_H$1/Vκ8 S29A) | P | P | P | P | P | P |

Single-Cycle Kinetics Analysis of Recombined $V_H$ with Lead $V_L$ Antibodies:

Single-cycle kinetics using transient HEK supernatant was performed as described previously. The fitted data for the single-cycle kinetics are shown Table 20.

Eight variants were found to have relative $K_D$s greater than four-fold compared to parent. Of these, five achieved $K_D$s greater than six-fold better than the parent (bold in Table 20). Five antibodies, 8H3_9B3/CP08E05, 8H3_9B3/CP08F05, 8H3_9B3/V$_\kappa$8 S29A, 8H3_9C2/CP08F05 and 9B3_9E5/CP08E05, were taken forward for larger scale production and Protein A purification for further analysis.

TABLE 20

Single-cycle kinetic constants for the recombined lead humanized affinity matured IgG4 $V_H$ variants with either parent Vκ or one of the two lead humanized affinity matured κ light chains. The relative $K_D$ compared to parent was calculated by dividing the $K_D$ of the humanized and affinity matured variants by that of the parent assayed in the same experiment. The variants which were > six-fold better than parent are highlighted in bold. The CDRs containing the mutations are indicated with "+". All variable light chains contain a S29A mutation in CDR1L (Kabat numbering scheme, corresponding to a S28A mutation in the primary amino acid sequence of the variable light chain).

| Variant | $V_H$ CDR1 | $V_H$ CDR3 B1 | $V_H$ CDR3 B2 | VL CDR3 | $k_a$ (1/Ms) | $k_d$ (1/s) | $K_D$ (M) | Relative $K_D$ to parent |
|---|---|---|---|---|---|---|---|---|
| Parent ($V_H$1/Vκ8 S29A) | | | | | $9.4 \times 10^4$ | $5.3 \times 10^{-2}$ | $5.6 \times 10^{-7}$ | 1 |
| 8H3_9B3/CP08E05 | + | | + | + | $9.3 \times 10^4$ | $7.2 \times 10^{-3}$ | $7.7 \times 10^{-8}$ | 7.3 |
| 8H3_9B3/CP08F05 | + | | + | + | $9.0 \times 10^4$ | $6.3 \times 10^{-3}$ | $7.0 \times 10^{-8}$ | 8 |
| 8H3_9B3/Vκ8 S29A | + | | + | | $9.0 \times 10^4$ | $6.9 \times 10^{-3}$ | $7.7 \times 10^{-8}$ | 7.2 |
| 8H3_9C2/CP08E05 | + | + | + | | $6.7 \times 10^4$ | $7.1 \times 10^{-3}$ | $1.1 \times 10^{-7}$ | 5.3 |
| 8H3_9C2/CP08F05 | + | + | + | + | $6.6 \times 10^4$ | $6.1 \times 10^{-3}$ | $9.3 \times 10^{-8}$ | 6 |
| 8H3_9C2/Vκ8 S29A | + | + | + | | $6.5 \times 10^4$ | $7.1 \times 10^{-3}$ | $1.1 \times 10^{-7}$ | 5.1 |
| 8H3_9E5/CP08E05 | | + | + | + | $7.9 \times 10^4$ | $2.5 \times 10^{-2}$ | $3.2 \times 10^{-7}$ | 1.8 |
| 8H3_9E5/CP08F05 | | + | + | + | $7.7 \times 10^4$ | $2.8 \times 10^{-2}$ | $2.8 \times 10^{-7}$ | 2 |
| 8H3_9E5/Vκ8 S29A | | + | + | | $8.1 \times 10^5$ | $2.4 \times 10^{-2}$ | $3.0 \times 10^{-7}$ | 1.9 |
| 9B3_9E5/CP08E05 | | + | | + | $1.2 \times 10^5$ | $7.8 \times 10^{-3}$ | $6.7 \times 10^{-8}$ | 8.3 |
| 9B3_9E5/CP08F05 | | + | | + | $1.3 \times 10^5$ | $1.2 \times 10^{-2}$ | $9.5 \times 10^{-8}$ | 5.9 |
| 9B3_9E5/Vκ8 S29A | | + | | | $1.4 \times 10^5$ | $2.1 \times 10^{-2}$ | $1.5 \times 10^{-7}$ | 3.8 |
| 8H3_9C2 (CDR1)/ CP08E05 | + | | + | + | $7.3 \times 10^4$ | $1.9 \times 10^{-2}$ | $2.5 \times 10^{-7}$ | 2.2 |
| 8H3_9C2 (CDR1)/ CP08F05 | + | | + | + | $7.2 \times 10^4$ | $1.7 \times 10^{-2}$ | $2.4 \times 10^{-7}$ | 2.3 |
| 8H3_9C2 (CDR1)/ Vκ8 S29A | + | | + | | $8.8 \times 10^4$ | $1.8 \times 10^{-2}$ | $2.1 \times 10^{-7}$ | 2.7 |
| 9B3_9E5_8H3/CP08E05 | + | + | + | + | $8.2 \times 10^4$ | $2.2 \times 10^{-2}$ | $2.7 \times 10^{-7}$ | 1.9 |
| 9B3_9E5_8H3/CP08F05 | + | + | + | + | $8.6 \times 10^4$ | $1.8 \times 10^{-2}$ | $2.1 \times 10^{-7}$ | 2.4 |
| 9B3_9E5_8H3/Vκ8 S29A | + | + | + | | $9.5 \times 10^4$ | $2.0 \times 10^{-2}$ | $2.1 \times 10^{-7}$ | 2.4 |

Expression, Purification and Testing of Lead Antibodies

The six most improved combined variants (CP08H03/CP08E05, CP08H03/CP08F05, CP08H03/V$_\kappa$8 S29A, CP09B03/CP08E05, CP09C02/CP08E05, and CP09C02/CP08F05, highlighted in bold in Table 16) together with the five most improved $V_H$ CDR1 and $V_H$ CDR3 recombined variants (8H3_9B3/CP08E05, 8H3_9B3/CP08F05, 8H3_9B3/V$_\kappa$8 S29A, 8H3_9C2/CP08F05, and 9B3_9E5/CP08E05, highlighted in bold in Table 20) were transiently transfected into HEK EBNA adherent cells in triple flasks using the PEI method and incubated for 5-7 days post-transfection. Antibodies were purified from cell culture supernatants on Protein A sepharose columns, buffer exchanged into PBS pH 7.2 and quantified by $OD_{280\ nm}$ using an extinction coefficient based on the predicted amino acid sequence. 2 µg of each antibody was analyzed by SDS-PAGE and bands corresponding to the profile of a typical antibody were observed.

Single-Cycle Kinetics Analysis of Purified Lead Humanized and Affinity Matured Antibodies (Using Purified Proteins)

Single-cycle kinetics was performed as described above using purified antibodies instead of HEK supernatants. The fitted data for the single-cycle kinetics are shown in Table 21. Expression levels for the individual mutants are provided in Table 22.

All 11 lead variants bound >four-fold better than the parent antibody (see Table 21). Data obtained using purified IgG was consistent with data previously obtained using supernatants.

TABLE 21

Single-cycle kinetic constants for purified lead humanized affinity matured antibodies. The relative $K_D$ compared to parent was calculated by dividing the $K_D$ of the humanized and affinity matured variants by that of the parent assayed in the same experiment. A mutation of CDR CDR1H, CDR3H B1, CDR3H B2, or CDR1L is indicated with a "+" as applicable. All variable light chains contain a S29A mutation in CDR1L (Kabat numbering scheme, corresponding to a S28A mutation in the primary amino acid sequence of the variable light chain).

| Variant | $V_H$ CDR1 | $V_H$ CDR3 B1 | $V_H$ CDR3 B2 | $V_L$ CDR3 | $k_a$ (1/Ms) | $k_d$ (1/s) | $K_D$ (M) | Relative $K_D$ to parent |
|---|---|---|---|---|---|---|---|---|
| Parent ($V_H1$/Vx8 S29A) | | | | | $4.0 \times 10^5$ | $1.9 \times 10^{-1}$ | $4.8 \times 10^{-7}$ | 1 |
| CP08H03/CP08E05 | | | + | + | $7.6 \times 10^4$ | $8.0 \times 10^{-3}$ | $1.1 \times 10^{-7}$ | 4.5 |
| CP08H03/CP08F05 | | | + | + | $7.3 \times 10^4$ | $6.9 \times 10^{-3}$ | $9.5 \times 10^{-8}$ | 5.0 |
| CP08H03/Vκ8 S29A | | | + | | $6.3 \times 10^4$ | $7.5 \times 10^{-3}$ | $1.2 \times 10^{-7}$ | 4.0 |
| CP09B03/CP08E05 | + | | | + | $1.1 \times 10^5$ | $9.6 \times 10^{-3}$ | $9.0 \times 10^{-8}$ | 5.3 |
| CP09C02/CP08E05 | + | + | | + | $9.7 \times 10^4$ | $7.0 \times 10^{-3}$ | $7.2 \times 10^{-8}$ | 6.6 |
| CP09C02/CP08F05 | + | + | | + | $1.1 \times 10^5$ | $1.0 \times 10^{-2}$ | $9.5 \times 10^{-8}$ | 5.0 |
| 9B3_9E5/CP08E05 | + | + | | + | $1.1 \times 10^5$ | $7.0 \times 10^{-3}$ | $6.1 \times 10^{-8}$ | 7.8 |
| 8H3_9B3/CP08E05 | + | | + | + | $9.5 \times 10^4$ | $6.5 \times 10^{-3}$ | $6.9 \times 10^{-8}$ | 6.9 |
| 8H3_9B3/CP08F05 | + | | + | + | $9.5 \times 10^4$ | $5.6 \times 10^{-3}$ | $5.9 \times 10^{-8}$ | 8.0 |
| 8H3_9B3/Vκ8 S29A | + | | + | | $9.2 \times 10^4$ | $6.2 \times 10^{-3}$ | $6.7 \times 10^{-8}$ | 7.1 |
| 8H3_9C2/CP08F05 | + | + | + | + | $7.3 \times 10^4$ | $5.5 \times 10^{-3}$ | $7.6 \times 10^{-8}$ | 6.3 |

TABLE 22

Expression level for purified lead humanized affinity matured antibodies. A mutation of CDR CDR1H, CDR3H B1, CDR3H B2, or CDR1L is indicated with a "+" as applicable. All variable light chains contain a S29A mutation in CDR1L (Kabat numbering scheme, corresponding to a S28A mutation in the primary amino acid sequence of the variable light chain).

| Variant | $V_H$ CDR1 | $V_H$ CDR3 B1 | $V_H$ CDR3 B2 | $V_L$ CDR3 | Expression level (µg/ml) | Presence of G26E mutation |
|---|---|---|---|---|---|---|
| Parent ($V_H1$/Vx8 S29A) | | | | | 26.31 | |
| CP08H03/CP08E05 | | | + | + | 24.63 | |
| CP08H03/CP08F05 | | | + | + | 28.01 | |
| CP08H03/Vκ8 S29A | | | + | | 31.40 | |
| CP09B03/CP08E05 | + | | | + | 18.26 | |
| CP09C02/CP08E05 | + | + | | + | 37.04 | + |
| CP09C02/CP08F05 | + | + | | + | 20.39 | + |
| 9B3_9E5/CP08E05 | + | + | | + | 13.61 | |
| 8H3_9B3/CP08E05 | + | | + | + | 9.76 | |
| 8H3_9B3/CP08F05 | + | | + | + | 12.15 | |
| 8H3_9B3/Vκ8 S29A | + | | + | | 13.92 | |
| 8H3_9C2/CP08F05 | + | + | + | + | 16.88 | + |

Removal of Potential CD4+T Cell Epitopes

The sequences of the 11 lead antibodies (see Table 21) were analyzed using iTope™ technology for in silico analysis of peptide binding to human MHC class II alleles (Perry et al 2008), and using the TCED™ of known antibody sequence-related T cell epitopes (Bryson et al 2010) to ensure that no significant T cell epitopes had been introduced during the affinity maturation process. The CDR1 mutation (G26E, CDR definition according to IMGT) found in the heavy chain of CP09C02 is associated with the introduction of a promiscuous high epitope not observed in the parent sequence (see Table 21).

Selectivity Analysis of Lead Antibodies

Figure 11:
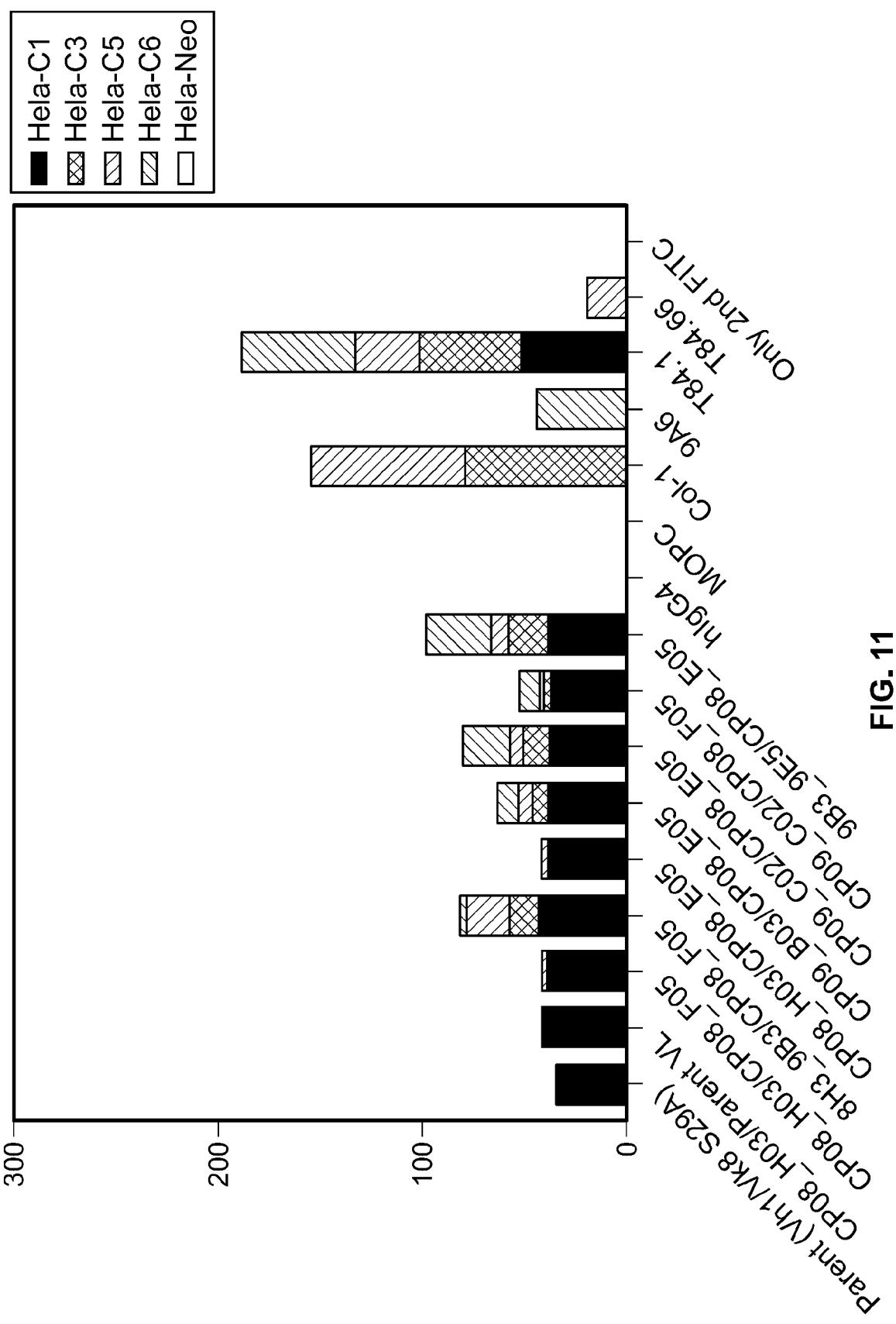
FIG. 11 illustrates the binding selectivity of different affinity-matured CEACAM1 antibodies. Affinity matured antibodies CP08H03/V$_K$8 S29A (labeled "CP08_H03/Parent VL"), CP08H03/CP08F05, 8H3_9B3/CP08F05, and CP08H03/CP08E05 contain a phenylalanine (F) at CDR3H residue 104. Affinity matured antibodies CP09B03/CP08E05, CP09C02/CP08E05, CP09C02/CP08F05, and 9B3_9E5/CP08E05 contain an aspartic acid residue (D) at CDR3H residue 104. HELA cells were transfected with vector alone (HeLa-Neo) or vectors expressing CEACAM1, CEACAM3, CEACAM5, or CEACAM6, respectively, and stained with the indicated antibodies. The y-axis shows % staining of each antibody with the transfected panel of cells. hIgG4=control antibody with identical stabilizing hinge mutation. MOPC=mouse IgG1 control antibody. Mouse antibodies as positive control for transfected CEACAM isoforms: Col-1=CEACAM3 and CEACAM5 antibody. 9A6=CEACAM6 antibody. T84.1=CEACAM cross-reactive antibody and T84.66=CEACAM5 antibody. Only 2$^{nd}$ FITC=No primary antibody, only secondary FITC conjugated antibody. Col-1 and 9A6 are commercially available antibodies (Dako) and T84.1 and T84.66 have been previously described (Neumaier M, J Immunol 1985; 135:3604-9). Data for affinity-matured antibodies 9B3_8H3/V$_K$8

An initial selectivity analysis of several lead antibodies indicated that antibodies with a phenylalanine (F) at CDR3H position 104 showed on average an increased selectivity for CEACAM1 as compared to antibodies with a aspartic acid (D) at CDR3H position 104 (FIG. 11).

Multi-Cycle Kinetic Analysis

Variants CP08H03/V$_κ$8 S29A and CP08H03/CP08F05 were further analyzed using multi-cycle kinetics analysis, using a Biacore T200 instrument running Biacore T200 Evaluation Software V3.0.1. The purified antibodies were diluted to a concentration of 1 µg/ml in HBS-P+. At the start of each cycle, each antibody was captured on the Protein A surface to give an RL of ~100 RU. Following capture, the surface was allowed to stabilize. Kinetic data was obtained using a flow rate of 80 µl/min to minimize any potential mass transfer effects. Multiple repeats of the blank (no CEACAM1) and a repeat of a single concentration of the analyte were programmed into the kinetic run in order to check the stability of both the surface and analyte over the kinetic cycles. For kinetic analysis, a two-fold dilution range was selected from 100 to 1.56 nM CEACAM1. The association phase of CEACAM1 was monitored for 150 seconds and the dissociation phase was measured for 150 seconds. Regeneration of the Protein A surface was conducted using two injections of 10 mM glycine-HCL pH 1.5 at the end of each cycle.

The signal from the reference channel Fc1 was subtracted from that of Fc2, Fc3 and Fc4 to correct for differences in non-specific binding to a reference surface, and a global Rmax parameter was used in the 1-to-1 binding model. The relative $K_D$ compared to Parent ($V_H1/V_\kappa 8$ S29A) was calculated by dividing the $K_D$ of the affinity matured composite human antibody variants by that of the Parent on the same chip. The kinetic parameters measured for the interaction of CEACAM1 with affinity matured CEACAM1 antibody variants CP08H03/$V_\kappa 8$ S29A and CP08H03/CP08F05 are shown in Table 23. Both affinity matured CEACAM1 antibody variants demonstrated affinity improvements of >four-fold compared to $V_H1/V_\kappa 8$ S29A parent.

TABLE 23

Multi-cycle kinetic data for antibody $V_H1/V\kappa 8$ S29A (parent), the chimeric antibody ($V_H0/V\kappa 0$) and two affinity matured leads binding to CEACAM1 as determined using the Biacore T200. The relative $K_D$ compared to the parent ($V_H1/V\kappa 8$ S29A) was calculated by dividing the $K_D$ of the affinity matured variants by that of the parent assayed on the same chip. All variable light chains contain a S29A mutation in CDR1L (Kabat numbering scheme, corresponding to a S28A mutation in the primary amino acid sequence of the variable light chain).

| | $V_H$ CDR1 | $V_H$ CDR3 B1 | $V_H$ CDR3 B2 | $V_L$ CDR3 | $k_a$ (1/Ms) | $k_d$ (1/s) | $K_D$ (M) | Relative $K_D$ to parent |
|---|---|---|---|---|---|---|---|---|
| Parent ($V_H1/V\kappa 8$ S29A) | | | | | $1.1 \times 10^5$ | $4.5 \times 10^{-2}$ | $4.2 \times 10^{-7}$ | 1 |
| Chimeric ($V_H0/V\kappa 0$) | | | | | $4.7 \times 10^5$ | $4.5 \times 10^{-2}$ | $9.5 \times 10^{-8}$ | 4.4 |
| CP08H03/V$\kappa$8 S29A | | + | | | $9.1 \times 10^4$ | $9.0 \times 10^{-3}$ | $9.9 \times 10^{-8}$ | 4.3 |
| Parent ($V_H1/V\kappa 8$ S29A) | | | | | $1.2 \times 10^5$ | $6.0 \times 10^{-2}$ | $4.9 \times 10^{-7}$ | 1 |
| Chimeric ($V_H0/V\kappa 0$) | | | | | $3.5 \times 10^5$ | $3.5 \times 10^{-2}$ | $1.0 \times 10^{-7}$ | 4.8 |
| CP08H03/CP08F05 | | + | + | | $1.3 \times 10^5$ | $7.8 \times 10^{-3}$ | $5.8 \times 10^{-8}$ | 8.4 |

Example 2: Selectivity of CEACAM1 Antibodies

To further assess the binding selectivity of CEACAM1 antibodies $V_H0/V_\kappa 0$, CP08H03/$V_\kappa 8$ S29A, CP08H03/CP08F05 CEACAM1 over other proteins, binding affinities to CEACAM1, CEACAM3, CEACAM5, and CEACAM6 were compared using single-cycle kinetics analysis performed as described above. Single cycle kinetics was conducted using CEACAM concentrations from 280 nM to 70 nM. Antibodies were loaded onto the chip at the following concentrations (taking into account the varying analyte MWs): 100 RU for CEACAM1, 375 RU for CEACAM3, 71.4 RU for CEACAM5, and 150 RU for CEACAM6. No significant binding of the three CEACAM1 antibodies, CP08H03/$V_\kappa 8$ S29A, CP08H03/CP08F05, and $V_H0/V_\kappa 0$, was observed for CEACAM3, CEACAM5, and CEACAM6 (see FIG. 12A).

These results were consistent with data obtained by measuring antibody specificity with an ELISA. For the ELISA experiments, a 96 well plate was coated with CEACAM1 at either 0.5 or 1.0 µg/ml. Non-specific binding was blocked with 2% BSA/Dulbecco's PBS. A 1:3 dilution series of CP08H03/$V_\kappa 8$ S29A, CP08H03/CP08F05, or $V_H0/V_\kappa 0$ (50 µg/mL starting concentration) was prepared in 2% BSA/PBS. 100 µL of the sample was added to the pre-coated plate and incubated for 1 h at RT. Anti-human Igκ chain—Peroxidase secondary antibody (AP502P) used to detect the CEACAM antibodies. Plates were developed with TMB and stopped with 3M HCl. Results were analyzed by subtracting the background. Essentially no binding of the three CEACAM1 antibodies, CP08H03/$V_\kappa 8$ S29A, CP08H03/CP08F05, and $V_H0/V_\kappa 0$ to CEACAM3, CEACAM5, or CEACAM6 was observed (see FIGS. 12B and 12C).

This high degree of selectivity can be observed despite the fact that the N-domains of different CEACAM share high degrees of homology: The N-domains of CEACAM1 and CEACAM3 are 88% identical, the N-domains of CEACAM1 and CEACAM5 are 89% identical, and N-domains of CEACAM1 and CEACAM6 are 90% identical, as indicated by a percent identity matrix created using Clustal2.1 (see FIG. 13).

Example 3: Epitope Analysis of CEACAM1 Antibodies

To determine which residues on CEACAM1 are involved in binding to certain CEACAM1 antibodies contemplated by the invention, single point mutations were introduced into FLAG-tagged CEACAM1. Each FLAG-tagged CEACAM1 mutant was transfected into 293T cells. 48 hours after transfection, CEACAM1 proteins were subjected to Western blotting. CEACAM1 antibodies $V_H0/V_\kappa 0$ (chimeric antibody), $V_H1/V_\kappa 8$, $V_H2/V_\kappa 4$, $V_H3/V_\kappa 1$, and $V_H4/V_\kappa 1$ were used as the antibody for detection. Mutation of CEACAM1 residues Y34, V39, G41, N42, R43, Q44, G47, and Q89, which are part of the CEACAM1 GFCC' face, lead to reduced binding of CEACAM1 to the CEACAM1 antibodies, indicating that these CEACAM1 residues may be involved in binding (see FIG. 14).

Example 4: Crystal Structure of a CEACAM Antibody and CEACAM1

To more precisely map the binding interface between CEACAM1 and CP08H03/$V_\kappa 8$ S29A, the crystal structure of human CEACAM1 in complex with a CP08H03/$V_\kappa 8$ S29A Fab fragment was determined.

CEACAM1 was expressed from E. coli transformed with a pET21D-based plasmid expressing a tagless version of CEACAM1. The protein was refolded in an arginine-containing buffer, and purified. The Fab fragment was prepared by digestion of the antibody, after concentrating to ~18 mg/ml, using immobilized papain resin and then purified by protein A affinity and gel filtration chromatography. Purified CEACAM1 and Fab were mixed at a 1:1 molar ratio prior to crystallization screening. Initial crystallization hits of the CEACAM1:Fab complex were identified and subsequently optimized. Diffraction quality crystals were grown at room temperature in a condition containing 18-20% PEG 6000, 50 mM potassium dihydrogen phosphate, 20 mM Tris pH 7.0, and 1% β-octylglucoside. SDS-PAGE analysis and silver staining of a washed crystal was used to verify crystallization of the complex. X-ray data from numerous crystals were collected from beamline NE-CAT 24-ID-E at the Advanced Photon Source of Argonne National Laboratory. The best data from two non-twinned isomorphous crystals were merged to produce a highly redundant dataset at 3.3 Å for structure determination and refinement. The structure of the complex was solved by molecular replacement and refined to final R and $R_{free}$ values of 24.9% and 32.8%, respectively.

The structure of the CEACAM1: CP08H03/$V_\kappa$8 S29A Fab complex was determined to 3.3 Å resolution. The CP08H03/$V_\kappa$8 S29A Fab binds to CEACAM1 in a 1:1 stoichiometric ratio (see FIG. 15). Part of the epitope on CEACAM1 for the Fab fragment is shown in a molecular surface representation of CEACAM1 in FIG. 16. Primary and secondary interactions between the Fab molecule and CEACAM1 are listed in Table 24 and Table 25.

TABLE 24

Primary interactions between CEACAM1 CP08H03/Vκ8 S29A Fab (interaction distance <4.0 Å).

| CDR residue (Kabat)# | CDR residue* | Antibody CDR | CEACAM1 Residue | Hydrogen bond (Å) | Hydrophobic interaction (Å) |
|---|---|---|---|---|---|
| Y58 | Y59 | HC CDR 2 | S93 | 2.49 | — |
| D98 | D102 | HC CDR 3 | T56 | 2.53 | — |
| Y99 | Y103 | HC CDR 3 | Y34 | 3.43 | — |
| Y99 | Y103 | HC CDR 3 | Q89 | 2.02 | — |
| Y100B | Y106 | HC CDR 3 | D94 | 3.14 | — |
| Y56 | Y57 | HC CDR 2 | F29 | — | Aromatic-Aromatic (~3.75) |
| F100 | F104 | HC CDR 3 | F29 | — | Aromatic-Aromatic (~4.0) |
| S31 | S30 | LC CDR 1 | E99 | 3.97 | — |
| Y32 | Y31 | LC CDR 1 | N97 | 2.31 | — |
| S52 | S51 | LC CDR 2 | D40 | 3.18 | — |
| N53 | N52 | LC CDR 2 | G41 | 2.69 | — |
| N53 | N52 | LC CDR 2 | N42 | 3.39 | — |

Numbering of residues based on Kabat numbering scheme.
*Numbering of residues based on primary amino acid sequence of the heavy variable chain.

TABLE 25

Secondary interactions between CEACAM1 CP08H03/Vκ8 S29A Fab (interaction distance >4.0 Å).

| CDR residue (Kabat)# | CDR residue* | Antibody CDR | CEACAM1 Residue | Hydrogen bond (Å) | Hydrophobic interaction (Å) |
|---|---|---|---|---|---|
| Y99 | Y103 | HC CDR 3 | S32 | 5.2 | — |
| Y99 | Y103 | HC CDR 3 | Q44 | 5.9 | — |
| F100 | F104 | HC CDR 3 | A49 | — | 4.32 |
| P100A | P105 | HC CDR 3 | I91 | — | 4.91 |
| S92 | S91 | LC CDR 3 | L95 | 5.10 | — |
| S93 | S92 | LC CDR 3 | V96 | 5.9 | — |

Numbering of residues based on Kabat numbering scheme.
*Numbering of residues based on primary amino acid sequence of the heavy variable chain.

With reference to an existing structure of the CEACAM1 dimer (FIG. 17), it is evident that the Fab binds to the interface of CEACAM1 involved in self-association. Presumably, this competitive interaction leads to dissociation of the dimer in solution. Residues targeted on CEACAM1 include four residues that form an YQQN pocket at the CEACAM1:CEACAM1 dimer interface (Y34, Q44, Q89, N97). Of note, several of the residues on CEACAM1 that bind to the antibody have also been predicted to be involved in binding to TIM-3, including CEACAM1 residues Y34, G41, N42, Q44, Q89, S93, D94, V96, and/or N97 (Huang et al., Nature. 2015 Jan. 15; 517 (7534): 386-90).

In the Fab light chain, residues in CDR1, CDR2, and CDR3 (FIG. 18) interact mainly with residues in two loops between β-strands of the main B-sheet in CEACAM1, and also with residues of a B-strand in the sheet. In the Fab heavy chain, residues of CDR2 and CDR3 interact mainly with residues distributed across four different β-strands of the central-sheet.

The interacting surfaces have a shape complementarity of 0.5, and complex formation buries 1607 Å2 of total solvent accessible surface. No interactions are seen between the antigen and the Fab heavy chain CDR1.

Alignments of human CEACAM family members indicated that CEACAM3, 5, 6, 7, and 8 all contain a valine residue at position 49, while human CEACAM1 contains an alanine in this location. In addition, human CEACAM5 contains histidine at position 89. The polymorphisms in hCEACAM-1 at these residues include Ala49Val (rs8110904) and Gln89His (rs8111468). To further examine the selective nature of CEACAM1 antibody CP08H03/$V_\kappa$8 S29A, a human CEACAM1 A49V/Q89H mutant was expressed and purified as described above. Note that a natural human allelic variant of human CEACAM1 exists which convert Q89 to H89 as described in Huang et al., Nature. 2015 Jan. 15; 517 (7534): 386-90. A structure of the CEACAM1 A49V/Q89H mutant was determined to 1.7 Å resolution and compared to the CEACAM1 wildtype: CP08H03/$V_\kappa$8 S29A Fab complex. As discussed above, CDR3H residue F104 of CP08H03/$V_\kappa$8 S29A makes contact with residue F29 in wildtype CEACAM1 (see FIG. 19, left panel). Notably, F29 of one CEACAM1 monomer binds F29 of a second monomer at the CEACAM1: CEACAM1 homodimeric interface. Binding of CDR3H residue F104 of CP08H03/$V_\kappa$8 S29A blocks F29-F29 interactions. CEACAM1 residue A49 is located close to the F104/F29 interaction site. Due to the increase in hydrophobicity of valine in non-CEACAM1 family members as compared to alanine in human CEACAM1, a mutation of human CEACAM1 residue A49 to valine causes hydrophobic CEACAM1 residue F29 to move closer to CEACAM1 V49 residue. This rotameric shift of F29 was also observed in human CEACAM5 (PDB code 2QSQ) and human CEACAM3 (PDB code 6AW1) crystal structures and is predicted to clash with CDR3H residue F104 (see FIG. 19, right panel). This is illustrated by the change in orientation displayed by the CEACAM1 F29 ring, which moves closer to the space previously occupied by CDR3H residue F104 (see FIG. 19, right panel). These data indicate that this steric hindrance caused by the A49V mutation interferes with binding of CEACAM1 antibody CP08H03/$V_K$8 S29A to other CEACAM1 family members containing a valine at position 49 and is, as such, a major contribution to the selectivity of the antibody. It is predicted that this rotameric shift of F29 ring could also affect the interaction between CDR2H residue Y57 and F29. Further, the CEACAM1 Ala49Val polymorphism (rs8110904) is linked to lymphedema caused by *Wuchereria bancrofti* (Debrah L, B. et. al Hum Genomics. 2017 Nov. 9; 11 (1): 26)—a filaria worm that invades the lymphatic system. Development of disease is linked to the Ala49Val polymorphism, which marks the alanine 49 residue found to be involved in binding to CP08H03/$V_K$8 S29A antibody. As such, it is expected that CP08H03/$V_K$8 S29A may also interfere with *Wucheria bancrofti* and other related pathogens or cancer processes that phenocopy worm interactions with lymphatics such as tumor invasion.

Example 5: CEACAM1 Antibodies Block CEACAM1: CEACAM1 Interactions

The ability of the CEACAM1 antibodies to block CEACAM1 homodimerization was tested. CEACAM1-CEACAM1 competition ELISA studies were done in triplicates to determine ability of the CP08H03/$V_K$8 S29A antibody (concentration range 0-1000 nM) to inhibit human CEACAM1 IgV domain tagless protein (1 µg/ml) and human CEACAM1-GST protein (37.5 µg/ml) binding. In addition, IgG4 antibody was used as a control (0-1000 nM). Goat polyclonal anti-GST-HSP antibody from Abcam (1:2000) was used and assays were developed by addition of TMB solution (Life technologies). OD values were read at 450 nm on a plate reader. Data was plotted in a Graphpad and best-fit IC-50 values were determined.

CEACAM1 antibody CP08H03/$V_K$8 S29A was shown to block CEACAM1:CEACAM1 homophilic interactions (see FIG. 20A).

Example 6: CEACAM1 Antibodies Block CEACAM1:TIM-3 Interactions

The ability of the CEACAM1 antibodies to reduce the binding of CEACAM1 to TIM-3 was examined. CEACAM1/TIM-3 competition ELISA studies were done in triplicates to determine ability of CP08H03/$V_K$8 S29A antibody (concentration range 0-300 nM) to inhibit human TIM-3 IgV domain tagless protein (3 µg/ml) and human CEACAM1-GST protein (37.5 µg/ml) binding. In addition, human IgG4 antibody was used as a control (0-1000 nM). Goat polyclonal anti-GST-HSP antibody from Abcam (1:2000) was used and assays were developed by addition of TMB solution (Life technologies). OD values were read at 450 nm on a plate reader. Data was plotted in a Graphpad and best-fit IC-50 values were determined. As shown in FIG. 20B, CEACAM antibody CP08H03/$V_K$8 S29A blocks CEACAM1:TIM-3 heterophilic interactions.

Example 7: CEACAM1 Antibodies Induce T Cell Proliferation

The ability of CEACAM antibodies CP08H03/$V_K$8 S29A and CP08H03/CP08F05 to induce T cell proliferation was investigated in humanized NOD scid gamma mice (NSG mice). See FIG. 21 for experimental setup. Freshly isolated human PBMCs (5×10^6) were transferred via intraperitoneal (i.p.) injection into NOD·Cg-Prkdc$^{scid}$Il2rg$^{tm1Wjl}$/SzJ (NSG) mice. 21 days post PBMCs injections, NSG animals were examined for human immune cells implantation by the tail-bleeding. 24 and 31 days post PBMCs injections, the humanized NSG mice were administered the first and the second doses of the indicated concentration of CEACAM1 antibody or isotype control antibody via i.p. injection. Upon study termination (34 days post PBMCs injection), mice were sacrificed and surgically dissected the spleens for further analyses. Single cell suspension from the engraft mice were stained with cell proliferation dye and cultured in-vitro for additional 2-days in the presence of soluble form of anti-human CD3 stimulation (2 µg/ml, OKT3 clone) and rIL-2 (40 U/ml) in completed RPMI medium. Cells were maintained at 10^7 cell/ml concentration. After in-vitro stimulation, cells were stained with antibodies to human CD45 pan leukocyte marker and assessed by flow cytometry.

No antibody-dependent cell-mediated cytotoxicity (ADCC) was observed in any of the groups tested (see FIG. 22). Administration of CEACAM antibody CP08H03/$V_K$8 S29A or CP08H03/CP08F05, respectively, lead to an increase in in vivo antibody induced T cell expansion (see FIG. 23).

Example 8: CEACAM1 Antibodies Reduce Tumor Growth in a Melanoma Model

To assess the ability of CEACAM1 antibodies to reduce tumor growth, 1×10^6 MALME-3M (human melanoma) were injected subcutaneously into 7-8 week old male NSG (NOD·Cg-Prkdc$^{scid}$ Il2rg$^{tm1Wjl}$/SzJ) mice with 5×10^6 human PBMC. The MALME-3M (BRAFV600E) cell line was established in 1975 from a metastatic site (lung) from a 43-year-old Caucasian male with metastatic melanoma. On days 7-9, it was confirmed that all mice exhibited a reconstituted T cell population (see FIG. 24A for experimental setup). The animals were treated on days 10, 13, 17, 20 and 24 with CEACAM antibody CP08H03/$V_K$8 S29A or the hIgG4 control antibody intraperitonally.

The human melanoma cell lines MALME-3M were kindly provided by Dr. Nicole Beauchemin (McGill University, Montreal, Canada). MALME-3M were established in year of 1975 from a metastatic site (lung) in a 43-year-old Caucasian male with metastatic melanoma with BRAFV600E. 2×10^7 MALME-3M were subcutaneously (s.c.) injection into NOD·Cg-Prkdc$^{scid}$ Il2$^{tm1Wjl}$/SzJ (NSG) mice. After a 30 min period of acclimation, freshly isolated human PBMCs (1×10^8) were then transferred via intraperitoneal (i.p.) injection into the tumor-bearing NSG mice. 7- to 9-days post PBMC injection, NSG animals were examined for human immune cell implantation by tail-bleeding. 10, 13, 17, 20, and 24 days post human cell injection the tumor-bearing humanized NSG mice received a total of five doses of the indicated concentrations of CEACAM1 antibody or isotype control antibody via i.p. injection. Upon study termination (34 days post human cell injection), mice were sacrificed and surgical dissection performed.

CEACAM1 antibody CP08H03/$V_\kappa$8 S29A was effective in reducing tumor growth at various concentrations and proliferation (see FIGS. 24B, 24C and 25), while not depleting T cell populations (see FIG. 22). Further, the proliferative capability of human CD4 and CD8 tumor infiltrating lymphocytes was restored by administration of the CEACAM1 antibody, see FIG. 25. Also observed deviation of CD8 T memory cells to primarily central-memory T cells upon treatment with CP08H03/$V_\kappa$8 S29A in vivo (FIG. 26). Note that CEACAM1 antibody CP08H03/$V_\kappa$8 S29A increased the relative proportion of $T_{em}$ to $T_{em}$ relative to that observed in the control treated animals, consistent with augmentation of an anti-cancer response.

Example 9: CEACAM1 Antibodies are Useful for the Treatment of Cancer Resistant to Checkpoint Inhibitors CEACAM1 is expressed on a significant portion of TILs derived from naïve or anti-PD-1 and/or anti-CTLA-4 therapy resistant melanoma patients; with CEACAM1 expression levels being greater than the expression levels of PD-1 or TIM-3 (see FIG. 27). About 80% of samples exhibit CEACAM1 expression on greater than 20% of the CD4$^+$ T cell population isolated from TILs. To compare the expression of CEACAM1 for patients that had acquired resistance to anti-PD-1 and/or anti-CTLA-4 therapy vs. patients that had no previous exposure to anti-PD-1 and/or anti-CTLA-4 therapy, tumor associated cells (TACs) were obtained from melanoma patients who were naïve (no previous exposure to anti-PD-1 and/or anti-CTLA-4 therapy) or those that acquired resistance to anti-PD-1 and/or anti-CTLA-4 therapy (acquired resistance). TACs were obtained by culturing tumor tissue in DMEM medium and the floating cells removed from the supernatant. The cells were stained for CD3, CD4 and CD8, and CEACAM1 expression on the CD3 CD4 and CD3 CD8 assessed. These studies show that tumor associated cells deprived of the tumor microenvironment in acquired resistance upregulate CEACAM1 expression relative to that observed on naïve patients (see FIG. 28), indicating that patients resistant to anti-PD-1 and/or anti-CTLA-4 therapy might benefit from anti-CEACAM1 antibodies or antigen-binding fragments thereof, such as the ones contemplated in the present disclosure.

As expected, there was a relative decrease in central memory ($T_{cm}$) relative to effector memory ($T_{em}$) cells among the CD8$^+$ T cells in patients resistant to anti-PD-1 and/or anti-CTLA-4 therapy as compared to patients that had no previous exposure to anti-PD-1 and/or anti-CTLA-4 therapy, consistent with a reduction of an anti-cancer response in the resistant patients (see FIG. 29). Tumor associated cells from melanoma patients with either naïve (treatment naïve patients) or resistant to immune check point inhibitor (treatment failure patients), were stained for CD44, CCR7 and CD62L and the relative amounts of central memory, $T_{cm}$ (CD44$^{high}$, CD62L$^{high}$, CCR7$^{high}$) and effector memory, $T_{em}$ (CD44$^{high}$, CD62L$^{low}$, CCR7$^{low}$) were indicated as percentage of total CD8 T cells present in the bulk tumor.

To assess the ability of CEACAM1 antibodies to reverse T cell exhaustion in patients that are resistant to treatment with checkpoint inhibitors such as PD-1/PD-L1 and CTLA-4 inhibitors, PBMCs and tumor associated cells were isolated from a melanoma patient with secondary resistance to Pembrolizumab (PD-1 inhibitor), Ipilimumab (CTLA-4 inhibitor)+Nivolumab (PD-1 inhibitor) and Dabrafenib (B-Raf inhibitor)+Trametinib (MEK inhibitor) and Stage IV disease. Tumor associated cells and PBMC were stained for CEACAM1, PD1 or TIM-3 and proportion of CD8 and CD4 T cells denoted (see FIG. 30, left panel). Tumor biopsies were subjected to either an enzymatic digest or to a commercial mechanical/enzymatic dissociation system (GentleMACS dissociator, Miltenyi Biotec). The enzymatic digest was based upon methodology previously established for the generation of melanoma TILs (Dudley et al, 2003, 2008). In brief, tumor biopsies were cut into small fragments ~2-3 mm in length and put in an enzyme digest mix consisting of 100 U ml 1 DNAse, 10 mg ml 1 collagenase VIII (Sigma-Aldrich) and incubated 45 min at 37° C. temperature under continuous rotation. GentleMACS dissociation was performed according to the manufacturer's protocol. Briefly, the tumour was cut into small fragments about 2-3 mm in length and put in a C-tube (Miltenyi Biotech) with RPMI 1640 (Lonza, Slough, UK) and solutions 1, 2 and 3 (all from Miltenyi Biotec) according to the manufacturer's recommendation; the digest mix containing the tumour was then subjected to three 36-second mechanical disaggregation steps (programs h_tumor_01.01, 02.01 and 03.01) in the GentleMACS dissociator interspersed by two 30-min incubations at 37° C. performed after the first and the second disaggregation steps, respectively. After disaggregation, TILs from the enzymatic digest and the GentleMACS dissociation were passed through 100-μm strainers for the further analyses. Dissociated tumor cells and the autologous PBMCs were stained with the following antibodies according to standard procedures: fluorochrome-conjugated monoclonal antibody specific for human CD3, CD4, CD8, TIM-3, PD1, CEACAM1, CD45 and viable dye. Data were acquired with a Cytoflex flow cytometer (Invitrogen) and analyzed with FlowJo software (TreeStar, V7.6.5 for Windows). PBMC or tumor associated cells were cultured with soluble anti-CD3 (2 μg/ml) and rIL-2 (40 units/ml) in complete media (RPMI 1640 (Lonza) supplemented with 10% fetal calf serum (FCS), 1% glutamine, 100 IU ml$^{-1}$ penicillin, 100 μg ml$^{-1}$ streptomycin (Life Technologies), 25 mM HEPES (Sigma-Aldrich) in 96-well plates in the presence of CP08H03/$V_\kappa$8 S29A or hIgG4 control. After 96 hours, cell-culture supernatants were collected for further TNF-α and IFN-γ ELISA (BD) analyses following the manufacturer procedures. CP08H03/$V_\kappa$8 S29A reverses T cell exhaustion in PD-1/CTLA-4 resistance tumors as evidenced by an increase in TNF-α and IFN-γ production both in tumor associated cells and PBMC (see FIG. 30, right panel).

Example 10: CEACAM1 Antibodies Contemplated by the Invention Show Improved Efficacy as Compared to Previously Known CEACAM1 Antibodies The properties of antibody CP08H03/$V_\kappa$8 S29A were compared to anti-CEACAM1 antibody CM-24 (WO2015/166484). Unlike CEACAM1 antibody CP08H03/$V_\kappa$8 S29A disclosed herein, CM-24 (i) binds to CEACAM1 away from the dimer interface based upon modeling, (ii) exhibits cross-reactivity with CEACAM3 and CEACAM5, (iii) shows a limited ability to reverse T cell tolerance in TILs, and (iv) functions as an agonistic, rather than antagonistic antibody in mouse models of metastatic melanoma.

CP08H03/$V_\kappa$8 S29A is selective for CEACAM1 and did not show significant binding to CEACAM3, CEACAM5, CEACAM6, or CEACAM8. CM-24 on the other hand showed significant cross-reactivity with CEACAM3 and CEACAM5 at higher antibody concentrations (FIGS. 31A and 31B). The cervical adenocarcinoma cell line HeLa (ATCC No CCL-2) as well as transfected cell lines HeLaCEACAM1, HeLaCEACAM3, HeLaCEACAM5, HeLaCEACAM6 and HeLaCEACAM8 used for flow cytometry experiments were cultured at 37° C., 5.0% $CO_2$ in Dulbecco's modified Eagle's medium supplemented with 10% fetal bovine serum, penicillin (100 U/ml) and dihydrostreptomycin (100 µg/ml). Cell lines were stained with the indicated antibodies followed by fluorochrome-conjugated monoclonal antibody specific for the indicated antibody isotypes such as human IgG4 or mouse IgG1 together with viable dye (DAPI). Data were acquired with a Cytoflex flow cytometer (Invitrogen) and analyzed with FlowJo software (TreeStar, V7.6.5 for Windows).

Further, CM-24 showed a limited ability to reserve T cell tolerance in tumor associated cells. Incubation of tumor associated cells with antibody CP08H03/$V_\kappa$8 S29A lead to a more extensive reversal of T cell tolerance over a range of antibody concentrations as compared to CM-24 in naïve Merkel cell carcinoma tumor cells (FIGS. 32A, 32B, and 32C). Merkel cell carcinoma biopsies were subjected to a commercial mechanical/enzymatic dissociation system (GentleMACS dissociator, Miltenyi Biotec), according to the manufacturer's protocol. Briefly, the tumour was cut into small fragments about 2-3 mm in length and put in a C-tube (Miltenyi Biotech) with RPMI 1640 (Lonza, Slough, UK) and solutions 1, 2 and 3 (all from Miltenyi Biotec) according to the manufacturer's recommendation; the digest mix containing the tumour was then subjected to three 36-second mechanical disaggregation steps (programs h_tumor_01.01, 02.01 and 03.01) in the GentleMACS dissociator interspersed by two 30-min incubations at 37° C. performed after the first and the second disaggregation steps, respectively. After disaggregation, TILs from the enzymatic digest and the GentleMACS dissociation were passed through 100-µm strainers for the further analyses. In vitro assay for T cell function in tumor milieu: Dissociated tumor cells and the autologous PBMCs were cultured in complete media (RPMI 1640 (Lonza) supplemented with 10% fetal calf serum (FCS), 1% glutamine, 100 IU ml 1 penicillin, 100 µg ml 1 streptomycin (Life Technologies), 25 mM HEPES (Sigma-Aldrich) in 96-well plates with 40 IU ml 1 recombinant IL-2 (NIH) and soluble CD3 (2 µg/ml) in the presence of various concentrations of antibodies or the relevant isotype controls. After 96 hours, cell-culture supernatants were collected for further TNF-α and IFN-γ ELISA (BD) analyses following the manufacture procedures.

In a metastic melanoma model (see FIG. 33A for experimental setup), mice treated in vivo with CP08H03/$V_\kappa$8 S29A showed a significant decrease in tumor cells as compared to the control mice in vivo treated with human IgG4 (hIgG4), and significant increases in TIL $CD4^+$ and $CD8^+$ lymphocytes (FIGS. 33B, 34A, 34B, and 34C). On the other hand, mice treated with CM-24 in vivo exhibited a large increase in tumor cells, and almost complete absence of TIL $CD4^+$ and CD8 lymphocytes as compared to the control mice treated with hIgG4 control (FIGS. 33B, 34A, 34B, and 34C). Further, the tumor cells exhibited decreased proliferation in the CP08H03/$V_\kappa$8 S29A treated animals relative to the hIgG4 control or the CM24 treated animals (FIG. 33C). Further, the CD4 T cells in the spleens of CP08H03/$V_\kappa$8 S29A treated animals exhibited increased proliferation relative to hIgG4 treated animals or CM24 treated mice (FIG. 33D). In contrast to CP08H03/$V_\kappa$8 S29A treated animals, the CM24 treated animals displayed decreased proliferation of spleen CD4 T cells (FIG. 33D). The human melanoma cell line MALME-3M was provided by Dr. Nicole Beauchemin (McGill University). MALME-3M were established in year of 1975 from a metastatic site (lung) in a 43-year-old Caucasian male with metastatic melanoma with $BRAF^{V600E}$. 2×10^7 MALME-3M were subcutaneously (s.c.) injected into NSG mice. After 30 min to allow the mice to absorb the tumor cells, freshly isolated human PBMCs (1×10^8) were then transferred via intraperitoneal (i.p.) injection into the tumor-bearing NSG mice. 7 to 9 days after PBMC injection, NSG animals were examined for human immune cell implantation by the tail-bleeding. At day 14, palpable tumor nodules were detected. Beginning at day 17 after human cell injection, the tumor-bearing humanized NSG mice received a total of four doses of the CP08H03/$V_\kappa$8 S29A antibody (2 mg/kg), CM-24 (2 mg/kg) or isotype control antibody (2 mg/kg) via i.p. injection twice weekly. Upon study termination (30 days post human cell injection), mice were sacrificed and surgically dissected. The metastatic tumor together with the spleens and lung and liver were saved for further analyses. Total cell counts and proliferation as well as the frequency of the CD4, CD8 and tumor cells characterized by being high in FSC and SSC and negative for human pan-leukocyte marker, CD45, expression.

FIGS. 34A, 34B, and 34C provide statistical comparisons of the results shown in FIG. 33B by the protocol shown in FIG. 33A. Animals treated with CM-24 showed larger tumors with no evidence of tumor associated T cells. On the other hand, increased quantities of infiltrating T cells and decreased tumor cells were observed in mice treated with CP08H03/$V_\kappa$8 S29A (FIG. 33B). As noted, assessment of tumor cell proliferation showed inhibition of tumor proliferation by CP08H03/$V_\kappa$8 S29A but not by CM-24 (FIG. 33C). Further, an increased proliferation of splenic CD4 T cells was observed in CP08H03/$V_\kappa$8 S29A treated mice, whereas a decreased proliferation of splenic CD4 T cells was observed in CM-24 treated mice (FIG. 33D).

Example 11: CEACAM1 Antibodies Block the Interaction Between CEACAM1 and HopQ

HopQ is expressed on the surface of *Helicobacter pylori*, a bacterium that specifically colonizes the human gastric epithelium and is the major causative agent for ulcer disease and gastric cancer development. The HopQ-CEACAM1 interaction has been suggested to promote gastric colonization and Hp-induced pathologies, for example by enabling translocation bacterial virulence factors into host cells and enhancing the release of pro-inflammatory mediators.

Published crystal structure data (PDB IDs 6AW2, 6GBH, 6GBG, see Bonsor, D, et. al. EMBO J. 2018 Jul. 2; 37 (13) and Moonens K et al. EMBO J. 2018 Jul. 2; 37 (13)) indicate that the GFCC' loop of CEACAM1 is involved in binding to HopQ and that CEACAM1 residues F29, Y34, N42, Q89, and N97 make various hydrogen bonded and hydrophobic interactions with HopQ residues (see FIG. 35A). Modelling based on the CECAM1:HopQ co-crystal and the CEACAM1:CP08H03/$V_\kappa$8 S29A Fab co-crystal indicates that CEACAM1 antibody CP08H03/$V_\kappa$8 S29A covers CEACAM1 binding site for HopQ (see FIG. 35B) and is as such capable of disrupting the CEACAM1:HopQ interaction.

Example 12: CEACAM1 Antibodies Promote Long-Term Survival

The ability of CEACAM1 antibody CP08H03/$V_\kappa$8 S29A to promote long-term survival of tumor-bearing mammals was investigated using a mouse melanoma model.

$10^6$ MALME-3M (human melanoma) cells, along with $5\times10^6$ human PBMC (from HLA-A2 matched donors) were injected subcutaneously into NSG mice. At day 10, the tumor tumors had reached 2-2.5 mm³, and the mice were randomized (n=4/group). Anti-CEACAM1 antibody CP08H03/V$_\kappa$8 S29A or a control human IgG4 antibody, respectively, were administered intraperitonally on days 10, 13, 17, 20, and 24. Survival was monitored for 104 days, at which point the surviving animal that exhibited vigorous clinical activity was sacrificed (arrow).

As shown in FIG. 36, treatment with the anti-CEACAM1 antibody significantly increased the survival rate of the tumor-bearing mice. Further, at autopsy, the antibody-treated animals exhibited local tumors with no visible metastasis consistent with control of disease. This data demonstrates that anti-CEACAM1 antibodies and fragments thereof disclosed herein are useful for treating cancer and increasing survival.

Example 13: CP08H03/V$_\kappa$8 S29A Increases the Immune Response in Tumor Cells Derived from Naïve Patients or Those with Secondary Resistance to Immunotherapy The ability of CEACAM1 antibody CP08H03/V$_\kappa$8 S29A to increase the immune response in tumors derived from melanoma patients who were naïve or who exhibited secondary resistance to immunotherapy was examined using isolated tumor specimens.

In one example, the isolated tumor specimen from a patient with secondary resistance was disrupted by mechanical dissociation and the dissociated cells treated for 4 days in culture medium with either CP08H03/V$_\kappa$8 S29A or a hIgG4 control antibody (2 µg/ml) in the presence of 2 µg/ml anti-CD3 and 40 units/ml recombinant IL-2. The cells were then examined by mass cytometry using the following antibodies to detect a variety of intracellular factors associated with immune responses to tumors in CD8$^+$ T cells using standard techniques: IFNγ (clone B27; 168Er), IL-17A (clone N49-653; 164Dy), IL-17F (clone SHLR17; 166Er); granzyme B (clone GB11; 171Yb); Perforin (clone B-D48; 175Lu); MIP1beta (clone D21-1351; 150Nd); TNFalpha (clone Mab11; 152Sm), CD3 (clone UCHT1; 170Er); CD8 (clone RPA78; 146Nd); intercalator (103Rh).

As shown in FIGS. 37A and 37B, treatment with the CP08H03/V$_\kappa$8 S29A antibody led to a significant induction of the factors indicated intracellularly within CD8 T cells as compared to the control human IgG4 antibody. These results directly indicate that the CP08H03/V$_\kappa$8 S29A antibody induces the production of a variety of factors in CD8 T cells that are potentially associated with a productive anti-tumor immune response.

In another example, the tumors specimens associated with two melanoma patients with either no prior treatment (subject 189) or with secondary resistance to immunotherapy (subject 185) were disrupted by mechanical dissociation (Miltenyi). $8\times10^5$/ml dissociated tumor cells were placed in a culture dish. Freshly isolated tumor dissociated cells were exposed to only 2 µg/ml CP08H03/V$_\kappa$8 S29A or human IgG4 isotype control antibody. After 96 hours, the supernatants were removed and ELISA analysis was performed in triplicate for detection of the presence of interferon-gamma.

As shown in FIGS. 38A and 38B, treatment with the CP08H03/V$_\kappa$8 S29A antibody induced significant levels of secretion of the cytokine interferon-γ relative to that observed with the control human IgG4 antibody into the supernatant of the tumor dissociated cells isolated from patients with either secondary resistance to immunotherapy treatment (FIG. 38A, subject 185) or naïve to immunotherapy treatment (FIG. 38B, subject 189).

In summary, these data demonstrate that anti-CEACAM1 antibodies and fragments thereof disclosed herein are useful for treating naïve cancer patients and those with secondary resistance to immunotherapy.

Overview of Sequences

| SEQ ID NO: | Sequence |
|---|---|
| 1 | $X_1HX_2X_3S$<br>wherein $X_1$ is A, D, N, or S;<br>wherein $X_2$ is A or G; and<br>wherein $X_3$ is an amino acid with a hydrophobic side chain including I or M |
| 2 | TISSGGTYTYYPDSVKG |
| 3 | $HX_4X_5DYX_6PX_7WFAX_8$<br>wherein $X_4$ is D, G, or P;<br>wherein $X_5$ is F or P;<br>wherein $X_6$ is D or F;<br>wherein $X_7$ is A or Y; and<br>wherein $X_8$ is L, H, or F |
| 4 | RANSAVSYMY |
| 5 | LTSNRAT |
| 6 | $QQX_9X_{10}X_{11}X_{12}PX_{13}T$<br>wherein $X_9$ is W or N;<br>wherein $X_{10}$ is S or T;<br>wherein $X_{11}$ is A or an amino acid with a neutral hydrophilic side chain including S, N, and T;<br>wherein $X_{12}$ is L, F, or N; and<br>wherein $X_{13}$ is P or F. |
| 7 | $HX_4X_5DYFPYWFAX_8$<br>wherein $X_4$ is D, G, or P;<br>wherein $X_5$ is F or P; and<br>wherein $X_8$ is L, H, or F; |
| 8 | $QQX_9SSX_{12}PX_{13}T$<br>wherein $X_9$ is W or N;<br>wherein $X_{12}$ is L, F, or N; and<br>wherein $X_{13}$ is P or F. |
| 9 | SHGMS |
| 10 | HDFDYFPYWFAH |
| 11 | QQWSSNPPT |
| 12 | QQWTSNPPT |
| 13 | EVQLLESGGGLVQPGGSLRLSCAASGFIFSSHGMSWVRQAP GKGLEWVATISSGGTYTYYPDSVKGRFTISRDNSKNTLYLQ MNSLKAEDTAMYYCARHDFDYFPYWFAHWGQGTLVTVSS |
| 14 | EIVLTQSPATLSLSPGERATLSCRANSAVSYMYWYQQKPGQ APRPWIYLTSNRATGVPARFSGSGSGTDYTLTISSLEPEDF AVYYCQQWSSNPPTFGQGTKLEIK |
| 15 | EIVLTQSPATLSLSPGERATLSCRANSAVSYMYWYQQKPGQ APRPWIYLTSNRATGVPARFSGSGSGTDYTLTISSLEPEDF AVYYCQQWTSNPPTFGQGTKLEIK |
| 16 | EIVLTQSPATLSLSPGERATLSCRANSSVSYMYWYQQKPGQ APRPWIYLTSNRATGVPARFSGSGSGTDYTLTISSLEPEDF AVYYCQQWSSNPPTFGQGTKLEIK |
| 17 | QLTTESMPFNVAEGKEVLLLVHNLPQQLFGYSWYKGERVDG NRQIVGYAIGTQQATPGPANSGRETIYPNASLLIQNVTQND TGFYTLQVIKSDLVNEEATGQFHVYPELPKPSISSNNSNPV EDKDAVAFTCEPETQDTTYLWWINNQSLPVSPRLQLSNGNR |

| SEQ ID NO: | Sequence |
|---|---|
|  | TLTLLSVTRNDTGPYECEIQNPVSANRSDPVTLNVTYGPDT PTISPSDTYYRPGANLSLSCYAASNPPAQYSWLINGTFQQS TQELFIPNITVNNSGSYTCHANNSVTGCNRTTVKTIIVTEL SPVVAKPQIKASKTTVTGDKDSVNLTCSTNDTGISIRWFFK NQSLPSSERMKLSQGNTTLSINPVKREDAGTYWCEVFNPIS KNQSDPIMLNVNYNALPQENGLSPGAIAGIVIGVVALVALI AVALACFLHFGKTGRASDQRDLTEHKPSVSNHTQDHSNDPP NKMNEVTYSTLNFEAQQPTQPTSASPSLTATEIIYSEVKKQ |
| 18 | RANSSVSYMY |
| 19 | EVQLLESGGGLVQPGGSLRLSCAASGFIFSSHGMSWVRQAP GKGLEWVATISSGGTYTYYPDSVKGRFTISRDNSKNTLYLQ MNSLKAEDTAMYYCARHDFDYDAAWFAYWGQGTLVTVSS |
| 20 | $X_{14}X_{15}X_{16}FX_{17}X_1HX_2$<br>wherein $X_{14}$ is G or E;<br>wherein $X_{15}$ is an amino acid with an aromatic side chain including F or Y;<br>wherein $X_{16}$ is T, S, or I;<br>wherein $X_{17}$ is an amino acid with a polar uncharged side chain including S, T, or N;<br>wherein $X_1$ is A, D, N, or S; and<br>wherein $X_2$ is A or G. |
| 21 | GFIFSHG |
| 22 | $X_{14}X_{15}X_{16}FX_{17}X_1HX_2X_3S$,<br>wherein $X_{14}$ is G or E;<br>wherein $X_{15}$ is an amino acid with an aromatic side chain including F or Y;<br>wherein $X_{16}$ is T, S, or I;<br>wherein $X_{17}$ is an amino acid with a polar uncharged side chain including S, T, or N;<br>wherein $X_1$ is A, D, N, or S;<br>wherein $X_2$ is A or G; and<br>wherein $X_3$ is an amino acid with a hydrophobic side chain including I or M |
| 23 | GFIFSSHGMS |
| 24 | $X_{18}HX_4X_5DYX_6PX_7WFAX_8$<br>wherein $X_{18}$ is R or K<br>wherein $X_4$ is D, G, or P<br>wherein $X_5$ is F or P;<br>wherein $X_6$ is D or F;<br>wherein $X_7$ is A or Y; and<br>wherein $X_8$ is L, H, or F. |
| 25 | RHDFDYFPYWFAH |
| 26 | MGHLSAPLHRVRVPWQGLLLTASLLTFWNPPTTAQLTTESM PFNVAEGKEVLLLVHNLPQQLFGYSWYKGERVDGNRQIVGY AIGTQQATPGPANSGRETIYPNASLLIQNVTQNDTGFYTLQ VIKSDLVNEEATGQFHVYPELPKPSISSNNSNPVEDKDAVA FTCEPETQDTTYLWWINNQSLPVSPRLQLSNGNRTLTLLSV TRNDTGPYECEIQNPVSANRSDPVTLNVTYGPDTPTISPSD TYYRPGANLSLSCYAASNPPAQYSWLINGTFQQSTQELFIP NITVNNSGSYTCHANNSVTGCNRTTVKTIIVTELSPVVAKP QIKASKTTVTGDKDSVNLTCSTNDTGISIRWFFKNQSLPSS ERMKLSQGNTTLSINPVKREDAGTYWCEVFNPISKNQSDPI MLNVNYNALPQENGLSPGAIAGIVIGVVALVALIAVALACF LHFGKTGRASDQRDLTEHKPSVSNHTQDHSNDPPNKMNEVT YSTLNFEAQQPTQPTSASPSLTATEIIYSEVKKQ |
| 27 | EVQLVESGGDLVKPGGSLKLACAASGFIFSSHGMSWVRQTP DKRLEWVATISSGGTYTYYPDSVKGRFTISRDNDKNTLYLQ MNSLKSEDTAMYYCARHDFDYDAAWFAYWGQGTLVTVSS |
| 28 | EVQLLESGGGLVQPGGSLRLSCAASGFIFSSHGMSWVRQAP GKGLEWVATISSGGTYTYYPDSVKGRFTISRDNSKNTLYLQ MNSLRAEDTAMYYCARHDFDYDAAWFAYWGQGTLVTVSS |
| 29 | EVQLLESGGGLVQPGGSLRLSCAASGFIFSSHGMSWVRQAP GKGLEWVATISSGGTYTYYADSVKGRFTISRDNSKNTLYLQ MNSLRAEDTAMYYCARHDFDYDAAWFAYWGQGTLVTVSS |
| 30 | EVQLLESGGGLVQPGGSLRLSCAASGFIFSSHGMSWVRQAP GKGLEWVSTISSGGTYTYYADSVKGRFTISRDNSKNTLYLQ MNSLRAEDTAVYYCARHDFDYDAAWFAYWGQGTLVTVSS |
| 31 | QIVLTQSPALMSASPGVKVTMTCSANSSVSYMYWYRQKPRS SPKPWIYLTSNLASGVPARFSGSGSGTSYSLTISSMEAEDA ATYYCQQWSSNPPTFGSGTKLEIK |
| 32 | QIVLTQSPALLSLSPGERATMSCSANSSVSYMYWYRQKPGQ APKPWIYLTSNLASGVPARFSGSGSGTDYTLTISSLEAEDF ATYYCQQWSSNPPTFGQGTKLEIK |
| 33 | EIVLTQSPATLSLSPGERATLSCRANSSVSYMYWYQQKPGQ APRPWIYLTSNRATGVPARFSGSGSGTDYTLTISSLEPEDF ATYYCQQWSSNPPTFGQGTKLEIK |
| 34 | EIVLTQSPATLSLSPGERATLSCRANSSVSYMAWYQQKPGQ APRPWIYLTSNRATGVPARFSGSGSGTDYTLTISSLEPEDF ATYYCQQWSSNPPTFGQGTKLEIK |
| 35 | EIVLTQSPATLSLSPGERATLSCRANSSVSYMYWYQQKPGQ APRPWIYLTSNRATGIPARFSGSGSGTDYTLTISSLEPEDF ATYYCQQWSSNPPTFGQGTKLEIK |
| 36 | EIVLTQSPATLSLSPGERATLSCRANSSVSYMAWYQQKPGQ APRLLIYLTSNRATGIPARFSGSGSGTDFTLTISSLEPEDF AVYYCQQWSSNPPTFGQGTKLEIK |
| 37 | DIQLTQSPSFLSASVGDRVTITCRANSSVSYMAWYQQKPGK APKLLIYLTSNLQSGVPSRFSGSGSGTEFTLTISSLQPEDF ATYYCQQWSSNPPTFGQGTKLEIK |
| 38 | EIVLTQSPATLSLSPGERATLSCRANSSVSYMYWYQQKPGQ APRPWIYLTSNRATGVPARFSGSGSGTDFTLTISSLEPEDF ATYYCQQWSSNPPTFGQGTKLEIK |
| 39 | EIVLTQSPATLSLSPGERATLSCRANSSVSYMYWYQQKPGQ APRPLIYLTSNRATGVPARFSGSGSGTDYTLTISSLEPEDF ATYYCQQWSSNPPTFGQGTKLEIK |
| 40 | EIVLTQSPATLSLSPGERATLSCRANSSVSYMYWYQQKPGQ APRPWIYLTSNRATGIPARFSGSGSGTDFTLTISSLEPEDF ATYYCQQWSSNPPTFGQGTKLEIK |
| 41 | EIVLTQSPATLSLSPGERATLSCRANSSVSYMYWYQQKPGQ APRPWIYLTSNRATGIPARFSGSGSGTDYTLTISSLEPEDF AVYYCQQWSSNPPTFGQGTKLEIK |
| 42 | EIVLTQSPATLSLSPGERATLSCRANSSVSYMYWYQQKPGQ APRPLIYLTSNRATGIPARFSGSGSGTDYTLTISSLEPEDF ATYYCQQWSSNPPTFGQGTKLEIK |
| 43 | $GXXXXX_1HX_2X_3S$;<br>wherein X is any amino acid;<br>wherein $X_1$ is A, D, N, or S;<br>wherein $X_2$ is A or G; and<br>wherein $X_3$ is an amino acid with a hydrophobic side chain including I or M |
| 44 | $HX_4X_5DYFPX_7WFAX_8$,<br>wherein $X_4$ is D, G, or P;<br>wherein $X_5$ is F or P;<br>wherein $X_7$ is A or Y; and<br>wherein $X_8$ is L, H, or F. |
| 45 | $HX_4X_5DYX_6X_{19}X_7WFAX20$<br>wherein $X_4$ is D, G, or P;<br>wherein $X_5$ is F or P;<br>wherein $X_6$ is D or F;<br>wherein $X_{19}$ is P or A; |

| SEQ ID NO: | Sequence |
|---|---|
| | wherein $X_7$ is A or Y; and<br>wherein $X_{20}$ is L, H, Y or F; |
| 46 | $X_{14}FX_{21}FX_{22}X_{23}HX_2X_3S$ (SEQ ID NO: 46);<br>wherein $X_{14}$ is G or E;<br>wherein $X_{21}$ is T or I;<br>wherein $X_{22}$ is N or S;<br>wherein $X_{23}$ is A, D, or S<br>wherein $X_2$ is A or G; and<br>wherein $X_3$ is an amino acid with a hydrophobic side chain including I or M; |
| 47 | $HX_{24}FDYX_6X_{19}X_7WFAX_{25}$<br>wherein $X_{24}$ is D or G;<br>wherein $X_6$ is D or F;<br>wherein $X_{19}$ is P or A;<br>wherein $X_7$ is A or Y; and<br>wherein $X_{25}$ is H or Y; |
| 48 | $QQWX_{10}X_{10}NPPT$<br>wherein $X_{10}$ is S or T; |
| 49 | $X_{14}FTFX_{22}X_{26}HAX_3S$ (SEQ ID NO: 49)<br>wherein $X_{14}$ is G or E;<br>wherein $X_{17}$ is S or N;<br>wherein $X_{22}$ is N or S;<br>wherein $X_{26}$ is A or D and<br>wherein $X_3$ is an amino acid with a hydrophobic side chain including I or M; |

While the foregoing written description of the invention enables one of ordinary skill to make and use what is considered presently to be the best mode thereof, those of ordinary skill will understand and appreciate the existence of variations, combinations, and equivalents of the specific embodiments, methods, and examples herein.

We claim:

1. An antibody or antigen-binding fragment thereof which binds to CEACAM1, the antibody or antigen-binding fragment thereof comprising a heavy chain variable region and a light chain variable region, wherein each of the heavy chain and the light chain variable regions comprises a CDR1, CDR2, and CDR3 and wherein:
   the sequence of CDR1H comprises the sequence SHGMS (SEQ ID NO:9);
   the sequence of CDR2H comprises the sequence TISSGGTYTYYPDSVKG (SEQ ID NO: 2);
   the sequence of CDR3H comprises the sequence HDFDYFPYWFAH (SEQ ID NO:10);
   the sequence of CDR1L comprises the sequence RANSAVSYMY (SEQ ID NO:4);
   the sequence of CDR2L comprises the sequence LTSNRAT (SEQ ID NO:5); and
   the sequence of CDR3L comprises the sequence QQWSSNPPT (SEQ ID NO:11).

2. The antibody or antigen-binding fragment thereof according to claim 1, wherein:
   the sequence of the heavy chain variable region comprises a sequence that is at least 90% identical to the heavy chain variable region amino acid sequence of SEQ ID NO: 13; and
   the sequence of the light chain variable region comprises a sequence that is at least 90% identical to the light chain variable region amino acid sequence of SEQ ID NO:14.

3. The antibody or antigen-binding fragment thereof according to claim 1, wherein:
   the sequence of the heavy chain variable region comprises SEQ ID NO: 13; and
   the sequence of the light chain variable region comprises SEQ ID NO: 14.

4. The antibody or antigen-binding fragment thereof according to claim 1, wherein the antibody or antigen-binding fragment thereof is a chimeric antibody, a CDR-grafted antibody, or a humanized antibody or antigen-binding fragment thereof.

5. The antibody or antigen-binding fragment thereof according to claim 1, wherein the antibody or antigen-binding fragment thereof is a multispecific or a bispecific antibody or antigen-binding fragment thereof.

6. The antibody or antigen-binding fragment thereof according to claim 5, wherein the antibody or antigen-binding fragment thereof is a bispecific antibody comprising a complementary region that binds to PD-1 or PD-L1.

7. The antibody or antigen-binding fragment thereof according to claim 1, wherein the antibody or antigen-binding fragment thereof has isotype IgG4.

8. The antibody or antigen-binding fragment thereof according to claim 1, wherein the antibody or antigen-binding fragment thereof contains a S241P substitution in the constant region of the heavy chain.

9. The antibody or antigen-binding fragment thereof according to claim 1, wherein the antibody or antigen-binding fragment thereof is deglycosylated.

10. The antibody or antigen-binding fragment thereof according to claim 1, wherein the antibody or antigen-binding fragment thereof is lacking a C-terminal lysine in the heavy chain.

11. The antibody or antigen-binding fragment thereof according to claim 1, wherein the antibody or antigen-binding fragment thereof is conjugated to one or more of a cytotoxin, a fluorescent label, and an imaging agent.

12. An isolated nucleic acid encoding the antibody or antigen-binding fragment thereof according to claim 1.

13. A vector comprising the nucleic acid according to claim 12.

14. A cell comprising the vector according to claim 13.

15. A T-cell with a chimeric antigen receptor comprising the CDRs of the antibody or antigen-binding fragment thereof according to claim 1.

16. A pharmaceutical composition comprising the antibody or antigen-binding fragment thereof according to claim 1, and a pharmaceutically acceptable excipient.

17. A method of reducing T cell tolerance in a subject in need thereof, the method comprising administering to the subject an effective amount of the antibody or antigen-binding fragment thereof according to claim 1.

18. A method of treating cancer in a subject in need thereof, the method comprising administering to the subject an effective amount of the antibody or antigen-binding fragment thereof according to claim 1.

19. The method of claim 18, wherein the cancer is melanoma, pancreatic cancer, thyroid cancer, lung cancer, colorectal cancer, squamous cancer, prostate cancer, breast cancer, bladder cancer, or gastric cancer.

20. A method of reducing tumor growth in a subject in need thereof, the method comprising administering to the subject an effective amount of the antibody or antigen-binding fragment thereof according to claim 1.

21. The method according to claim 18, the method further comprising administering a checkpoint inhibitor.

22. The method according to claim 21, wherein the checkpoint inhibitor is an inhibitor of CTLA-4, PD-1, PD-L1, PD-L2, TIM-3, ICOS, CD160, LAG3, TIGIT, and VISTA.

23. The method according to claim 18, the method further comprising administering one or more of an inhibitor LAP, Podoplanin, Protein C receptor, GITR, CD226, or CD160.

* * * * *